(12) United States Patent
Chinnaiyan et al.

(10) Patent No.: US 11,390,923 B2
(45) Date of Patent: Jul. 19, 2022

(54) NCRNA AND USES THEREOF

(71) Applicant: THE REGENTS OF THE UNIVERSITY OF MICHIGAN, Ann Arbor, MI (US)

(72) Inventors: Arul Chinnaiyan, Plymouth, MI (US); John Prensner, Ann Arbor, MI (US); Matthew Iyer, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

(21) Appl. No.: 16/453,195

(22) Filed: Jun. 26, 2019

(65) Prior Publication Data

US 2020/0165682 A1 May 28, 2020

Related U.S. Application Data

(63) Continuation of application No. 15/064,266, filed on Mar. 8, 2016, now abandoned, which is a continuation of application No. 13/299,000, filed on Nov. 17, 2011, now abandoned.

(60) Provisional application No. 61/415,490, filed on Nov. 19, 2010.

(51) Int. Cl.
C12Q 1/68 (2018.01)
C12Q 1/6886 (2018.01)
C12N 15/11 (2006.01)

(52) U.S. Cl.
CPC .......... C12Q 1/6886 (2013.01); *C12N 15/11* (2013.01); *C12Q 2600/118* (2013.01); *C12Q 2600/158* (2013.01); *C12Q 2600/16* (2013.01); *C12Q 2600/178* (2013.01)

(58) Field of Classification Search
None
See application file for complete search history.

(56) References Cited

U.S. PATENT DOCUMENTS

| | | |
|---|---|---|
| 2005/0118625 A1 | 6/2005 | Mounts |
| 2007/0172841 A1 | 7/2007 | Wang |
| 2008/0076674 A1 | 3/2008 | Litman et al. |
| 2009/0239221 A1 | 6/2009 | Chinnaiyan |
| 2016/0251729 A1 | 9/2016 | Chinnaiyan |
| 2016/0348184 A1 | 12/2016 | Chinnaiyan |

FOREIGN PATENT DOCUMENTS

| | | |
|---|---|---|
| CN | 101835902 A | 9/2010 |
| WO | WO 199845420 A1 | 10/1998 |
| WO | WO 200166753 A1 | 9/2001 |
| WO | WO 2004037972 A2 | 5/2004 |
| WO | WO 2008086478 A2 | 7/2008 |
| WO | WO 2009020905 A2 | 2/2009 |
| WO | WO 2012068383 A2 | 5/2012 |

OTHER PUBLICATIONS

Bannert et al., "Retroelements and the human genome: new perspectives on an old relation." Proc Natl Acad Sci U S A. Oct. 5, 2004; 101 Suppl 2:14572-9.
Birney et al., "Identification and analysis of functional elements in 1% of the human genome by the ENCODE pilot project." Nature. Jun. 14, 2007; 447(7146):799-816.
Boorjian et al., "Long-term risk of clinical progression after biochemical recurrence following radical prostatectomy: the impact of time from surgery to recurrence." Eur Urol. Jun. 2011; 59(6):893-9.
Brouha et al., "Hot L1s account for the bulk of retrotransposition in the human population." Proc Natl Acad Sci U S A. Apr. 29, 2003; 100(9):5280-5.
Bussemakers et al., "DD3: a new prostate-specific gene, highly overexpressed in prostate cancer." Cancer Res. Dec. 1, 1999; 59(23):5975-9.
Carninci et al., "The transcriptional landscape of the mammalian genome." Science. Sep. 2, 2005; 309(5740):1559-63.
Chalitchagorn et al., "Distinctive pattern of LINE-1 methylation level in normal tissues and the association with carcinogenesis." Oncogene. Nov. 18, 2004; 23(54):8841-6.
Cho et al., "Hypermethylation of CpG island loci and hypomethylation of LINE-1 and Alu repeats in prostate adenocarcinoma and their relationship to clinicopathological features." J Pathol. Feb. 2007; 211(3):269-77.
Chow et al., "LINE-1 activity in facultative heterochromatin formation during X chromosome inactivation." Cell. Jun. 11, 2010; 141(6):956-69.
Cordaux et al., "The impact of retrotransposons on human genome evolution." Nat Rev Genet. Oct. 2009; 10(10):691-703.
Day et al., "Estimating enrichment of repetitive elements from high-throughput sequence data." Genome Biol. 2010; 11(6):R69.
De Klein et al., "A cellular oncogene is translocated to the Philadelphia chromosome in chronic myelocytic leukaemia." Nature. Dec. 23, 1982; 300(5894):765-7.
Dechassa et al. "Architecture of the SWI/SNF-nucleosome complex." Mol Cell Biol. Oct. 2008; 28(19):6010-21.
Dhanasekaran et al., "Delineation of prognostic biomarkers in prostate cancer." Nature. Aug. 23, 2001; 412(6849):822-6.
Fu et al., "Regulation of apoptosis by a prostate-specific and prostate cancer-associated noncoding gene, PCGEM1." DNA Cell Biol. Mar. 2006; 25(3):135-41.
Gupta et al., "Long non-coding RNA Hotair reprograms chromatin state to promote cancer metastasis." Nature. Apr. 15, 2010; 464(7291):1071-6.
Guttman et al., "Ab initio reconstruction of cell type-specific transcriptomes in mouse reveals the conserved multi-exonic structure of lincRNAs." Nat Biotechnol. May 2010; 28(5):503-10.
Guttman et al., "Chromatin signature reveals over a thousand highly conserved large non-coding RNAs in mammals." Nature. Mar. 12, 2009; 458(7235):223-7.

(Continued)

*Primary Examiner* — Jehanne S Sitton
(74) *Attorney, Agent, or Firm* — Casimir Jones, S.C.; Tanya A. Arenson

(57) ABSTRACT

The present invention relates to compositions and methods for cancer diagnosis, research and therapy, including but not limited to, cancer markers. In particular, the present invention relates to ncRNAs as diagnostic markers and clinical targets for prostate, lung, breast and pancreatic cancer.

7 Claims, 54 Drawing Sheets

Specification includes a Sequence Listing.

(56) References Cited

OTHER PUBLICATIONS

He et al., "The antisense transcriptomes of human cells." Science. Dec. 19, 2008; 322(5909):1855-7.

Huarte & Rinn, "Large non-coding RNAs: missing links in cancer?" Human Molecular Genetics 2010,19(2): R152-R161.

Jones et al., "Frequent mutations of chromatin remodeling gene ARID1A in ovarian clear cell carcinoma." Science. Oct. 8, 2010; 330(6001):228-31.

Kunarso et al., "Transposable elements have rewired the core regulatory network of human embryonic stem cells." Nat Genet. Jul. 2010; 42(7):631-4.

Lin et al., "Nuclear receptor-induced chromosomal proximity and DNA breaks underlie specific translocations in cancer." Cell. Dec. 11, 2009; 139(6):1069-83.

Mitelman, "Recurrent chromosome aberrations in cancer", Mutation Research 2000, 462: 247-253.

Oosumi et al., "Mariner transposons in humans." Nature. Dec. 14, 1995; 378(6558):672.

Prensner et al., "Transcriptome sequencing across a prostate cancer cohort identifies PCAT-1, an unannotated lincRNA implicated in disease progression." 29(8): 742-749.

Rabbitts, "Chromosomal translocations in human cancer", Nature Nov. 10, 1994, 372: 143-149.

Reis et al., "Antisense intronic non-coding RNA levels correlate to the degree of tumor differentiation in prostate cancer." Oncogene. Aug. 26, 2004;23(39):6684-92.

Rinn et al., "Functional demarcation of active and silent chromatin domains in human HOX loci by noncoding RNAs." Cell. Jun. 29, 2007; 129(7):1311-23.

Roberts et al., "The SWI/SNF complex-chromatin and cancer." Nat Rev Cancer. Feb. 2004; 4(2):133-42.

Robertson et al., "Reconstructing the ancient mariners of humans." Nat Genet. Apr. 1996; 12(4):360-1.

Rowley, "A new Consistent Chromosomal Abnormality in Chronic Myelogenous Leukaemia Identified by Quinacrine Fluorescence and Giemsa Staining", Nature Jun. 1, 1973, 243:290-293.

Rowley, "Chromosome translocations: dangerous liaisons revisited", Nature Reviews: Cancer Dec. 2001, (1):245-250.

Shen et al., "The SWI/SNF ATPase Brm is a gatekeeper of proliferative control in prostate cancer." Cancer Res. Dec. 15, 2008; 68(24):10154-62.

Simmons et al., "Natural history of biochemical recurrence after radical prostatectomy: risk assessment for secondary therapy." Eur Urol. May 2007; 51(5):1175-84.

Slotkin et al., "Transposable elements and the epigenetic regulation of the genome." Nat Rev Genet. Apr. 2007; 8(4):272-85.

Srikantan et al., "PCGEM1, a prostate-specific gene, is overexpressed in prostate cancer." Proc Natl Acad Sci U S A. Oct. 24, 2000;97(22):12216-21.

Stavenhagen et al., "An ancient provirus has imposed androgen regulation on the adjacent mouse sex-limited protein gene." Cell. Oct. 21, 1988; 55(2):247-54.

Sun et al., "Aberrant expression of SWI/SNF catalytic subunits BRG1/BRM is associated with tumor development and increased invasiveness in prostate cancers." Prostate. Feb. 1, 2007; 67(2):203-13.

Taft et al., "Non-coding RNAs: regulators of disease." J Pathol. Jan. 2010; 220(2):126-39.

Tomlins et al., "Distinct classes of chromosomal rearrangements create oncogenic ETS gene fusions in prostate cancer." Nature. Aug. 2, 2007; 448(7153):595-9.

Varela et al., "Exome sequencing identifies frequent mutation of the SWI/SNF complex gene PBRM1 in renal carcinoma." Nature. Jan. 27, 2011; 469(7331):539-42.

Versteege et al., "Truncating mutations of hSNF5/INI1 in aggressive paediatric cancer." Nature. Jul. 9, 1998; 394(6689):203-6.

Wiegand et al., "ARID1A mutations in endometriosis-associated ovarian carcinomas." N Engl J Med. Oct. 14, 2010; 363(16):1532-43.

Yap et al., "Molecular interplay of the noncoding RNA ANRIL and methylated histone H3 lysine 27 by polycomb CBX7 in transcriptional silencing of INK4a." Mol Cell. Jun. 11, 2010; 38(5):662-74.

Yegnasubramanian et al., "DNA hypomethylation arises later in prostate cancer progression than CpG island hypermethylation and contributes to metastatic tumor heterogeneity." Cancer Res. Nov. 1, 2008;68(21):8954-67.

Yelin et al., "Widespread occurrence of antisense transcription in the human genome." Nat Biotechnol. Apr. 2003; 21(4):379-86.

Yu et al., "An integrated network of androgen receptor, polycomb, and TMPRSS2-ERG gene fusions in prostate cancer progression." Cancer Cell. May 18, 2010; 17(5):443-54.

International Search Report of PCT application No. PCT/US2011/061204, dated Jun. 19, 2012, 11 pages.

Office Action of related AU Appl. No. 2015242941, dated May 18, 2017, 4 pages.

EP Search Report, EP Patent Application No. 18155318.1, dated Apr. 24, 2018, 9 pages.

d

| Rank | Gene | Chromosomal Location | Outlier Score |
|---|---|---|---|
| 1 | CRISP3 | chr6:49803053-49813070 | 294.5644568 |
| 2 | SPINK1 | chr5:147184335-147191453 | 177.1951756 |
| 3 | PCAT-107 | chrX:66691350-66692032 | 130.7349145 |
| 4 | PCAT-108 | chr16:79420131-79423590 | 127.0430957 |
| 5 | PCAT-109 | chr2:180689090-180696402 | 123.5416436 |
| 6 | ERG | chr21:38673821-38792298 | 119.4460029 |
| 7 | C7orf68 | chr7:127883119-127885708 | 105.1850442 |
| 8 | CSRP3 | chr11:19160153-19180106 | 101.129471 |
| 9 | COL2A1 | chr12:46653014-46684552 | 99.16632908 |
| 10 | C1orf64 | chr1:16203317-16205771 | 98.0859221 |
| 11 | COL9A2 | chr1:40538749-40555526 | 74.40844283 |
| 12 | PLA2G7 | chr6:46780012-46811389 | 69.5211751 |
| 13 | AGT | chr1:228904891-228916959 | 69.31988642 |
| 14 | PCAT-113 | chr1:20685471-20686432 | 68.3572507 |
| 15 | ETV1 | chr7:13897382-13992664 | 68.21856853 |
| 16 | MUC6 | chr11:1002823-1026706 | 64.73280043 |
| 17 | PCAT-114 | chr10:42652247-42653596 | 60.91841567 |
| 18 | PCAT-115 | chr4:102257900-102306678 | 59.24997694 |
| 19 | RGL3 | chr19:11365731-11391018 | 57.5286889 |
| 20 | TMEM45B | chr11:129190950-129235108 | 55.88784464 |

Figure 28

PCAT-1

Exon 1: chr8:128,094,581-128,095,201 (SEQ ID NO:1)

ACACATGGATATTGGATATCTGCATAGGCAGCTTGCTCCACGCCAGTGCCTACCTGTGCAGATGGGAAGGAA
AGGAAAGTGGCAAGGAGGCAGAGAAAGCATCTGTACCCTTACAATTTGGTGAGACAAGAATGTATGAATTCC
CACAGGTCAAATTATAATGAAGAAAGGAACCTCTCTTGAGTACAAAGAGCTACCTATGGTGGTCTGGAGCCG
GAGGACCACAGCATCAAAGGATATAAGATGCATAGCCAACTGAGGAACCTGAGCAATTAAAGAGATCCACAG
TTAAGTCACACTTAACTGGCACTTGTGGAAGCCCCGCAAGGCCTGAAGGAGAGCTGACATAGGCACCCCGGA
GAGCCAGAATCTGGATCCCATCTTAATAAGGCCATGAACACCAGTGGAGAAGAGGCAGAAACACCAATGGAT
AAGGAACATTCACATCTTTCTTCCCATGTGCCTCTAAGTGCCAGTGCAGGCCCCACAGGCCAAGCTACAGGGA
GAAAGGAGATGACGCAAAGGAACCTAACTGGACTTTAATCACTAGAAGTGAGAAGAGAAATCTATTGGAACC
TCCCAAGATAATGCCAAGGGTCAAAGGGTGCGCAGATACATAAG

Exon 2: chr8:128,101,071-128,102,441 (SEQ ID NO:2)

ACCATGGAAATAATATCAGACAAAAAGCAGATTAGAGCAATTTTCTTTTTCGAGTTCAAAATGGGTTATAAAG
CAGCGGAGACAAACCGCAACATCACCAACGCCTTTGGCCCAGGAACTGCTAATGAAGGTACAGTGCAGTCAC
TGTTCAGGAAGTTTTGCAAAGGAGACTAGAGCCTTGAAGATGAGGAGCATAGTGACCAGCCATTGGAAGTCG
ACAAAGACCAATTGAGAGGAATCATTGAAGCTGATCATCTTACAACTACACGAGAAGTTGTCAAAGAACGCA
ATGTTGACCATTGTGTGGTCTTTTCGCATTTGAAGCAAATTGGAAAGGTGAAAAACTTGATAAGTGGGTGCCT
TGTGAGCTCAGCAAAAATCCAAAAAAATAATCATTTTTAAGTGTTGTCTTCTCTTATTCTACGCAACAACAATAA
CCATTTTGCAATCGGATTGTGATGTGCAATGAAAAGTGGATTTGGGGCCGGGCGCGGTGGCTCACGCCTGTA
ATCTCAGCACTTTGGAAGGCCAAGGCGGGCAGATCACGAGGTCAGGAGATCAAGACCGTCCTGGCTAACACG
GTGAAACCCCGTCTCTACTGAAAATACAAAAAATTAGCCGGGTGTGGTGGCTGGCGCCTGTAGTCCCAGCTAC
AGGCTGAGGCAGGAGAATGGCATGAACCTGGGAGGCGGAGCTTGCAGTGAGCCGAGACCGTGCCACTGCAC
TCCAGCCTGGGCGACAGAGCGATACTCCGTCAAAAAAAAAAAAAAAAAAAAAAAAAAGACAAGTGGATTTTAT
ATATGGCAACCAGCAATGACCAGCTCAGTGGCTGGACTGAGAAGAAGCTCCAAAGCACTTCCCAAAGCCAAA
CTTGCACCAAAAAAAAGGTCAGGGTCACTGTTTGGTGGTCTGCTGCTGGTCTGATCCACCGCTGCTCTCTGAAT
CCTGGCAAAACCATTACATCTGAGAAGTATGCTCAACAAATCAATGAGCTACGCCAAAAACTGCAGCATCTGC
AGCTGGCATTGGTCAACATAACGGGTCCAATTCTTCTCCACGACAACGCTCAACTGCACCTTGCGCAAGCAGC
GCTTCAAAAGTTGAACAAATTGGGCTACATAGTTTTTCCTCATCCGCCATATTCACCTGACGTCTTGCCAACTAA
CTACCACTTCTTCAAGTATCTCAACAACTTTTTGCAGGGAAAACACTTCCACAACCAGCAGGATGCAGAACACG
CTTTCCAAGAGTTTGTCGAATCCTGACGCACAGATTTTTATGCTACAGGAATAAACTAACTTATTTCTCATTGGC
AAAAATGTGTTGATTGTAATGGTTCCTATTTTGATGAATAAATGTGTGTTTGAGCCTA

Figure 28 (cont)

PCAT-14, isoform 1

Exon 1: chr22:22,209,086-22,209,323 (SEQ ID NO:3)

ATGCTGAGCGCCGGTCCCCTGGGCCCACTTTTCTTTCTCTATACTTTGTCTCTGTTGTCTTTCTTTTCTCAAGTCT
CTCGTTCCACCTGAGGAGAAATGCCCACAGCTGTGGAGGCGCAGGCCACTCCATCTGGTGCCCAACGTGGAT
GCTTTTCTCTAGGGTGAAGGGACTCTCGAGTGTGGTCATTGAGGACAAGTCAACGAGAGATTCCCGAGTACG
TCTACAGTGAGCCTTGTG

Exon 2: chr22:22,210,948-22,211,026 (SEQ ID NO:4)

GGTGAAGGTACTCTACAGTGTGGTCATTGAGGACAAGTTGACGAGAGAGTCCCAAGTACGTCCACGGTCAGC
CTTGCGG

Exon 3: chr22:22,216,415-22,216,493 (SEQ ID NO:5)

ACATTTAAAGTTCTACAATGAACTCACTGGAGATGCAAAGAAAAGTGTGGAGATGGAGACACCCCAATCGAC
TCGCCAG

Exon 4: chr22:22,218,673-22,219,354 (SEQ ID NO:6)

TCTACAGGTGTATCCAGCAGCTCCAAAGAGACAGCAACCAGCAAGAATGGGCCATAGTGACGATGGTGGTTT
TGTCAAAAAGAAAAGGGGGGGATATGTAAGGAAAAGAGAGATCAGACTTTCACTGTGTCTATGTAGAAAAG
GAAGACATAAGAAACTCCATTTTGATCTGTACTAAGAAAAATTGTTTTGCCTTGAGATGCTGTTAATCTGTAAC
TTTAGCCCCAACCCTGTGCTCACGGAAACATGTGCTGTAAGGTTTAAGGGATCTAGGGCTGTGCAGGATGTAC
CTTGTTAACAATATGTTTGCAGGCAGTATGTTTGGTAAAAGTCATCGCCATTCTCCATTCTCGATTAACCAGGG
GCTCAATGCACTGTGGAAAGCCACAGGAACCTCTGCCCAAGAAAGCCTGGCTGTTGTGGGAAGTCAGGGACC
CCGAATGGAGGGACCAGCTGGTGCTGCATCAGGAAACATAAATTGTGAAGATTTCTTGGACATTTATCAGTTT
CCAAAATTAATACTTTTATAATTTCTTACACCTGTCTTACTTTAATCTCTTAATCCTGTTATCTTTGTAAGCTGAG
GATATACGTCACCTCAGGACCACTATTGTACAAATTGATTGTAAAACATGTTCACATGTGTTTGAACAATATGA
AATCAGTGCACCTTGAAAATGAA

PCAT-14, isoform 2

Exon 1: chr22:22,209,086-22,209,323 (SEQ ID NO:7)

Figure 28 (cont)

ATGCTGAGCGCCGGTCCCCTGGGCCCACTTTTCTTTCTCTATACTTTGTCTCTGTTGTCTTTCTTTTCTCAAGTCT
CTCGTTCCACCTGAGGAGAAATGCCCACAGCTGTGGAGGCGCAGGCCACTCCATCTGGTGCCCAACGTGGAT
GCTTTTCTCTAGGGTGAAGGGACTCTCGAGTGTGGTCATTGAGGACAAGTCAACGAGAGATTCCCGAGTACG
TCTACAGTGAGCCTTGTG

Exon 2: chr22:22,210,860-22,216,414 (SEQ ID NO:8)

TCTCTCATCCCTCCTGACGAGAAATACCCACAGGTGTGGAGGGGCTGGCCCCCTTCATCTGATGCCCAATGTG
GGTGCCTTTCTCTAGGGTGAAGGTACTCTACAGTGTGGTCATTGAGGACAAGTTGACGAGAGAGTCCCAAGT
ACGTCCACGGTCAGCCTTGCGGTAAGCTTGTGTGCTTAGAGGAACCCAGGGTAACGATGGGGCAAACTGAAA
GTAAATATGCCTCTTATCTCAGCTTTATTAAAATTCTTTTAAGAAGAGGGGGAGTTAGAGCTTCTACAGAAAAT
CTAATTACGCTATTTCAAACAATAGAACAATTCTGCCCATGGTTTCCAGAACAGGGAACTTTAGATCTAAAAGA
TTGGGAAAAAATTGGCAAAGAATTAAAACAAGCAAATAGGGAAGGTAAAATCATCCCACTTACAGTATGGAA
TGATTGGGCCATTATTAAAGCAACTTTAGAACCATTTCAAACAGGAGAAGATATTGTTTCAGTTTCTGATGCCC
CTAAAAGCTGTGTAACAGATTGTGAAGAAGAGGCAGGGACAGAATCCCAGCAAGGAACGGAAAGTTCACAT
TGTAAATATGTAGCAGAGTCTGTAATGGCTCAGTCAACGCAAAATGTTGACTACAGTCAATTACAGGAGATAA
TATACCCTGAATCATCAAAATTGGGGAAGGAGGTCCAGAATCATTGGGGCCATCAGAGCCTAAACCACGAT
CGCCATCAACTCCTCCTCCCGTGGTTCAGATGCCTGTAACATTACAACCTCAAACGCAGGTTAGACAAGCACAA
ACCCCAAGAGAAATCAAGTAGAAAGGGACAGAGTCTCTATCCCGGCAATGCCAACTCAGATACAGTATCCA
CAATATCAGCCGGTAGAAAATAAGACCCAACCGCTGGTAGTTTATCAATACCGGCTGCCAACCGAGCTTCAGT
ATCGGCCTCCTTCAGAGGTTCAATACAGACCTCAAGCGGTGTGTCCTGTGCCAAATAGCACGGCACCATACCA
GCAACCCACAGCGATGGCGTCTAATTCACCAGCAACACAGGACGCGGCGCTGTATCCTCAGCCGCCCACTGTG
AGACTTAATCCTACAGCATCACGTAGTGGACAGGGTGGTGCACTGCATGCAGTCATTGATGAAGCCAGAAAA
CAGGGCGATCTTGAGGCATGGCGGTTCCTGGTAATTTTACAACTGGTACAGGCCGGGGAAGAGACTCAAGTA
GGAGCGCCTGCCCGAGCTGAGACTAGATGTGAACCTTTCACCATGAAAATGTTAAAAGATATAAAGGAAGGA
GTTAAACAATATGGATCCAACTCCCCTTATATAAGAACATTATTAGATTCCATTGCTCATGGAAATAGACTTACT
CCTTATGACTGGGAAATTTTGGCCAAATCTTCCCTTTCATCCTCTCAGTATCTACAGTTTAAAACCTGGTGGATT
GATGGAGTACAAGAACAGGTACGAAAAAATCAGGCTACTAAGCCCACTGTTAATATAGACGCAGACCAATTG
TTAGGAACAGGTCCAAATTGGAGCACCATTAACCAACAATCAGTGATGCAGAATGAGGCTATTGAACAAGTA
AGGGCTATTTGCCTCAGGGCCTGGGGAAAAATTCAGGACCCAGGAACAGCTTTCCCTATTAATTCAATTAGAC
AAGGCTCTAAAGAGCCATATCCTGACTTTGTGGCAAGATTACAAGATGCTGCTCAAAAGTCTATTACAGATGA
CAATGCCCGAAAAGTTATTGTAGAATTAATGGCCTATGAAAATGCAAATCCAGAATGTCAGTCGGCCATAAAG
CCATTAAAAGGAAAAGTTCCAGCAGGAGTTGATGTAATTACAGAATATGTGAAGGCTTGTGATGGGATTGGA
GGAGCTATGCATAAGGCAATGCTAATGGCTCAAGCAATGAGGGGGCTCACTCTAGGAGGACAAGTTAGAAC
ATTTGGGAAAAATGTTATAATTGTGGTCAAATCGGTCATCTGAAAAGGAGTTGCCCAGGCTTAAATAAACAG
AATATAATAAATCAAGCTATTAACAGCAAAAAATAAAAAGCCATCTGGCCTGTGTCCAAAATGTGGAAAAGCA
AAACATTGGGCCAATCAATGTCATTCTAAATTTGATAAAGATGGGCAACCATTGTCTGGAAACAGGAAGAGG
GGC

Figure 28 (cont)

CAGCCTCAGGCCCCCCAACAAACTGGGGCATTCCCAGTTAAACTGTTTGTTCCTCAGGGTTTTCAAGGACAACA
ACCCCTACAGAAAATACCACCACTTCAGGGAGTCAGCCAATTACAACAATCCAACAGCTGTCCCGCGCCACAG
CAGGCAGCACCGCAGTAGATTTATGTTCCACCCAAATGGTCTTTTTACTCCCTGGAAAGCCCCCACAAAAGATT
CCTAGAGGGGTATATGGCCCGCTGCCAGAAGGGAGGGTAGGCCTTTGAGGGAGATCGTCTAAATTTGAAGG
GAGTCCAAATTCATACTGGGGTAATTTATTCAGATTATAAAGGGGGAATTCAGTTAGTGATCAGCTCCACTGTT
CCCCGGAGTGCCAATCCAGGTGATAGAATTGCTCAATTACTGCTTTTGCCTTATGTTAAAATTGGGGAAAACA
AAAAGGAAAGAACAGGAGGGTTTGGAAGTACCAACCCTGCAGGAAAAGCTGCTTATTGGGCTAATCAGGTCT
CAGAGGATAGACCCGTGTGTACAGTCACTATTCAGGGAAAGAGTTTGAAGGATTAGTGGATACCCAGGCTGA
TGTTTCTGTCATCGGCATAGGTACTGCCTCAGAAGTGTATCAAAGTGCCATGATTTTACATTGTCCAGGATCTG
ATAATCAAGAAAGTACGGTTCAGCCTGTGATCACTTCATTCCAATCAATTTATGGGGCCGAGACTTGTTACAAC
AATGGCATGCAGAGATTACTATCCCAGCCTCCCTATACAGCCCCAGGAATAAAAAAATCATGACTAAAATGGG
ATAGCTCCCTAAAAAGGGACTAGGAAAGAAGTCCCAATTGAGGCTGAAAAAAATCAAAAAAGAAAAGGAAT
AGGGCATCCTTTTTAGGAGCGGTCACTGTAGAGCCTCCAAAACCCATTCCATTAACTTGGGGGAAAAAAAAAC
AACTGTATGGTAAATCAGCAGCGCTTCCAAAACAAAAACTGGAGGCTTTACATTTATTAGCAAAGAAACAATT
AGAAAAAGGACATTGAGCCTTCATTTTCGCCTTGGAATTCTGTTTGTAATTCAGAAAAAATCCGGCAGATGGC
GTATAATGCCGTAATTCAACCCATGGGGCTCTCCCACCCCGGTTGCCCTCTCCAGCCATGGTCCCCTTTAATT
ATAATTGATCTGAAGGATTGCTTTTTTACCATTCCTCTGGCAAAACAGGATTTTGAAAAATTTGCTTTTACCACA
CCAGCCTAAATAATAAAGAACCAGCCACCAGGTTTCAGTGGAAAGTATTGCCTCAGGGAATGCTTAATAGTTC
AACTATTTGTCAGCTCAAGCTCTGCAACCAGTTAGAGACAAGTTTTCAGACTGTTACATCGTTCACTATGTTGA
TATTTTGTGTGCTGCAGAAACGAGAGACAAATTAATTGACCGTTACACATTTCTGCAGACAGAGGTTGCCAAC
GCGGGACTGACAATAACATCTGATAAGATTCAAACCTCTACTCCTTTCCGTTACTTGGGAATGCAGGTAGAGG
AAAGGAAAATTAAACCACAAAAATAGAAATAAGAAAAGACACATTAAAAGCATTAAATGAGTTTCAAAAGT
TGCTAGGAGATACTAATTGGATTTGGAGATATTAATTGGATTTGGCCAACTCTAGGCATTCCTACTTATGCCAT
GTCAAATTTGTTCTCTTTCTTAAGAGGGGACTCGGAATTAAATAGTGAAAGAACGTTAACTCCAGAGGCAACT
AAAGAAATTAAATTAATTGAAGAAAAAATTCGGTCAGCACAAGTAAATAGAATAGATCACTTGGCCCCACTCC
AAATTTTGATTTTTGCTACTGCACATTCCCTAACAGGCATCATTGTTCAAAATACAGATCTTGTGGAGTGGTCCT
TCCTTCCTCACAGTACAATTAAGACTTTTACATTGTACTTGGATCAAATGGCTACATTAATTGGTCAGGGAAGA
TTATGAATAATAACATTGTGTGGAAATGACCCAGATAAAATCACTGTTCCTTTCAACAAGCAACAGGTTAGACA
AGCCTTTATCAATTCTGGTGCATGGCAGATTGGTCTTGCCGATTTTGTGGGAATTATTGACAATCGTTACCCCA
AAACAAAAATCTTCCAGTTTTTAAAATTGACTACTTGGATTTTACCTAAAGTTACCAAACATAAGCCTTTAAAAA
ATGCTCTGGCAGTGTTTACTGATGGTTCCAGCAATGGAAAAGTGGCTTACACCGGGCCAAAAGAATGAGTCAT
CAAAACTCAGTATCACTTGACTCAAAGAGCAGAGTTGGTTGCCGTCATTACAGTGTTAACAAGATTTTAATCAG
TCTATTAACATTGTATCAGATTCTGCATATGTAGTACAGGCTACAAAGGATATTGAGAGAGCCCTAATCAAATA
CATTATGGATGATCAGTTAAACCCGCTGTTTAATTTGTTACAACAAAATGTAAGAAAAGAAATTTCCCATTTT
ATATTACTCATATTCGAGCACACACTAATTTACCAGGGCCTTTAACTAAAGCAAATGAACAAGCTGACTTGCTA
GTATCATCTGCATTCATGGAAGCACAAGAACTTCATGCCTTGACTCATGTAAATGCAATAGGATTAAAAAATAA
ATTTGATATCACATGGAAACAGACAAAAAATATTGTACAACATTGCACCCAGTGTCAGATTCTACACCTGGCCA
CTCAGGAGGCAAGAGTTAATCCCAGAGGTCTATGTCCTAATGTGTTATGGCAAATGGATGTCATGCACGTACC
TTCATTTGGAAAATTGTCATTTGTCCATGTGACAGTTGATACTTATTCACATTTCATATGGGCAACCTGCCAGAC
AGGAGAAAGTACTTCCCATGTTAAAAGACATTTATTATCTTGTTTTCCTGTCATGGGAGTTCCAGAAAAAGTTA
AAACAGACAATGGGCCAGGTTACTGTAGTA

Figure 28 (cont)

AAGCAGTTCAAAAATTCTTAAATCAGTGGAAAATTACACATACAATAGGAATTCTCTATAATTCCCAAGGACAG
GCCATAATTGAAAGAACTAATAGAACACTCAAAGCTCAATTGGTTAAACAAAAAAAAGGAAAAGACAGGAGT
ATAACACTCCCCAGATGCAACTTAATCTAGCACTCTATACTTTAAATGTTTTAAACATTTATAGAAATCAGACCA
CTACCTCTGCAGAACAACATCTTACTGGTAAAAGGAACAGCCCACATGAAGGAAAACTGATTTGGTGGAAAG
ATAATAAAAATAAAACATGGGAAATGGGGAAGGTGATAACGTGGGGGAGAGGTTTTGCTTGTGTTTCACCAG
GAGAAAATCAGCTTCCTGTTTGGATACCCACTAG

PCAT-14, isoform 3

Exon 1: chr22:22,216,494-22,218,672 (SEQ ID NO:9)

GTAAACAAAATGGTGATATCAGAAGAACAGAAAAAGTTGCCTTCCATCAAGGAAGCAGAGTTGCCAATATAG
GCACAATTAAAGAAGCTGACACAGTTAGCTAAAAAAAAAAGCCTAGAGAATACAAAGGTGACACCAACTCCA
GAGAATATGCTGCTTGCAGCTCTGATGATTGTATCAACGGTGGTAAGTCTTCCCAAGTCTGCAGGAGCAGCTG
CAGCTAATTATACTTACTGGGCCTATGTGCCTTTCCCACCCTTAATTCGGGCAGTTACATAGATGGATAATCCTA
TTGAAGTAGATGTTAATAATAGTGCATGGGTGCCTGGCCCCACAGATGACTGTTGCCCTGCCCAACCTGAAGA
AGGAATGATGATGAATATTTCCATTGGGTATCCTTATCCTCCTGTTTGCCTAGGGAAGGCACCAGGATGCTTAA
TGCCTACAACCCAAAATTGGTTGGTAGAAGTACCTACAGTCAGTGCTACCAGTAGATTTACTTATCACATGGTA
AGTGGAATGTCACAGATAAATAATTTACAGGACCCTTCTTATCAAAGATCATTACAATGTAGGCCTAAGGGGA
AGGCTTGCCCCAAGGAAATTCCCAAAGAATCAAAAAGCCCAGAAGTCTTAGTCTGCGGAGAATGTGTGGCTG
ATACTGCAGTGTAGTACAAAACAATGAATTTTGAACTATGATAGACTGGGTCCCTTGAGGCCAATTATATCATA
ACTGTACAGGCCAGACTCATTCATGTTCACAGGCCCCATCCATCTGGCCCATTAATCCAGCCTATGACGGTGAT
GTAACTGAAAGGCTGGACCAGGTTTATAGAAGGTTAGAATCACTCTGTCCAAGGAAATGGGGTGAAAAGGG
AATTTCATCACCTTGACCAAAGTTAGTCCTGTTACTGGTCCTGAACATCCAGAATTAGGAAGCTTACTGTGGCC
TCACACCACATTAGAATTTGTTCTGGAAATCAAGCTATAGGAACAAGAGATCGTAAGTCATATTATACTATCAA
CCTAAATTCCAGTCTGACAATTCCTTTGCAAAATTGTGTAAAACTCCCTTATATTGCTAGTTGTAGGAAAAACAT
AGTTATTAAACCTGATTCCCAAACCATAATCTGTGAAAATTGTGGAATGTTACTTGCATTGATTTGACTTTTAA
TTGGCAGCACCGTATTCTACTAGGAAGAGCAAGAGAGGGTGTGTGGATCCTTGTGTCCATGGACCGACCATG
GGAGGCTTCGCTATCCATCCATATTTTAACGGAAGTATTAAAAGGAATTCTAACTAGATCCAAAAGATTCATTT
TTACTTTGATGGCAGTGATTATGGGCCTCATTGCAGTCACAGCTACTGCTGCGGCTGCTGGAATTGCTTTACAC
TCCTCTGTTCAAACTGCAGAATACGTAAATGATTGGCAAAAGAATTCCTCAAAATTGTGGAATTCTCAGATCCA
AATAGATCAAAAATTGGCAAACCAAATTAATGATCTTAGACAAACTGTCATTTGGATGGGAGAGGCTCATGAG
CTTGGAATATCTTTTTCAGTTACGATGTGACTGGAATACATCAGATTTTTGTGTTACACCACAAGCCTATAATGA
GTCTGAGCATCACTGGGACATGGTTAGATGCCATCTGCAAGGAGGAGAAGATAATCTTACTTTAGACATTTCA
AAATTAAAAGAATTTTTTTTTTCTTTGAGACAGAGTCTCGCTCTGTCGCCCAGGCTGGAGTGCAGTGGCGTGAT
CTCAGCTCACTGCAAGTTCCGCCTCCTGGGTTTACACCATTCTCCTGCCTCAGCCTCCCAAGTAGTTGGGACTAC
AGGAGCCCACCACCATGCCTGGCTAATTTTTTTGGGTTTTTAATAGAGATGGAGTTTCACCGTGTTAGCCAGG
ATGGTCTCGATCTCCTGACCTTGTGATCTGCCCACCTTGGCCTCCCAAAGTGCTGGGATTACAGTCGT

Figure 28 (cont)

GAGCCACCGTGCCCAGCCAAGAAAAAATTTTTGAGGCATCAAAAGCCCATTTAAATTTGGTGCCAGGAACGG
AGACAATCGTGAAAGCTGCTGATAGCCTCACAAATCTTAAGCCAGTCACTTGGGTTAAAAGCATCAGAAGTTT
CACTATTGTAAATTTCATATTAATCCTTGTATGCCTGTTCTGTCTGTTGTTAG

NCRNA AND USES THEREOF

This application is a continuation of U.S. patent application Ser. No. 15/064,266, filed Mar. 8, 2016, which is a continuation of U.S. patent application Ser. No. 13/299,000, filed Nov. 17, 2011, which claims priority to provisional application 61/415,490, filed Nov. 19, 2010, which is herein incorporated by reference in its entirety.

STATEMENT REGARDING FEDERALLY SPONSORED RESEARCH OR DEVELOPMENT

This invention was made with government support under CA069568, CA132874 and CA111275 awarded by the National Institutes of Health and W81XWH-09-2-0014 awarded by the Army Medical Research and Material Command. The government has certain rights in the invention.

FIELD OF THE INVENTION

The present invention relates to compositions and methods for cancer diagnosis, research and therapy, including but not limited to, cancer markers. In particular, the present invention relates to ncRNAs as diagnostic markers and clinical targets for prostate, lung, breast and pancreatic cancer.

BACKGROUND OF THE INVENTION

A central aim in cancer research is to identify altered genes that are causally implicated in oncogenesis. Several types of somatic mutations have been identified including base substitutions, insertions, deletions, translocations, and chromosomal gains and losses, all of which result in altered activity of an oncogene or tumor suppressor gene. First hypothesized in the early 1900's, there is now compelling evidence for a causal role for chromosomal rearrangements in cancer (Rowley, *Nat Rev Cancer* 1: 245 (2001)). Recurrent chromosomal aberrations were thought to be primarily characteristic of leukemias, lymphomas, and sarcomas. Epithelial tumors (carcinomas), which are much more common and contribute to a relatively large fraction of the morbidity and mortality associated with human cancer, comprise less than 1% of the known, disease-specific chromosomal rearrangements (Mitelman, *Mutat Res* 462: 247 (2000)). While hematological malignancies are often characterized by balanced, disease-specific chromosomal rearrangements, most solid tumors have a plethora of non-specific chromosomal aberrations. It is thought that the karyotypic complexity of solid tumors is due to secondary alterations acquired through cancer evolution or progression.

Two primary mechanisms of chromosomal rearrangements have been described. In one mechanism, promoter/enhancer elements of one gene are rearranged adjacent to a proto-oncogene, thus causing altered expression of an oncogenic protein. This type of translocation is exemplified by the apposition of immunoglobulin (IG) and T-cell receptor (TCR) genes to MYC leading to activation of this oncogene in B- and T-cell malignancies, respectively (Rabbitts, *Nature* 372: 143 (1994)). In the second mechanism, rearrangement results in the fusion of two genes, which produces a fusion protein that may have a new function or altered activity. The prototypic example of this translocation is the BCR-ABL gene fusion in chronic myelogenous leukemia (CML) (Rowley, *Nature* 243: 290 (1973); de Klein et al., *Nature* 300: 765 (1982)). Importantly, this finding led to the rational development of imatinib mesylate (Gleevec), which successfully targets the BCR-ABL kinase (Deininger et al., *Blood* 105: 2640 (2005)). Thus, diagnostic methods that specifically identify epithelial tumors are needed.

SUMMARY OF THE INVENTION

The present invention relates to compositions and methods for cancer diagnosis, research and therapy, including but not limited to, cancer markers. In particular, the present invention relates to ncRNAs as diagnostic markers and clinical targets for prostate, lung, breast and pancreatic cancer.

Embodiments of the present invention provide compositions, kits, and methods useful in the detection and screening of prostate cancer. Experiments conducted during the course of development of embodiments of the present invention identified upregutation of non-coding RNAs in prostate cancer. Some embodiments of the present invention provide compositons and methods for detecting expression levels of such ncRNAs. Identification of ncRNAs finds use in screening, diagnostic and research uses.

For example, in some embodiments, the present invention provides a method of screening for the presence of prostate cancer in a subject, comprising contacting a biological sample from a subject with a reagent for detecting the level of expression of one or more non-coding RNAs (ncRNA) (e.g., PCAT1, PCAT14, PCAT43 and PCAT 109); and detecting the level of expression of the ncRNA in the sample, for example, using an in vitro assay, wherein an increased level of expression of the ncRNA in the sample (e.g., relative to the level in normal prostate cells, increase in level relative to a prior time point, increase relative to a pre-established threshold level, etc.) is indicative of prostate cancer in the subject. In some embodiments, the ncRNAs are described by SEQ ID NOs: 1-9. In some embodiments, the sample is tissue, blood, plasma, serum, urine, urine supernatant, urine cell pellet, semen, prostatic secretions or prostate cells. In some embodiments, the detection is carried out utilizing a sequencing technique, a nucleic acid hybridization technique, a nucleic acid amplification technique, or an immunoassay. However, the invention is not limited to the technique employed. In some embodiments, the nucleic acid amplification technique is polymerase chain reaction, reverse transcription polymerase chain reaction, transcription-mediated amplification, ligase chain reaction, strand displacement amplification or nucleic acid sequence based amplification. In some embodiments, the prostate cancer is localized prostate cancer or metastatic prostate cancer. In some embodiments, the reagent is a pair of amplification oligonucleotides or an oligonucleotide probe.

Additional embodiments provide a method of screening for the presence of prostate cancer in a subject, comprising contacting a biological sample from a subject with a reagent for detecting the level of expression of two or more (e.g., 10 or more, 25 or more, 50 or more, 100 or more or all 121) non-coding RNAs (ncRNA) selected from, for example, PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, or PCAT121; and detecting the level of expression of the ncRNA in the sample using an in vitro assay, wherein an increased level of expression of the ncRNA in the sample relative to the level in normal prostate cells in indicative of prostate cancer in the subject.

Further embodiments of the present invention provide an array, comprising reagents for detecting the level of expression of two or more (e.g., 10 or more, 25 or more, 50 or more, 100 or more or all 121) non-coding RNAs (ncRNA) selected from, for example, PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, or PCAT121. In some embodiments, the reagent is a pair of amplification oligonucleotides or an oligonucleotide probe.

In some embodiments, the present invention provides a method for screening for the presence of lung cancer in a subject, comprising contacting a biological sample from a subject with a reagent for detecting the level of expression of one or more non-coding RNAs (e.g., M41 or ENST-75); and detecting the level of expression of the ncRNA in the sample, for example, using an in vitro assay, wherein an increased level of expression of the ncRNA in the sample (e.g., relative to the level in normal lung cells, increase in level relative to a prior time point, increase relative to a pre-established threshold level, etc.) is indicative of lung cancer in the subject.

In some embodiments, the present invention provides a method for screening for the presence of breast cancer in a subject, comprising contacting a biological sample from a subject with a reagent for detecting the level of expression of one or more non-coding RNAs (e.g., TU0011194, TU0019356, or TU0024146); and detecting the level of expression of the ncRNA in the sample, for example, using an in vitro assay, wherein an increased level of expression of the ncRNA in the sample (e.g., relative to the level in normal breast cells, increase in level relative to a prior time point, increase relative to a pre-established threshold level, etc.) is indicative of breast cancer in the subject.

In some embodiments, the present invention provides a method for screening for the presence of pancreatic cancer in a subject, comprising contacting a biological sample from a subject with a reagent for detecting the level of expression of one or more non-coding RNAs (e.g., TU0009141, TU0062051, or TU0021861); and detecting the level of expression of the ncRNA in the sample, for example, using an in vitro assay, wherein an increased level of expression of the ncRNA in the sample (e.g., relative to the level in normal pancreatic cells, increase in level relative to a prior time point, increase relative to a pre-established threshold level, etc.) is indicative of pancreatic cancer in the subject.

Additional embodiments are described herein.

RACE. Sequence analysis of PCAT-1 shows that it is a viral long terminal repeat (LTR) promoter splicing to a marriner family transposase that has been bisected by an Alu repeat. e. qPCR on a panel of prostate and non-prostate samples shows prostate-specific expression and upregulation in prostate cancers and metastases compared to benign prostate samples. f. Four matched tumor/normal pairs included in the analysis in e. demonstrate somatic upregulation of PCAT-1 in matched cancer samples.

Figure 5:
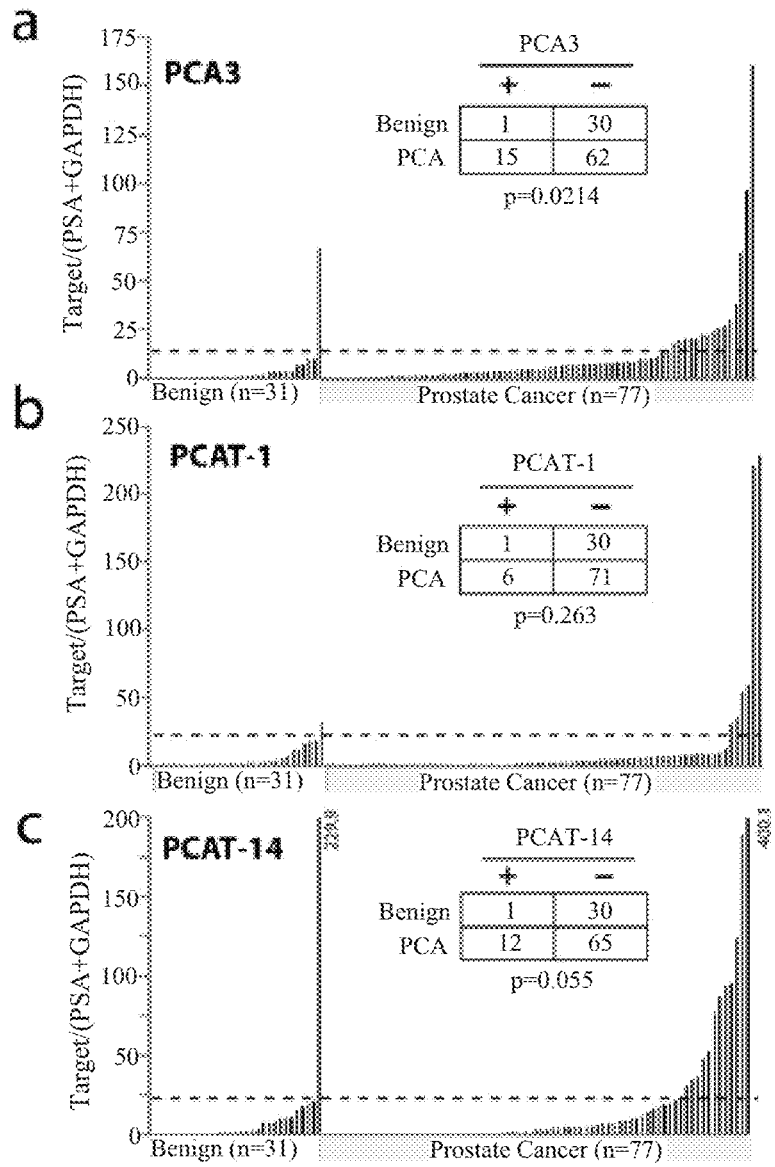
Figure 5:
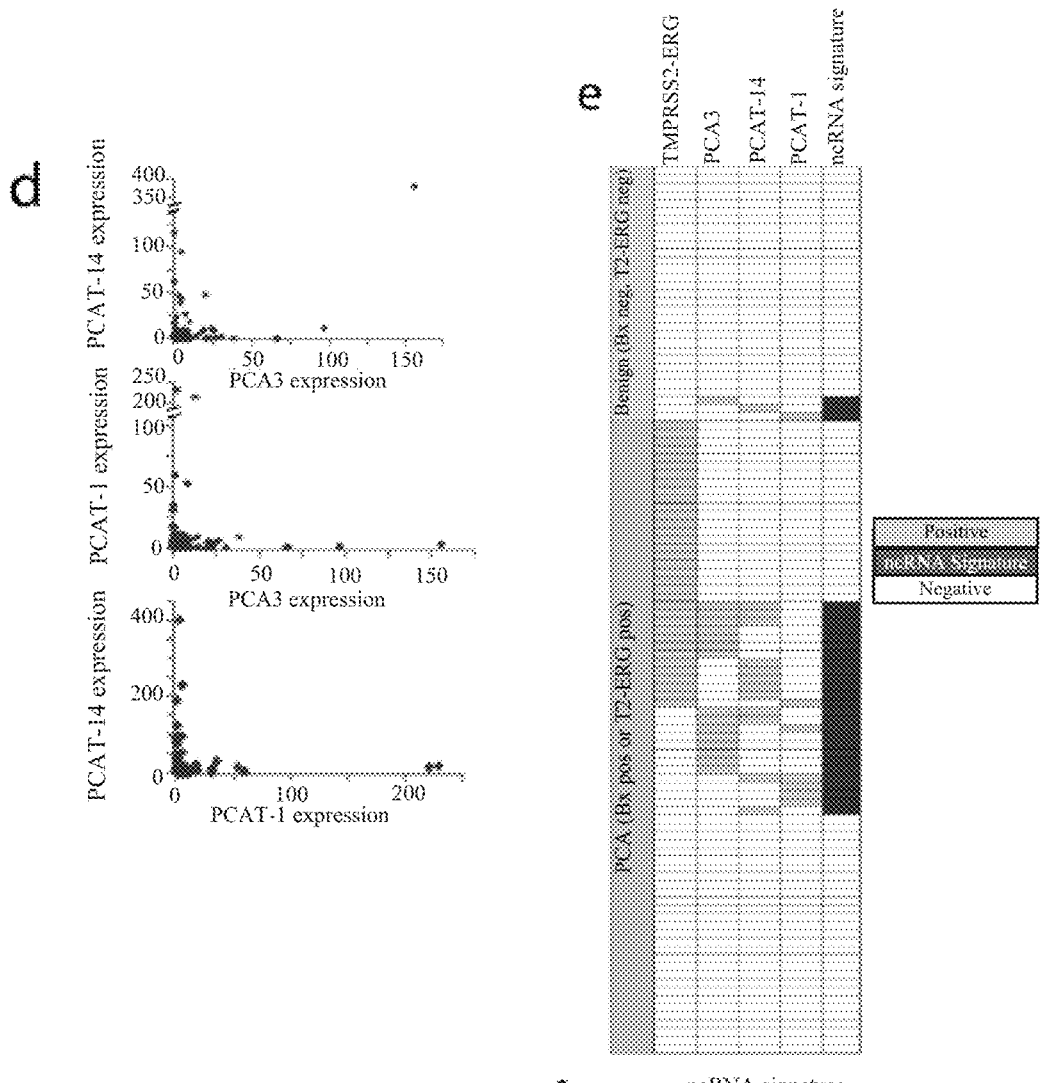
Figure 5:
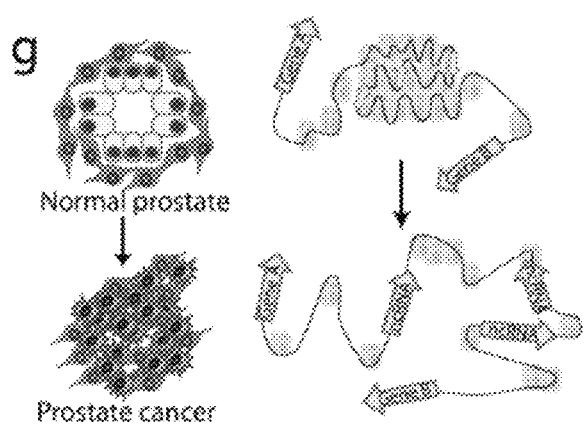

FIG. 5 shows that ncRNAs serve as urine biomarkers for prostate cancer. a-c. Three ncRNAs displaying biomarker status in prostate cancer tissues were evaluated on a cohort of urine samples from 77 patients with prostate cancer and 31 controls with negative prostate biopsy results and absence of the TMPRSS2-ERG fusion transcript. PCA3 (a); PCAT-1 (b); and PCAT-14 (c). d. Scatter plots demonstrating distinct patient subsets scoring positively for PCA3, PCAT-1, or PCAT-14 expression. e. A heatmap displaying patients positive and negative for several different prostate cancer biomarkers in urine sediment samples. f. A table displaying the statistical significance of the ncRNA signature. g. A model for non-coding RNA (ncRNA) activation in prostate cancer.

Figure 6:
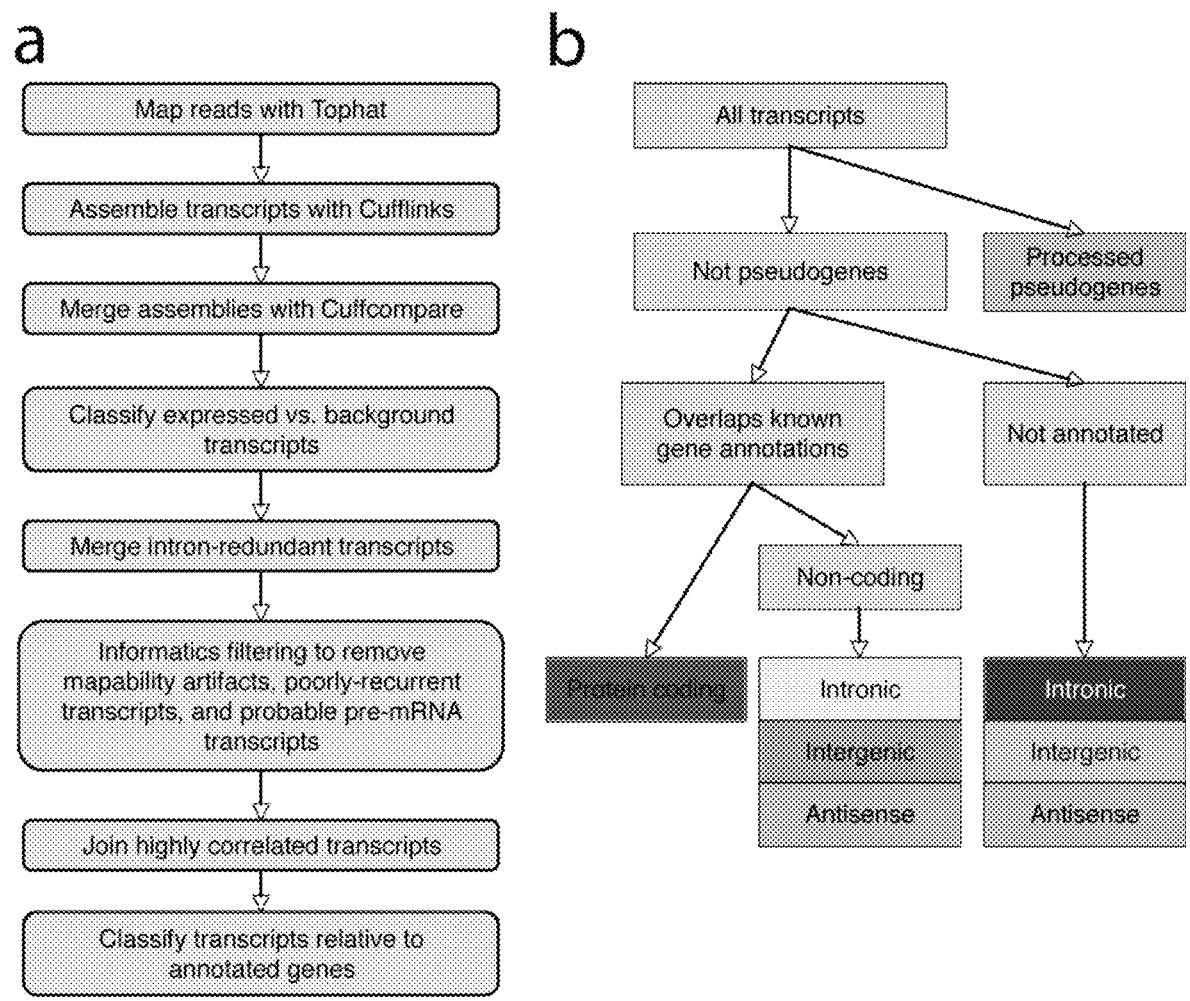

FIG. 6 shows Ab initio assembly of the prostate cancer transcriptome. (a) Reads were mapped with TopHat and assembled into library-specific transcriptomes by Cufflinks. (b) Transcripts corresponding to processed pseudogenes were isolated, and the remaining transcripts were categorized based on overlap with an aggregated set of known gene annotations.

Figure 7:
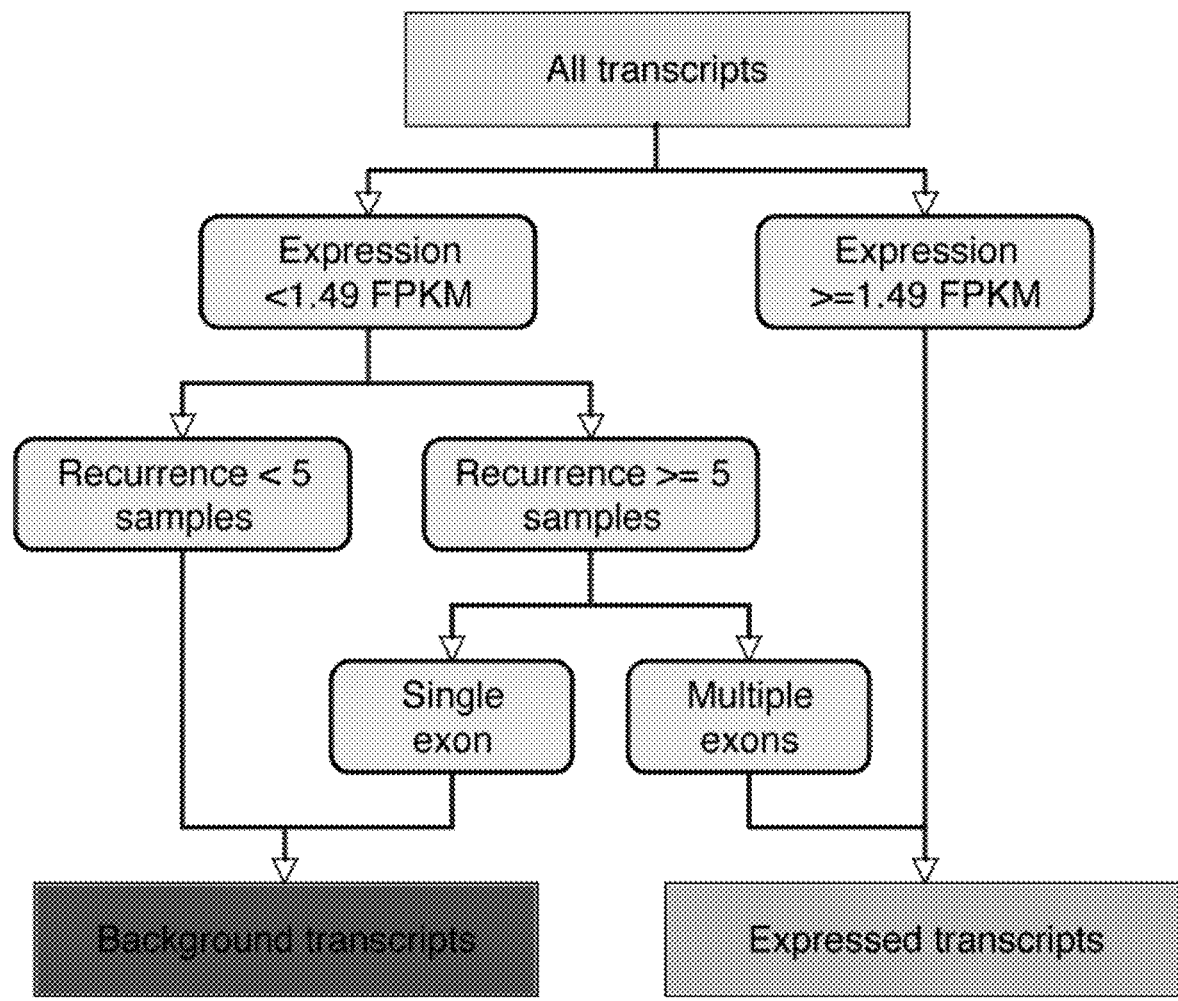

FIG. 7 shows classification tree results for Chromosome 1. The recursive regression and partitioning trees (rpart) machine learning algorithm was used to predict expressed transcripts versus background signal.

Figure 8:
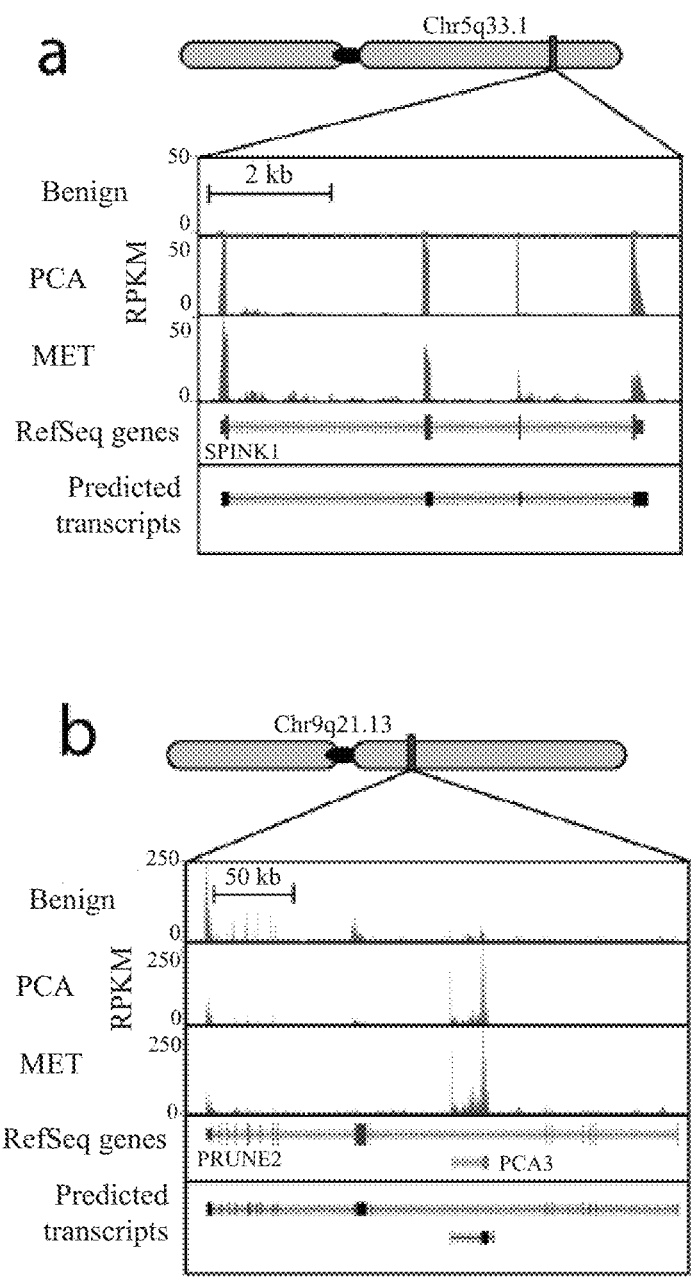
Figure 8:
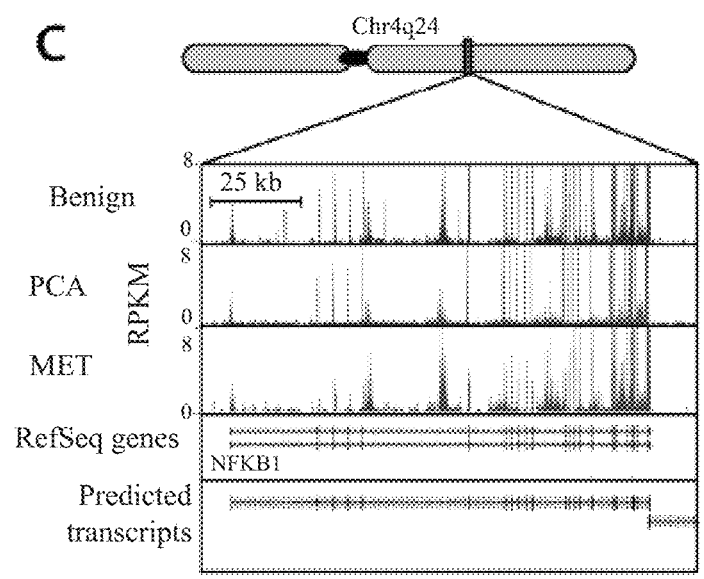
Figure 8:
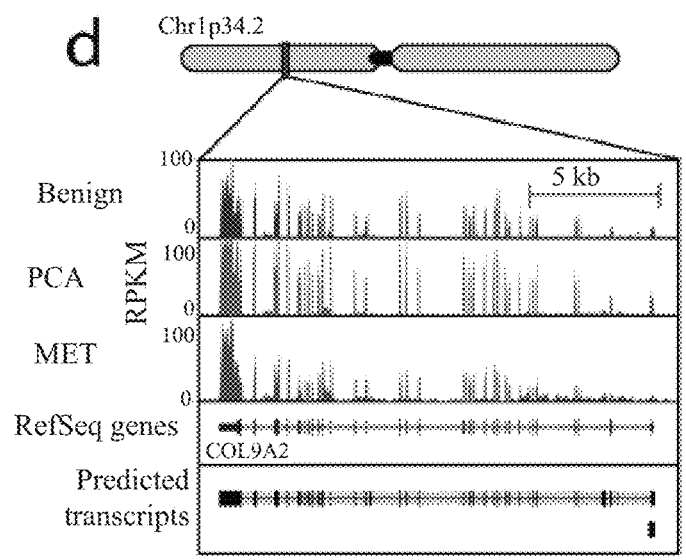

FIG. 8 shows transcript assembly of known genes. ab initio transcript assembly on prostate transcriptome sequencing data was used to reconstruct the known prostate transcriptome. a. SPINK1, a biomarker for prostate cancer. b. PRUNE2 with the PCA3 non-coding RNA within its intronic regions. c. NFKB1. d. COL9A2.

Figure 9:
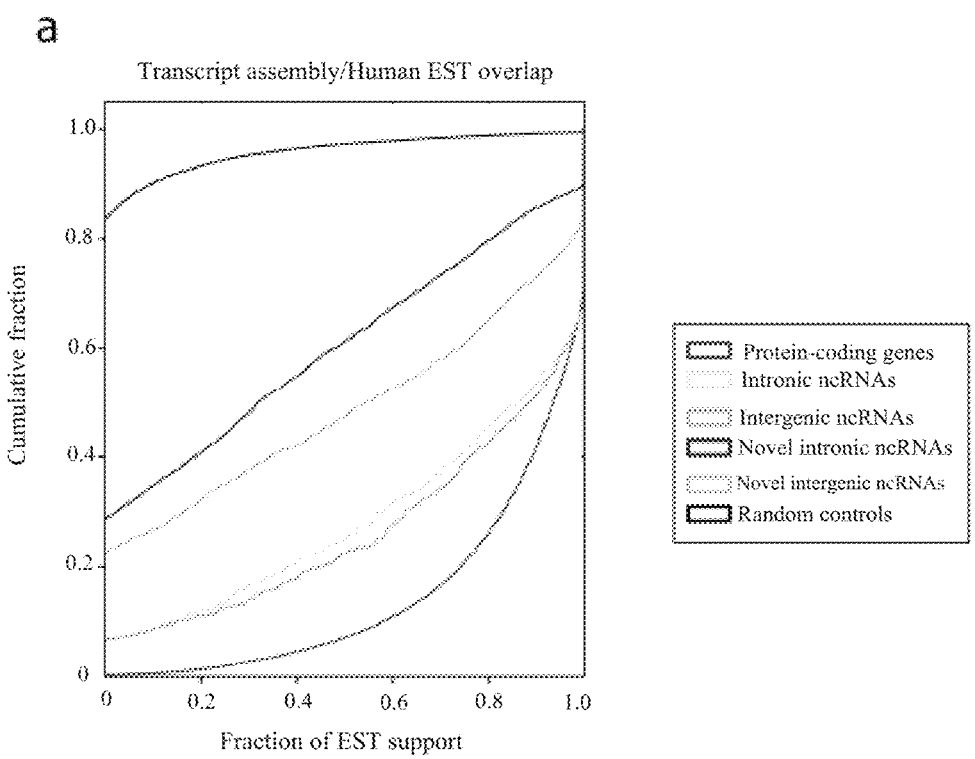
Figure 10:
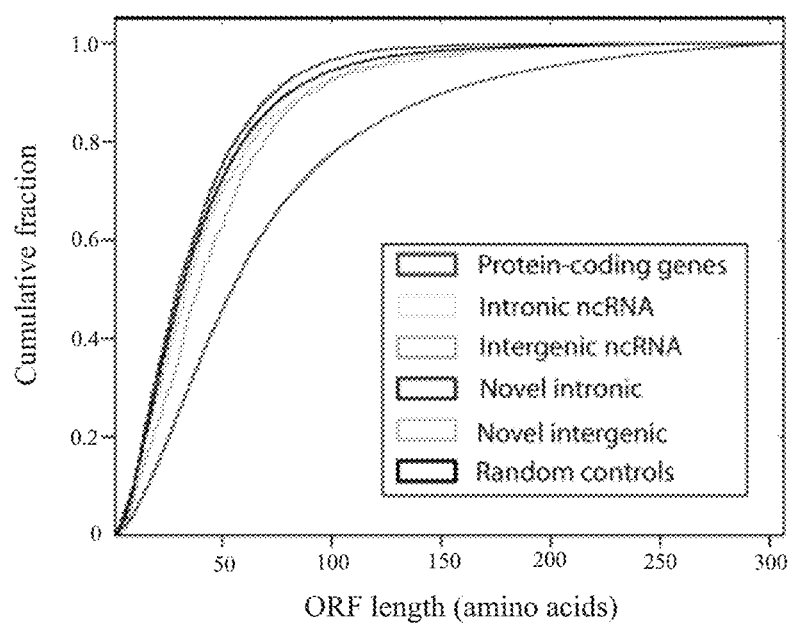

FIG. 9 shows analysis of EST support for exemplary transcripts. ESTs from the UCSC database table "Human ESTs" were used to evaluate the amount of overlap between ESTs and novel transcripts. a. A line graph showing the fraction of genes whose transcripts are supported by a particular fraction of ESTs. b. A table displaying the number of ESTs supporting each class of transcripts FIG. 10 shows analysis of coding potential of unannotated transcripts. DNA sequences for each transcript were extracted and searched for open reading frames (ORFs) using the txCdsPredict program from the UCSC source tool set.

Figure 11:
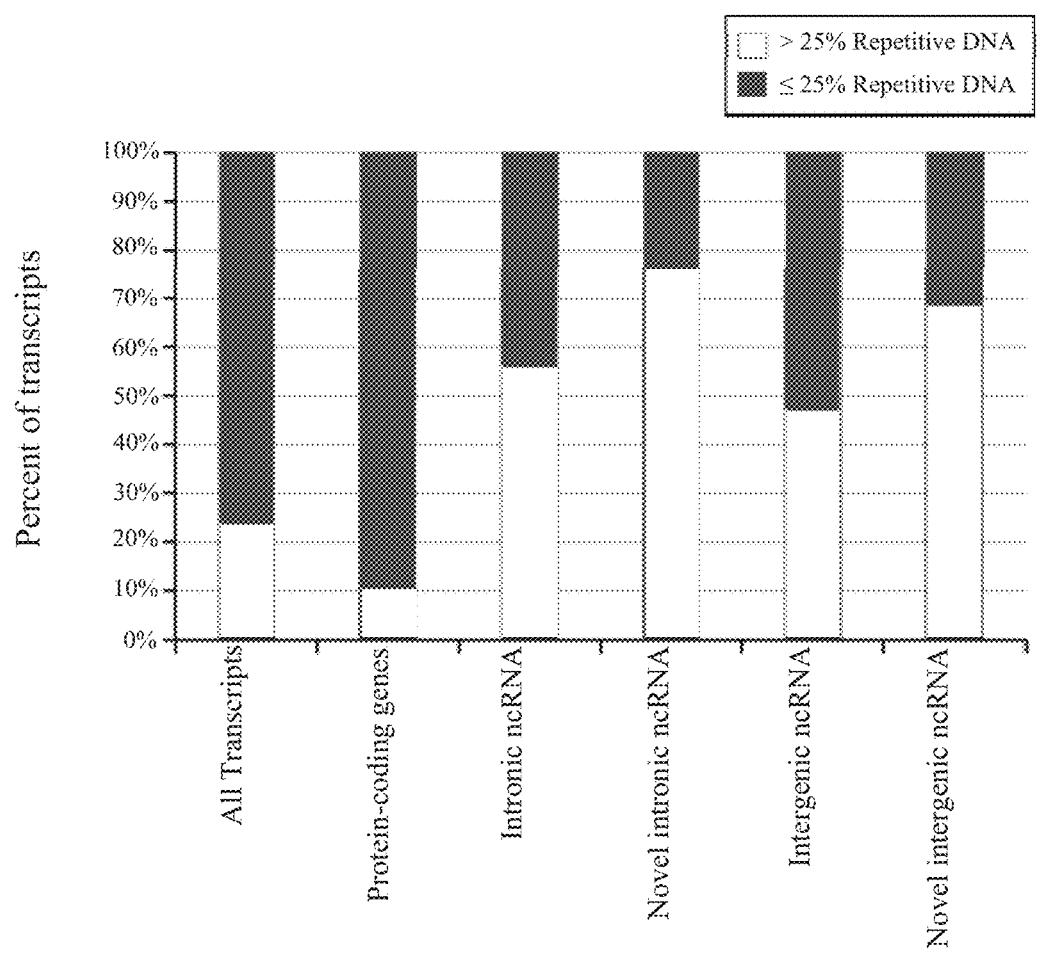

FIG. 11 shows repetitive content of novel transcripts. The percentage of repetitive sequences was assessed in all transcripts by calculating the percentage of repeatmasked nucleotides in each sequence.

Figure 12:
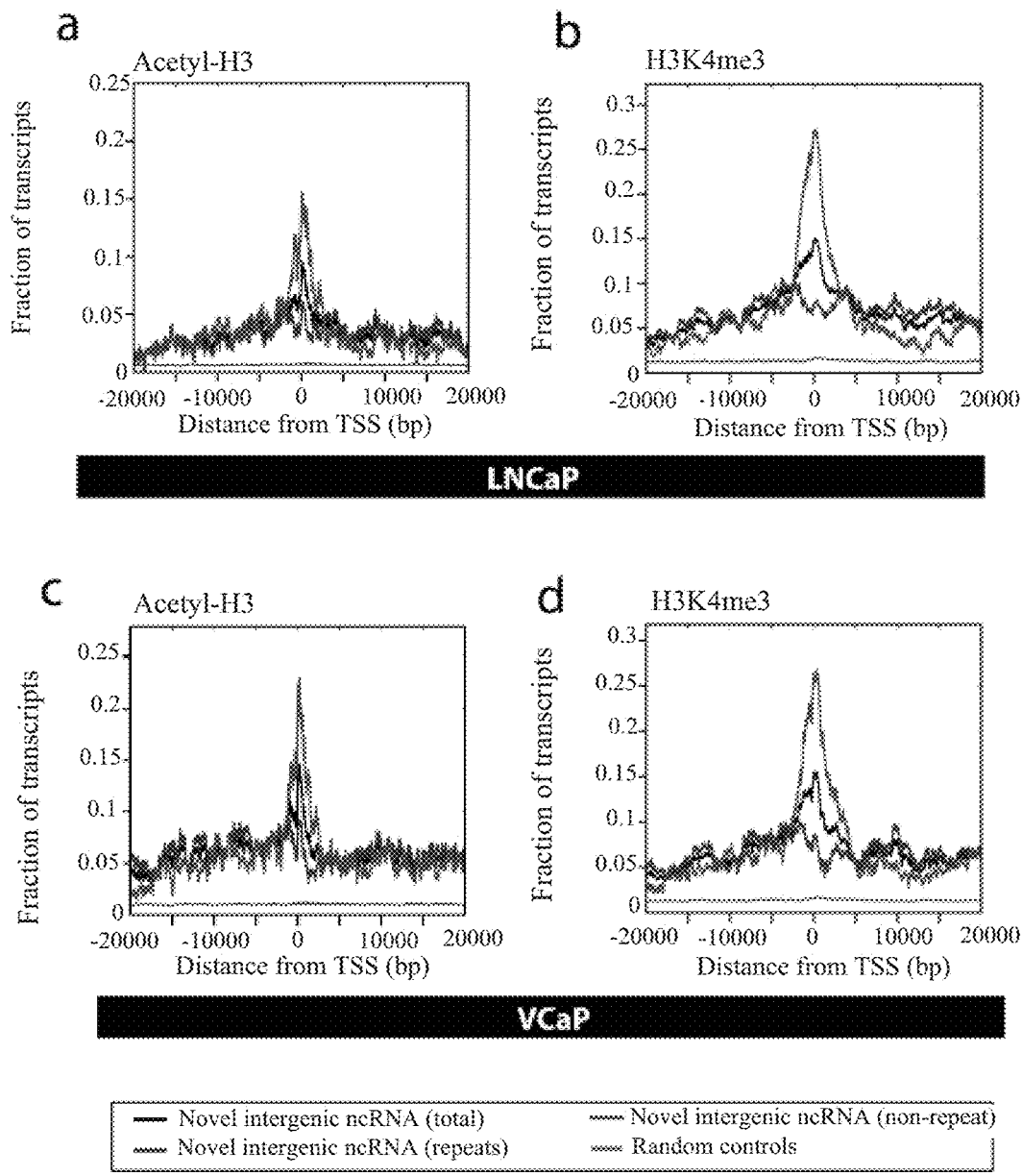

FIG. 12 shows distinct ChIP-Seq signatures for repeat-associated and nonrepeat novel ncRNAs. Unannotated transcripts were divided into two groups, repeat-associated and non-repeat, and intersected with ChIP-Seq data for Acetyl-H3 and H3K4me3, two histone modifications strongly associated with transcriptional start sites (TSS), in two prostate cancer cell lines. a. Acetyl-H3 in LNCaP cells. b. H3K4me3 in LNCaP cells. c. Acetyl-H3 in VCaP cells. d. H3K4me3 in VCaP cells.

Figure 13:
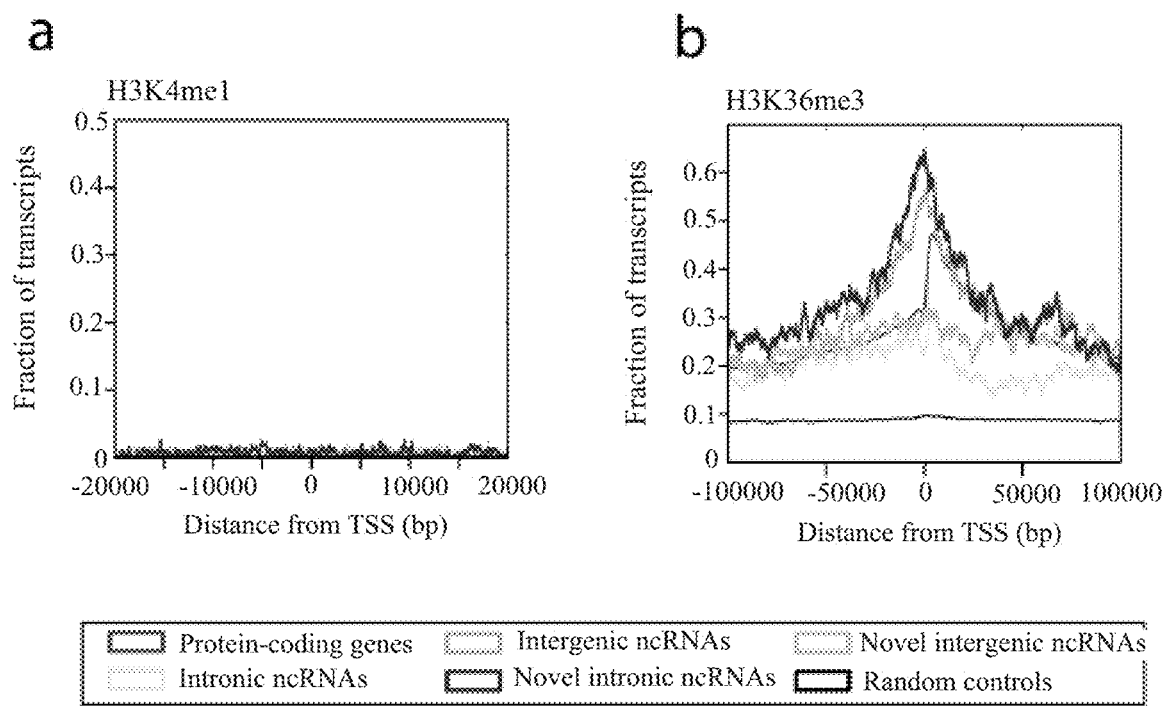

FIG. 13 shows overlap of unannotated transcripts with ChIP-Seq data in VCaP cells. Perviously published ChIP-Seq data for VCaP prostate cancer cells were intersected with unannotated prostate cancer transcripts and annotated control genes. a. H3K4me1 b. H3K36me3.

Figure 14:
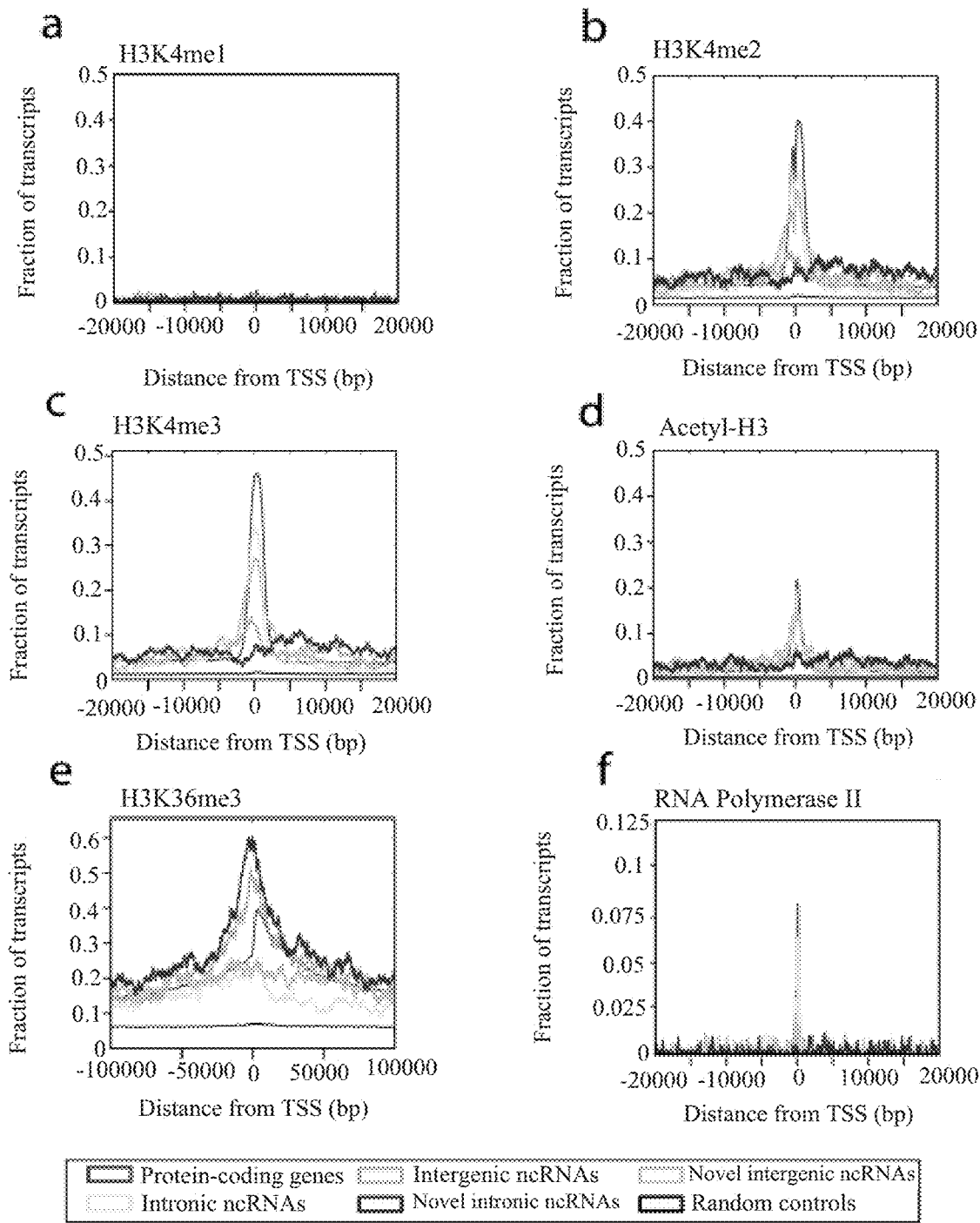

FIG. 14 shows overlap of unannotated transcripts with ChIP-Seq data in LNCaP cells. ChIP-Seq data for LNCaP prostate cancer cells were intersected with unannotated transcripts and annotated control genes. ncRNAs were divided into intergenic and intronic. a. H3K4me1 b. H3K4me2 c. H3K4me3 d. Acetyl-H3 e. H3K36me3 f. RNA polymerase II.

Figure 15:
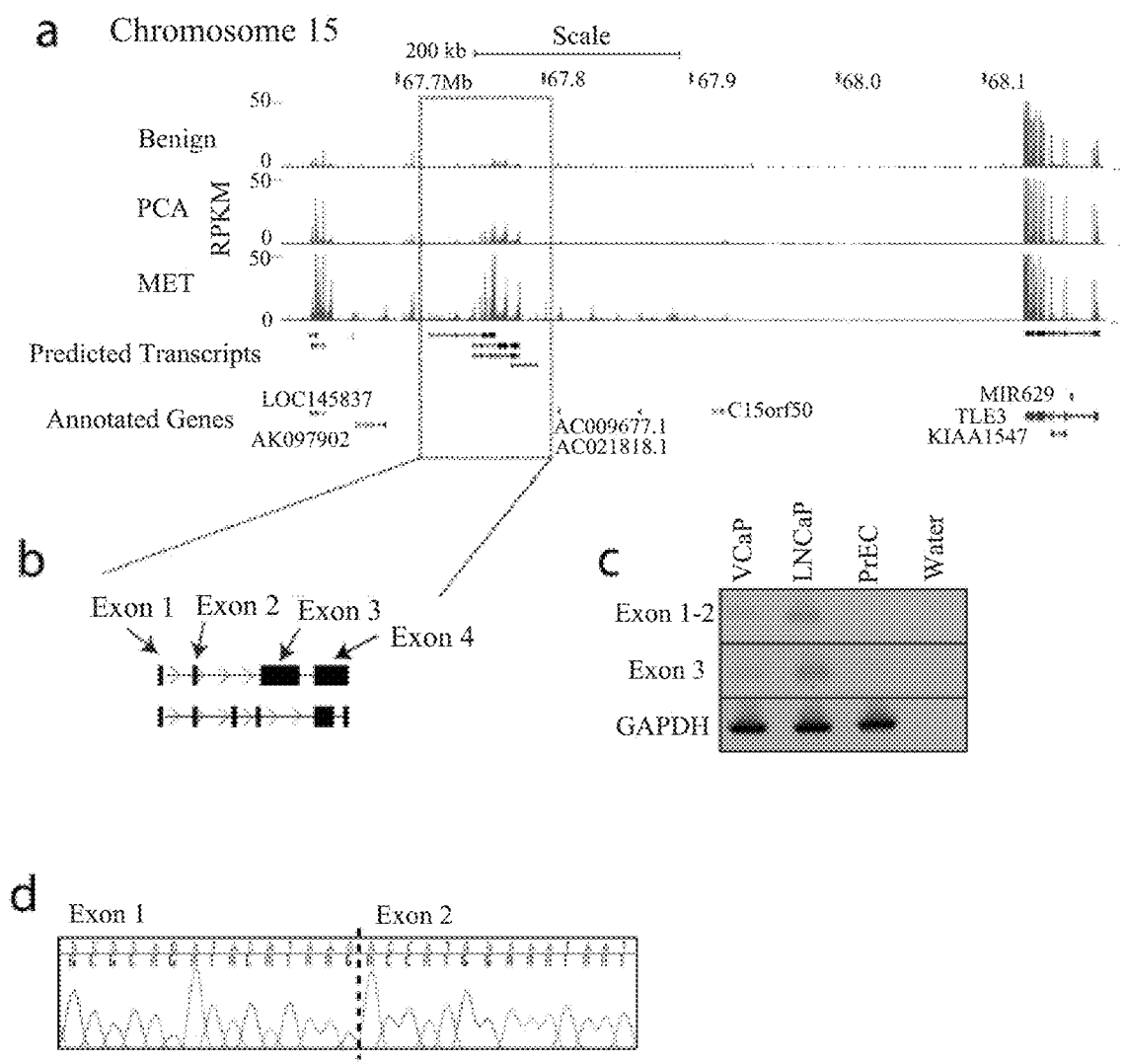

FIG. 15 shows validation of a novel transcript on chromosome 15. a. Coverage maps showing the average expression levels (RPKM) across the benign, localized tumor, and metastatic samples shows upregulation of a novel transcript downstream of TLE3. b. Several predicted isoforms of this transcript were nominated which retained common exons 1 and 2. c. The exon-exon boundary between exons 1 and 2, as well as an internal portion of exon 3, was validated by RT-PCR in prostate cell line models. d. Sanger sequencing of the RT-PCR product confirmed the junction of exon 1 and exon 2.

Figure 16:
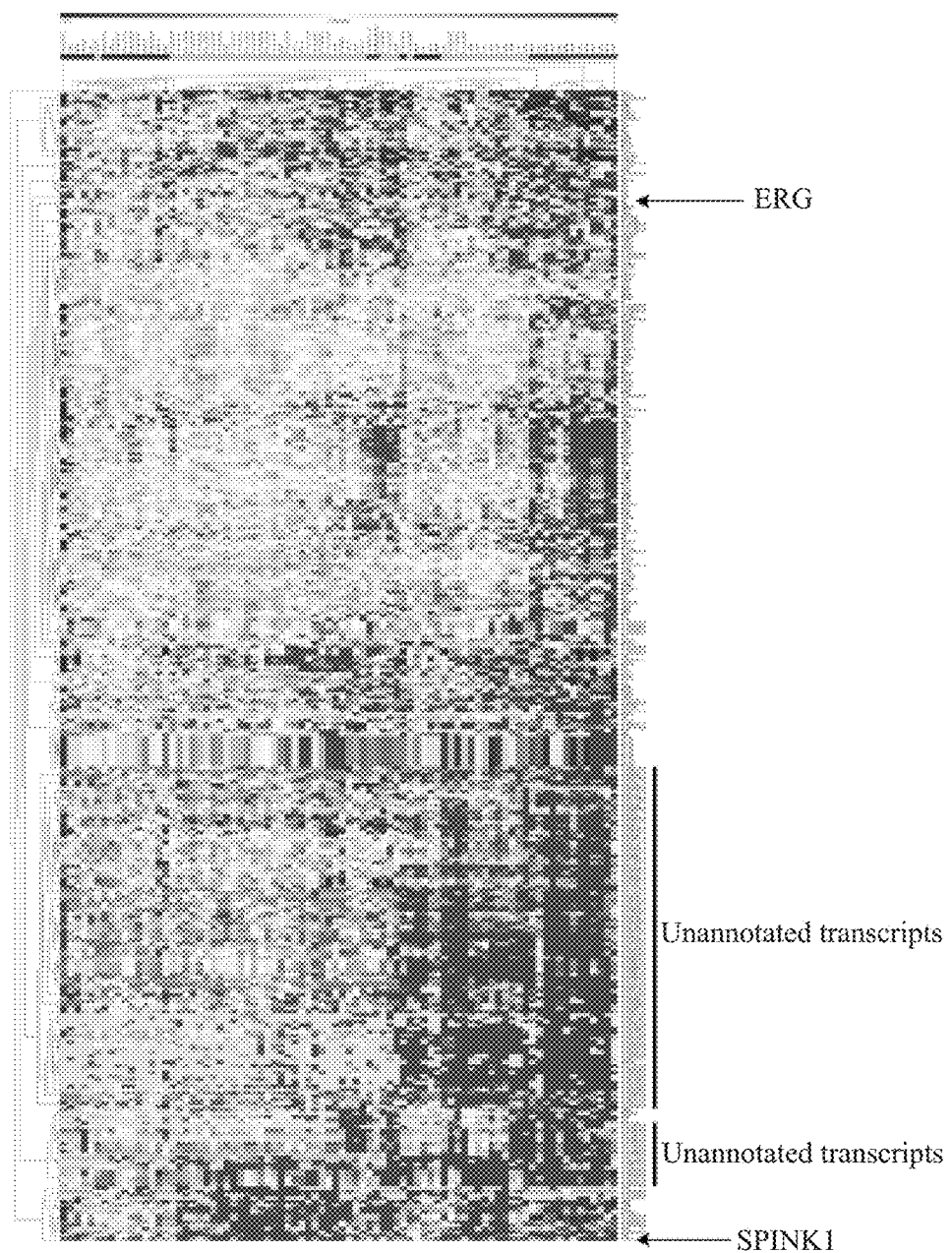

FIG. 16 shows clustering of prostate cancer with outliers. Transcripts with outlier profile scores in the top 10% were clustered using hierarchical trees.

Figure 17:
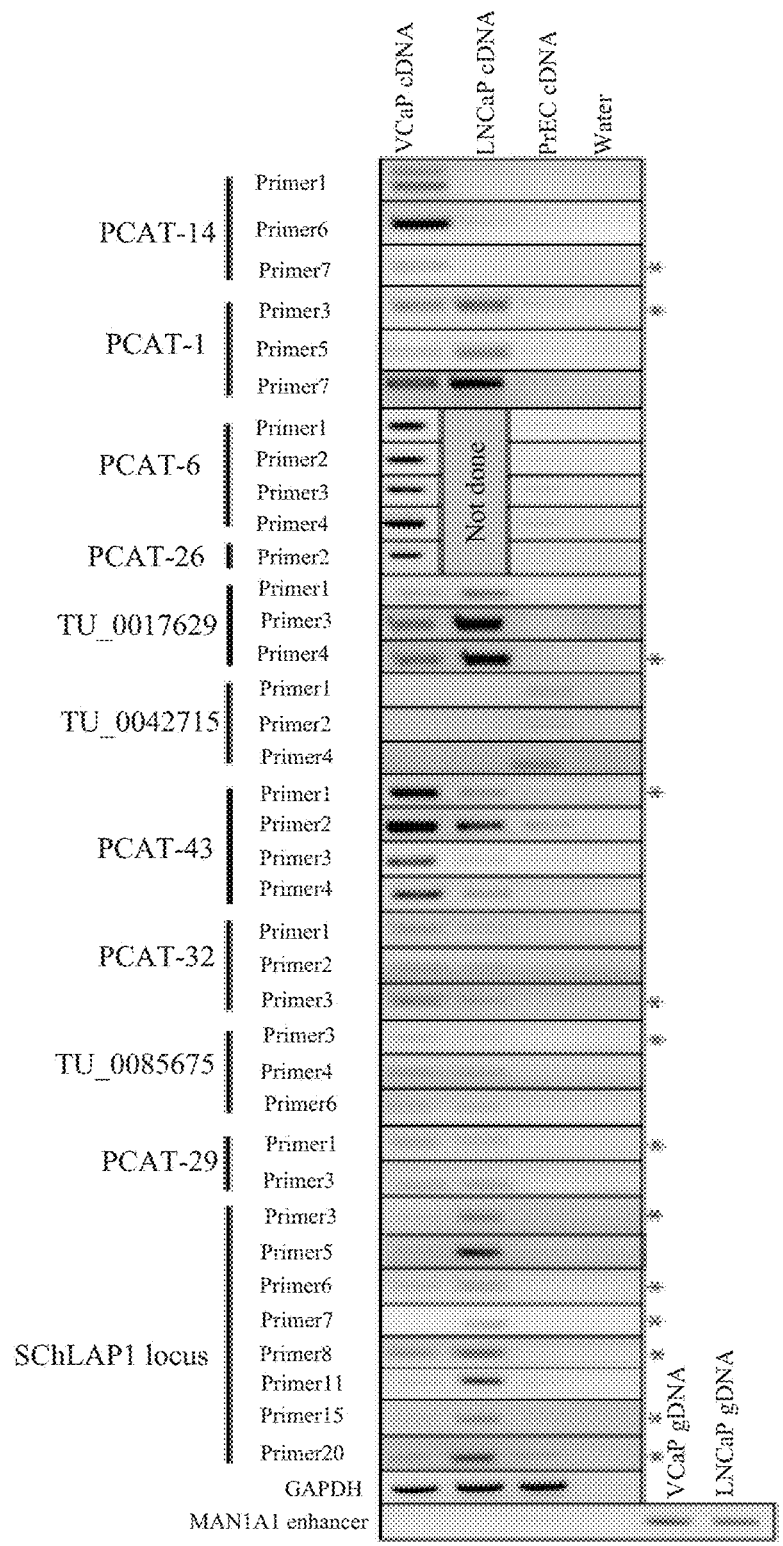
Figure 17:
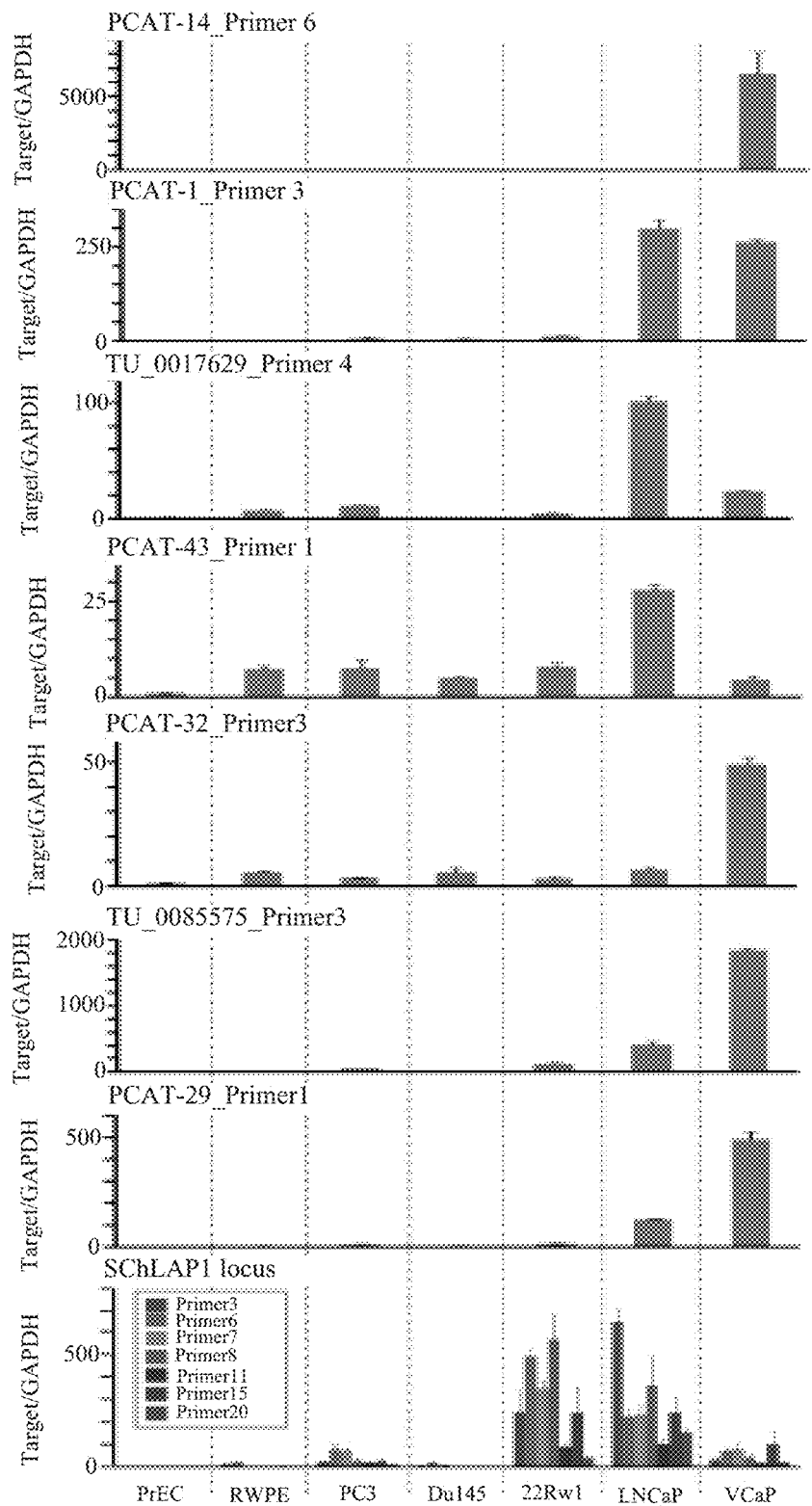

FIG. 17 shows validation of novel transcripts in prostate cell lines. 11/14 unannotated transcripts selected for validation by RT-PCR and qPCR were confirmed in cell line models. a. RT-PCR gels showing expected bands for the 11 transcripts that validated. b. Representative qPCR results using primers selected from a. The primers used in b are indicated by a red asterisk in a.

Figure 18:
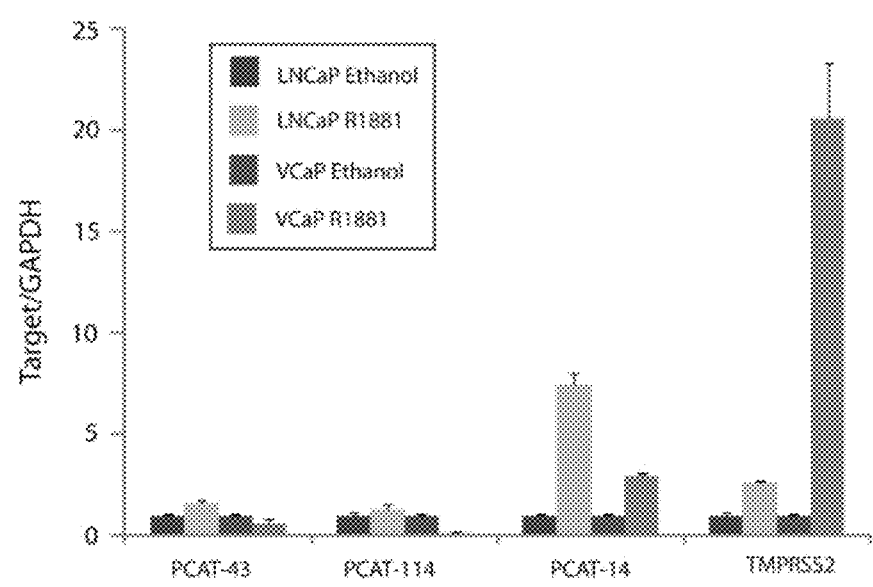

FIG. 18 shows that PCAT-14 is upregulated by androgen signaling. VCaP and LNCaP cells were treated 5 nM R1881 or vehicle (ethanol) control.

Figure 19:
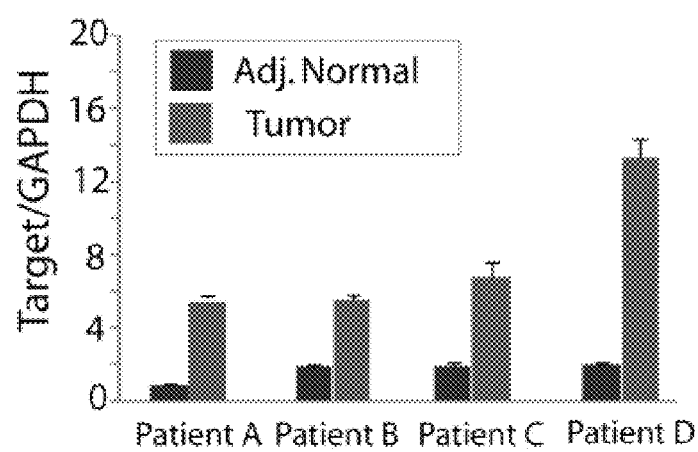

FIG. 19 shows that PCAT-14 is upregulated in matched tumor tissues. Four matched tumor-normal patient tissue samples were assayed for PCAT-14 expression by qPCR.

Figure 20:
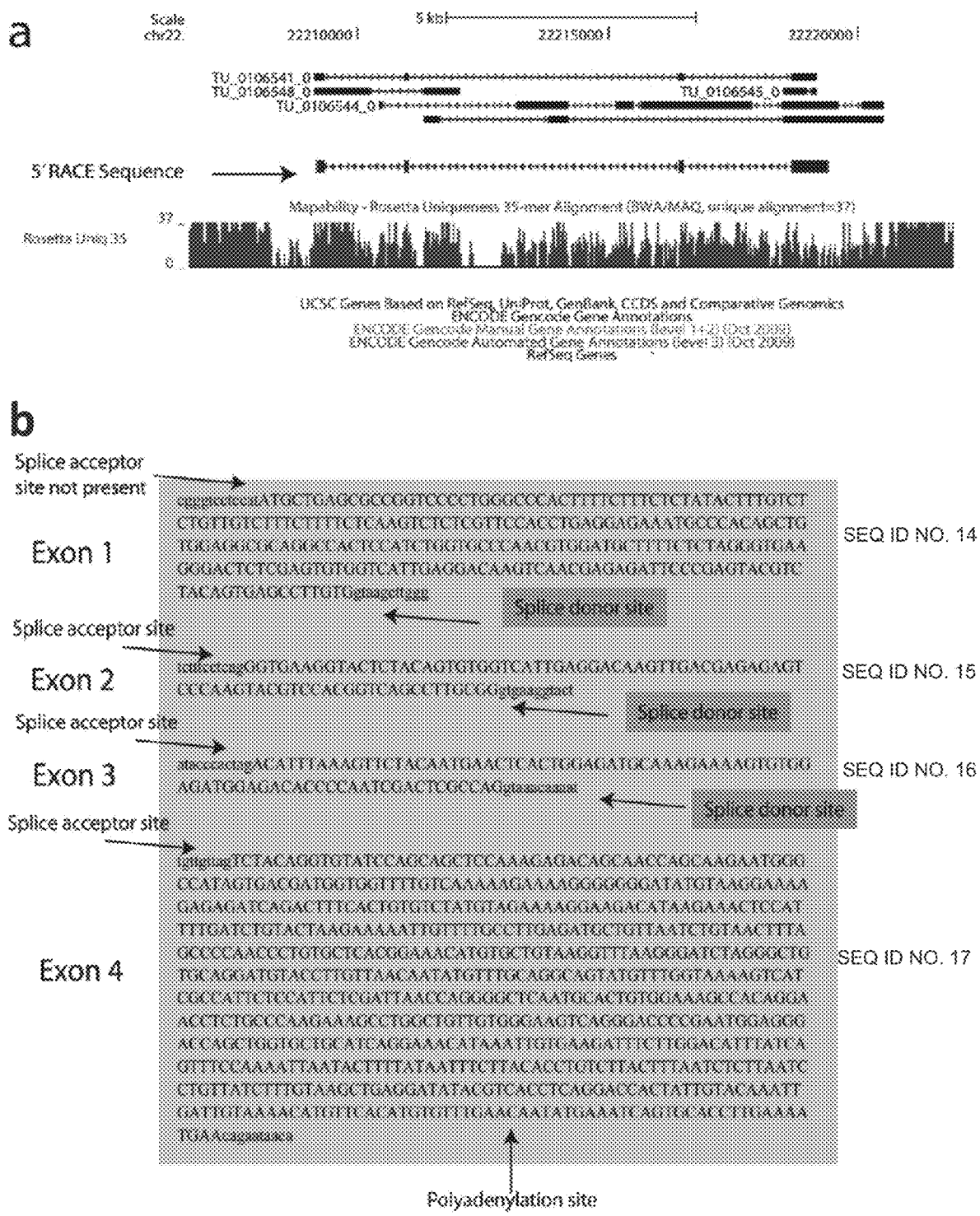

FIG. 20 shows analysis of PCAT-14 transcript structure. a. Representative 5'RACE results using a 3' primer confirms the presence of the sense transcript PCAT-14. Predicted novel transcripts are displayed above the RACE results. b. DNA sequence analysis of PCAT-14 indicates expected splice donor sites, splice acceptor sites, and a polyadenylation site.

Figure 21:
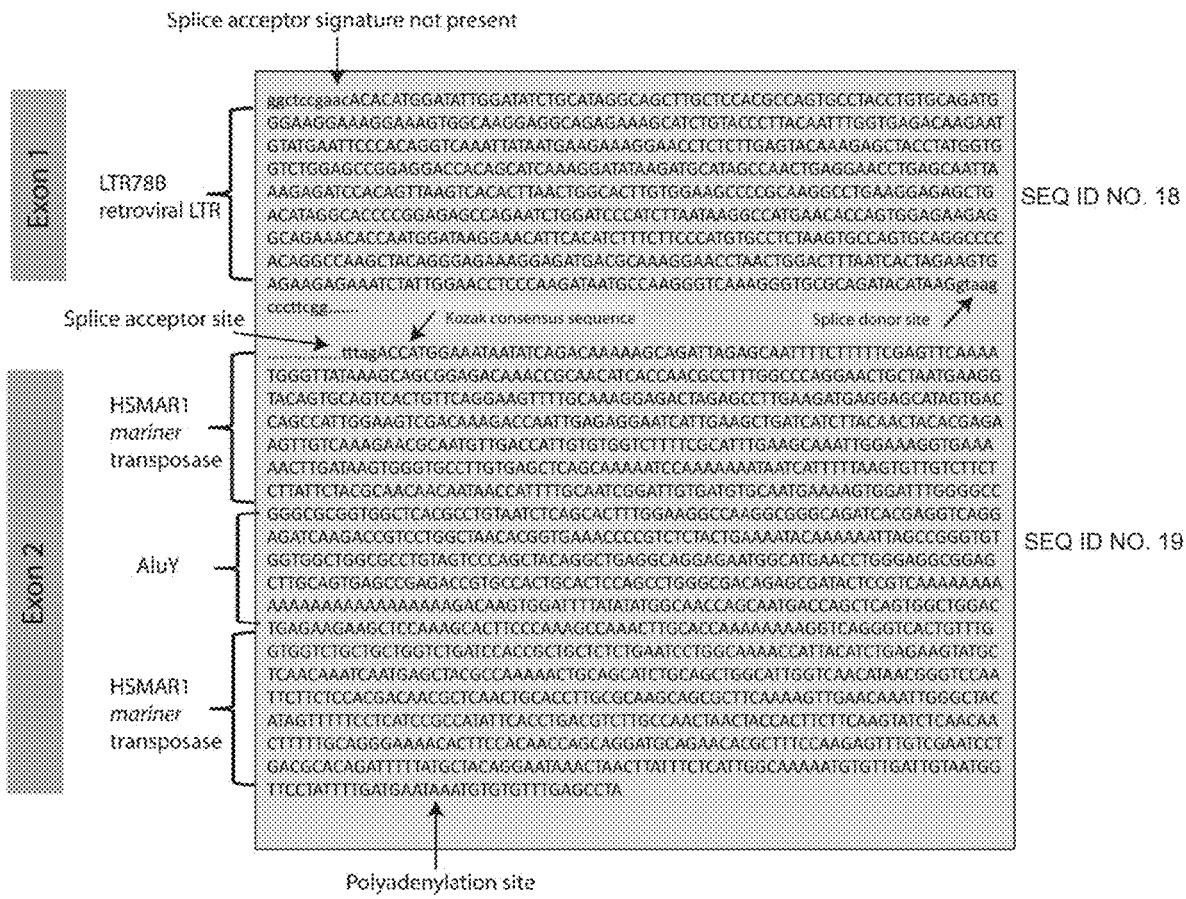

FIG. 21 shows analysis of PCAT-1 transcript structure. 5' and 3' RACE experiments showed a ncRNA transcript containing two exons.

Figure 22:
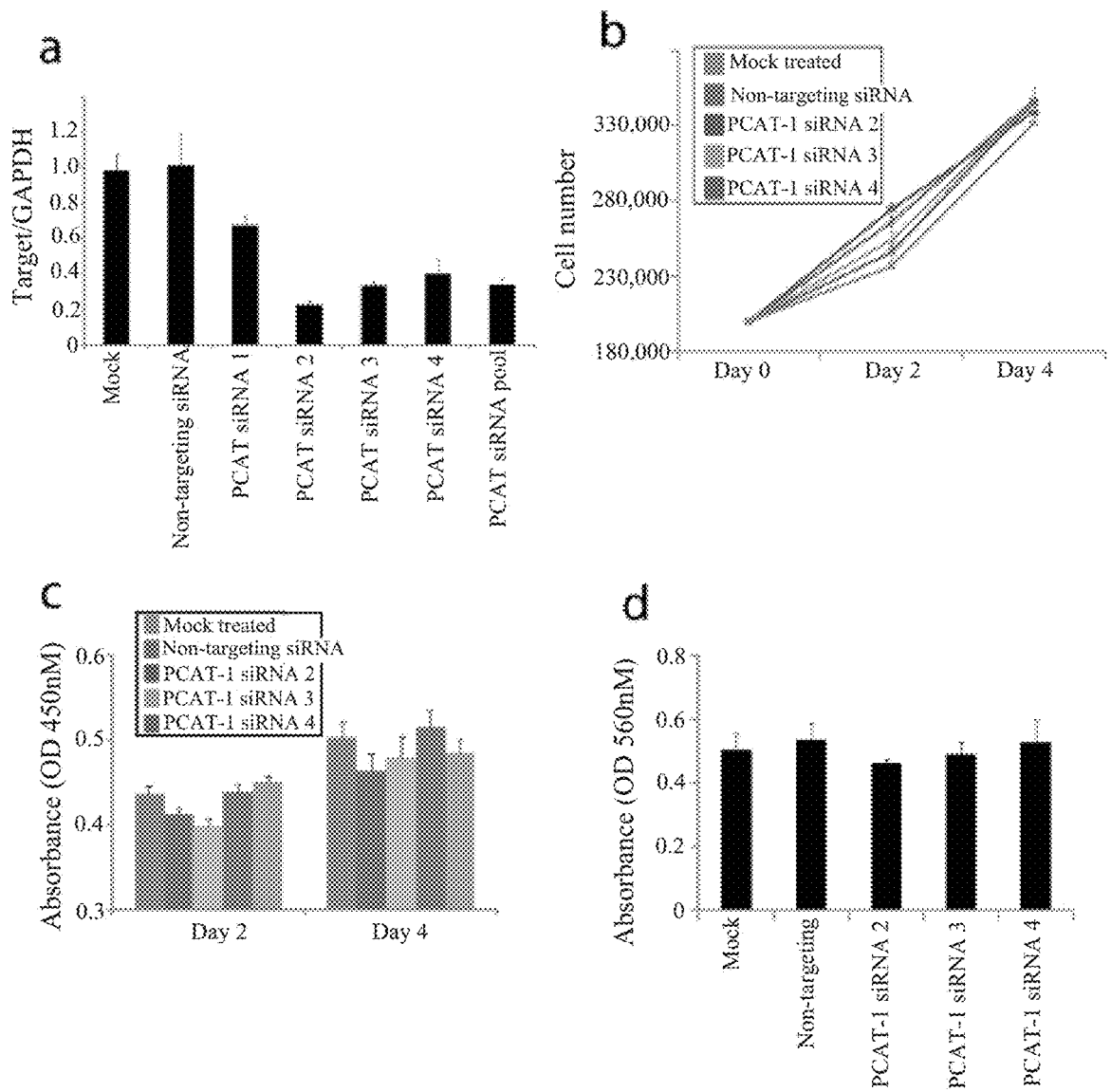

FIG. 22 shows that knockdown of PCAT-1 does not affect invasion or proliferation of VCaP cells. VCaP cells were transfected with custom-made siRNAs targeting PCAT-1 or non-targeting controls. a. Knockdown efficiency for four siRNA oligos individually and pooled. b.-d. siRNAs 2-4 were tested for functional effect due to their higher efficiency of knockdown. b. A cell proliferation assay performed with a Coulter counter shows no significant difference in cell proliferation following knockdown of PCAT-1. c. A WST-1 assay indicates no change in VCaP cell viability following PCAT-1 knockdown. d. A transmembrane invasion assay shows no change in VCaP cell invasiveness following PCAT-1 knockdown.

Figure 23:
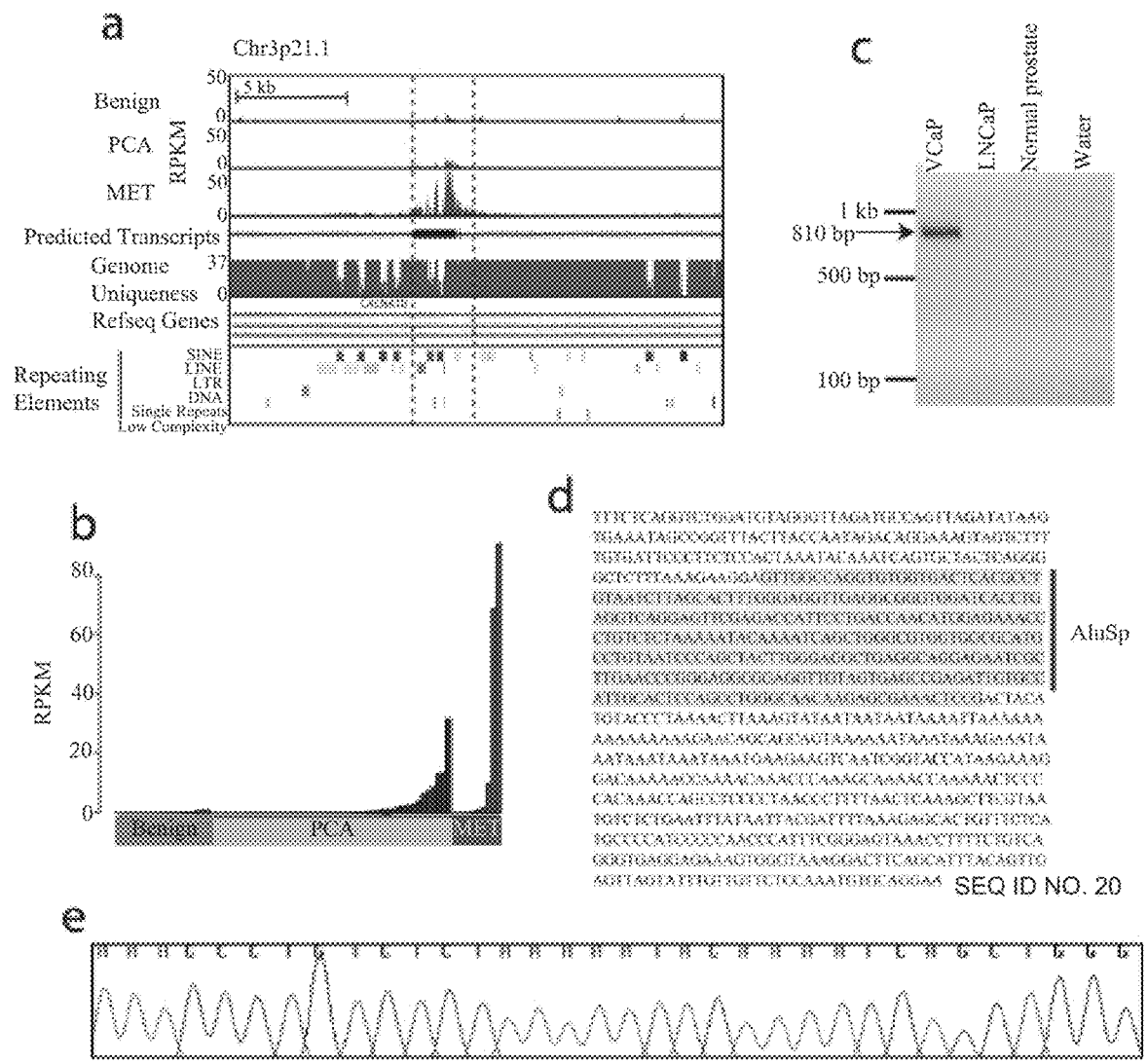

FIG. 23 shows transcription of two Alu elements in a CACNA1D intron. a. Coverage maps representing average expression in RPKM in benign samples, localized tumors, and prostate metastases. b. RPKM expression values for the CACNA1D Alu transcript across the prostate transcriptome sequencing cohort. c. RT-PCR validation of the Alu transcript in cell line models. d. Sanger sequencing confirmation of RT-PCR fragments verifies the presence of AluSp transcript sequence. e. Raw sequencing data of a portion of the AluSp sequence.

Figure 24:
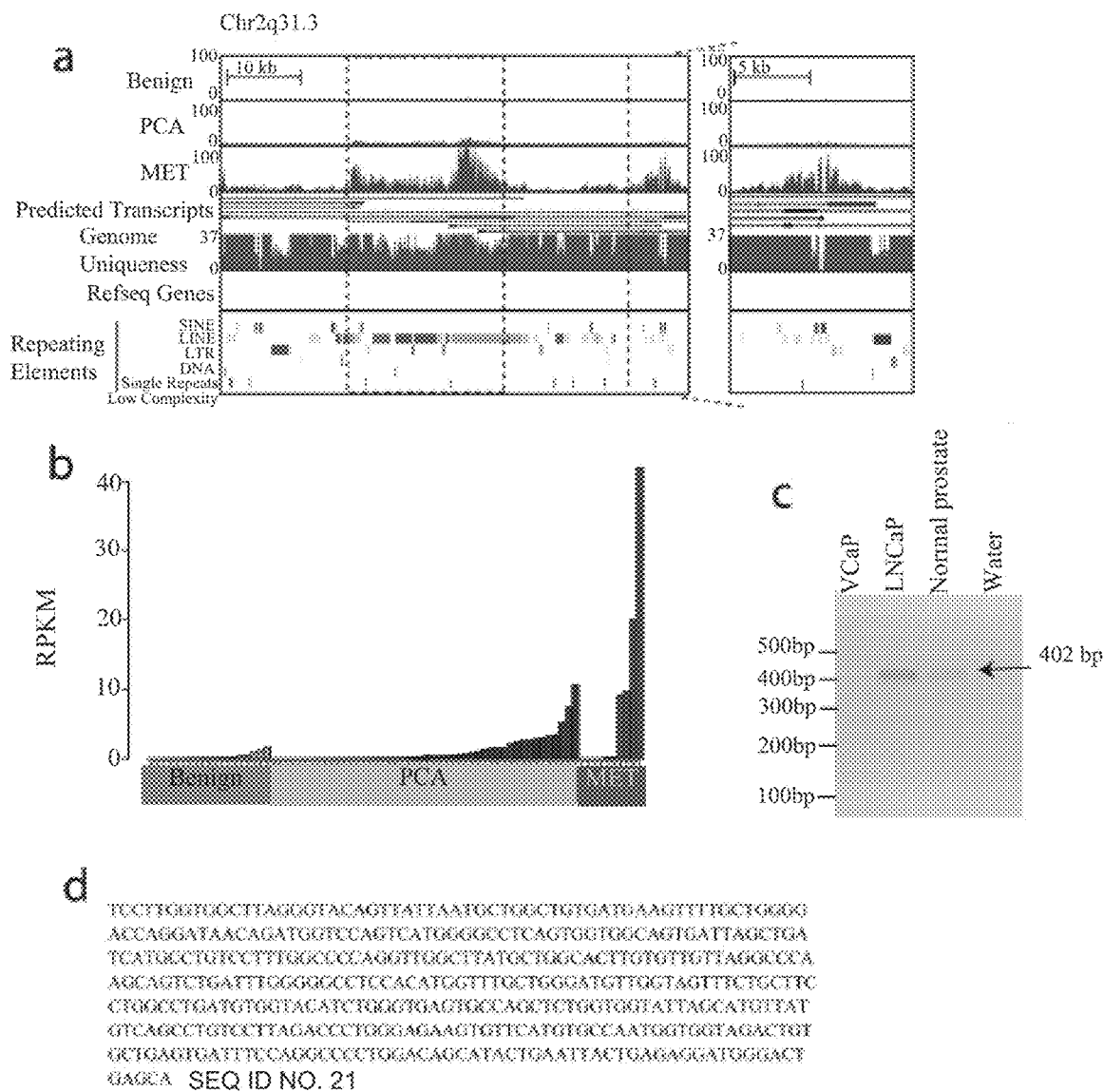

FIG. 24 shows transcription of numerous repeat elements at the SChLAP1 locus. a. Coverage maps representing repeat elements transcribed at the chr2q31.3 locus. b. RPKM expression values for the LINE-1 repeat region on chr2q31.3 across the prostate transcriptome sequencing cohort. c. RTPCR validation of the LINE-1 repetitive element in cell line models. A 402 bp fragment was amplified. d. Sanger sequencing of the PCR fragment confirms identity of the LINE-1 amplicon.

Figure 25:
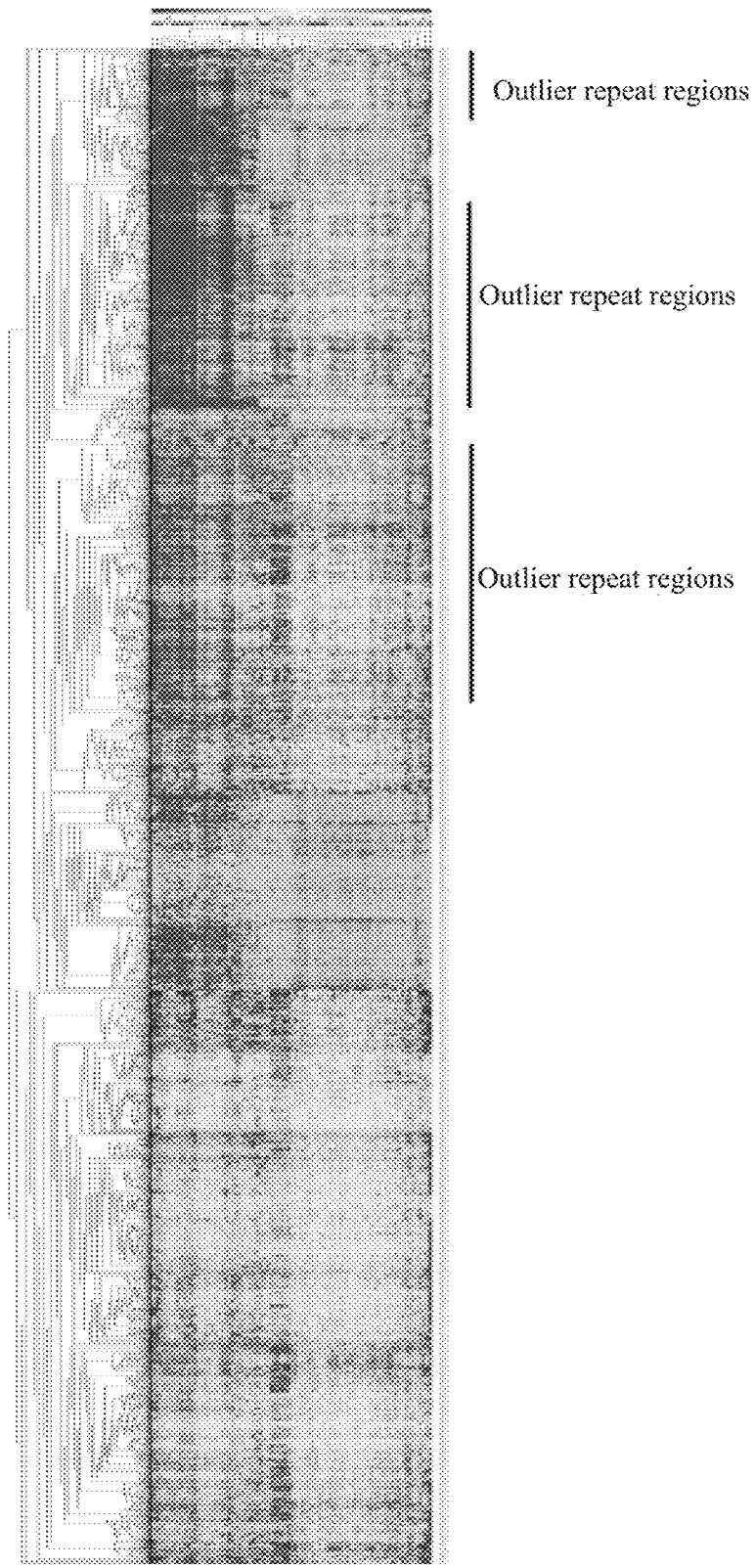

FIG. 25 shows a heatmap of repeats clusters prostate cancer samples. Unannotated transcripts that contained repeat elements were used to cluster prostate cancer samples in an unsupervised manner.

Figure 26:
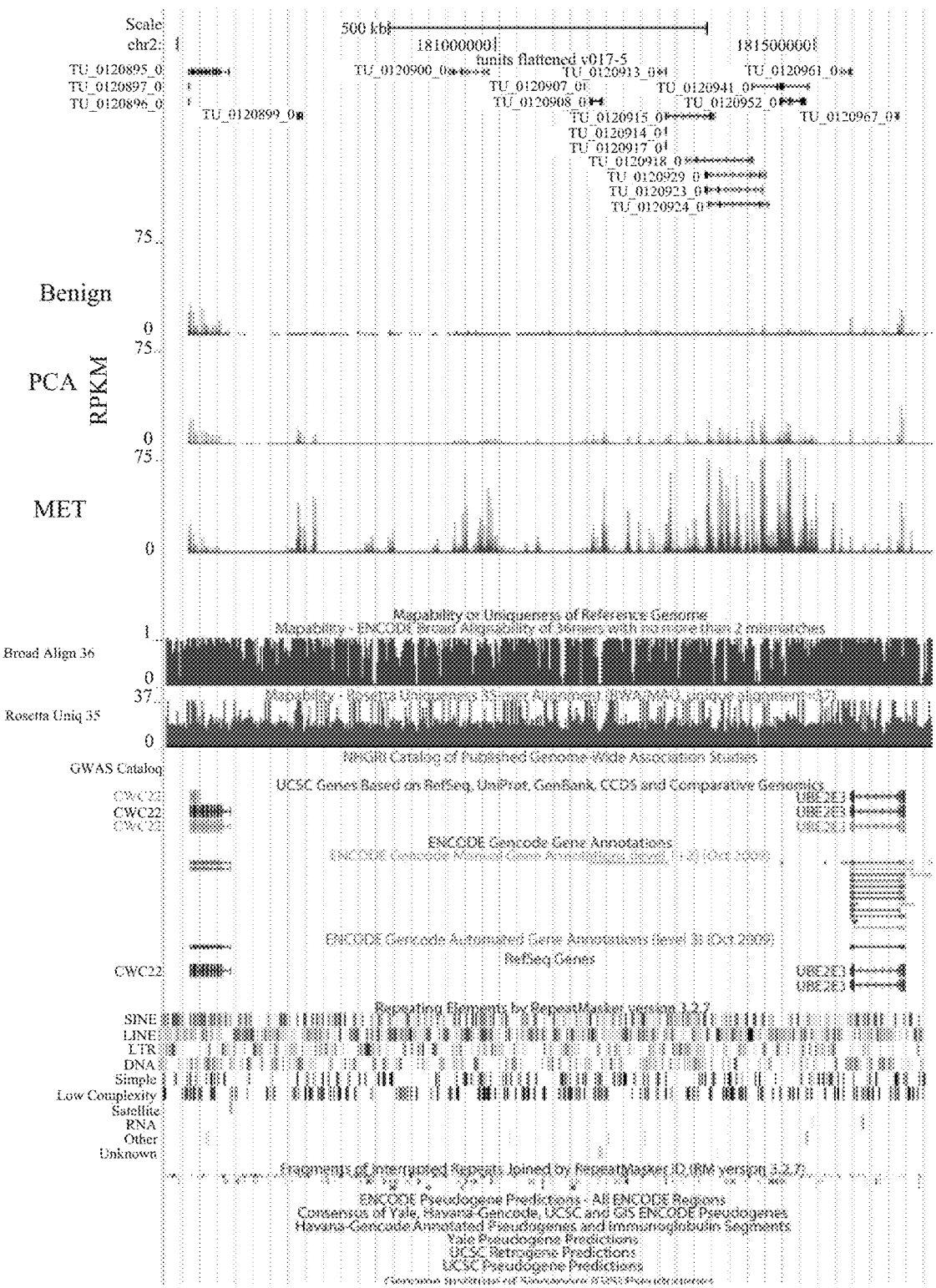

FIG. 26 shows that the SChLAP1 locus spans >500 kb. Visualization of transcriptome sequencing data in the UCSC genome browser indicates that a large, almost 1 Mb section of chromosome 2 is highly activated in cancer, contributing to many individual transcripts regulated in a coordinated fashion.

Figure 1:
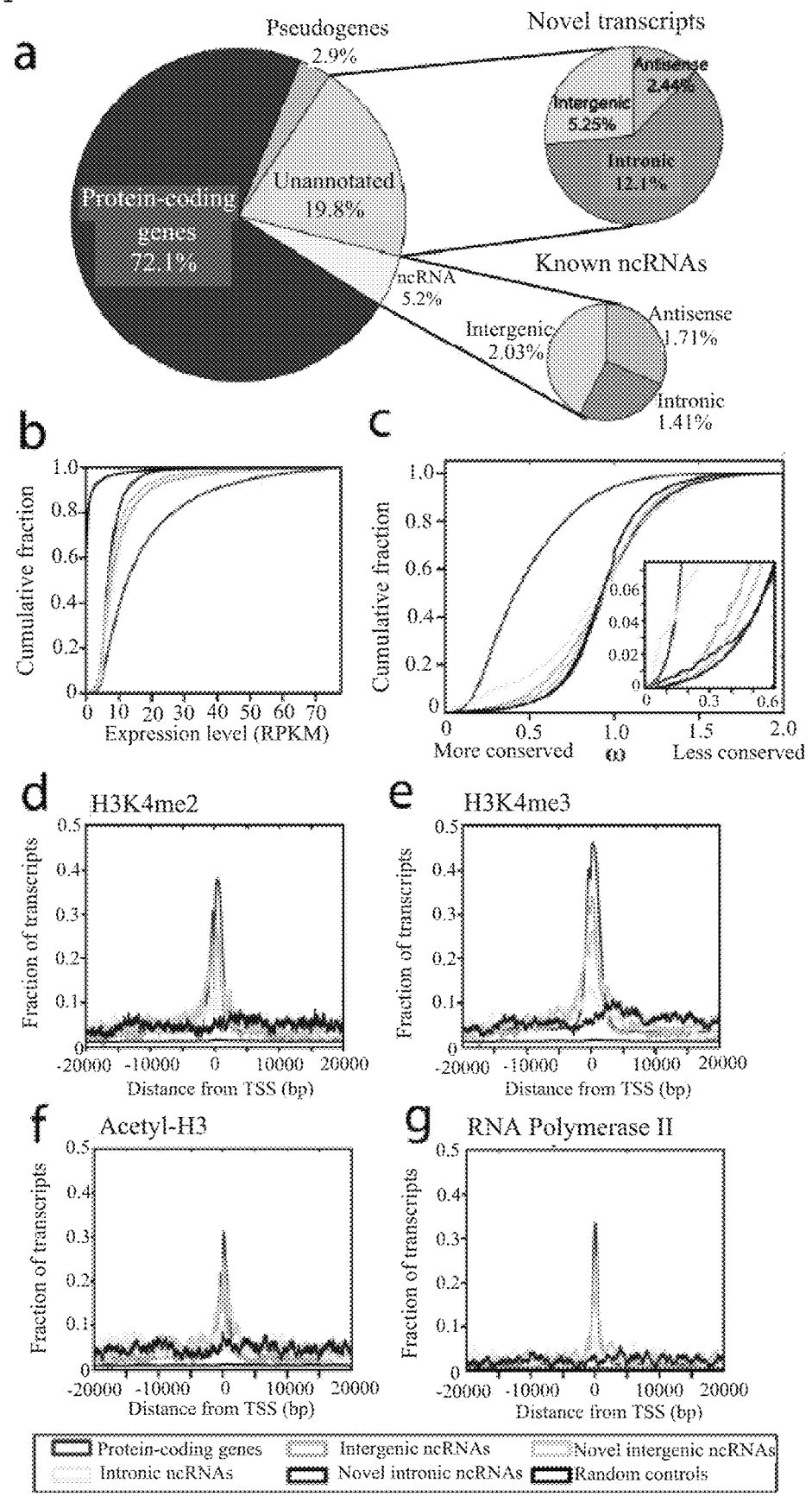
FIG. 1 shows that prostate cancer transcriptome sequencing reveals dysregulation of exemplary transcripts identified herein. a. A global overview of transcription in prostate cancer. b. A line graph showing the cumulative fraction of genes that are expressed at a given RPKM level. c. Conservation analysis comparing unannotated transcripts to known genes and intronic controls shows a low but detectable degree of purifying selection among intergenic and intronic unannotated transcripts. d.-g. Intersection plots displaying the fraction of unannotated transcripts enriched for H3K4me2 (d), H3K4me3 (e), Acetyl-H3 (f) or RNA polymerase II (g) at their transcriptional start site (TSS) using ChIP-Seq and RNA-Seq data for the VCaP prostate cancer cell line. h. A heatmap representing differentially expressed transcripts, including novel unannotated transcripts, in prostate cancer.
Figure 1:
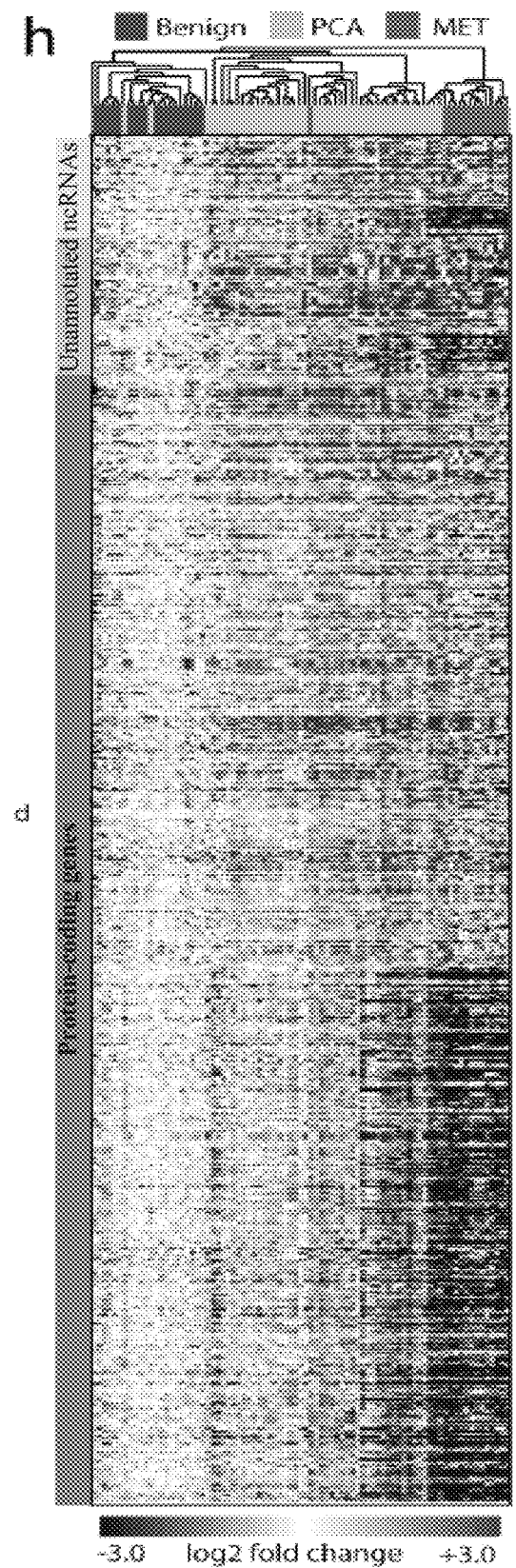
Figure 2:
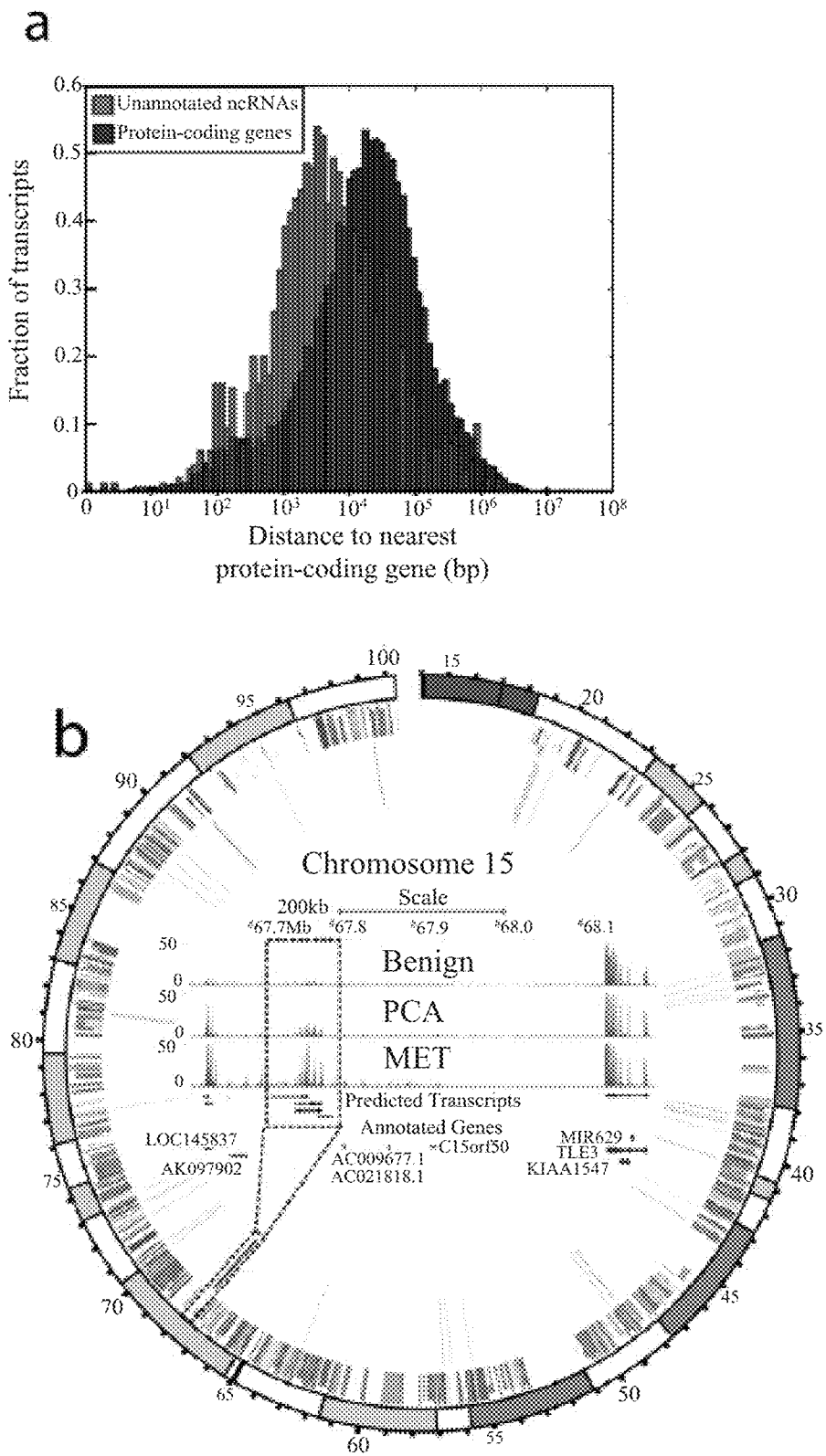
FIG. 2 shows that unannotated intergenic transcripts differentiate prostate cancer and benign prostate samples. a. A histogram plotting the genomic distance between an unannotated ncRNA and the nearest protein-coding gene. b. A Circos plot displaying the location of annotated transcripts and unannotated transcripts on Chr15q. c. A heatmap of differentially expressed or outlier unannotated intergenic transcripts clusters benign samples, localized tumors, and metastatic cancers by unsupervised clustering analyses. d. Cancer outlier profile analysis (COPA) outlier analysis for the prostate cancer transcriptome reveals known outliers (SPINK1, ERG, and ETV1), as well as numerous unannotated transcripts.
Figure 2:
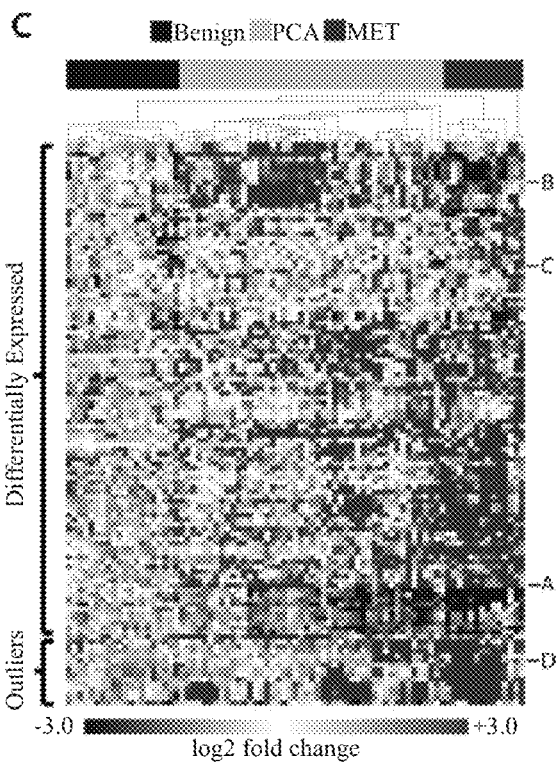
Figure 3:
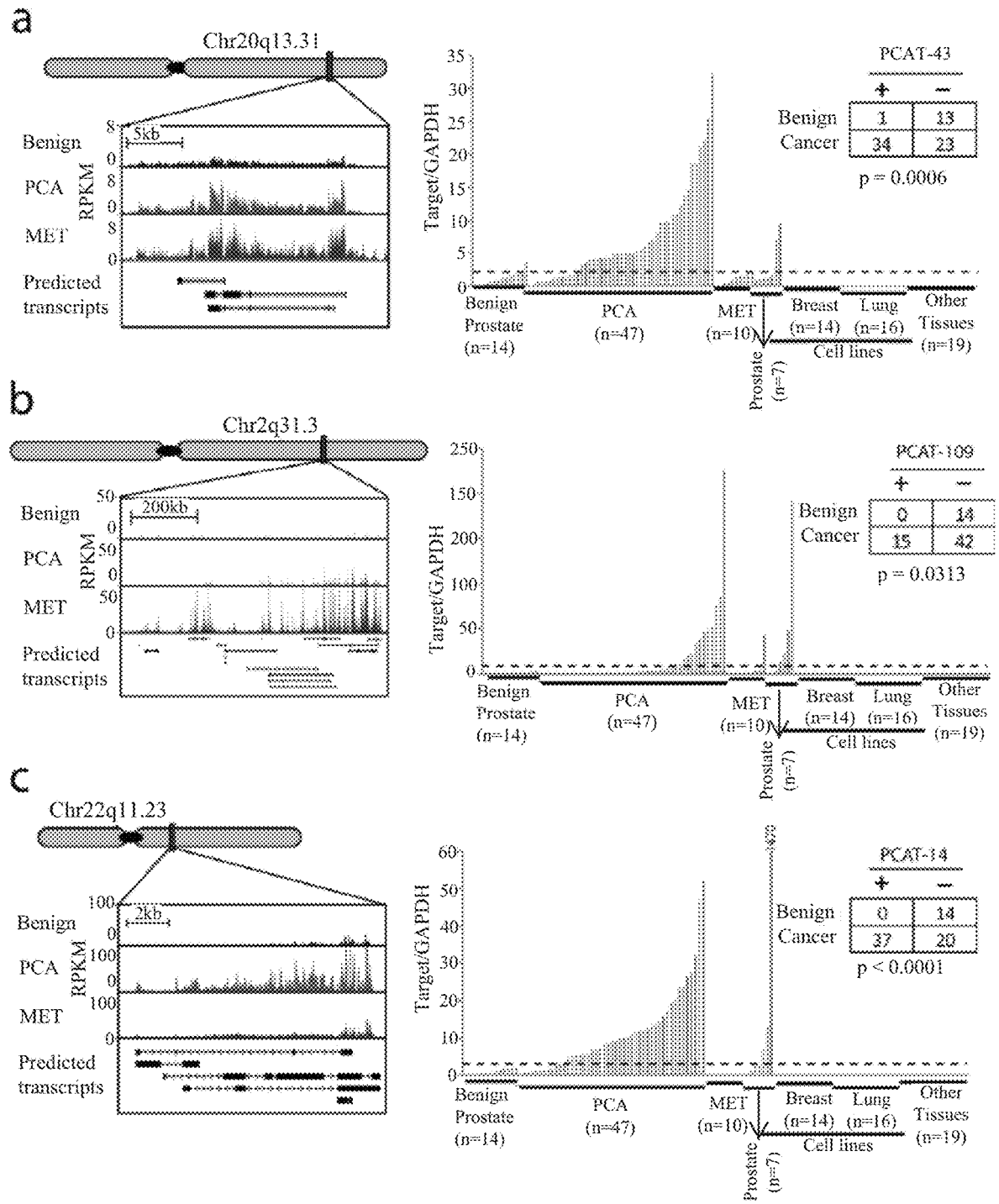
FIG. 3 shows validation of tissue-specific prostate cancer-associated non-coding RNAs. a-c. Quantitative real-time PCR was performed on a panel of prostate and non-prostate samples to measure expression levels of three nominated non-coding RNAs (ncRNAs), PCAT-43, PCAT-109, and PCAT-14, upregulated in prostate cancer compared to normal prostate tissues. a. PCAT-43 is a 20 kb ncRNA located 40 kb upstream of PMEPA1 on chr20q13.31. b. PCAT-109, located in a large, 0.5 Mb gene desert region on chr2q31.3 displays widespread transcription in prostate tissues, particularly metastases. c. PCAT-14, a genomic region on chr22q11.23 encompassing a human endogenous retrovirus exhibits marked upregulation in prostate tumors but not metastases.
Figure 27:
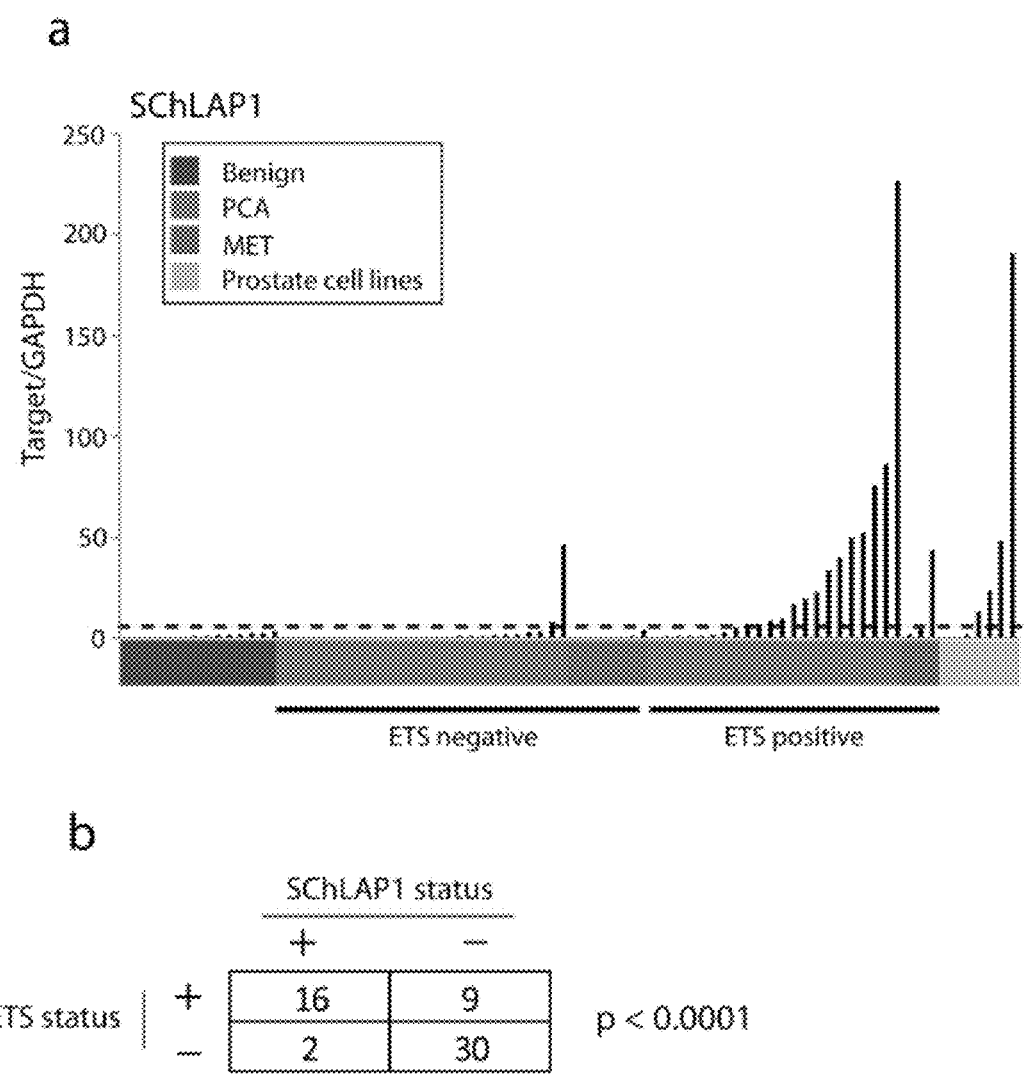

FIG. 27 shows that the SChLAP1 locus is associated with ETS positive tumors. a. Expression of the SChLAP1 locus was assayed by qPCR as display in FIG. 3$b$ on a cohort of 14 benign prostate tissues, 47 localized prostate tumors and 10 metastatic prostate cancers. b. Quantification of the SChLAP1 association with ETS status using the threshold indicated by the blue dotted line in a.

FIG. 28 shows the sequence of PCAT-1 and PCAT-14.

Figure 29:
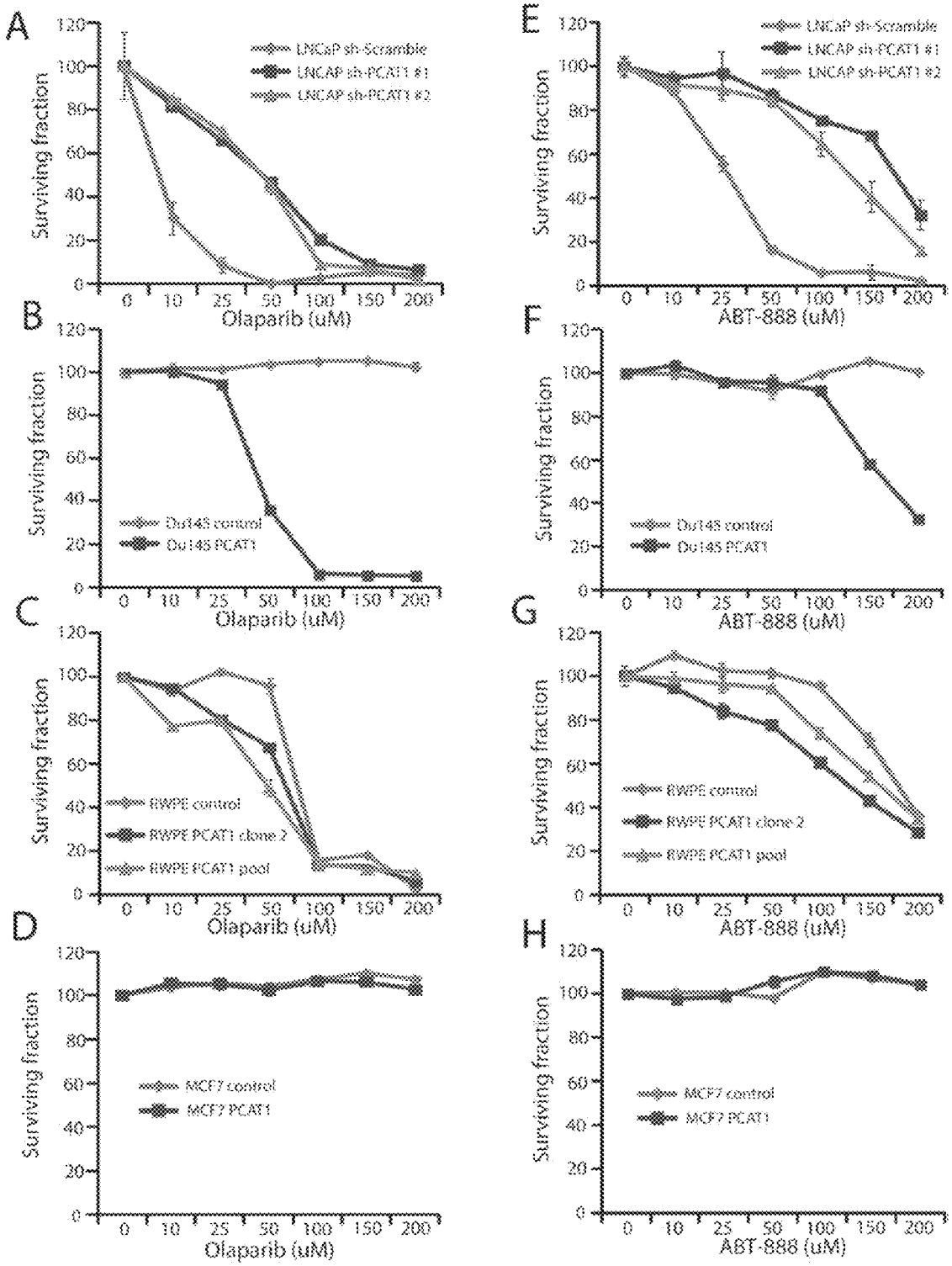

FIG. 29 shows that PCAT-1 expression sensitizes prostate cancer cells to treatment with PARP-1 inhibitors. (a-d) treatment with the PARP1 inhibitor olaparib, (e-h) treatment with the PARP1 inhibitor ABT-888. Stable PCAT-1 knockdown in LNCAP prostate cells reduces sensitivity to olaparib (a) and ABT-888 (e). Stable overexpression in Du145 prostate cancer and RWPE benign prostate cells increases sensitivity to olaparib (b,c) and ABT-888 (f,g). Overexpression of PCAT-1 in MCF7 breast cancer cells does not recapitulate this effect (d,h).

Figure 30:
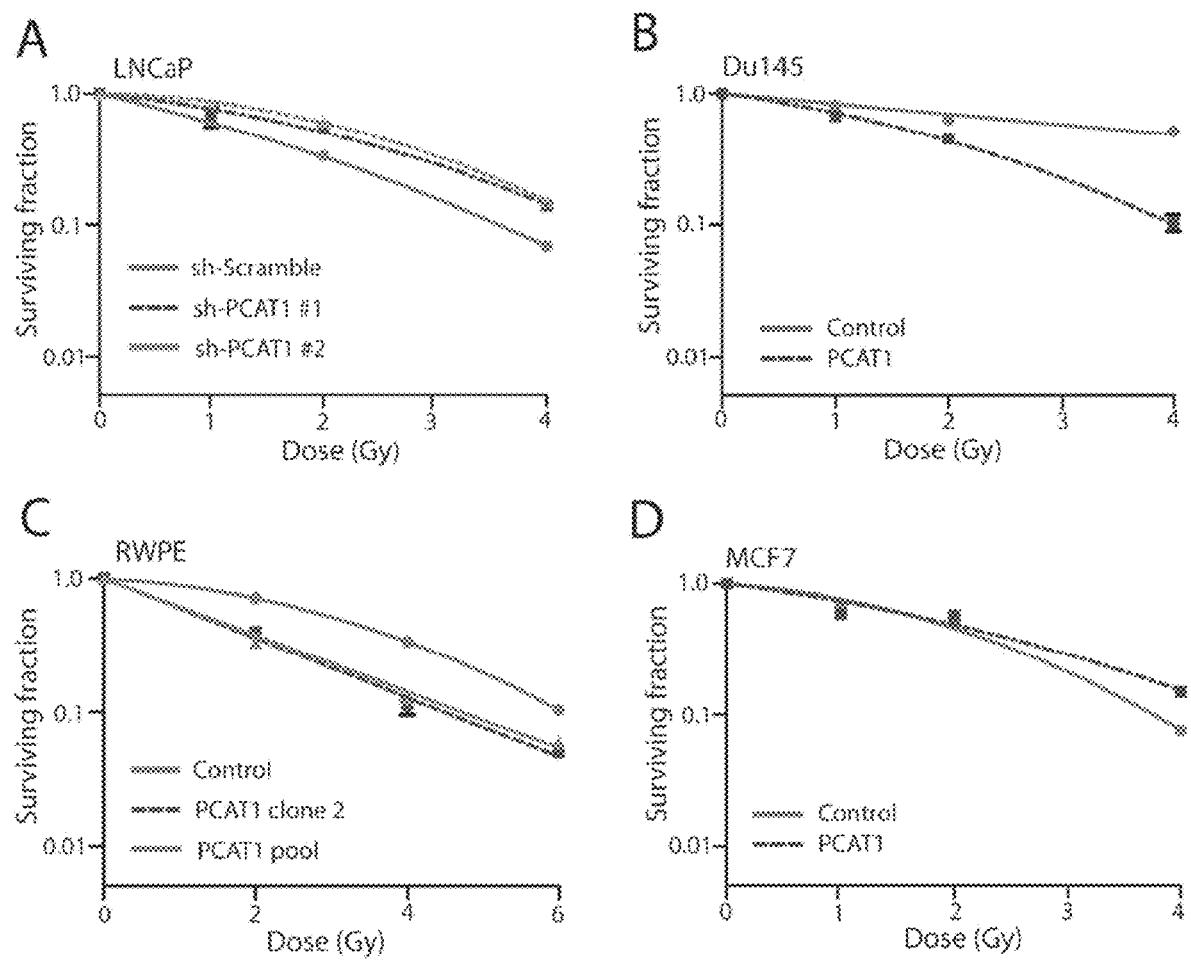

FIG. 30 shows that PCAT-1 expression sensitizes prostate cancer cells to radiation treatment. (a) Stable PCAT-1 knockdown in LNCAP prostate cells reduces sensitivity to radiation. (b,c) Stable overexpression in Du145 prostate cancer and RWPE benign prostate cells increases sensitivity to radiation. (d). Overexpression of PCAT-1 in MCF7 breast cancer cells does not recapitulate this effect.

Figure 31:
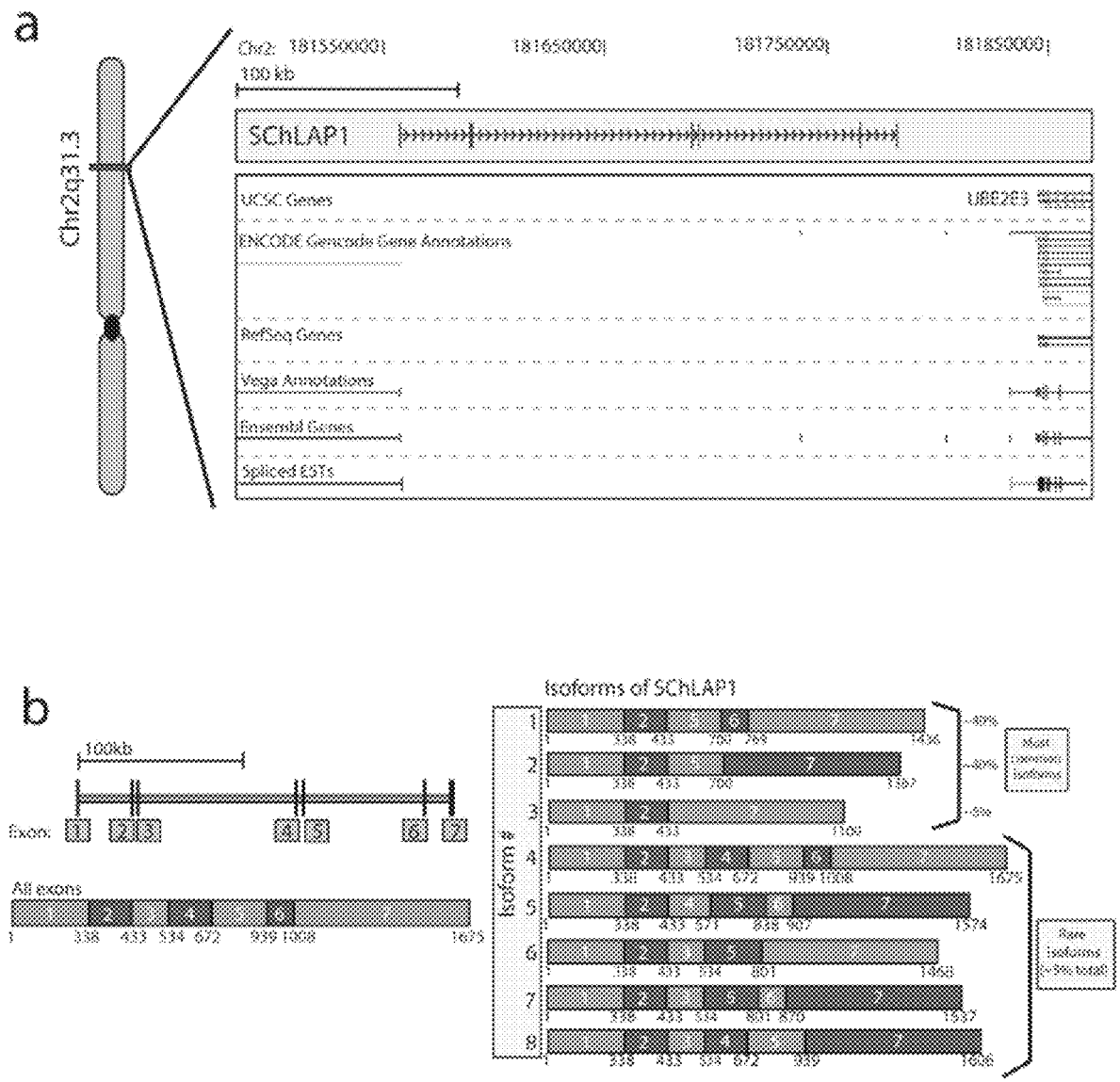
Figure 31:
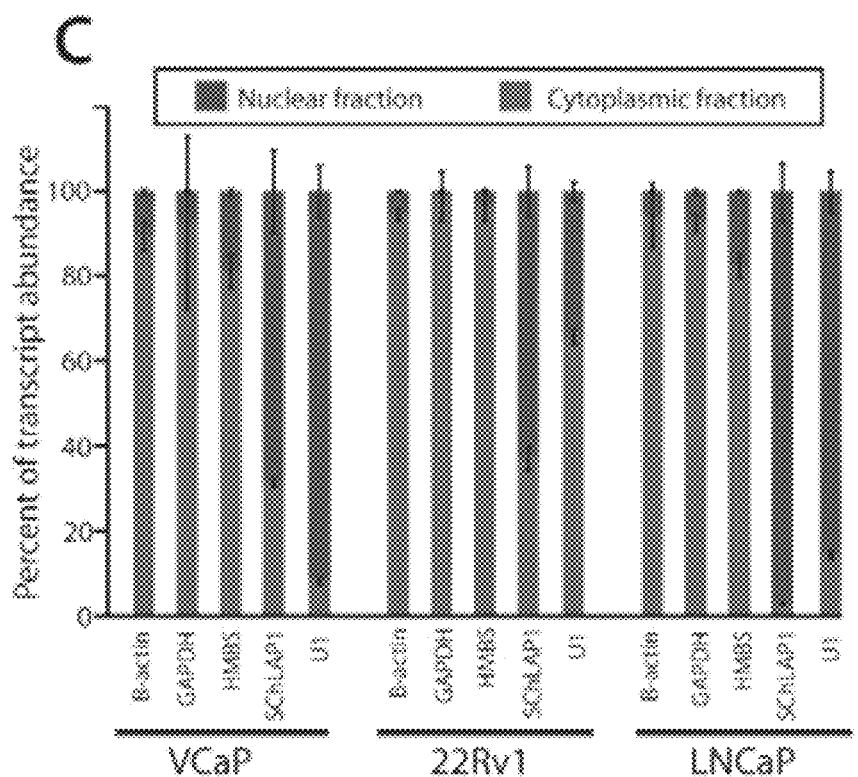
Figure 31:
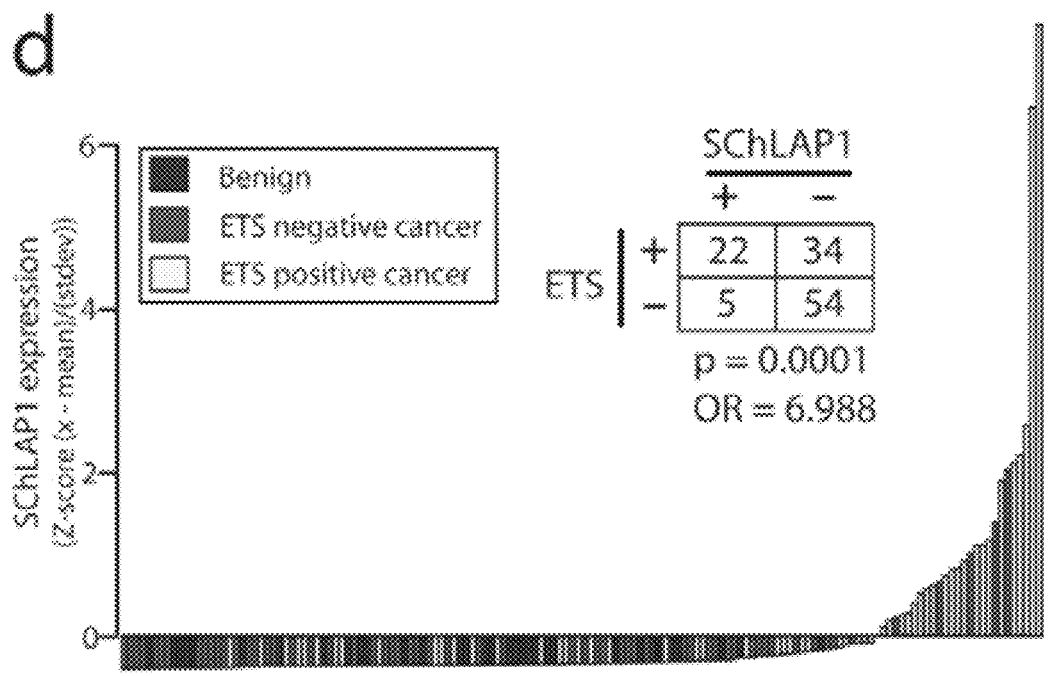

FIG. 31 shows that unannotated intergenic transcripts differentiate prostate cancer and benign samples. (a) The genomic location and exon structure of SChLAP-1. SChLAP-1 is located on chromosome 2 in a previously unannotated region. (b) The isoform structure of SChLAP-1. (c) Cell fractionation into nuclear and cytoplasmic fractions demonstrates that SChLAP-1 is predominantly nuclear in its localization. (d) Expression of SChLAP-1 in a cohort of prostate cancer and benign tissues indicates that SChLAP-1 is a prostate cancer outlier associated with cancers.

Figure 32:
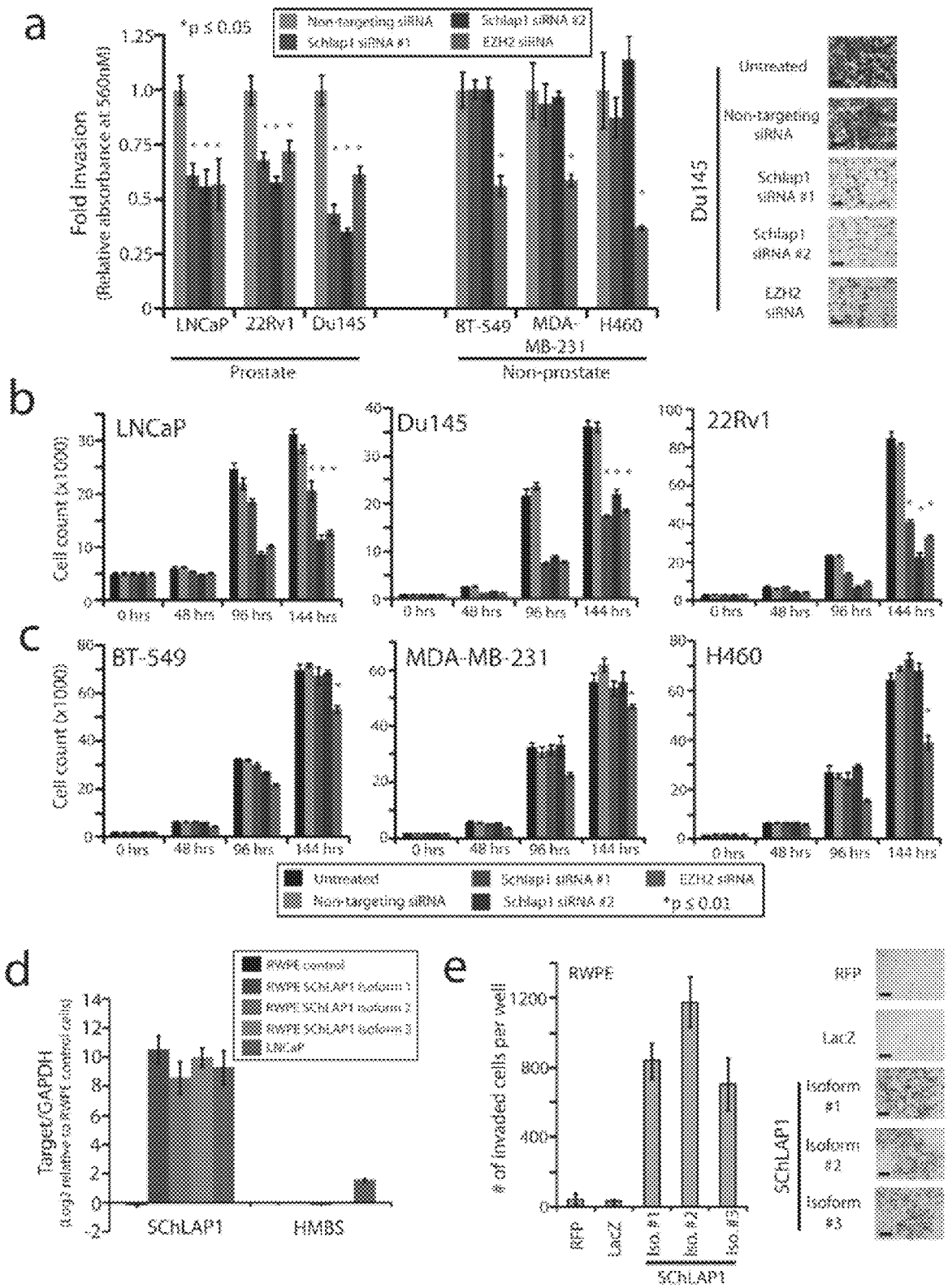

FIG. 32 shows that SChLAP-1 is required for prostate cancer cell invasion and proliferation. (a) Prostate and non-prostate cancer cell lines were treated with SChLAP-1 siRNAs.
(b and c) As in (a), prostate and non-prostate cell lines were assayed for cell proliferation following SChLAP-1 knockdown. (d) The three most abundant isoforms of SChLAP-1 were cloned and overexpressed in RWPE benign immortalized prostate cells at levels similar to LNCaP cancer cells. (e) RWPE cells overexpressing SChLAP-1 isoforms show an increased ability to invade through Matrigel in Boyden chamber assays.

Figure 33:
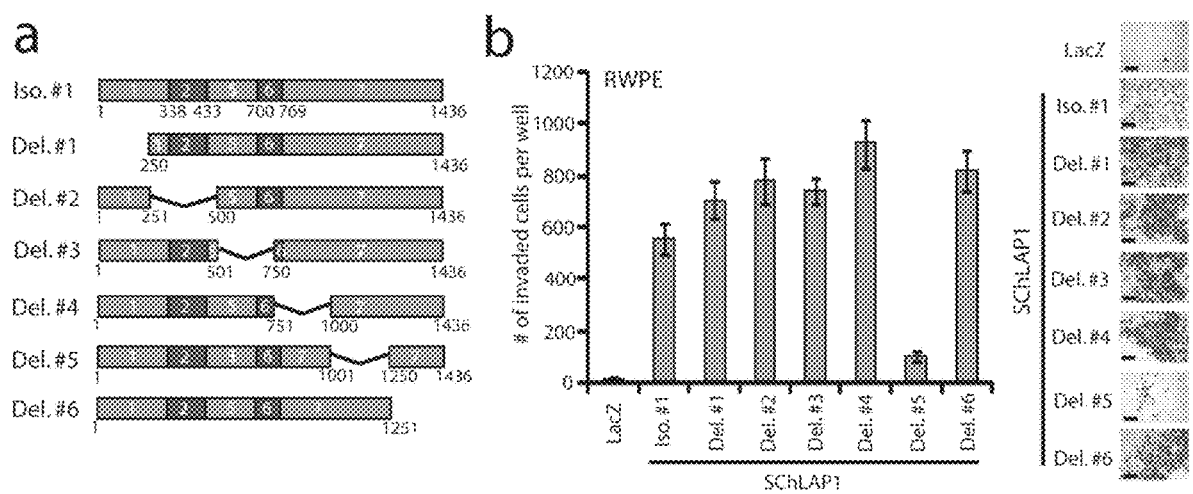

FIG. 33 shows that deletion analysis of SChLAP-1 identifies a region essential for its function. (a) RWPE cells overexpressing SChLAP-1 deletion constructs or full-length isoform #1 were generated as shown in the schematic of the constructs. (b) RWPE cells overexpressing SChLAP-1 deletion constructs demonstrated an impaired ability to invade through Matrigel, while the other deletion constructs showed no reduction in their ability to induce RWPE cell invasion compared to the wild type SChLAP-1.

Figure 34:
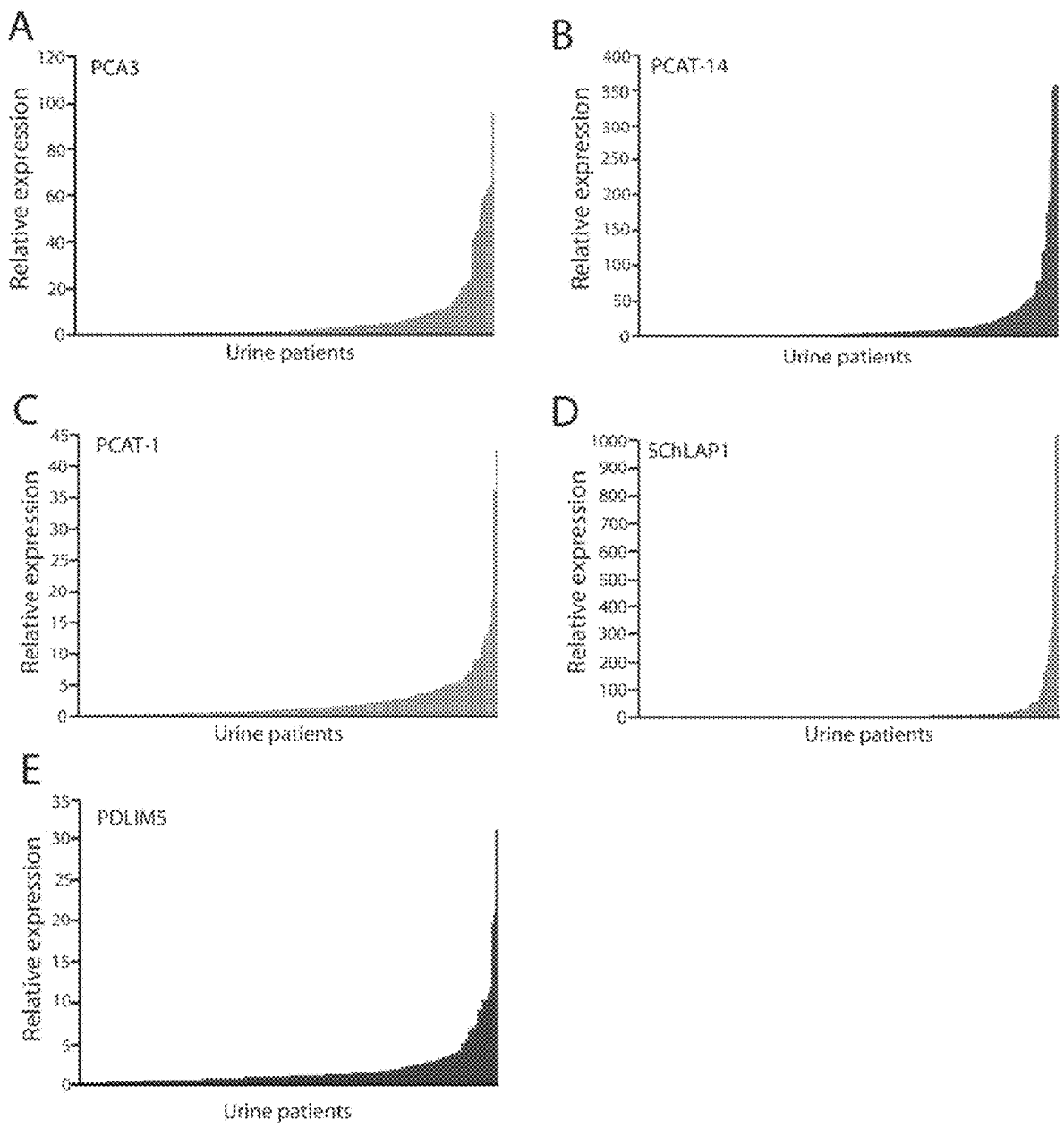

FIG. 34 shows detection of prostate cancer RNAs in patient urine samples. (a-e). (a) PCA3 (b) PCAT-14 (c) PCAT-1 (d) SChLAP-1 (e) PDLIM5

Figure 35:
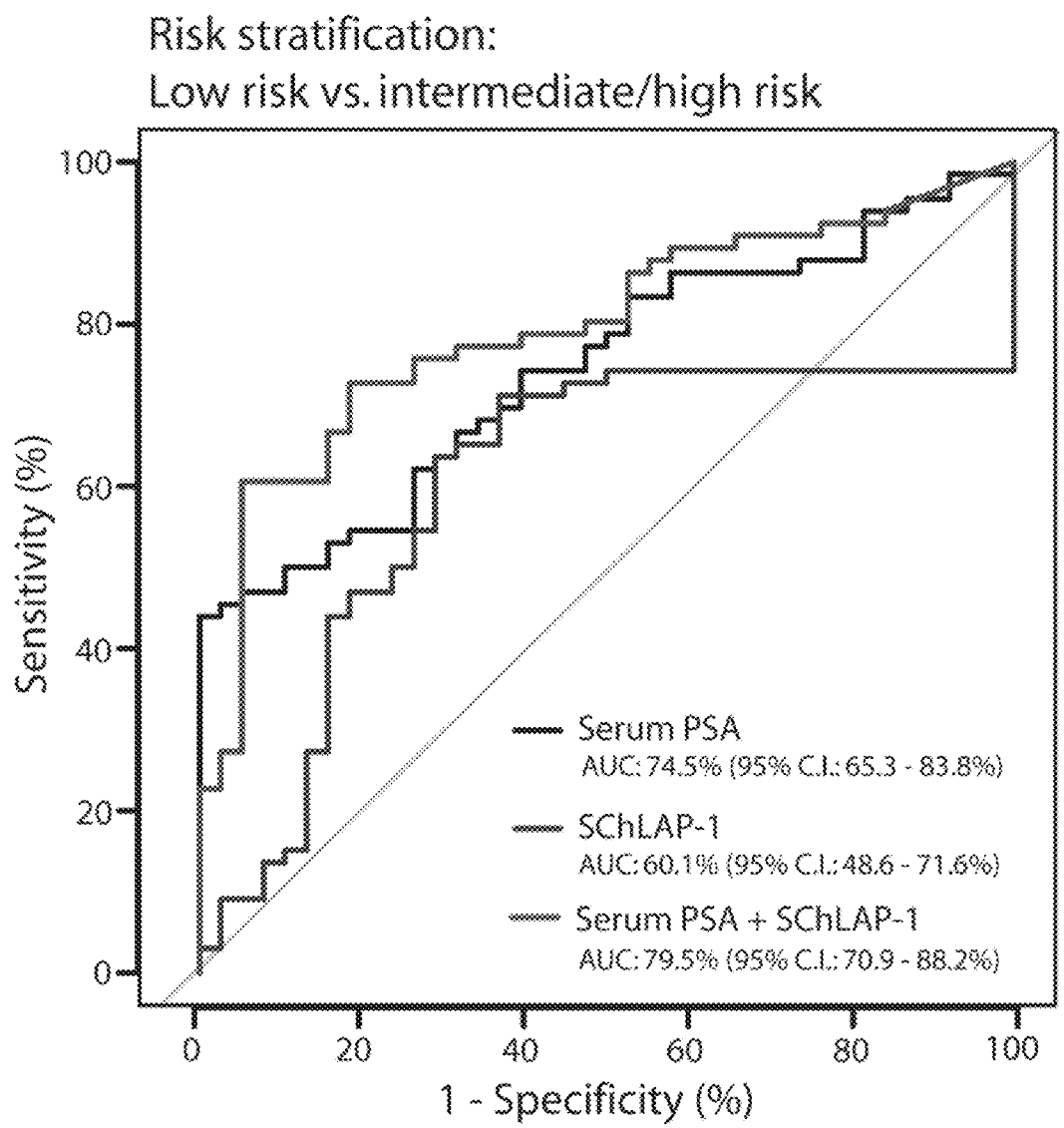

FIG. 35 shows multiplexing urine SChLAP-1 measurements with serum PSA improves prostate cancer risk stratification.

Figure 36:
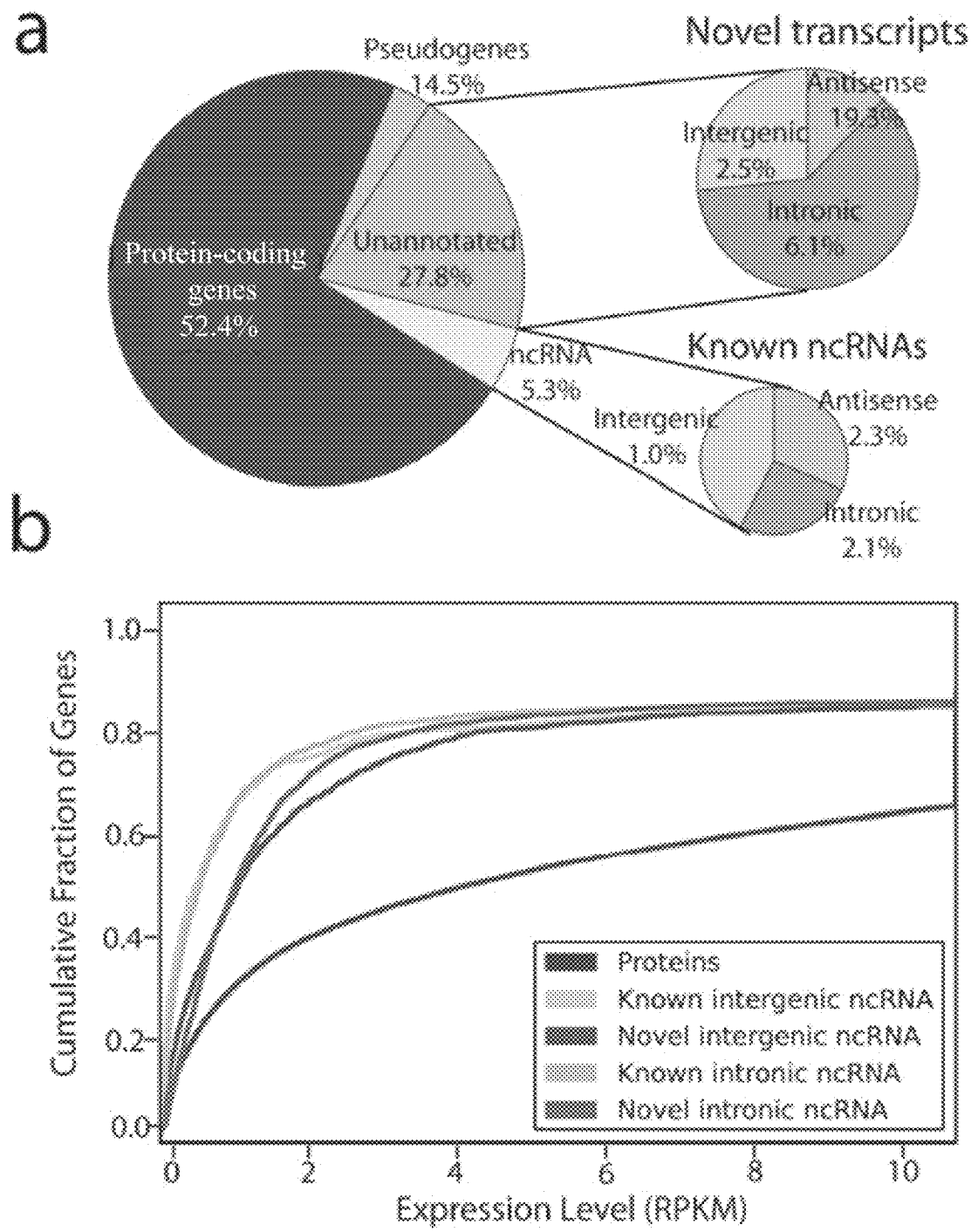
Figure 36:
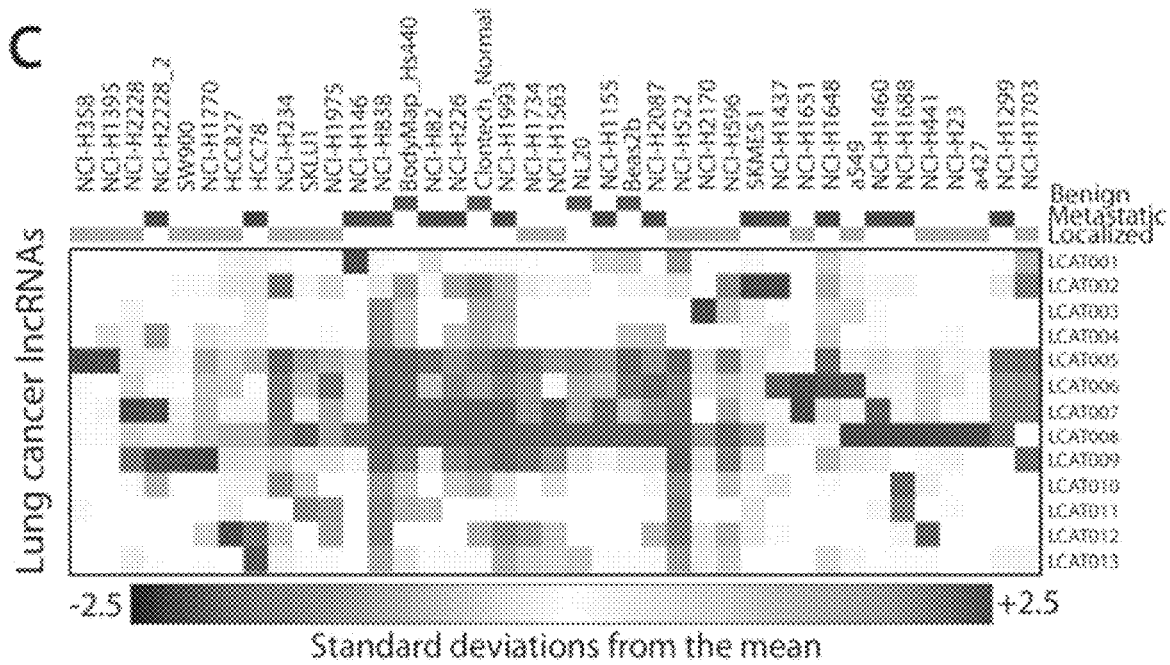

FIG. 36 shows analysis of the lung cancer transcriptome. (a) 38 lung cell lines were analyzed by RNA-Seq and then lncRNA transcripts were reconstructed. (b) Expression levels of transcripts observed in lung cell lines. (c) An outlier analyses of 13 unannotated transcripts shows the presence of novel lncRNAs in subtypes of lung cancer cell lines.

Figure 37:
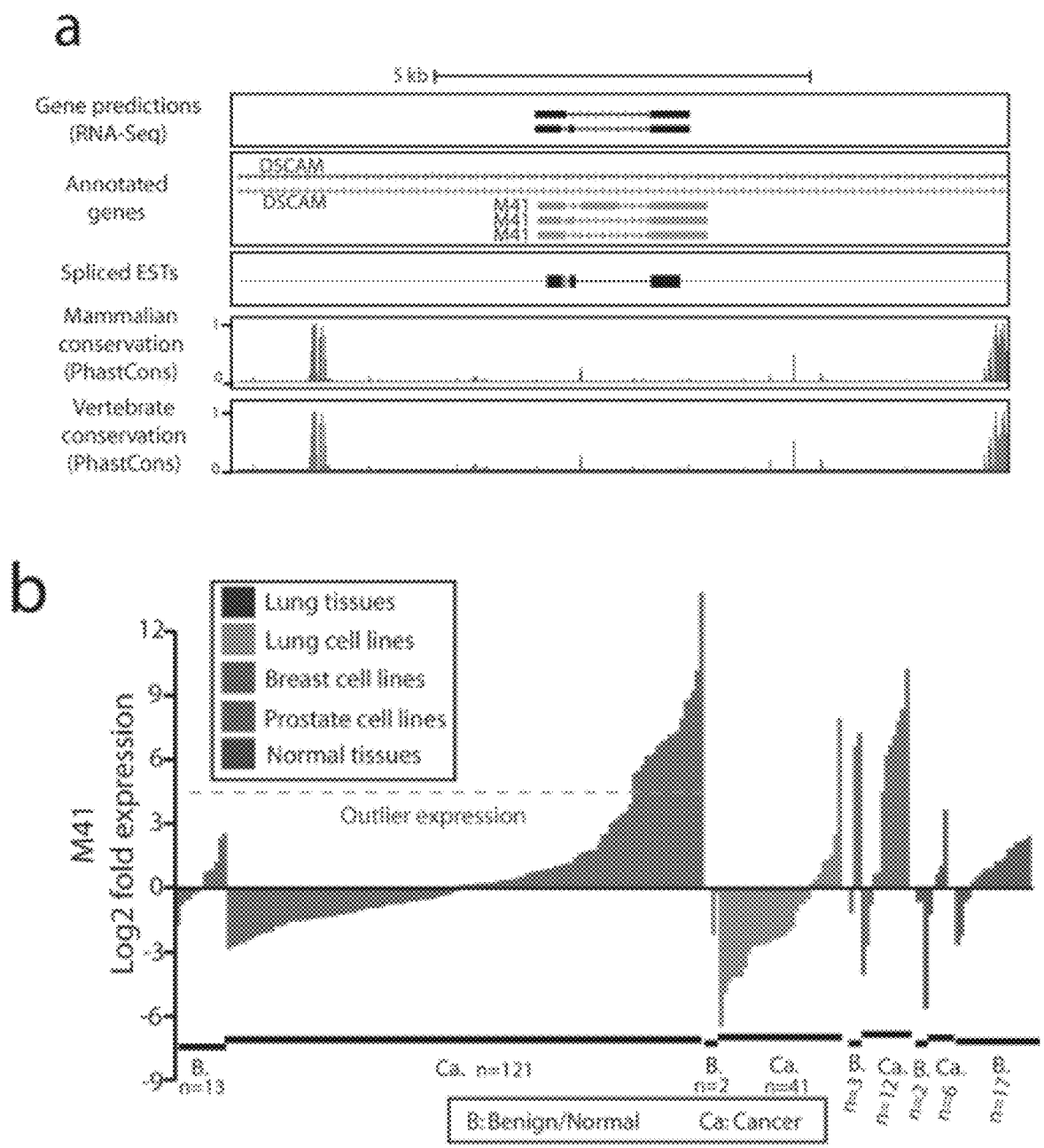
Figure 37:
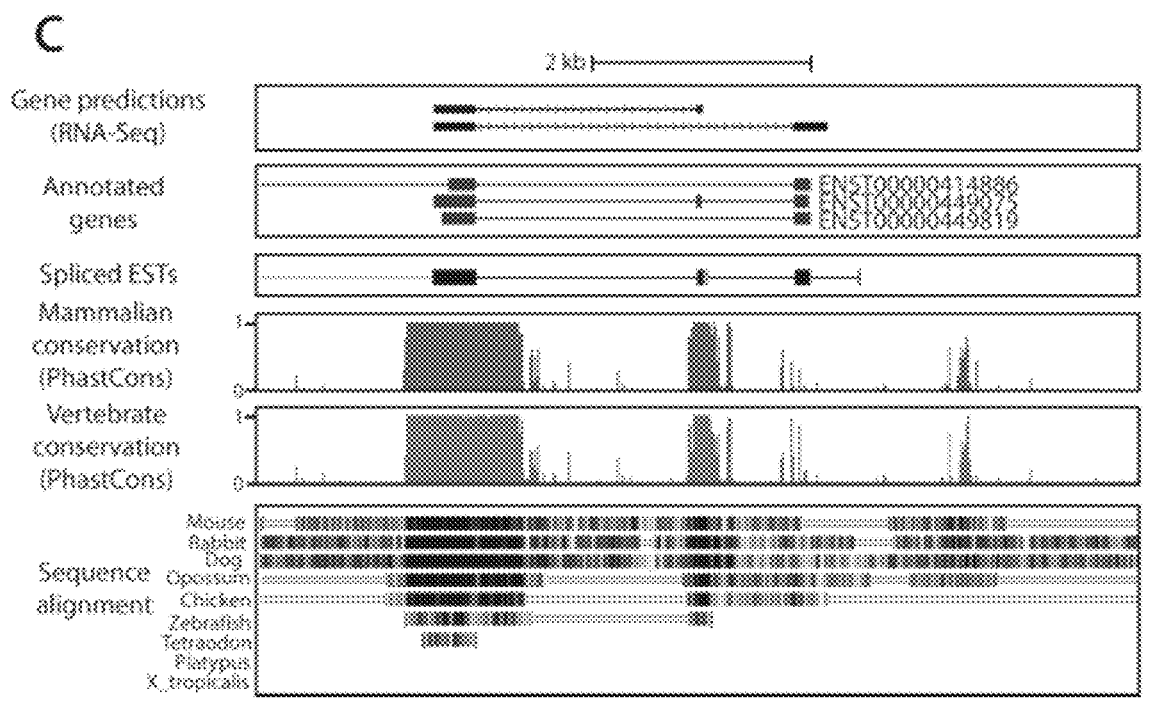
Figure 37:
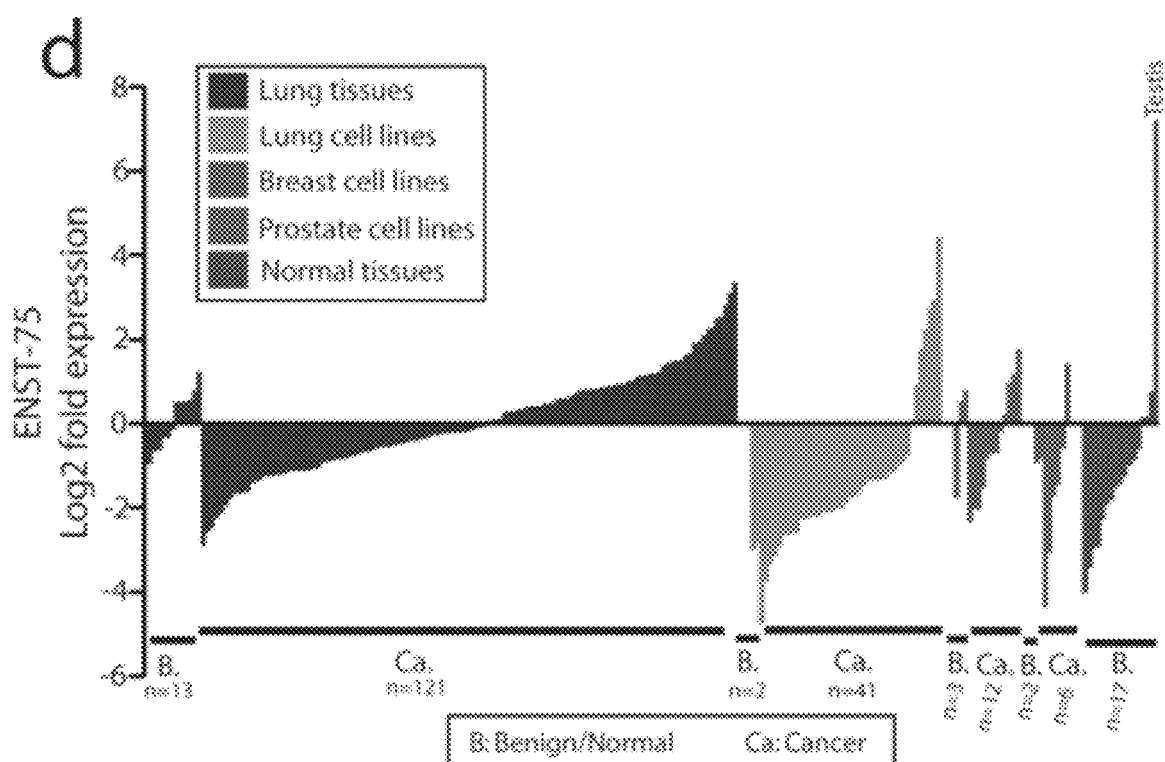

FIG. 37 shows discovery of M41 and ENST-75 in lung cancer. (a) The genomic location of M41, which resides in an intron of DSCAM. M41 is poorly conserved across species. (b) qPCR of M41 demonstrates outlier expression in 15-20% of lung adenocarcinomas as well as high expression in breast cells. (c) The genomic location of ENST-75, which demonstrates high conservation across species. (d) qPCR of ENST-75 shows up-regulation in lung cancer but not breast or prostate cancers. High expression is observed in normal testis.

Figure 38:
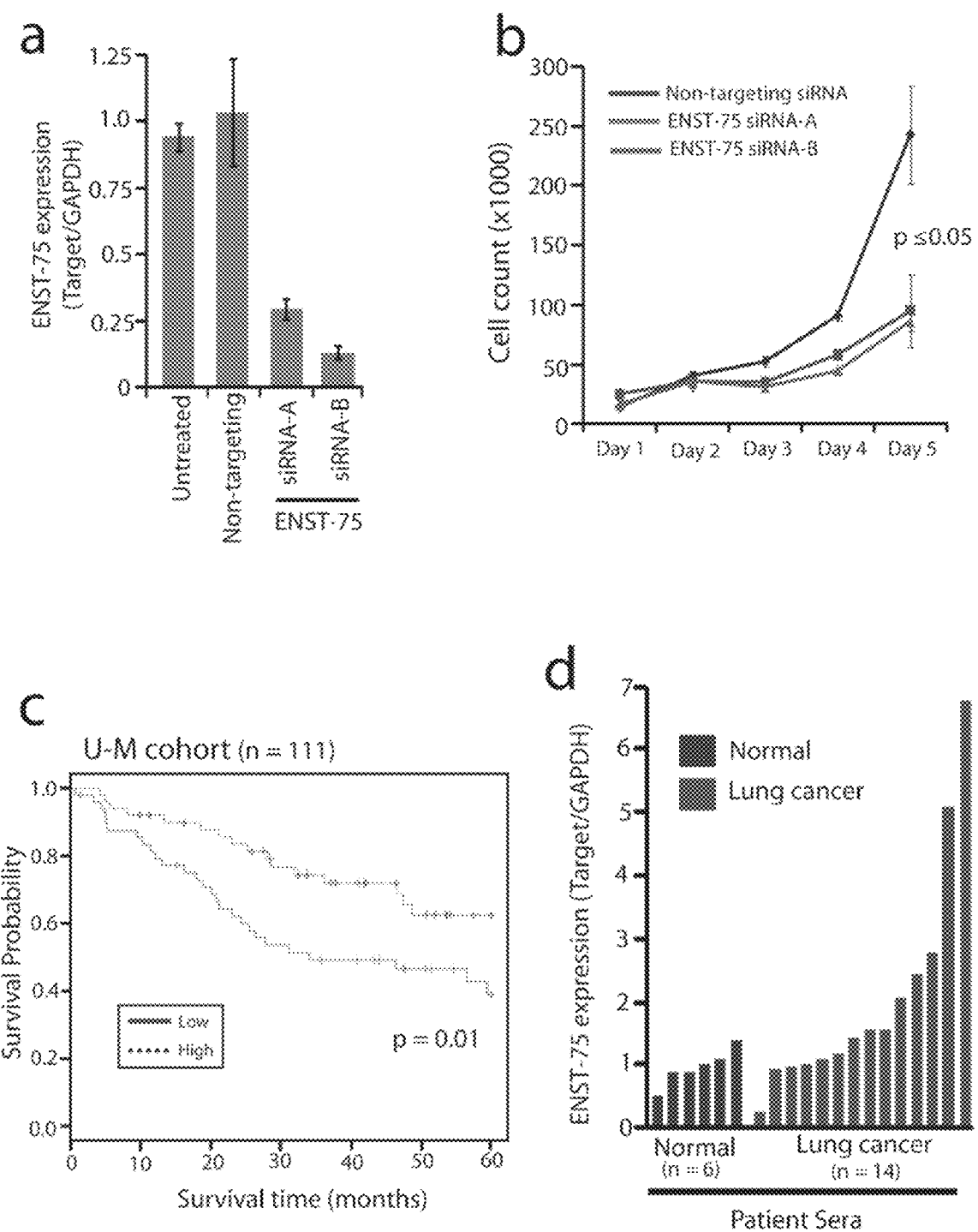
Figure 38:
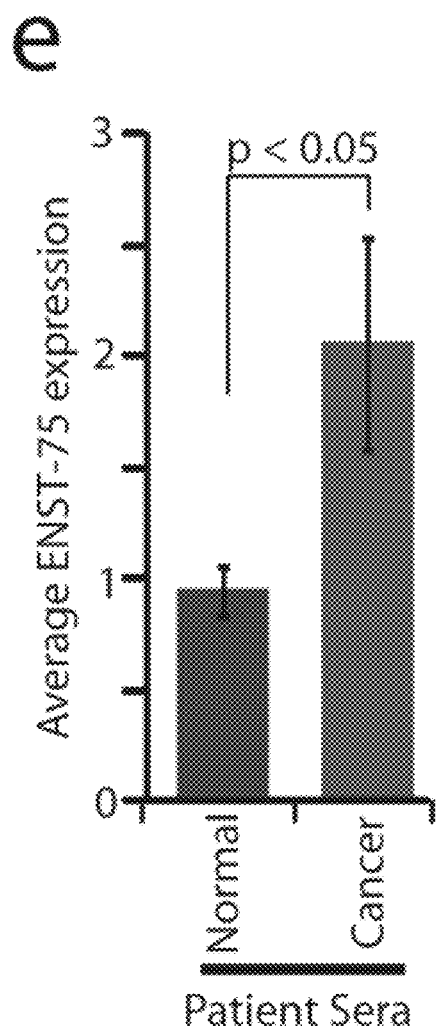

FIG. 38 shows lncRNAs are drivers and biomarkers in lung cancer. (a) Knockdown of ENST-75 in H1299 cells with independent siRNAs achieving >70% knockdown. (b) Knockdown of ENST-75 in H1299 cells impairs cell proliferation. Error bars represent s.e.m. (c) ENST-75 expression in lung adenocarcinomas stratifies patient overall survival. (d) Serum detection levels of ENST-75 in normal and lung cancer patients. (e) Average ENST-75 expression in lung cancer patient sera compared to normal patient sera. Error bars represent s.e.m.

Figure 39:
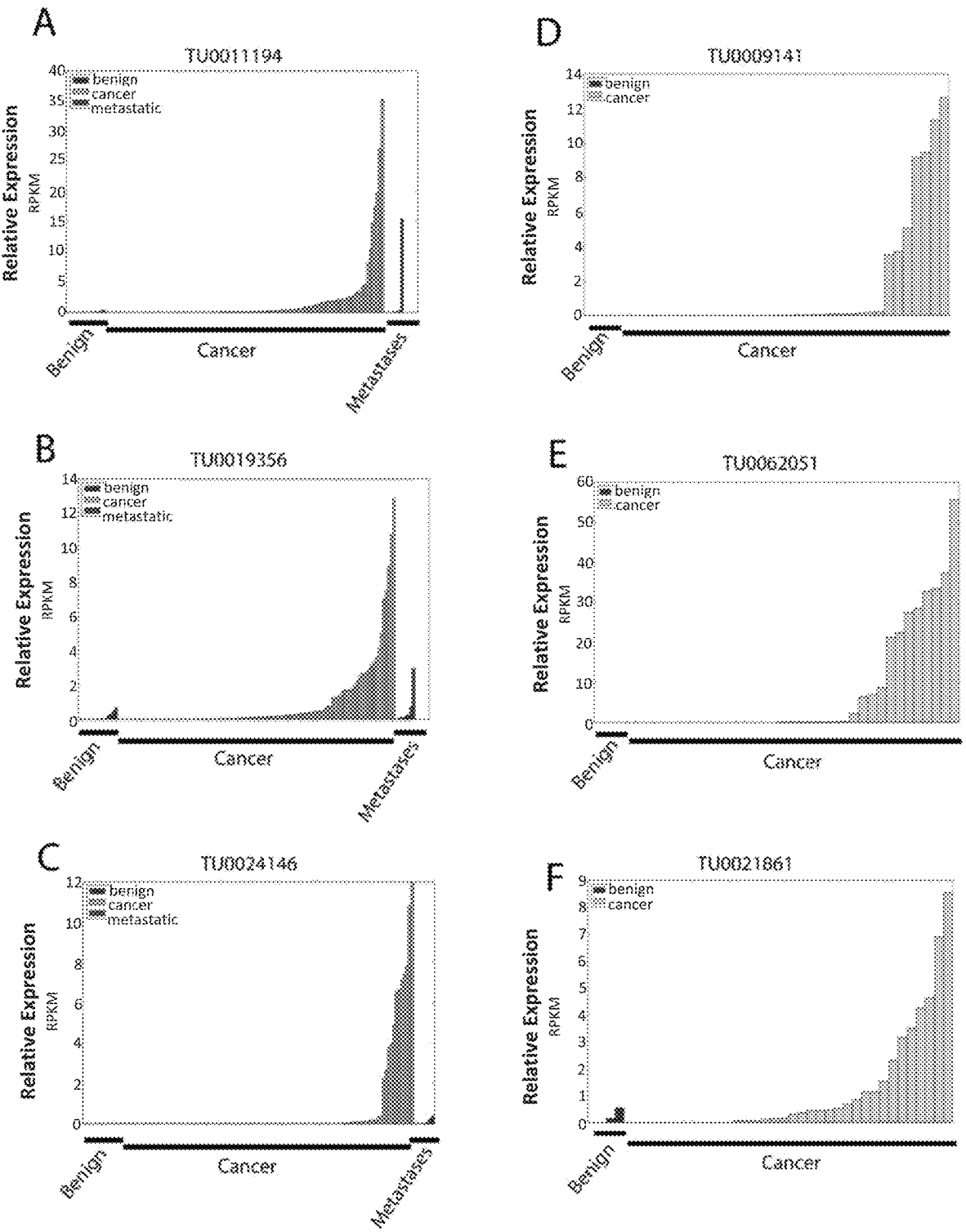

FIG. 39 shows nomination of cancer-associated lncRNAs in breast and pancreatic cancer. (a-c) (a) TU0011194 (b) TU0019356 (c) TU0024146 (d-f) Three novel pancreatic cancer lncRNAs nominated from RNA-Seq data. All show outlier expression patterns in pancreatic cancer samples but not benign samples. (d) TU0009141 (e) TU0062051 (f) TU0021861

DEFINITIONS

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "subject" refers to any organisms that are screened using the diagnostic methods described herein. Such organisms preferably include, but are not limited to, mammals (e.g., murines, simians, equines, bovines, porcines, canines, felines, and the like), and most preferably includes humans.

The term "diagnosed," as used herein, refers to the recognition of a disease by its signs and symptoms, or genetic analysis, pathological analysis, histological analysis, and the like.

A "subject suspected of having cancer" encompasses an individual who has received an initial diagnosis (e.g., a CT scan showing a mass or increased PSA level) but for whom the stage of cancer or presence or absence of ncRNAs indicative of cancer is not known. The term further includes people who once had cancer (e.g., an individual in remission). In some embodiments, "subjects" are control subjects that are suspected of having cancer or diagnosed with cancer.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the ncRNAs disclosed herein.

As used herein, the term "characterizing prostate tissue in a subject" refers to the identification of one or more properties of a prostate tissue sample (e.g., including but not limited to, the presence of cancerous tissue, the presence or absence of ncRNAs, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragments are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF THE INVENTION

The present invention relates to compositions and methods for cancer diagnosis, research and therapy, including but not limited to, cancer markers. In particular, the present invention relates to ncRNAs as diagnostic markers and clinical targets for prostate, lung, breast and pancreatic cancer.

Experiments conducted during the development of embodiments of the present invention utilized RNA-Seq analyses of tissue samples and ab initio transcriptome assembly to predict the complete polyA+ transcriptome of prostate cancer. 6,144 novel ncRNAs found in prostate cancer were identified, including 121 ncRNAs that associated with disease progression (FIGS. 1, 2, 16 and 25). These data demonstrate the global utility of RNA-Seq in defining functionally-important elements of the genome.

The present invention is not limited to a particular mechanism. Indeed, an understanding of the mechanism is not necessary to practice the present invention. Nonetheless, although the biological role of these RNAs, especially the differentially-expressed ones, is not yet known, these results indicate a model in which specific intergenic loci are activated in prostate cancer, enabling the transcription of numerous disease-specific and tissue-specific ncRNAs (FIG. 5g). Clinically, these ncRNA signatures are suitable for urine-based assays to detect and diagnose prostate cancer in a non-invasive manner (See e.g., Example 1). It is further contemplated that specific ncRNA signatures occur universally in all disease states and applying these methodologies to other diseases reveals clinically important biomarkers, particularly for diseases that currently lack good protein biomarkers.

While traditional approaches have focused on the annotated reference genome, data generated during the course of development of embodiments of the present invention implicate large swaths of unannotated genomic loci in prostate cancer progression and prostate-specific expression. One example of this is the SChLAP1 locus, which represents a >500 kb stretch of coordinately regulated expression, and the chr8q24 locus, which contains a prostate specific region with the prostate cancer biomarker PCAT-1. The fact that the SChLAP1 locus is almost exclusively expressed in prostate cancers harboring an ETS gene fusion further confirms the capacity of ncRNAs to identify patient disease subtypes. In addition, these analyses reveal novel cancer-specific drivers of tumorigenesis. For example, the long ncRNA HOTAIR is known to direct cancer-promoting roles for EZH2 in breast cancer (Gupta et al., *Nature* 464 (7291), 1071 (2010)), while in the PC3 prostate cancer cell line a similar role has been proposed for the ANRIL ncRNA (Yap et al., *Mol Cell* 38 (5), 662 (2010)).

I. Diagnostic and Screening Methods

As described above, embodiments of the present invention provide diagnostic and screening methods that utilize the detection of ncRNAs (e.g., PCAT-1, PCAT-14, PCAT-43 and PCAT-109; SEQ ID NOs: 1-9). Exemplary, non-limiting methods are described below.

Any patient sample suspected of containing the ncRNAs may be tested according to methods of embodiments of the present invention. By way of non-limiting examples, the sample may be tissue (e.g., a prostate biopsy sample or a tissue sample obtained by prostatectomy), blood, urine, semen, prostatic secretions or a fraction thereof (e.g., plasma, serum, urine supernatant, urine cell pellet or prostate cells). A urine sample is preferably collected immediately following an attentive digital rectal examination (DRE), which causes prostate cells from the prostate gland to shed into the urinary tract.

In some embodiments, the patient sample is subjected to preliminary processing designed to isolate or enrich the sample for the ncRNAs or cells that contain the ncRNAs. A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

The ncRNAs may be detected along with other markers in a multiplex or panel format. Markers are selected for their predictive value alone or in combination with the gene fusions. Exemplary prostate cancer markers include, but are not limited to: AMACR/P504S (U.S. Pat. No. 6,262,245); PCA3 (U.S. Pat. No. 7,008,765); PCGEM1 (U.S. Pat. No. 6,828,429); prostein/P501S, P503S, P504S, P509S, P510S, prostase/P703P, P710P (U.S. Publication No. 20030185830); RAS/KRAS (Bos, Cancer Res. 49:4682-89 (1989); Kranenburg, Biochimica et Biophysica Acta 1756: 81-82 (2005)); and, those disclosed in U.S. Pat. Nos. 5,854, 206 and 6,034,218, 7,229,774, each of which is herein incorporated by reference in its entirety. Markers for other cancers, diseases, infections, and metabolic conditions are also contemplated for inclusion in a multiplex or panel format.

In some embodiments, multiplex or array formats are utilized to detected multiple markers in combination. For example, in some embodiments, the level of expression of two or more (e.g., 10 or more, 25 or more, 50 or more, 100 or more or all 121) non-coding RNAs (ncRNA) selected from, for example, PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, or PCAT121 is utilized in the research, screening, diagnostic and prognositic compositions and methods described herein.

i. DNA and RNA Detection

The ncRNAs of the present invention are detected using a variety of nucleic acid techniques known to those of ordinary skill in the art, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts (e.g., ncRNAs) within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, ncRNAs are detected using fluorescence in situ hybridization (FISH). In some embodiments, FISH assays utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on human prostate cells, human prostate tissue or on the fluid surrounding said human prostate cells or human prostate tissue. Specific protocols are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

3. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., ncRNAs) by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Nucleic acids (e.g., ncRNAs) may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified nucleic acids can be detected by any conventional means. For example, the ncRNAs can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

ii. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of a ncRNA) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

iii. In Vivo Imaging ncRNAs may also be detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of embodiments of the present invention are useful in the identification of cancers that express ncRNAs (e.g., prostate cancer). In vivo imaging is used to visualize the presence or level of expression of a ncRNA. Such techniques allow for diagnosis without the use of an unpleasant biopsy. The in vivo imaging methods of embodiments of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin Onc 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the ncRNA, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

iv. Compositions & Kits

Compositions for use in the diagnostic methods described herein include, but are not limited to, probes, amplification oligonucleotides, and the like.

The probe and antibody compositions of the present invention may also be provided in the form of an array.

II. Drug Screening Applications

In some embodiments, the present invention provides drug screening assays (e.g., to screen for anticancer drugs). The screening methods of the present invention utilize ncRNAs. For example, in some embodiments, the present invention provides methods of screening for compounds that alter (e.g., decrease) the expression or activity of ncRNAs. The compounds or agents may interfere with transcription, by interacting, for example, with the promoter region. The compounds or agents may interfere with mRNA (e.g., by RNA interference, antisense technologies, etc.). The compounds or agents may interfere with pathways that are upstream or downstream of the biological activity of ncRNAs. In some embodiments, candidate compounds are antisense or interfering RNA agents (e.g., oligonucleotides) directed against ncRNAs. In other embodiments, candidate compounds are antibodies or small molecules that specifically bind to a ncRNAs regulator or expression products inhibit its biological function.

In one screening method, candidate compounds are evaluated for their ability to alter ncRNAs expression by contacting a compound with a cell expressing a ncRNA and then assaying for the effect of the candidate compounds on expression. In some embodiments, the effect of candidate compounds on expression of ncRNAs is assayed for by detecting the level ncRNA expressed by the cell. mRNA expression can be detected by any suitable method.

EXPERIMENTAL

The following examples are provided in order to demonstrate and further illustrate certain preferred embodiments and aspects of the present invention and are not to be construed as limiting the scope thereof.

Example 1

A. Methods

Methods Summary

All prostate tissue samples were obtained from the University of Michigan Specialized Program Of Research Excellence (S.P.O.R.E.) using an IRB-approved informed consent protocol. Next generation sequencing and library preparation was performed as previously described (Maher et al., *Proc Natl Acad Sci USA* 106 (30), 12353 (2009)). Uniquely mapping sequencing reads were aligned with TopHat and sequencing data for all samples was merged. Ab initio transcriptome assembly was performed by aligning sequences with TopHat and using uniquely mapped read positions to build transcripts with Cufflinks. Informatics approaches were used to refine the assembly and predict expressed transcriptional units. Unannotated transcripts were nominated based upon their absence in the UCSC, RefSeq, ENSEMBL, ENCODE, and Vega databases. Differential expression was determined using the Significance Analysis of Microarrays (SAM) algorithm (Tusher et al., *Proc Natl Acad Sci USA* 98 (9), 5116 (2001)) on log 2 mean expression in benign, cancer, and metastatic samples. Cancer outlier profile analysis (COPA) was performed as previously described (Tomlins et al., *Science* 310 (5748), 644 (2005)) with slight modifications. PCR experiments were performed according to standard protocols, and RACE was performed with the GeneRacer Kit (Invitrogen) according to manufacturer's instructions. ChIP-seq data was obtained from previously published data (Yu et al., *Cancer Cell* 17 (5), 443). siRNA knockdown was performed with custom siRNA oligos (Dharmacon) with Oligofectamine (Invitrogen). Transmembrane invasion assays were performed with Matrigel (BD Biosciences) and cell proliferation assays were performed by cell count with a Coulter counter. Urine analyses were performed as previously described (Laxman et al., *Cancer Res* 68 (3), 645 (2008)) with minor modifications.

Cell Lines and Tissues

The benign immortalized prostate cell line RWPE as well as PC3, Du145, LNCaP, VCaP, 22Rv1, CWR22, C4-2B, NCI-660, MDA PCa 2b, WPMY-1, and LAPC-4 prostate cell lines were obtained from the American Type Culture Collection (Manassas, Va.). Benign non-immortalized prostate epithelial cells (PrEC) and prostate smooth muscle cells (PrSMC) were obtained from Lonza (Basel, Switzerland). Cell lines were maintained using standard media and conditions. For androgen treatment experiments, LNCaP and VCaP cells were grown in androgen depleted media lacking phenol red and supplemented with 10% charcoal-stripped serum and 1% penicillin-streptomycin. After 48 hours, cells were treated with 5 nM methyltrienolone (R1881, NEN Life Science Products) or an equivalent volume of ethanol. Cells were harvested for RNA at 6, 24, and 48 hours post-treatment. Prostate tissues were obtained from the radical prostatectomy series and Rapid Autopsy Program at the University of Michigan tissue core. These programs are part of the University of Michigan Prostate Cancer Specialized Program Of Research Excellence (S.P.O.R.E.). All tissue samples were collected with informed consent under an Institutional Review Board (IRB) approved protocol at the University of Michigan.

PC3, Du145, LNCaP, 22Rv1, and CRW22 cells were grown in RPMI 1640 (Invitrogen) and supplemented with 10% fetal bovine serum (FBS) and 1% penicillin-streptomycin. LNCaP CDS parent cells were grown in RPMI 1640 lacking phenol red (Invitrogen) supplemented with 10% charcoal-dextran stripped FBS (Invitrogen) and 1% penicillin-streptomycin. LNCaP CDS 1, 2, and 3 are androgen-independent subclones derived from extended cell culture in androgendepleted media. VCaP and WPMY-1 cells were grown in DMEM (Invitrogen) and supplemented with 10% fetal bovine serum (FBS) with 1% penicillin-streptomycin. NCI-H660 cells were grown in RPMI 1640 supplemented with 0.005 mg/ml insulin, 0.01 mg/ml transferring, 30 nM sodium selenite, 10 nM hydrocortisone, 10 nM beta-estradiol, 5% FBS and an extra 2 mM of L-glutamine (for a final concentration of 4 mM). MDA PCa 2b cells were grown in F-12K medium (Invitrogen) supplemented with 20% FBS, 25 ng/ml cholera toxin, 10 ng/ml EGF, 0.005 mM phosphoethanolamine, 100 µg/ml hydrocortisone, 45 nM selenious acid, and 0.005 mg/ml insulin. LAPC-4 cells were grown in Iscove's media (Invitrogen) supplemented with 10% FBS and 1 nM R1881. C4-2B cells were grown in 80% DMEM supplemented with 20% F12, 5% FBS, 3 g/L NaCo3, 5 µg/ml insulin, 13.6 pg/ml triiodothyonine, 5 µg/ml transferrin, 0.25 µg/ml biotin, and 25 µg/ml adenine. PrEC cells were grown in PrEGM supplemented with 2 ml BPE, 0.5 ml hydrocortisone, 0.5 ml EGF, 0.5 ml epinephrine, 0.5 ml transferring, 0.5 ml insulin, 0.5 ml retinoic acid, and 0.5 ml triiodothyronine, as part of the PrEGM BulletKit (Lonza). PrSMC cells were grown in SmGM-2 media supplemented with 2 ml BPE, 0.5 ml hydrocortisone, 0.5 ml EGF, 0.5 ml epinephrine, 0.5 ml transferring, 0.5 ml insulin, 0.5 ml retinoic acid, and 0.5 ml triiodothyronine, as part of the SmGM-2 BulletKit (Lonza).

RNA-Seq Library Preparation.

Next generation sequencing of RNA was performed on 21 prostate cell lines, 20 benign adjacent prostates, 47 localized tumors, and 14 metastatic tumors according to Illumina's protocol using 2 µg of RNA. RNA integrity was measured using an Agilent 2100 Bioanalyzer, and only samples with a RIN score >7.0 were advanced for library generation. RNA was poly-A+ selected using the OligodT beads provided by Ilumina and fragmented with the Ambion Fragmentation Reagents kit (Ambion, Austin, Tex.). cDNA synthesis, end-repair, A-base addition, and ligation of the Illumina PCR adaptors (single read or paired-end where appropriate) were performed according to Illumina's protocol. Libraries were then size-selected for 250-300 bp cDNA fragments on a 3.5% agarose gel and PCR-amplified using Phusion DNA polymerase (Finnzymes) for 15-18 PCR cycles. PCR products were then purified on a 2% agarose gel and gel-extracted. Library quality was credentialed by assaying each library on an Agilent 2100 Bioanalyzer of product size and concentration. Libraries were sequenced as 36-45mers on an Illumina Genome Analyzer I or Genome Analyzer II flow-cell according to Illumina's protocol. All single read samples were sequenced on a Genome Analyzer I, and all paired-end samples were sequenced on a Genome Analyzer II.

RNA Isolation and cDNA Synthesis

Total RNA was isolated using Trizol and an RNeasy Kit (Invitrogen) with DNase I digestion according to the manufacturer's instructions. RNA integrity was verified on an Agilent Bioanalyzer 2100 (Agilent Technologies, Palo Alto, Calif.). cDNA was synthesized from total RNA using Superscript III (Invitrogen) and random primers (Invitrogen).

Quantitative Real-Time PCR

Quantitative Real-time PCR (qPCR) was performed using Power SYBR Green Mastermix (Applied Biosystems, Foster City, Calif.) on an Applied Biosystems 7900HT Real-Time PCR System. All oligonucleotide primers were obtained from Integrated DNA Technologies (Coralville, Iowa) and are listed in Table 13. The housekeeping gene, GAPDH, was used as a loading control. Fold changes were calculated relative to GAPDH and normalized to the median value of the benign samples.

Reverse-Transcription PCR

Reverse-transcription PCR (RT-PCR) was performed for primer pairs using Platinum Taq High Fidelity polymerase (Invitrogen). PCR products were resolved on a 2% agarose gel. PCR products were either sequenced directly (if only a single product was observed) or appropriate gel products were extracted using a Gel Extraction kit (Qiagen) and cloned into per4-TOPO vectors (Invitrogen). PCR products were bidirectionally sequenced at the University of Michigan Sequencing Core using either gene-specific primers or M13 forward and reverse primers for cloned PCR products. All oligonucleotide primers were obtained from Integrated DNA Technologies (Coralville, Iowa) and are listed in Table 13.

RNA-Ligase-Mediated Rapid Amplification of cDNA Ends (RACE)

5' and 3' RACE was performed using the GeneRacer RLM-RACE kit (Invitrogen) according to the manufacturer's instructions. RACE PCR products were obtained using Platinum Taq High Fidelity polymerase (Invitrogen), the supplied GeneRacer primers, and appropriate gene-specific primers indicated in Table 13. RACEPCR products were separated on a 2% agarose gels. Gel products were extracted with a Gel Extraction kit (Qiagen), cloned into per4-TOPO vectors (Invitrogen), and sequenced bidirectionally using M13 forward and reverse primers at the University of Michigan Sequencing Core. At least three colonies were sequenced for every gel product that was purified.

Paired-End Next-Generation Sequencing of RNA

2 µg total RNA was selected for polyA+ RNA using Sera-Mag oligo(dT) beads (Thermo Scientific), and paired-end next-generation sequencing libraries were prepared as previously described (Maher et al., supra) using Illumina-supplied universal adaptor oligos and PCR primers (Illumina). Samples were sequenced in a single lane on an Illumina Genome Analyzer II flowcell using previously described protocols (Maher et al., supra). 36-45 mer paired-end reads were according to the protocol provided by Illumina.

siRNA Knockdown Studies

Cells were plated in 100 mM plates at a desired concentration and transfected with 20 µM experimental siRNA oligos or non-targeting controls twice, at 12 hours and 36 hours post-plating. Knockdowns were performed with Oligofectamine and Optimem. Knockdown efficiency was determined by qPCR. 72 hours post-transfection, cells were trypsinized, counted with a Coulter counter, and diluted to 1 million cells/mL. For proliferation assays, 200,000 cells were plated in 24-well plates and grown in regular media. 48 and 96 hours post-plating, cells were harvested and counted using a Coulter counter. For invasion assays, Matrigel was diluted 1:4 in serum-free media and 100 µL of the diluted Matrigel was applied to a Boyden chamber transmembrane insert and allowed to settle overnight at 37° C. 200,000 cells suspended in serum-free media were applied per insert and 500 µL of serum-containing media was placed in the bottom of the Boyden (fetal bovine serum functioning as a chemoattractant). Cells were allowed to invade for 48 hours, at which time inserts were removed and noninvading cells and Matrigel were gently removed with a cotton swab. Invading cells were stained with crystal violet for 15 minutes and air-dried. For colorimetric assays, the inserts were treated with 200 µl of 10% acetic acid and the absorbance at 560 nm was measured using a spectrophotometer. For WST-1 assays, 20,000 cells were plated into 96-well plates and grown in 100 µL of serum-containing media. 48 and 96 hours post-plating, cells were measured for viability by adding 10 µL of WST-1 reagent to the cell media, incubating for 2 hours at 37° C. and measuring the absorbance at 450 nM using a spectrophotomer.

Urine qPCR

Urine samples were collected from 120 patients with informed consent following a digital rectal exam before either needle biopsy or radical prostatectomy at the University of Michigan with Institutional Review Board approval as described previously (Laxman et al., *Cancer Res* 68 (3), 645 (2008)). Isolation of RNA from urine and TransPlex whole transcriptome amplification were performed as described previously (Laxman et al., *Neoplasia* 8 (10), 885 (2006)). qPCR on urine samples was performed for KLK3 (PSA), TMPRSS2-ERG, GAPDH, PCA3, PCAT-1 and PCAT-14 using Power SYBR Mastermix (Applied Biosystems) as described above. Raw Ct values were extracted and normalized in the following manner. First, samples with GAPDH Ct values >25 or KLK3 Ct values >30 were removed from analysis to ensure sufficient prostate cell collection, leaving $10^8$ samples for analysis. The GAPDH and KLK3 raw Ct values were average for each sample. ΔCt analysis was performed by measuring each value against the average of CtGAPDH and CtKLK3, and ΔCt values were normalized to the median ΔCt of the benign samples. Fold change was then calculated at 2−ΔCt. Samples were considered to be prostate cancer if histopathological analysis observed cancer or if the TMPRSS2-ERG transcript achieved a Ct value <37. Benign samples were defined as samples with normal histology and TMPRSS2-ERG transcript Ct values >37.

Statistical Analyses for Experimental Studies

All data are presented as means±s.e.m. All experimental assays were performed in duplicate or triplicate.

Bioinformatics Analyses

To achieve an ab initio prediction of the prostate cancer transcriptome existing publicly tools for mapping, assembly, and quantification of transcripts were supplemented with additional informatics filtering steps to enrich the results for the most robust transcript predictions (FIG. 6a). Transcripts were then identified and classified by comparing them against gene annotation databases (FIG. 6b). Details of the bioinformatics analyses are provided below.

Mapping Reads with TopHat

Reads were aligned using TopHat v1.0.13 (Feb. 5, 2010) (Trapnell et al., *Bioinformatics* 25, 1105-11 (2009)), a gapped aligner capable of discovering splice junctions ab initio. Briefly, TopHat aligns reads to the human genome using Bowtie (Langmead et al., *Genome Biol* 10, R25 (2009)) to determine a set of "coverage islands" that may represent putative exons. TopHat uses these exons as well as the presence of GT-AG genomic splicing motifs to build a second set of reference sequences spanning exon-exon junctions. The unmapped reads from the initial genome alignment step are then remapped against this splice junction reference to discover all the junction-spanning reads in the sample. TopHat outputs the reads that successfully map to either the genome or the splice junction reference in SAM format for further analysis. For this study a maximum intron size of 500 kb, corresponding to over 99.98% of RefSeq (Wheeler et al. *Nucleic Acids Res* 28, 10-4 (2000)) introns was used. For sequencing libraries the insert size was determined using an Agilent 2100 Bioanalyzer prior to data analysis, and it was found that this insert size agreed closely with software predictions. An insert size standard deviation of 20 bases was chosen in order to match the most common band size cut from gels during library preparation. In total, 1.723 billion fragments were generated from 201 lanes of sequencing on the Illumina Genome Analyzer and Illumina Genome Analyzer II. Reads were mapped to the human genome (hg18) downloaded from the UCSC genome browser website (Karolchik et al., *Nucleic Acids Res* 31, 51-4 (2003); Kent et al., *Genome Res* 12, 996-1006 (2002)). 1.418 billion unique alignments were obtained, including 114.4 million splice junctions for use in transcriptome assembly. Reads with multiple alignments with less than two mismatches were discarded.

Ab Initio Assembly and Quantification with Cufflinks

Aligned reads from TopHat were assembled into sample-specific transcriptomes with Cufflinks version 0.8.2 (Mar. 26, 2010) (Trapnell et al., *Nat Biotechnol* 28, 511-5). Cufflinks assembles exonic and splice-junction reads into transcripts using their alignment coordinates. To limit false positive assemblies a maximum intronic length of 300 kb, corresponding to the 99.93% percentile of known introns was used. After assembling transcripts, Cufflinks computes isoform-level abundances by finding a parsimonious allocation of reads to the transcripts within a locus. Transcripts with abundance less than 15% of the major transcript in the locus, and minor isoforms with abundance less than 5% of the major isoform were filtered. Default settings were used for the remaining parameters.

The Cufflinks assembly stage yielded a set of transcript annotations for each of the sequenced libraries. The transcripts were partitioned by chromosome and the Cuffcompare utility provided by Cufflinks was used to merge the transcripts into a combined set of annotations. The Cuffcompare program performs a union of all transcripts by merging transcripts that share all introns and exons. The 5' and 3' exons of transcripts were allowed to vary by up to 100 nt during the comparison process.

Distinguishing Transcripts from Background Signal

Cuffcompare reported a total of 8.25 million distinct transcripts. Manual inspection of these transcripts in known protein coding gene regions indicated that most of the transcripts were likely to be poor quality reconstructions of overlapping larger transcripts. Also, many of the transcripts were unspliced and had a total length smaller than the size selected fragment length of approximately ~250 nt. Furthermore, many of these transcripts were only present in a single sample. A statistical classifier to predict transcripts over background signal was designed to identify highly recurrent transcripts that may be altered in prostate cancer. AceView (Thierry-Mieg et al. *Genome Biol* 7 Suppl 1, S12 1-14 (2006)) were used. For each transcript predicted by Cufflinks the following statistics were collected: length (bp), number of exons, recurrence (number of samples in which the transcript was predicted), 95th percentile of abundance (measured in Fragments per Kilobase per Million reads (FPKM)) across all samples, and uniqueness of genomic DNA harboring the transcript (measured using the Rosetta uniqueness track from UCSC (Rhead et al. 2010. *Nucleic Acids Res* 38, D613-9). Using this information, recursive partitioning and regression trees in R (package rpart) were used to predict, for each transcript, whether its expression patterns and structural properties resembled those of annotated genes. Classification was performed independently for each chromosome in order to incorporate the effect of gene density variability on expression thresholds. Transcripts that were not classified as annotated genes were discarded, and the remainder were subjected to additional analysis and filtering steps. By examining the decision tree results it was observed that the 95th percentile of expression across all samples as well as the recurrence of each transcript were most frequently the best predictors of expressed versus background transcripts (FIG. 7).

Refinement of Transcript Fragments

The statistical classifier predicted a total 2.88 million (34.9%) transcript fragments as "expressed" transcripts. A program was developed to extend and merge intron-redundant transcripts to produce a minimum set of transcripts that describes the assemblies produced by Cufflinks. The merging step produced a total of 123,554 independent transcripts. Transcript abundance levels were re-computed for these revised transcripts in Reads per Kilobase per Million (RPKM) units. These expression levels were used for the remainder of the study. Several additional filtering steps were used to isolate the most robust transcripts. First, transcripts with a total length less than 200 nt were discarded. Single exon transcripts with greater than 75% overlap to another longer transcript were also discarded. Transcripts that lacked a completely unambiguous genomic DNA stretch of at least 40 nt were also removed. Genomic uniqueness was measured using the Rosetta uniqueness track downloaded from the UCSC genome browser website. Transcripts that were not present in at least 5% of the cohort (>5 samples) at more than 5.0 RPKM were retained.

In certain instances transcripts were observed that were interrupted by poorly mappable genomic regions. Additionally, for low abundance genes fragmentation due to the lack of splice junction or paired-end read evidence needed to connect nearby fragments were observed. The difference in the Pearson correlation between expression of randomly chosen exons on the same transcript versus expression of spatially proximal exons on different transcripts was measured and it was found that in the cohort, a Pearson correlation >0.8 had a positive predictive value (PPV) of >95% for distinct exons to be part of the same transcript. Using this criteria, hierarchical agglomerative clustering to extend transcript fragments into larger transcriptional units was performed. Pairs of transcripts further than 100 kb apart, transcripts on opposite strands, and overlapping transcripts were not considered for clustering. Groups of correlated transcripts were merged, and introns <40 nt in length were removed.

Comparison with Gene Annotation Databases

The 44,534 transcripts produced by the bioinformatics pipeline were classified by comparison with a comprehensive list of "annotated" transcripts from UCSC, RefSeq, ENCODE, Vega, and Ensembl. First, transcripts corresponding to processed pseudogenes were separated. This was done to circumvent a known source of bias in the TopHat read aligner. TopHat maps reads to genomic DNA in its first step, predisposing exon-exon junction reads to align to their spliced retroposed pseudogene homologues. Next, transcripts with >1 bp of overlap with at least one annotated gene on the correct strand were designated "annotated", and the remainder were deemed "unannotated". Transcripts with no overlap with protein coding genes were subdivided into intronic, intergenic, or partially intronic antisense categories based on their relative genomic locations.

Informatics Filtering of Unspliced Pre-mRNA Isoforms

An increase in the percentage of intronic transcripts in the assembly relative to known intronic ncRNAs was observed. This led to the observation that in many cases unspliced pre mRNAs appear at sufficient levels to escape the filtering steps employed by Cufflinks during the assembly stage. Intronic and antisense transcripts that were correlated (Pearson correlation >0.5) to their overlapping protein coding genes were removed. This effectively removed transcripts within genes such as PCA3 and HPN that were obvious premRNA artifacts, while leaving truly novel intronic transcripts—such as those within FBXL7 and CDH13—intact. These steps produced a consensus set of 35,415 transcripts supporting long polyadenylated RNA molecules in human prostate tissues and cell lines. Per chromosome transcript counts closely mirrored known transcript databases (Table 2), indicating that the informatics procedures employed compensate well for gene density variability across chromosomes. Overall a similar number of transcripts as present in the either the RefSeq or UCSC databases (Wheeler et al. *Nucleic Acids* Res 28, 10-4 (2000)) were detected.

Coding Potential Analysis

To analyze coding potential, DNA sequences for each transcript were extracted and searched for open reading frames (ORFs) using the txCdsPredict program from the UCSC source tool set (Kent et al. *Genome Res* 12, 996-1006 (2002)). This program produces a score corresponding to the protein coding capacity of a given sequence, and scores >800 are ~90% predictive of protein coding genes. This threshold was used to count transcripts with coding potential, and found only 5 of 6,641 unannotated genes with scores >800, compared with 1,669 of 25,414 protein coding transcripts. Additionally, it was observed that protein coding genes possess consistently longer ORFs than either unannotated or annotated ncRNA transcripts, indicating that the vast majority of the unannotated transcripts represent ncRNAs (FIG. 10).

Separation of Transcripts into Repetitive and Non-Repetitive Categories

To separate transcripts into "repeat" and "non-repeat" transcripts, the genomic DNA corresponding to the transcript exons was extracted and the fraction of repeat-masked nucleotides in each sequence were calculated. For the designation of repeat classes, RepMask 3.2.7 UCSC Genome Browser track (Kent, supra) was used. It was observed that transcripts enriched with repetitive DNA tended to be poorly conserved and lacked ChIP-seq marks of active chromatin (FIG. 12). Transcripts containing >25% repetitive DNA (FIG. 11) were separated for the purposes of the ChIP-seq and conservation analyses discussed below.

Conservation Analysis

The SiPhy package (Garber et al. *Bioinformatics* 25, i54-62 (2009)) was used to estimate the locate rate of variation (ω) of all non-repetitive transcript exons across 29 placental mammals. The program was run as described on the SiPhy website.

ChIP-Seq Datasets

Published ChIP-Seq datasets for H3K4me1, H3K4me2, H3K4me3, Acetylated H3, Pan-H3, and H3K36me3 were used (Yu et al. *Cancer Cell* 17, 443-54). These data are publically available through the NCBI Geo Omnibus (GEO GSM353632). The raw ChIP-Seq data was analyzed using MACS34 (H3K4me1, H3K4me2, H3K4me3, Acetylated H3, and Pan-H3) or SICER35 (H3K36me3) peak finder programs using default settings. These peak finders were used based upon their preferential suitability to detect different types of histone modifications (Pepke et al., *Nat Methods* 6, S22-32 (2009)). The H3K4me3-H3K36me3 chromatin signature used to identify lincRNAs was determined from the peak coordinates by associating each H3K4me3 peak with the closest H3K36me3-enriched region up to a maximum of 10 kb away. The enhancer signature (H3K4me1 but not H3K4me3) was determined by subtracting the set of overlapping H3K4me3 peaks from the entire set of H3K4me1 peaks. These analyses were performed with the bx-python libraries distributed as part of the Galaxy bioinformatics infrastructure.

Differential Expression Analysis

To predict differentially expressed transcripts a matrix of log-transformed, normalized RPKM expression values was prepared by using the base 2 logarithm after adding 0.1 to all RPKM values. The data were first centered by subtracting the median expression of the benign samples for each transcript. The Significance Analysis of Microarrays (SAM) method (Tusher et al., *Proc Natl Acad Sci USA* 98, 5116-21 (2001)) with 250 permutations of the Tusher et al. SO selection method was used to predict differentially expressed genes. A delta value corresponding to the 90th percentile FDR desired for individual analyses was used. The Multi-Experiment Viewer application (Chu et al., *Genome Biol* 9, R118 (2008)) was used to run SAM and generate heatmaps. It was confirmed that the results matched expected results through comparison with microarrays and known prostate cancer biomarkers.

Outlier Analysis

A modified COPA analysis was performed on the 81 tissue samples in the cohort. RPKM expression values were used and shifted by 1.0 in order to avoid division by zero. The COPA analysis had the following steps (MacDonald & Ghosh, *Bioinformatics* 22, 2950-1 (2006); Tomlins et al. *Science* 310, 644-8 (2005)): 1) gene expression values were median centered, using the median expression value for the gene across the all samples in the cohort. This sets the gene's median to zero. 2) The median absolute deviation (MAD) was calculated for each gene, and then each gene expression value was scaled by its MAD. 3) The 80, 85, 90, 98 percentiles of the transformed expression values were calculated for each gene and the average of those four values was taken. Then, genes were rank ordered according to this "average percentile", which generated a list of outliers genes arranged by importance. 4) Finally, genes showing an outlier profile in the benign samples were discarded. Six novel transcripts ranked as both outliers and differentially-expressed genes in the analyses. These six were manually classified either as differentially-expressed or outlier status based on what each individual's distribution across samples indicated.

Repeat Enrichment Analysis

To assess the enrichment of repetitive elements in the assembly, 100 random permutations of the transcript positions on the same chromosome and strand were generated. To mirror the original constraints used to nominate transcripts it was ensured that permuted transcript positions contained a uniquely mappable stretch of genomic DNA at least 50 nt long. To account for the effects of mappability difficulties, each exon was padded by ±0 bp, 50 bp, 100 bp, or 500 bp of additional genomic sequence before intersecting the exons with repeat elements in the RepeatMasker 3.2.7 database. It was observed that padding by more than 50 bp did not improve enrichment results and padded exons by ±50 bp in subsequent analyses and tests (Table 9). Finally, the Shapiro-Wilk test for normality was performed and it was verified that the number of matches to highly abundant repetitive element types was approximately normally distributed.

B. Results

Prostate Cancer Transcriptome Sequencing

Transcriptome sequencing (RNA-Seq) was performed on 21 prostate cell lines, 20 benign adjacent prostates (benign), 47 localized tumors (PCA), and 14 metastatic tumors (MET). A total of 201 RNA-Seq libraries from this cohort were sequenced yielding a total of 1.41 billion mapped reads, with a median 4.70 million mapped reads per sample (Table 1 for sample information).

To analyze these data a method for ab initio transcriptome assembly to reconstruct transcripts and transcript abundance levels was used (FIG. 6 and Table 2) (Trapnell et al., *Nat Biotechnol* 28 (5), 511; Trapnell et al., *Bioinformatics* 25 (9), 1105 (2009)). Sample-specific transcriptomes were predicted and individual predication were merged into a consensus transcriptome and the most robust transcripts were retained (FIG. 7). The ab initio transcriptome assembly and subsequent refinement steps yielded 35,415 distinct transcriptional loci (see FIG. 8 for examples).

The assembled transcriptome was compared to the UCSC, Ensembl, Refseq, Vega, and ENCODE gene databases to identify and categorize transcripts. While the majority of the transcripts (77.3%) corresponded to annotated protein coding genes (72.1%) and noncoding RNAs (5.2%), a significant percentage (19.8%) lacked any overlap and were designated "unannotated" (FIG. 1a). These included partially intronic antisense (2.44%), totally intronic (12.1%), and intergenic transcripts (5.25%). These results agree with previous data indicating that large fractions of the transcriptome represent unannotated transcription (Birney et al., *Nature* 447 (7146), 799 (2007); Carninci et al., *Science* 309 (5740), 1559 (2005) and that significant percentages of genes may harbor related antisense transcripts (He et al., *Science* 322 (5909), 1855 (2008); Yelin et al., *Nat Biotechnol* 21 (4), 379 (2003)). Due to the added complexity of characterizing antisense or partially intronic transcripts without strand-specific RNA-Seq libraries, studies focused on totally intronic and intergenic transcripts.

Characterization of Novel Transcripts

Global characterization of novel transcripts corroborated previous reports that they are relatively poorly conserved and more lowly expressed than protein coding genes (Guttman et al., *Nat Biotechnol* 28 (5), 503; Guttman et al., *Nature* 458 (7235), 223 (2009)). Expression levels of unannotated prostate cancer transcripts were consistently higher than randomly permuted controls, but lower than annotated ncRNAs or protein coding genes (FIG. 1b). Unannotated transcripts also showed less overlap with known expressed sequence tags (ESTs) than protein-coding genes but more than randomly permuted controls (FIG. 5). Unannotated transcripts showed a clear but subtle increase in conservation over control genomic intervals (novel intergenic transcripts p=2.7×10-4±0.0002 for 0.4<ω<0.8; novel intronic transcripts p=2.6×10-5±0.0017 for 0<ω<0.4, FIG. 1c). Only a small subset of novel intronic transcripts showed increased conservation (FIG. 1c insert), but this conservation was quite profound. By contrast, a larger number of novel intergenic transcripts showed more mild increases in conservation. Finally, analysis of coding potential revealed that only 5 of 6,144 transcripts harbored a high quality open reading frame (ORF), indicating that the overwhelming majority of these transcripts represent ncRNAs (FIG. 10).

Next, published prostate cancer ChIP-Seq data for two prostate cell lines (Yu et al., Cancer Cell 17 (5), 443; VCaP and LNCaP was used in order to interrogate the overlap of unannotated transcripts with histone modifications supporting active transcription (H3K4me1, H3K4me2, H3K4me3, H3K36me3, Acetyl-H3 and RNA polymerase II, see Table 3). Because unannotated ncRNAs showed two clear subtypes, repeat-associated and non-repeats (FIG. 11 and discussed below), it was contemplated that these two subtypes may display distinct histone modifications as noted in previous research (Day et al., Genome Biol 11 (6), R69). Whereas non-repeat transcripts showed strong enrichment for histone marks of active transcription at their putative transcriptional start sites (TSSs), repeat-associated transcripts showed virtually no enrichment (FIG. 12), and for the remaining ChIP-Seq analyses non-repeat transcripts only were considered. In this set of unannotated transcripts, strong enrichment for histone modifications characterizing TSSs and active transcription, including H3K4me2, H3K4me3, Acetyl-H3 and RNA Polymerase II (FIG. 1d-g) but not H3K4me1 was observed, which characterizes enhancer regions (FIGS. 13 and 14). Intergenic ncRNAs performed much better in these analyses than intronic ncRNAs (FIG. 1d-g). To elucidate global changes in transcript abundance between prostate cancer and benign tissues, differential expression was performed analysis for all transcripts. 836 genes differentially-expressed between benign and PCA samples (FDR<0.01) were found, with protein-coding genes constituting 82.8% of all differentially-expressed genes (FIG. 1h and Table 4). This category contained the most significant transcripts, including numerous known prostate cancer genes such as AMACR32 and Hepsin (Dhanasekaran et al., Nature 412 (6849), 822 (2001)). Annotated ncRNAs represented 7.4% of differentially-expressed genes, including the ncRNA PCA334, which resides within an intron of the PRUNE2 gene and ranked #4 overall (12.2 fold change; adj. p<2×10-4, Wilcoxon rank sum test, Benjamini-Hochberg correction) (FIG. 8). Finally, 9.8% of differentially-expressed genes corresponded to unannotated ncRNAs, including 3.2% within gene introns and 6.6% in intergenic regions, indicating that these species contribute significantly to the complexity of the prostate cancer transcriptome.

Dysregulation of Unannotated Non-Coding RNAs

Recent reports of functional long intervening non-coding RNAs (Dhanasekaran et al., Nature 412 (6849), 822 (2001); Gupta et al., Nature 464 (7291), 1071; Rinn et al., Cell 129 (7), 1311 (2007); Guttman et al., Nature 458 (7235), 223 (2009)) (lincRNAs) in intergenic regions led to an exploration of intergenic ncRNAs further. A total of 1859 unannotated intergenic RNAs were found throughout the human genome. The present invention is not limited to a particular mechanism. Indeed, an understanding of the mechanism is not necessary to practice the present invention. Nonetheless it is contemplated that this is an underestimate due to the inability to detect small RNAs eliminated by the ~250 bp size selection performed during RNA-Seq library generation (Methods). Overall, novel intergenic RNAs resided closer to protein-coding genes than protein-coding genes do to each other (the median distance to the nearest protein-coding gene is 4292 kb for novel genes and 8559 kb for protein-coding genes, FIG. 2a). For instance, if two protein-coding genes, Gene A and Gene B, are separated by the distance AB, then the furthest an unannotated ncRNA can be from both of them is 0.5*AB, which is exactly what was observed (4292/8559=0.501). Supporting this observation, 34.1% of unannotated transcripts are located ≥10 kb from the nearest protein-coding gene. As an example, the Chr15q arm was visualized using the Circos program. Eighty-nine novel intergenic transcripts were nominated across this chromosomal region, including several differentially-expressed loci centromeric to TLE3 (FIG. 2b) which were validated by PCR in prostate cancer cell lines (FIG. 15). A focused analysis of the 1859 novel intergenic RNAs yielded 106 that were differentially expressed in localized tumors (FDR<0.05; FIG. 2c). These Prostate Cancer Associated Transcripts (PCATs) were ranked according to their fold change in localized tumor versus benign tissue (Tables 5 and 6).

Similarly, performing a modified cancer outlier profile analysis (COPA) on the RNA-Seq dataset re-discovered numerous known prostate cancer outliers, such as ERG7, ETV17, SPINK135, and CRISP336,37, and nominated numerous unannotated ncRNAs as outliers (FIG. 2d and Tables 6 and 7). Merging the results from the differential expression and COPA analyses resulted in a set of 121 unannotated transcripts that accurately discriminated benign, localized tumor, and metastatic prostate samples by unsupervised clustering (FIG. 2c). These data provide evidence that PCATs serve as biomarkers for prostate cancer and novel prostate cancer subtypes. Clustering analyses using novel ncRNA outliers also provide disease subtypes (FIG. 16).

Confirmation and Tissue-Specificity of ncRNAs

Validation studies were performed on 14 unannotated expressed regions, including ones both included and not present in the list of differentially expressed transcripts. Reverse transcription PCR (RT-PCR) and quantitative real-time PCR (qPCR) experiments demonstrated a ~78% (11/14) validation rate in predicted cell line models for both transcript identity and expression level (FIG. 17). Next, three transcripts (PCAT-109, PCAT-14, and PCAT-43) selectively upregulated in prostate cancer compared to normal prostate were examined. From the sequencing data, each genomic loci shows significantly increased expression in prostate cancer and metastases, except for PCAT-14, which appears absent in metastases (FIG. 3a-c). PCAT-109 also ranks as the #5 best outlier in prostate cancer, just ahead of ERG (FIG. 2d and Table 6). qPCR on a cohort of 14 benign prostates, 47 tumors, and 10 metastases confirmed expression of these transcripts (FIG. 3a-c). All three appear to be prostate-specific, with no expression seen in breast or lung cancer cell lines or in 19 normal tissue types (Table 8). This tissue specificity was not necessarily due to regulation by androgen signaling, as only PCAT-14 expression was induced by treatment of androgen responsive VCaP and LNCaP cells with the synthetic androgen R1881, consistent with previous data from this genomic locus (FIG. 18) (Tomlins et al., Nature 448 (7153), 595 (2007); Stavenhagen et al., Cell 55 (2), 247 (1988)). PCAT-14, but not PCAT-109 or PCAT-43, also showed differential expression when tested on a panel of matched tumor-normal samples, indicating that this transcript, which is comprised of an endogenous retrovirus in the HERV-K family (Bannert and Kurth, Proc Natl

Figure 4:
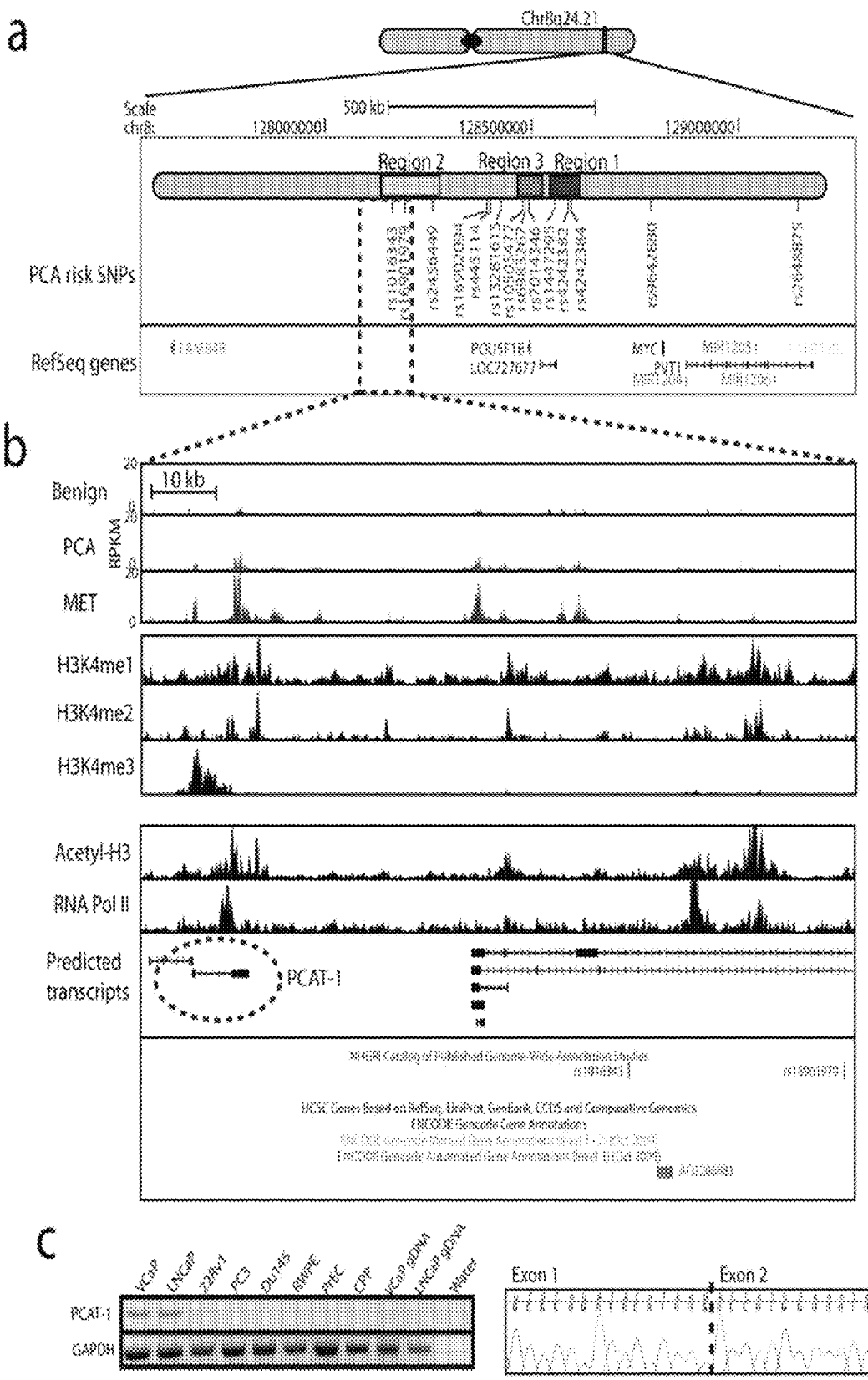
FIG. 4 shows that prostate cancer ncRNAs populate the Chr8q24 gene desert. a. A schematic of the chr8q24 region. b. Comprehensive analysis of the chr8q24 region by RNA-Seq and ChIP-Seq reveals numerous transcripts supported by histone modifications, such as Acetyl-H3 and H3K4me3, demarcating active chromatin. c. RT-PCR and Sanger sequencing validation of the PCAT-1 exon-exon junction. d. The genomic location of PCAT-1 determined by 5' and 3'
Figure 4:
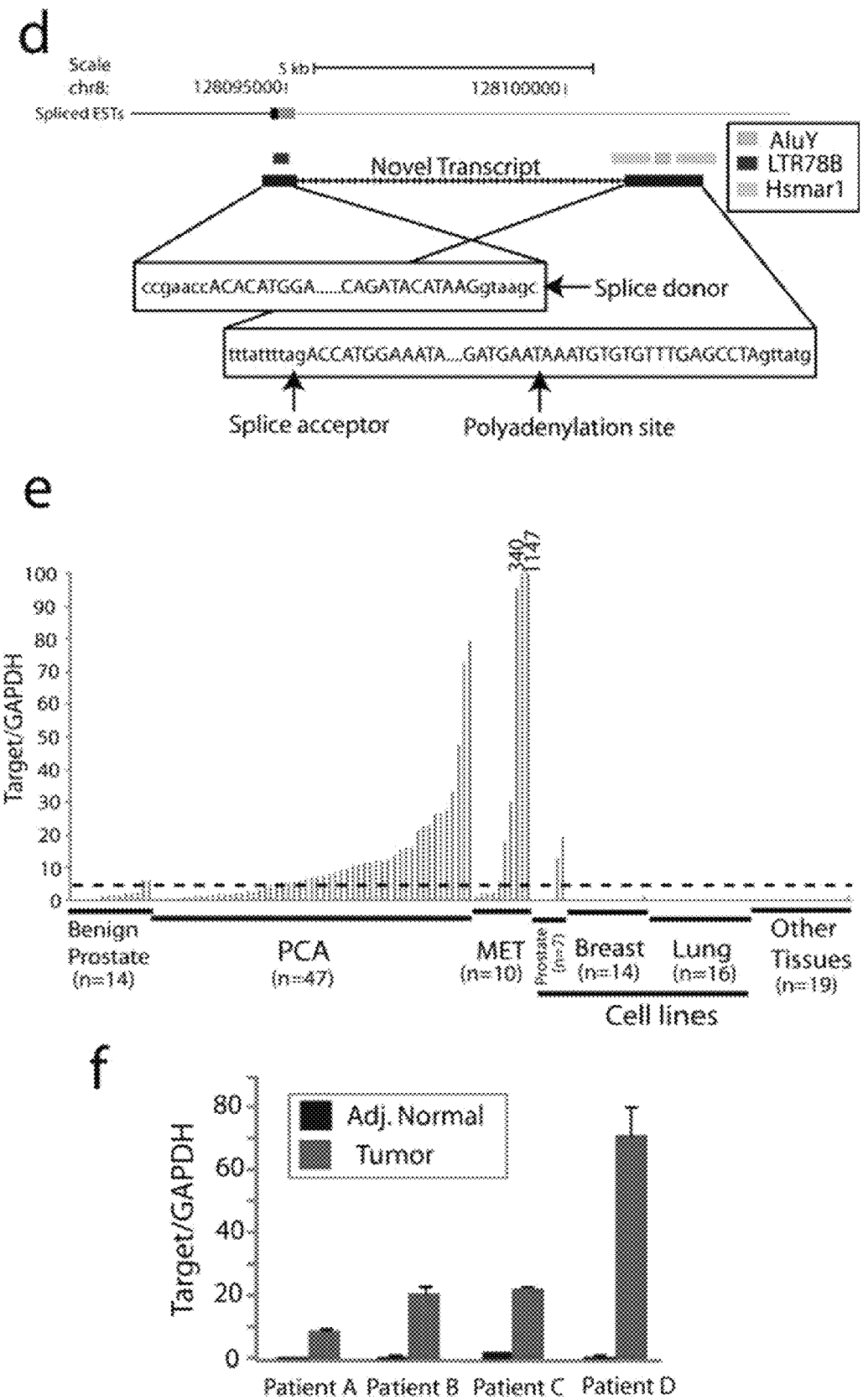

*Acad Sci USA* 101 Suppl 2, 14572 (2004)), can be used as a somatic marker for prostate cancer (FIG. 19). 5' and 3' rapid amplification of cDNA ends (RACE) at this locus revealed the presence of individual viral protein open reading frames (ORFs) and a transcript splicing together individual ORF 5' untranslated region (UTR) sequences (FIG. 20). It was observed that the top-ranked intergenic ncRNA resided in the chromosome 8q24 gene desert nearby to the c-Myc oncogene. This ncRNA, termed PCAT-1, is located on the edge of the prostate cancer susceptibility region 240-43 (FIG. 4a) and is about 0.5 Mb away from c-Myc. This transcript is supported by clear peaks in H3K4me3, Acetyl-H3, and RNA polymerase II ChIP-Seq data (FIG. 4b). The exon-exon junction in cell lines was validated by RT-PCR and Sanger sequencing of the junction (FIG. 4c), and 5' and 3' RACE was performed to elucidate transcript structure (FIG. 4d). By this analysis, PCAT-1 is a mariner family transposase (Oosumi et al., *Nature* 378 (6558), 672 (1995); Robertson et al., *Nat Genet* 12 (4), 360 (1996)) interrupted by an Alu retrotransposon and regulated by a viral long terminal repeat (LTR) promoter region (FIG. 4d and FIG. 21). By qPCR, PCAT-1 expression is specific to prostate tissue, with striking upregulation in prostate cancers and metastases compared to benign prostate tissue (FIG. 4e). PCAT-1 ranks as the second best overall prostate cancer biomarker, just behind AMACR (Table 3), indicating that this transcript is a powerful discriminator of this disease. Matched tumor normal pairs similarly showed marked upregulation in the matched tumor samples (FIG. 4f). RNA interference (RNAi) was performed in VCaP cells using custom siRNAs targeting PCAT-1 sequences and no change in the cell proliferation or invasion upon PCAT-1 knockdown was observed (FIG. 22)

Selective Re-Expression of Repetitive Elements in Cancer

The presence of repetitive elements in PCAT-1 led to an exploration of repetitive elements. Repetitive elements, such as Alu and LINE-1 retrotransposons, are broadly known to be degenerate in humans (Oosumi et al, supra; Robertson et al., supra; Cordaux et al., *Nat Rev Genet* 10 (10), 691 (2009), with only ~100 LINE-1 elements (out of 12~500,000) showing possible retrotransposon activity (Brouha et al., *Proc Natl Acad Sci USA* 100 (9), 5280 (2003)). While transcription of these elements is frequently repressed through DNA methylation and repressive chromatin modifications (Slotkin and Martienssen, *Nat Rev Genet* 8 (4), 272 (2007)), in cancer widespread hypomethylation has been reported (Cho et al., *J Pathol* 211 (3), 269 (2007); Chalitchagorn et al., *Oncogene* 23 (54), 8841 (2004); Yegnasubramanian et al., *Cancer Res* 68 (21), 8954 (2008)). Moreover, recent evidence indicates that these elements have functional roles in both normal biology (Kunarso et al., *Nat Genet.*) and cancer (Lin et al., *Cell* 139 (6), 1069 (2009)), even if their sequences have mutated away from their evolutionary ancestral sequence (Chow et al., *Cell* 141 (6), 956). To date, only RNA-Seq platforms enable discovery and quantification of specific transposable elements expressed in cancer. As described above, it was observed that >50% of unannotated exons in the assembly overlap with at least one repetitive element (FIG. 11). Since these elements pose mappability challenges when performing transcriptome assembly with unique reads, these loci typically appear as "mountain ranges" of expression, with uniquely mappable regions forming peaks of expression separated by unmappable "ravines" (FIGS. 23 and 24). PCR and Sanger sequencing experiments were performed to confirm that these transposable elements of low mappability are expressed as part of these loci (FIGS. 23 and 24). To probe this observation further, the exons from unannotated transcripts in the assembly, with the addition of the flanking 50, 100, or 500 bp of additional genomic sequence to the 5' and 3' end of the exons were generated, the overlap of these intervals with repetitive elements to randomly permuted genomic intervals of similar sizes was performed. A highly significant enrichment for repetitive elements in the dataset was observed (OR 2.82 (95% CI 2.68-2.97), p<10-100, Table 9). Examination of the individual repetitive element classes revealed a specific enrichment for SINE elements, particularly Alus (p≤2×10-16, Tables 10 and 11). A subset of LINE-1 and Alu transposable elements demonstrate marked differential expression in a subset of prostate cancer tumors (FIG. 25). One locus on chromosome 2 (also highlighted in FIG. 3b) is a 500+ kb region with numerous expressed transposable elements (FIG. 26). This locus, termed Second Chromosome Locus Associated with Prostate-1 (SChLAP1), harbors transcripts that perform extremely well in outlier analyses for prostate cancer (Tables 6 and 7). PCAT-109, discussed above, is one outlier transcript in this region. Moreover, the SChLAP1 locus is highly associated with patients positive for ETS gene fusions (p<0.0001, Fisher's exact test, FIG. 27), whereas this association was not observed with other expressed repeats. A direct regulatory role for ERG on this region was not identified using siRNA-mediated knockdown of ERG in the VCaP cell line. These data indicate that the dysregulation of repeats in cancer is highly specific, and that this phenomenon associates with only a subset of tumors and metastases. Thus, the broad hypomethylation of repeat elements observed in cancer (Cho et al., *J Pathol* 211 (3), 269 (2007); Chalitchagorn et al., *Oncogene* 23 (54), 8841 (2004); Yegnasubramanian et al., *Cancer Res* 68 (21), 8954 (2008)) does not account for the high specificity of repeat expression.

Non-Invasive Detection of ncRNAs in Urine

Taken together, these data show an abundance of novel ncRNA biomarkers for prostate cancer, many of which appear to have tissue specificity. 77 urine sediments obtained from patients with prostate cancer and 31 control patients without known disease (Table 12 for sample details) were analyzed (Laxman et al., *Cancer Res* 68 (3), 645 (2008)). The control patients are defined as those lacking cancer histology upon prostate biopsy and lacking the TMPRSS2-ERG fusion transcript in urine sediment RNA (Laxman et al., supra). PCAT-1 and PCAT-14, as well as the known ncRNA biomarker PCA3, were selected for evaluation on this urine panel due to their biomarker status in patient tissue samples. qPCR analysis led to an observation of specificity in their ability to detect prostate cancer patients and not patients with normal prostates (FIG. 5a-c). In several cases, patients with ETS-negative prostate cancer that were misclassified as "benign" are clearly evident (FIGS. 5a and 5c). Moreover, PCAT-14 appears to perform almost as well as PCA3 as a urine biomarker, nearly achieving statistical significance (p=0.055, Fisher's exact test) despite the small number of patients used for this panel. It was next evaluated whether these unannotated ncRNAs identified a redundant set of patients that would also be identified by other urine tests, such as PCA3 or TMPRSS2-ERG transcripts. Comparing PCAT-1 and PCAT-14 expression in urine samples to PCA3 or to each other revealed that these ncRNAs identified distinct patient sets, indicating that a patient's urine typically harbors PCAT-1 or PCAT-14 transcripts but not both (FIG. 5d). Using the cut-offs displayed in FIG. 5a-c, a binary heatmap comparing these three ncRNAs with patients' TMPRSS2-ERG status was generated (FIG. 5e). The ncR- NAs were able to detect additional ETS-negative patients with prostate cancer through this urine test, indicating that they have clinical utility as highly specific markers for prostate cancer using a multiplexed urine test. Combining PCAT-1, PCAT-14 and PCA3 into a single "non-coding RNA signature" generated a highly specific urine signature (p=0.0062, Fisher's exact test, FIG. 5f) that identifies a number of prostate cancer patients that is broadly comparable to the TMPRSS2-ERG fusion (33% vs. 45%).

FIG. 34 shows detection of prostate cancer RNAs in patient urine samples using qPCR. All RNA species were detectable in urine. FIG. 35 shows that multiplexing urine SChLAP-1 measurements with serum PSA improves prostate cancer risk stratification. Individually, SChLAP-1 is a predictor for prostate cancers with intermediate or high clinical risk of aggressiveness. Multiplexing this measurement with serum PSA improves upon serum PSA's ability to predict for more aggressive disease.

Additional Characterization

Additional experiments were conducted related to PCAT-1 and SChLAP-1 region in prostate cancer. FIG. 29 demonstrates that PCAT-1 expression sensitizes prostate cancer cells to treatment with PARP-1 inhibitors. FIG. 30 demonstrates that PCAT-1 expression sensitizes prostate cells to radiation treatment.

FIG. 31 demonstrates that unannotated intergeic transcripts in SChLAP-1 differentiate prostate cancer and benign samples. FIG. 32 demonstrates that SChLAP-1 is required for prostate cancer cell invasion and proliferation. Prostate cell lines, but not non-prostate cells, showed a reduction in invasion by Boyden chamber assays. EZH2 and non-targeting siRNAs served as positive and negative controls, respectively. Deletion analysis of SChLAP-1 was performed. FIG. 33 shows that a regionessential for its function was identified.

ncRNAs in Lung, Breast, and Pancreatic Cancers

Analysis of the lung cancer transcriptome (FIG. 36) was performed. 38 lung cell lines were analyzed by RNA-Seq and then lncRNA transcripts were reconstructed. Unannotated transcripts accounted for 27% of all transcripts. Novel transcripts well more highly expressed than annotated ncRNAs but not protein-coding transcripts. An outlier analyses of 13 unannotated transcripts shows novel lncRNAs in subtypes of lung cancer cell lines. FIG. 37 shows discovery of M41 and ENST-75 ncRNAs in lung cancer. FIG. 38 shows that lncRNAs are drivers and biomarkers in lung cancer. FIG. 39 shows identification of cancer-associated lncRNAs in breast and pancreatic cancer. Three novel breast cancer lncRNAs were nominated from RNA-Seq data (TU0011194, TU0019356, and TU0024146). All show outlier expression patterns in breast cancer samples but not benign samples. Three novel pancreatic cancer lncRNAs were nominated from RNA-Seq data (TU0009141, TU0062051, and TU0021861). All show outlier expression patterns in pancreatic cancer samples but not benign samples.

TABLE 1

| Library | Sample | Type | Sample Type | Read Type | Read Length | Total Reads (2 for PE) | Top-Hat Mapped Reads | Top-Hat Splice Junction Reads | % Splice | Diagnosis | ETS Status |
|---|---|---|---|---|---|---|---|---|---|---|---|
| ctp_41808AAXX_2 | PWP-1f | RNA-Seq | Cell Line | paired_end | 40 | 7363040 | 8367325 | 1693179 | 13.04% | Benign | Negative |
| mtcp_30077NAAXX_5 | PrEC | RNA-Seq | Cell Line | single_read | 40 | 3078463 | 955130 | 107311 | 11.24% | Benign | Negative |
| mtcp_209ENAAXX_8 | PrEC | RNA-Seq | Cell Line | single_read | 30 | 3319068 | 371580 | 67630 | 7.76% | Benign | Negative |
| mtcp_31472AAXX_1 | PrEC | RNA-Seq | Cell Line | paired_end | 40 | 7748627 | 7441379 | 747751 | 10.05% | Benign | Negative |
| mtcp_30351AAXX_7 | PrEC | RNA-Seq | Cell Line | paired_end | 40 | 2883459 | 9562343 | 892520 | 9.33% | Benign | Negative |
| mtcp_31472AAXX_2 | PYSMC | RNA-Seq | Cell Line | paired_end | 40 | 3464529 | 5676281 | 835503 | 20.54% | Benign | Negative |
| mtcp_20E6CAAXX_6 | RWPE | RNA-Seq | Cell Line | single_read | 36 | 5300180 | 1693164 | 149583 | 8.02% | Benign | Negative |
| mtcp_20E6CAAXX_7 | RWPE | RNA-Seq | Cell Line | single_read | 36 | 5347764 | 1718762 | 150130 | 8.78% | Benign | Negative |
| mtcp_30E6AAXX_6 | RWPE | RNA-Seq | Cell Line | single_read | 36 | 4778245 | 1539225 | 135956 | 8.84% | Benign | Negative |
| mtcp_20F65AAXX_6 | RWPE | RNA-Seq | Cell Line | single_read | 36 | 4033616 | 156520 | 1565250 | 8.78% | Benign | Negative |
| mtcp_20F6BAAXX_7 | RWPE | RNA-Seq | Cell Line | single_read | 36 | 5005497 | 1523033 | 145125 | 8.83% | Benign | Negative |
| mtcp_30F6BAAXX_8 | RWPE | RNA-Seq | Cell Line | single_read | 36 | 4955663 | 1507224 | 141352 | 8.80% | Benign | Negative |
| mtcp_20F6GAAXX_7 | RWPE | RNA-Seq | Cell Line | single_read | 36 | 4066436 | 1560635 | 138224 | 8.81% | Benign | Negative |
| mtcp_20F6GAAXX_8 | RWPE | RNA-Seq | Cell Line | single_read | 36 | 4009135 | 1550957 | 136045 | 8.77% | Benign | Negative |
| mtcp_20F6GAAXX_5 | RWPE | RNA-Seq | Cell Line | single_read | 36 | 4904457 | 1580424 | 138674 | 8.77% | Benign | Negative |
| mtcp_42603AAXX_3 | WPM1-2 | RNA-Seq | Cell Line | paired_end | 40 | 7593911 | 8101303 | 1613035 | 12.49% | Benign | Negative |
| mtcp_23969AAXX_1 | 32Fv1 | RNA-Seq | Cell Line | single_read | 36 | 5301735 | 2345205 | 169157 | 7.22% | Localized | Negative |
| mtcp_314NPAAXX_6 | 32Fv1 | RNA-Seq | Cell Line | paired_end | 40 | 9216420 | 9800615 | 1663132 | 11.07% | Localized | Negative |
| mtcp_42974AAXX_5 | CA-HPV-20 | RNA-Seq | Cell Line | paired_end | 40 | 13845951 | 14731620 | 1750425 | 12.89% | Localized | Negative |

TABLE 1-continued

| Library | Sample | Type | Sample Type | Read Type | Read Length | Total Reads (2 for PE) | Top-Hat Mapped Reads | Top-Hat Splice Junction Reads | % Splice | Diagnosis | ETS Status |
|---|---|---|---|---|---|---|---|---|---|---|---|
| mtcp_42974AAXX_7 | CWR72 | RNA-Seq | Cell Line | paired_end | 40 | 13952984 | 1479135 | 1530796 | 10.25% | Localized | Negative |
| mtcp_30D1DAAXX_2 | VCaP | RNA-Seq | Cell Line | single_read | 45 | 8275960 | 1450656 | 267746 | 21.58% | Metastatic | ERG+ |
| mtcp_20CCAAAXX_7 | VCaP | RNA-Seq | Cell Line | single_read | 36 | 5372814 | 981204 | 89560 | 9.14% | Metastatic | ERG+ |
| mtcp_20CCAAAXX_6 | VCaP | RNA-Seq | Cell Line | single_read | 36 | 5230393 | 957549 | 26139 | 9.00% | Metastatic | ERG+ |
| mtcp_20CCAAAXX_4 | VCaP | RNA-Seq | Cell Line | single_read | 36 | 5220542 | 956623 | 58342 | 9.23% | Metastatic | ERG+ |
| mtcp_20CCAAAXX_3 | VCaP | RNA-Seq | Cell Line | single_read | 36 | 5405126 | 985972 | 96075 | 9.11% | Metastatic | ERG+ |
| mtcp_20CCAAAXX_2 | VCaP | RNA-Seq | Cell Line | single_read | 36 | 5091526 | 938273 | 25147 | 9.07% | Metastatic | ERG+ |
| mtcp_20CCAAAXX_1 | VCaP | RNA-Seq | Cell Line | single_read | 36 | 4273323 | 304030 | 72304 | 9.05% | Metastatic | ERG+ |
| mtcp_20CCAAAXX_1 | VCaP | RNA-Seq | Cell Line | single_read | 36 | 4727324 | 861856 | 75361 | 9.07% | Metastatic | ERG+ |
| mtcp_20CCAAAXX_9 | VCaP | RNA-Seq | Cell Line | single_read | 36 | 5034304 | 926234 | 25638 | 9.23% | Metastatic | ERG+ |
| mtcp_20CCAAAXX_3 | VCaP | RNA-Seq | Cell Line | single_read | 36 | 4491727 | 807597 | 73636 | 9.11% | Metastatic | ERG+ |
| mtcp_20F0GAAXX_4 | NCI-H559 | RNA-Seq | Cell Line | paired_end | 40 | 12322636 | 15104197 | 1377700 | 9.12% | Metastatic | ERG+ |
| mtcp_20F0GAAXX_4 | LNCaP | RNA-Seq | Cell Line | single_read | 36 | 5109403 | 1430548 | 129270 | 8.35% | Metastatic | STV1+ |
| mtcp_30F0GAAXX_1 | LNCaP | RNA-Seq | Cell Line | single_read | 36 | 5018345 | 1402514 | 127293 | 8.36% | Metastatic | STV1+ |
| mtcp_20F0GAAXX_3 | LNCaP | RNA-Seq | Cell Line | single_read | 36 | 5106734 | 1476834 | 119452 | 8.37% | Metastatic | STV1+ |
| mtcp_20F0GAAXX_2 | LNCaP | RNA-Seq | Cell Line | single_read | 36 | 4990356 | 1393161 | 127850 | 8.43% | Metastatic | STV1+ |
| mtcp_20E6GAAXX_2 | LNCaP | RNA-Seq | Cell Line | single_read | 36 | 4893719 | 1370920 | 214874 | 8.30% | Metastatic | STV1+ |
| mtcp_20E6GAAXX_3 | LNCaP | RNA-Seq | Cell Line | single_read | 36 | 5402666 | 1512040 | 126177 | 8.36% | Metastatic | STV1+ |
| mtcp_20E6GAAXX_4 | LNCaP | RNA-Seq | Cell Line | single_read | 36 | 4851947 | 1304247 | 112485 | 8.52% | Metastatic | STV1+ |
| mtcp_42FMUAAXX_6 | LNCaP CD52 | RNA-Seq | Cell Line | paired_end | 36 | 10714839 | 10272130 | 1657574 | 10.30% | Metastatic | Negative |
| mtcp_42FMUAAXX_7 | LNCaP CD53 | RNA-Seq | Cell Line | paired_end | 36 | 9643473 | 9586206 | 973617 | 10.36% | Metastatic | Negative |
| mtcp_42TASAAXX_7 | DU-145 | RNA-Seq | Cell Line | paired_end | 36 | 13804352 | 23651384 | 1370597 | 10.04% | Metastatic | Negative |
| mtcp_42TASAAXX_7 | DU-145 | RNA-Seq | Cell Line | paired_end | 38 | 15765349 | 13915891 | 1570336 | 8.85% | Metastatic | Negative |
| mtcp_42TASAAXX_5 | DU-145 | RNA-Seq | Cell Line | paired_end | 38 | 14197743 | 14960979 | 1488834 | 9.93% | Metastatic | Negative |
| mtcp_42TASAAXX_3 | DU-145 | RNA-Seq | Cell Line | paired_end | 38 | 13150298 | 23047948 | 1330224 | 10.17% | Metastatic | Negative |
| mtcp_42TASAAXX_2 | DU-145 | RNA-Seq | Cell Line | paired_end | 38 | 12863746 | 13715378 | 13716578 | 10.09% | Metastatic | Negative |
| mtcp_42TA3AAXX_5 | DU-145 | RNA-Seq | Cell Line | paired_end | 38 | 10904533 | 5437287 | 653992 | 10.36% | Metastatic | Negative |
| mtcp_42TA3AAXX_8 | DU-145 | RNA-Seq | Cell Line | paired_end | 36 | 9229144 | 10026773 | 1053731 | 10.15% | Metastatic | Negative |
| mtcp_42PFSAAXX_5 | LNCaP CD5 parent | RNA-Seq | Cell Line | paired_end | 36 | 13259574 | 9518929 | 356543 | 10.15% | Metastatic | Negative |
| mtcp_42PFSAAXX_5 | LNCaP CD51 | RNA-Seq | Cell Line | paired_end | 36 | 12459565 | 13995952 | 1411356 | 10.08% | Metastatic | Negative |
| mtcp_205C5AAXX_8 | DU-145 | RNA-Seq | Cell Line | single_read | 36 | 5351486 | 2560642 | 135383 | 9.18% | Metastatic | Negative |
| mtcp_205569AAXX_2 | DU-145 | RNA-Seq | Cell Line | single_read | 35 | 5069345 | 2437193 | 225574 | 9.26% | Metastatic | Negative |
| mtcp_30D1DAAXX_3 | DU-145 | RNA-Seq | Cell Line | single_read | 45 | 3586532 | 4162580 | 498466 | 11.97% | Metastatic | Negative |
| mtcp_42974AAXX_1 | LAFC-4 | RNA-Seq | Cell Line | paired_end | 40 | 14795926 | 16711955 | 2790230 | 10.71% | Metastatic | Negative |
| mtcp_3064XAAXX_1 | PC3 | RNA-Seq | Cell Line | paired_end | 40 | 10267396 | 30291560 | 1185473 | 11.52% | Metastatic | Negative |
| mtcp_20559AAXX_3 | PC3 | RNA-Seq | Cell Line | single_read | 35 | 5364050 | 2547308 | 237597 | 9.33% | Metastatic | Negative |

TABLE 1-continued

| Library | Sample | Type | Sample Type | Read Type | Read Length | Total Reads (2 for PE) | Top-Hat Mapped Reads | Top-Hat Splice Junction Reads | % Splice | Diagnosis | ETS Status |
|---|---|---|---|---|---|---|---|---|---|---|---|
| mtcp_42974AAXX_2 | CA-2B | RNA-Seq | Cell Line | paired_end | 40 | 12755939 | 12823209 | 1591197 | 12.41% | Metastatic | Negative |
| mtcp_42974AAXX_6 | MDA PCe 2a | RNA-Seq | Cell Line | paired_end | 40 | 13341323 | 14969546 | 1839513 | 10.96% | Metastatic | Negative |
| mtcp_42807AAXX_4 | WPEI NB26 | RNA-Seq | Cell Line | paired_end | 40 | 10593920 | 9530521 | 1240043 | 12.49% | Metastatic | Negative |
| mtcp_42643AAXX_4 | PrBe10015 | RNA-Seq | Tissue | paired_end | 40 | 15313335 | 13040527 | 1435670 | 7.96% | Benign | Negative |
| mtcp_30WU2AAXX_5 | PrBe10013 | RNA-Seq | Tissue | paired_end | 38 | 9822744 | 12263152 | 927590 | 7.56% | Benign | Negative |
| mtcp_42B80AAXX_0 | PrBe20014 | RNA-Seq | Tissue | paired_end | 40 | 13242542 | 9035078 | 715451 | 7.92% | Benign | Negative |
| mtcp_428FAAAXX_6 | PrBe20014 | RNA-Seq | Tissue | paired_end | 38 | 5646551 | 6389375 | 471383 | 7.38% | Benign | Negative |
| mtcp_30WU2AAXX_6 | PrBe20014 | RNA-Seq | Tissue | paired_end | 36 | 3977105 | 4353696 | 321691 | 7.56% | Benign | Negative |
| mtcp_42CUAAXX_7 | PrBe20015 | RNA-Seq | Tissue | paired_end | 40 | 7584410 | 7927754 | 632270 | 7.90% | Benign | Negative |
| mtcp_42N14AAXX_7 | PrBe20015 | RNA-Seq | Tissue | paired_end | 38 | 14331227 | 12877194 | 936538 | 7.27% | Benign | Negative |
| mtcp_42648AAXX_1 | PrBe20016 | RNA-Seq | Tissue | paired_end | 40 | 12122396 | 11750531 | 820750 | 6.98% | Benign | Negative |
| mtcp_42N14AAXX_3 | PrBe20016 | RNA-Seq | Tissue | paired_end | 30 | 11809596 | 11367853 | 741489 | 6.53% | Benign | Negative |
| mtcp_30WUZAAXX_7 | PrBe20017 | RNA-Seq | Tissue | paired_end | 38 | 1959393 | 1256367 | 152020 | 7.05% | Benign | Negative |
| mtcp_42CJFAAXX_5 | PrBe20017 | RNA-Seq | Tissue | paired_end | 40 | 14245713 | 14383797 | 1025161 | 7.13% | Benign | Negative |
| mtcp_42820AAXX_5 | PrBe20018 | RNA-Seq | Tissue | paired_end | 30 | 16616393 | 17004216 | 1465145 | 8.62% | Benign | Negative |
| mtcp_42NY4AAXX_5 | PrBe10813 | RNA-Seq | Tissue | paired_end | 38 | 15877854 | 16459392 | 1428434 | 8.60% | Benign | Negative |
| mtcp_42D3NAAXX_5 | aN10_5 | RNA-Seq | Tissue | paired_end | 40 | 10162958 | 11540204 | 935298 | 7.85% | Benign | Negative |
| mtcp_3054YAAXX_2 | aN11_1 | RNA-Seq | Tissue | paired_end | 40 | 9792955 | 10708080 | 644033 | 7.98% | Benign | Negative |
| mtcp_42P6UAAXX_1 | aN11_1 | RNA-Seq | Tissue | paired_end | 40 | 14658075 | 10917492 | 323116 | 7.54% | Benign | Negative |
| mtcp_3057WAAXX_1 | aN13_2 | RNA-Seq | Tissue | paired_end | 40 | 14755517 | 15347555 | 1174999 | 7.56% | Benign | Negative |
| mtcp_42P6UAAXX_4 | aN13_2 | RNA-Seq | Tissue | paired_end | 40 | 16107801 | 16070565 | 1331934 | 7.57% | Benign | Negative |
| mtcp_306YWAAXX_3 | aN14_4 | RNA-Seq | Tissue | paired_end | 40 | 9282092 | 9326550 | 733493 | 7.70% | Benign | Negative |
| mtcp_42P6UAAXX_2 | aN14_4 | RNA-Seq | Tissue | paired_end | 40 | 12317092 | 11960962 | 394323 | 7.47% | Benign | Negative |
| mtcp_30553AAXX_5 | PrBe10002 | RNA-Seq | Tissue | paired_end | 40 | 20282216 | 3430927 | 198504 | 5.47% | Benign | Negative |
| mtcp_306YNAAXX_6 | PrBe10002 | RNA-Seq | Tissue | paired_end | 40 | 4359340 | 577146 | 39125 | 4.45% | Benign | Negative |
| mtcp_306YNAAXX_7 | PrBe10003 | RNA-Seq | Tissue | paired_end | 40 | 4724195 | 362030 | 17010 | 4.45% | Benign | Negative |
| mtcp_42P6UAAXX_3 | aN15_3 | RNA-Seq | Tissue | single_read | 40 | 14035929 | 10690595 | 928350 | 6.53% | Benign | Negative |
| mtcp_3054YAAXX_7 | aN15_3 | RNA-Seq | Tissue | single_read | 40 | 8772663 | 8161379 | 714429 | 8.82% | Benign | Negative |
| mtcp_300MZAAXX_6 | aN23 | RNA-Seq | Tissue | paired_end | 35 | 6359099 | 2998000 | 171398 | 5.72% | Benign | Negative |
| mtcp_300MZAAXX_6 | aN25 | RNA-Seq | Tissue | paired_end | 35 | 5162304 | 2181784 | 100935 | 4.53% | Benign | Negative |
| mtcp_300MZAAXX_3 | aN25 | RNA-Seq | Tissue | single_read | 35 | 5867482 | 2632682 | 1238775 | 4.70% | Benign | Negative |
| mtcp_300MZAAXX_1 | aN37 | RNA-Seq | Tissue | single_read | 35 | 4771661 | 1856628 | 93266 | 5.02% | Benign | Negative |
| mtcp_300MZAAXX_2 | aN27 | RNA-Seq | Tissue | single_read | 35 | 5643508 | 2090978 | 103542 | 4.95% | Benign | Negative |
| mtcp_300MZAAXX_7 | aN29 | RNA-Seq | Tissue | single_read | 35 | 5661652 | 1555510 | 87547 | 4.63% | Benign | Negative |
| mtcp_300MZAAXX_8 | aN29 | RNA-Seq | Tissue | single_read | 35 | 5201944 | 1472975 | 23463 | 5.67% | Benign | Negative |
| mtcp_20FGKAAXX_1 | aN31 | RNA-Seq | Tissue | single_read | 36 | 4306556 | 2642651 | 122140 | 7.44% | Benign | Negative |
| mtcp_20FGKAAXX_2 | aN31 | RNA-Seq | Tissue | single_read | 35 | 3524043 | 2504370 | 107996 | 7.18% | Benign | Negative |

TABLE 1-continued

| Library | Sample | Type | Sample Type | Read Type | Read Length | Total Reads (2 for PE) | Top-Hat Mapped Reads | Top-Hat Splice Junction Reads | % Splice | Diagnosis | ETS Status |
|---|---|---|---|---|---|---|---|---|---|---|---|
| mtcp_20FGKAAXX_4 | aN32 | RNA-Seq | Tissue | single_read | 36 | 4445596 | 1666001 | 113140 | 6.33% | Benign | Negative |
| mtcp_20FGKAAXX_3 | aN32 | RNA-Seq | Tissue | single_read | 36 | 4352455 | 1835242 | 215876 | 6.31% | Benign | Negative |
| mtcp_20FGKAAXX_7 | aN33 | RNA-Seq | Tissue | single_read | 35 | 5375947 | 2024782 | 122564 | 6.05% | Benign | Negative |
| mtcp_20FCKAAXX_2 | aN33 | RNA-Seq | Tissue | single_read | 35 | 3974268 | 1397869 | 96704 | 6.05% | Benign | Negative |
| mtcp_42D3NAAXX_6 | aT12_4 | RNA-Seq | Tissue | single_read | 40 | 10323732 | 19700318 | 891273 | 8.34% | Localized | ERG+ |
| mtcp_42P6UAAXX_6 | aT12_4 | RNA-Seq | Tissue | single_read | 40 | 12591651 | 12687329 | 1035642 | 8.16% | Localized | ERG+ |
| mtcp_1GAGMAAXX_7 | aT54 | RNA-Seq | Tissue | paired_end | 35 | 4951150 | 2395362 | 153160 | 6.39% | Localized | ERG+ |
| mtcp_302YWAAXX_3 | aT5_5 | RNA-Seq | Tissue | paired_end | 40 | 14290070 | 15157510 | 1231918 | 8.13% | Localized | ERG+ |
| mtcp_20ADMAAXX_8 | aT62 | RNA-Seq | Tissue | single_read | 35 | 5144018 | 2594526 | 146253 | 5.65% | Localized | ERG+ |
| mtcp_20693AAXX_3 | aT76 | RNA-Seq | Tissue | paired_end | 30 | 4492645 | 3095390 | 77035 | 3.58% | Localized | ERG+ |
| mtcp_42D3NAAXX_7 | aT78_3 | RNA-Seq | Tissue | single_read | 40 | 5949944 | 10269473 | 745408 | 7.35% | Localized | ERG+ |
| mtcp_42P6UAAXX_7 | aT78_2 | RNA-Seq | Tissue | single_read | 40 | 13165443 | 12753018 | 925562 | 7.25% | Localized | ERG+ |
| mtcp_2GAGMAAXX_6 | aT20 | RNA-Seq | Tissue | paired_end | 35 | 4905934 | 2380289 | 168032 | 7.05% | Localized | STV1+ |
| mtcp_30Y5NAAXX_5 | aT52 | RNA-Seq | Tissue | paired_end | 34 | 9555248 | 11236237 | 579323 | 5.16% | Localized | STV1+ |
| mtcp_20393AAXX_4 | PrCa10001 | RNA-Seq | Tissue | single_read | 30 | 5073375 | 2003733 | 51777 | 4.08% | Localized | Negative |
| mtcp_30YNAAXX_2 | PrCa10002 | RNA-Seq | Tissue | paired_end | 40 | 1579845 | 2573690 | 142307 | 9.04% | Localized | Negative |
| mtcp_20093AAXX_7 | PrCa10002 | RNA-Seq | Tissue | single_read | 30 | 5337734 | 2185509 | 134758 | 6.17% | Localized | Negative |
| mtcp_300W7AAXX_4 | PrCa10003 | RNA-Seq | Tissue | single_read | 40 | 7245008 | 3325450 | 200975 | 6.04% | Localized | Negative |
| mtcp_300YNAAXX_1 | PrCa10003 | RNA-Seq | Tissue | single_read | 40 | 2232676 | 996717 | 47049 | 4.72% | Localized | Negative |
| mtcp_20095AAXX_6 | PrCa10003 | RNA-Seq | Tissue | single_read | 30 | 4209584 | 1069531 | 80219 | 4.29% | Localized | Negative |
| mtcp_20033AAXX_2 | PrCa10004 | RNA-Seq | Tissue | single_read | 30 | 4277613 | 2429573 | 101279 | 4.17% | Localized | Negative |
| mtcp_300W7AAXX_3 | PrCa10004 | RNA-Seq | Tissue | single_read | 40 | 2503651 | 4337932 | 26532 | 6.03% | Localized | Negative |
| mtcp_20095AAXX_2 | PrCa10005 | RNA-Seq | Tissue | single_read | 30 | 4597349 | 2219405 | 86343 | 3.39% | Localized | Negative |
| mtcp_300W7AAXX_5 | PrCa10005 | RNA-Seq | Tissue | single_read | 40 | 7780454 | 3825883 | 211003 | 5.52% | Localized | Negative |
| mtcp_30WU2AAXX_5 | PrCa10015 | RNA-Seq | Tissue | paired_end | 38 | 7094073 | 8465055 | 698526 | 6.25% | Localized | Negative |
| mtcp_42FFAAXX_3 | PrCa10013 | RNA-Seq | Tissue | paired_end | 38 | 13129950 | 14850359 | 1205327 | 6.12% | Localized | Negative |
| mtcp_42CJFAAXX_4 | PrCa10013 | RNA-Seq | Tissue | paired_end | 40 | 11855634 | 13593357 | 1193752 | 8.79% | Localized | Negative |
| mtcp_42808AAXX_5 | PrCa10014 | RNA-Seq | Tissue | paired_end | 40 | 11559996 | 11373993 | 923458 | 8.19% | Localized | Negative |
| mtcp_42808AAXX_3 | PrCa10014 | RNA-Seq | Tissue | paired_end | 40 | 9529325 | 7576253 | 705179 | 9.31% | Localized | Negative |
| mtcp_42C3JAAXX_5 | PrCa10014 | RNA-Seq | Tissue | paired_end | 40 | 15125424 | 13200396 | 1326961 | 7.71% | Localized | Negative |
| mtcp_30WU2AAXX_1 | PrCa10014 | RNA-Seq | Tissue | paired_end | 38 | 13833345 | 15792364 | 1323174 | 7.11% | Localized | Negative |
| mtcp_42643AAXX_3 | PrCa10015 | RNA-Seq | Tissue | paired_end | 40 | 14322439 | 14744516 | 1043965 | 7.08% | Localized | Negative |
| mtcp_30WU3AAXX_4 | PrCa10015 | RNA-Seq | Tissue | paired_end | 38 | 9081533 | 10020115 | 675680 | 6.75% | Localized | Negative |
| mtcp_42NY4AAXX_4 | PrCa10015 | RNA-Seq | Tissue | paired_end | 38 | 11879130 | 13526717 | 954576 | 7.06% | Localized | Negative |
| mtcp_42848AAXX_6 | PrCa10016 | RNA-Seq | Tissue | paired_end | 40 | 11383818 | 13459171 | 1027559 | 7.53% | Localized | Negative |
| mtcp_42848AAXX_2 | PrCa10017 | RNA-Seq | Tissue | paired_end | 40 | 7503235 | 7558611 | 522237 | 8.24% | Localized | Negative |
| mtcp_42PFAAXX_1 | PrCa10017 | RNA-Seq | Tissue | paired_end | 38 | 13554764 | 11359051 | 352274 | 7.53% | Localized | Negative |

TABLE 1-continued

| Library | Sample | Type | Sample Type | Read Type | Read Length | Total Reads (2 for PE) | Top-Hat Mapped Reads | Top-Hat Splice Junction Reads | % Splice | Diagnosis | ETS Status |
|---|---|---|---|---|---|---|---|---|---|---|---|
| mtcp_42NY4AAXX_3 | PrCa10018 | RNA-Seq | Tissue | paired_end | 38 | 26107721 | 12636010 | 1473950 | 7.90% | Localized | Negative |
| mtcp_42CJFAAXX_2 | PrCa10018 | RNA-Seq | Tissue | paired_end | 40 | 12506692 | 14935373 | 1301243 | 8.71% | Localized | Negative |
| mtcp_30Y5NAAXX_4 | PrCa10018 | RNA-Seq | Tissue | paired_end | 34 | 8565125 | 10521603 | 649435 | 6.17% | Localized | Negative |
| mtcp_42C1JAAXX_9 | PrCa10019 | RNA-Seq | Tissue | paired_end | 40 | 14204491 | 12345166 | 984250 | 7.23% | Localized | Negative |
| mtcp_42843AAXX_5 | PrCa10021 | RNA-Seq | Tissue | paired_end | 40 | 14583654 | 15470222 | 1347556 | 7.42% | Localized | Negative |
| mtcp_43CJFAAXX_2 | PrCa10023 | RNA-Seq | Tissue | paired_end | 40 | 5473417 | 11040935 | 939157 | 6.51% | Localized | Negative |
| mtcp_42CIJAAXX_6 | PrCa10024 | RNA-Seq | Tissue | paired_end | 40 | 5249645 | 5541745 | 432904 | 7.81% | Localized | Negative |
| mtcp_42PF0AAXX_3 | PrCa10024 | RNA-Seq | Tissue | paired_end | 30 | 8109134 | 7303966 | 341558 | 7.21% | Localized | Negative |
| mtcp_42CJFAAXX_3 | PrCa10028 | RNA-Seq | Tissue | paired_end | 40 | 3344365 | 6256991 | 516414 | 6.25% | Localized | Negative |
| mtcp_42T69AAXX_3 | PrCa10030 | RNA-Seq | Tissue | paired_end | 38 | 17239720 | 16212019 | 125021 | 6.95% | Localized | Negative |
| mtcp_42TB9AAXX_2 | PrCa10031 | RNA-Seq | Tissue | paired_end | 38 | 17981940 | 19792732 | 1356072 | 6.95% | Localized | Negative |
| mtcp_42TB9AAXX_6 | PrCa10032 | RNA-Seq | Tissue | paired_end | 38 | 16392204 | 12313947 | 460799 | 7.75% | Localized | Negative |
| mtcp_42TB9AAXX_2 | PrCa10033 | RNA-Seq | Tissue | paired_end | 38 | 10735020 | 7143288 | 460799 | 6.45% | Localized | Negative |
| mtcp_42TB9AAXX_7 | PrCa10034 | RNA-Seq | Tissue | paired_end | 38 | 16494766 | 15635452 | 1426932 | 7.61% | Localized | Negative |
| mtcp_4296UAAXX_5 | aT1_2 | RNA-Seq | Tissue | paired_end | 40 | 14031093 | 1328365 | 1089323 | 7.30% | Localized | Negative |
| mtcp_302YWAAXX_2 | aT_3 | RNA-Seq | Tissue | paired_end | 40 | 14019721 | 15424771 | 1120415 | 7.26% | Localized | Negative |
| mtcp_42B43AAXX_7 | aT30 | RNA-Seq | Tissue | paired_end | 40 | 14021075 | 14206815 | 1075647 | 7.57% | Localized | Negative |
| mtcp_30Y5NAAXX_3 | aT38 | RNA-Seq | Tissue | paired_end | 34 | 9148041 | 10857079 | 634116 | 5.84% | Localized | Negative |
| mtcp_42Y27AAXX_2 | aT42 | RNA-Seq | Tissue | paired_end | 38 | 15907739 | 17336936 | 1112428 | 5.41% | Localized | Negative |
| mtcp_30DJDAAXX_5 | aT42 | RNA-Seq | Tissue | single_read | 45 | 9446722 | 4597917 | 345802 | 7.52% | Localized | Negative |
| mtcp_42Y2TAAXX_3 | aT45 | RNA-Seq | Tissue | paired_end | 38 | 16395435 | 13743230 | 814457 | 5.92% | Localized | Negative |
| mtcp_30DJDAAXX_6 | aT45 | RNA-Seq | Tissue | single_read | 45 | 9154922 | 3913914 | 273181 | 5.97% | Localized | Negative |
| mtcp_42508AAXX_7 | aT53 | RNA-Seq | Tissue | paired_end | 40 | 12154542 | 13040032 | 1055173 | 5.09% | Localized | Negative |
| mtcp_20F66AAXX_6 | aT56 | RNA-Seq | Tissue | single_read | 36 | 4655382 | 2003131 | 309230 | 5.46% | Localized | Negative |
| mtcp_30CW7AAXX_2 | aT56 | RNA-Seq | Tissue | single_read | 40 | 7556627 | 5043288 | 359576 | 6.22% | Localized | Negative |
| mtcp_20F65AAXX_1 | aT56 | RNA-Seq | Tissue | single_read | 36 | 4594327 | 1965966 | 108306 | 5.50% | Localized | Negative |
| mtcp_30U35AAXX_4 | aT57 | RNA-Seq | Tissue | paired_end | 40 | 9490697 | 3403761 | 618453 | 7.32% | Localized | Negative |
| mtcp_42CJFAAXX_9 | aT59 | RNA-Seq | Tissue | paired_end | 40 | 4160393 | 4703591 | 385743 | 9.27% | Localized | Negative |
| mtcp_42503AAXX_3 | aT51 | RNA-Seq | Tissue | paired_end | 40 | 10252280 | 10445106 | 710210 | 5.08% | Localized | Negative |
| mtcp_20F66AAXX_7 | aT56 | RNA-Seq | Tissue | single_read | 36 | 5026117 | 2455183 | 153987 | 5.27% | Localized | Negative |
| mtcp_30CW7AAXX_1 | aT56 | RNA-Seq | Tissue | single_read | 40 | 3055624 | 3791022 | 269311 | 7.05% | Localized | Negative |
| mtcp_20F65AAXX_2 | aT56 | RNA-Seq | Tissue | single_read | 36 | 5184870 | 2368556 | 149538 | 6.31% | Localized | Negative |
| mtcp_42P6UAAXX_6 | aT6_1 | RNA-Seq | Tissue | paired_end | 40 | 936249 | 595194 | 78695 | 7.80% | Localized | Negative |
| mtcp_42CJFAAXX_7 | aF6_1 | RNA-Seq | Tissue | paired_end | 40 | 9420907 | 7353536 | 524419 | 7.13% | Localized | Negative |
| mtcp_42PFAAAXX_4 | aF6_1 | RNA-Seq | Tissue | paired_end | 38 | 13242928 | 9178336 | 610109 | 6.65% | Localized | Negative |
| mtcp_30CW5AAXX_7 | PrCa10007 | RNA-Seq | Tissue | single_read | 42 | 7909935 | 3245264 | 903093 | 9.36% | Localized | Negative |
| mtcp_42D3NAAXX_2 | PrCa10025 | RNA-Seq | Tissue | paired_end | 40 | 8614308 | 9085904 | 903693 | 9.94% | Localized | Negative |

TABLE 1-continued

| Library | Sample | Type | Sample Type | Read Type | Read Length | Total Reads (2 for PE) | Top-Hat Mapped Reads | Top-Hat Splice Junction Reads | % Splice | Diagnosis | ETS Status |
|---|---|---|---|---|---|---|---|---|---|---|---|
| mtcp_42D3NAAXX_1 | PrCa10025 | RNA-Seq | Tissue | paired_end | 40 | 7701261 | 8539677 | 801237 | 9.39% | Localized | Negative |
| mtcp_43D3NAAXX_3 | PrCa10027 | RNA-Seq | Tissue | paired_end | 40 | 10505382 | 11427244 | 1110543 | 9.72% | Localized | Negative |
| mtcp_42TB9AAXX_4 | PrCa10029 | RNA-Seq | Tissue | paired_end | 38 | 8674521 | 9910831 | 734269 | 7.41% | Localized | Negative |
| mtcp_4276WAAXX_6 | PrCa10029 | RNA-Seq | Tissue | paired_end | 38 | 13229893 | 14063533 | 1060520 | 7.54% | Localized | Negative |
| mtcp_3054YAAXX_4 | 582927 | RNA-Seq | Tissue | paired_end | 40 | 9642505 | 8623237 | 638903 | 7.41% | Localized | Negative |
| mtcp_42B3YAAXX_1 | aT47 | RNA-Seq | Tissue | paired_end | 40 | 7806523 | 7010750 | 354001 | 5.05% | Localized | Negative |
| mtcp_20F56AAXX_3 | aM23 | RNA-Seq | Tissue | single_read | 36 | 4660303 | 2045530 | 115179 | 5.67% | Metastic | ERG+ |
| mtcp_20F56AAXX_4 | aM23 | RNA-Seq | Tissue | single_read | 36 | 4913495 | 2187836 | 327972 | 5.85% | Metastic | ERG+ |
| mtcp_20F59AAXX_4 | aM28 | RNA-Seq | Tissue | single_read | 36 | 5374558 | 1203543 | 93339 | 4.51% | Metastic | ERG+ |
| mtcp_20LVSAAXX_5 | aM29 | RNA-Seq | Tissue | single_read | 30 | 5217555 | 2234529 | 79072 | 3.54% | Metastic | ERG+ |
| mtcp_30LVSAAXX_7 | aM28 | RNA-Seq | Tissue | single_read | 30 | 5548786 | 2250821 | 80013 | 3.55% | Metastic | ERG+ |
| mtcp_2GAGMAAXX_4 | aM29 | RNA-Seq | Tissue | single_read | 35 | 4905432 | 1839767 | 75792 | 4.01% | Metastic | ERG+ |
| mtcp_20FETAAXX_5 | aM29 | RNA-Seq | Tissue | single_read | 36 | 5092573 | 1777721 | 73454 | 4.13% | Metastic | ERG+ |
| mtcp_2074VAAXX_1 | aM30 | RNA-Seq | Tissue | single_read | 36 | 5126432 | 2559949 | 150950 | 5.90% | Metastic | ERG+ |
| mtcp_300NNAAXX_2 | aM38 | RNA-Seq | Tissue | single_read | 40 | 4759734 | 2287003 | 139731 | 6.11% | Metastic | ERG+ |
| mtcp_303YGAAXX_3 | aM30 | RNA-Seq | Tissue | paired_end | 40 | 5778934 | 3539592 | 21553 | 7.60% | Metastic | ERG+ |
| mtcp_42620AAXX_6 | aM15 | RNA-Seq | Tissue | paired_end | 38 | 13925325 | 11684423 | 950874 | 5.14% | Metastic | ERG+ |
| mtcp_2074VAAXX_3 | aM15 | RNA-Seq | Tissue | single_read | 36 | 4746456 | 1087670 | 95102 | 4.56% | Metastic | ERG+ |
| mtcp_2074VAAXX_5 | aM37 | RNA-Seq | Tissue | single_read | 36 | 4509553 | 1941952 | 91631 | 4.72% | Metastic | STV1+ |
| mtcp_205K4AAXX_2 | aM41 | RNA-Seq | Tissue | single_read | 36 | 4480734 | 1702019 | 74575 | 4.38% | Metastic | STV1+ |
| mtcp_20FETAAXX_6 | aM41 | RNA-Seq | Tissue | single_read | 36 | 5372905 | 2051694 | 82655 | 4.03% | Metastic | STV1+ |
| mtcp_2074YAAXX_2 | aM41 | RNA-Seq | Tissue | single_read | 36 | 5222746 | 2184030 | 80786 | 4.05% | Metastic | STV1+ |
| mtcp_3054YAAXX_5 | ULMB-11239-97 | RNA-Seq | Tissue | paired_end | 40 | 9663726 | 10247077 | 1004315 | 9.30% | Metastic | Negative |
| mtcp_3054YAAXX_5 | ULMB-2440-97 | RNA-Seq | Tissue | paired_end | 40 | 9532376 | 10358562 | 931593 | 9.15% | Metastic | Negative |
| mtcp_20E7PAAXX_7 | aM11 | RNA-Seq | Tissue | single_read | 36 | 5201585 | 2533757 | 108578 | 4.65% | Metastic | Negative |
| mtcp_42CJFAAXX_6 | aM20 | RNA-Seq | Tissue | paired_end | 40 | 9038499 | 8021509 | 572135 | 5.49% | Metastic | Negative |
| mtcp_20E4PAAXX_6 | aM36 | RNA-Seq | Tissue | single_read | 36 | 5587558 | 2277795 | 104747 | 4.60% | Metastic | Negative |
| mtcp_30CW7AAXX_6 | aM36 | RNA-Seq | Tissue | single_read | 40 | 9198611 | 3033469 | 193679 | 5.05% | Metastic | Negative |
| mtcp_307YGAAXX_1 | aM35 | RNA-Seq | Tissue | paired_end | 40 | 7749518 | 2430308 | 141723 | 5.83% | Metastic | Negative |
| mtcp_205K4AAXX_1 | aM35 | RNA-Seq | Tissue | single_read | 36 | 5097473 | 1217307 | 126214 | 5.65% | Metastic | Negative |
| mtcp_20EYPAAXX_2 | aM39 | RNA-Seq | Tissue | single_read | 36 | 5516549 | 2339252 | 113774 | 4.86% | Metastic | Negative |
| mtcp_307YGAAXX_1 | aM39 | RNA-Seq | Tissue | paired_end | 40 | 6279578 | 5563921 | 235294 | 5.52% | Metastic | Negative |
| mtcp_205ETAAXX_7 | aM39 | RNA-Seq | Tissue | single_read | 36 | 5354844 | 2117551 | 102001 | 4.82% | Metastic | Negative |
| mtcp_20ETPAAXX_6 | aM43 | RNA-Seq | Tissue | single_read | 36 | 5497785 | 1630052 | 72729 | 4.33% | Metastic | Negative |
| mtcp_30CW7AAXX_7 | aM43 | RNA-Seq | Tissue | single_read | 40 | 8459324 | 5952621 | 200253 | 5.07% | Metastic | Negative |
| | | | TOTAL | | | 1723713421 | 1417627939 | 114448741 | 9.07% | | |

TABLE 2

| Chromosome | Cuffcompare | Classification tree filter | Merge intron-redundant transcripts | Informatic filters | Join transcript fragments | Filter Intronic pre-mRNA | UCSC Canonical | Refseq |
|---|---|---|---|---|---|---|---|---|
| chr1 | 759121 | 272072 | 12701 | 5030 | 4489 | 3652 | 2499 | 3334 |
| chr2 | 581574 | 206281 | 9353 | 3224 | 2856 | 2361 | 1579 | 2023 |
| chr3 | 518621 | 167071 | 5706 | 2917 | 2560 | 2053 | 1312 | 1816 |
| chr4 | 329950 | 103113 | 5160 | 2019 | 1731 | 1444 | 977 | 1738 |
| chr5 | 380613 | 126139 | 5833 | 2365 | 2067 | 1694 | 1104 | 1465 |
| chr6 | 396848 | 145607 | 7580 | 2590 | 2309 | 1874 | 1370 | 1607 |
| chr7 | 432152 | 134051 | 6432 | 2355 | 2132 | 1703 | 1326 | 1583 |
| chr8 | 308935 | 97724 | 4226 | 1729 | 1529 | 1243 | 848 | 1210 |
| chr9 | 359300 | 122626 | 4069 | 1937 | 1767 | 1402 | 1114 | 1272 |
| chr10 | 354625 | 103512 | 3509 | 1672 | 1508 | 1226 | 998 | 1382 |
| chr11 | 424606 | 165211 | 6909 | 2922 | 2640 | 2102 | 1566 | 2023 |
| chr12 | 425280 | 138650 | 6872 | 2653 | 2373 | 1858 | 1233 | 1668 |
| chr13 | 159649 | 68284 | 3616 | 1118 | 908 | 751 | 425 | 549 |
| chr14 | 261497 | 123741 | 4842 | 1806 | 1619 | 1308 | 885 | 1102 |
| chr15 | 291241 | 108058 | 5816 | 1884 | 1626 | 1321 | 1362 | 1127 |
| chr16 | 364747 | 124182 | 3968 | 2002 | 1835 | 1386 | 1093 | 1311 |
| chr17 | 473261 | 168469 | 5581 | 2780 | 2582 | 1950 | 1480 | 1907 |
| chr18 | 144300 | 49112 | 2504 | 785 | 682 | 539 | 377 | 459 |
| chr19 | 494738 | 189411 | 7209 | 3543 | 3239 | 2269 | 1668 | 2314 |
| chr20 | 217223 | 70308 | 3059 | 1243 | 1158 | 907 | 659 | 926 |
| chr21 | 113368 | 29728 | 939 | 495 | 436 | 354 | 306 | 427 |
| chr22 | 223385 | 73509 | 2401 | 1156 | 1068 | 798 | 633 | 771 |
| chrX | 222743 | 94591 | 4997 | 1516 | 1349 | 1161 | 959 | 1841 |
| chrY | 15190 | 4039 | 277 | 81 | 71 | 59 | 148 | 254 |
| Total | 8253710 | 2885489 | 123554 | 49822 | 44534 | 35415 | 25921 | 33669 |

TABLE 3

| GEO ID | File name | Pubmed ID | Antibody used | Antibody vendor | Peak Finder Used | # Uniquely mapped reads (in millions) | # Peaks Called |
|---|---|---|---|---|---|---|---|
| GSM353631 | VCaP_regular_medium_H3K4me1 | 20478527 | ab8895 | Abcam | MACS | 6.96 | 23116 |
| GSM353632 | VCaP_regular_medium_H3K4me2 | 20478527 | ab7766 | Abcam | MACS | 5.97 | 74153 |
| GSM353620 | VCaP_regular_medium_H3K4me3 | 20478527 | ab8580 | Abcam | MACS | 10.95 | 30043 |
| GSM353624 | VCaP_regular_medium_H3K36me3 | 20478527 | ab9050 | Abcam | SICER | 9.91 | 29860 |
| GSM353629 | VCaP_regular_medium_Ace_H3 | 20478527 | 06-599 | Millipore | MACS | 4.76 | 41971 |
| GSM353622 | VCaP_regular_medium_Pan_H3 | 20478527 | ab1791 | Abcam | MACS | 5.91 | control |
| GSM353623 | VCaP_regular_medium_PolI1 | 20478527 | ab817 | Abcam | MACS | 6.88 | 16941 |
| GSM353634 | LN_CaP_regular_medium_H3K4me1 | 20478527 | ab8895 | Abcam | MACS | 6.19 | 31109 |
| GSM353635 | LN_CaP_regular_medium_H3K4me2 | 20478527 | ab7766 | Abcam | MACS | 6.14 | 62061 |
| GSM353626 | LN_CaP_regular_medium_H3K4me3 | 20478527 | ab8580 | Abcam | MACS | 10.22 | 19638 |
| GSM353627 | LN_CaP_regular_medium_H3K36me3 | 20478527 | ab9050 | Abcam | SICER | 9.15 | 24932 |
| GSM353628 | LN_CaP_regular_medium_Ace_H3 | 20478527 | 06-599 | Millipore | MACS | 4.76 | 33211 |
| GSM353617 | LNCaP_EthI_PolI1 | 20478527 | ab817 | Abcam | MACS | 1.36 | 8232 |
| GSM353353 | tissue_H3K4me3 | 20478527 | ab8580 | Abcam | 51459 | 11.85 | 23750 |

TABLE 4

| Category | Type | Name | Interval | Fold change (Unlogged) | SAM score ((r)/(s + s0)) |
|---|---|---|---|---|---|
| PROTEIN | UPREG. | TU_0084471_0 | chr5: 33980375-34087770 | 12.75 | 7.71 |
| NOVEL | UPREG. | TU_0099865_0 | chr8: 128087842-128095202 | 7.07 | 7.41 |
| PROTEIN | UPREG. | TU_0123088_0 | chr2: 238147710-238169707 | 3.01 | 7.01 |
| ncRNA | UPREG. | TU_0102832_0 | chr9: 78569118-78593537 | 12.23 | 6.93 |
| PROTEIN | UPREG. | TU_0078322_0 | chr12: 32260254-32260805 | 4.52 | 6.82 |
| ncRNA | UPREG. | TU_0101270_0 | chr21: 41853044-41875166 | 9.82 | 6.79 |
| PROTEIN | UPREG. | TU_0027326_0 | chrX: 16874726-17077384 | 3.31 | 6.79 |
| PROTEIN | UPREG. | TU_0092114_0 | chr11: 60223535-60239968 | 7.40 | 6.65 |
| PROTEIN | UPREG. | TU_0044448_0 | chr13: 51509122-51537693 | 4.77 | 6.59 |
| PROTEIN | UPREG. | TU_0023159_0 | chr19: 40224450-40249318 | 3.69 | 6.56 |
| PROTEIN | UPREG. | TU_0092116_0 | chr11: 60238519-60239968 | 7.50 | 6.44 |
| PROTEIN | UPREG. | TU_0123090_0 | chr2: 238164428-238165452 | 3.57 | 6.24 |

TABLE 4-continued

| Category | Type | Name | Interval | Fold change (Unlogged) | SAM score ((r)/(s + s0)) |
|---|---|---|---|---|---|
| ncRNA | UPREG. | TU__0046239__0 | chr4: 1185645-1201937 | 5.19 | 6.22 |
| PROTEIN | UPREG. | TU__0122750__0 | chr2: 231610299-231625861 | 4.56 | 6.14 |
| PROTEIN | UPREG. | TU__0082723__0 | chr12: 120142512-120219979 | 3.26 | 6.13 |
| PROTEIN | UPREG. | TU__0123089__0 | chr2: 238164428-238165452 | 4.22 | 6.12 |
| PROTEIN | UPREG. | TU__0101111__0 | chr21: 36989329-37045253 | 4.04 | 6.04 |
| PROTEIN | UPREG. | TU__0090152__0 | chr11: 4965638-4969515 | 6.38 | 5.99 |
| PROTEIN | UPREG. | TU__0101113__0 | chr21: 36994126-37045253 | 3.76 | 5.98 |
| PROTEIN | UPREG. | TU__0045026__0 | chr13: 94660907-94668260 | 3.68 | 5.97 |
| ncRNA | UPREG. | TU__0101274__0 | chr21: 41869930-41870631 | 8.95 | 5.88 |
| PROTEIN | UPREG. | TU__0046235__0 | chr4: 1181913-1189142 | 4.28 | 5.87 |
| NOVEL | UPREG. | TU__0054603__0 | chr16: 82380933-82394836 | 7.25 | 5.84 |
| PROTEIN | UPREG. | TU__0101308__0 | chr21: 42605257-42608791 | 4.97 | 5.83 |
| PROTEIN | UPREG. | TU__0084137__0 | chr5: 13981150-13997615 | 3.91 | 5.80 |
| PROTEIN | UPREG. | TU__0084127__0 | chr5: 13882635-13892514 | 4.95 | 5.79 |
| PROTEIN | UPREG. | TU__0101119__0 | chr21: 37034016-37045253 | 3.56 | 5.78 |
| PROTEIN | UPREG. | TU__0054919__0 | chr16: 88188842-88191143 | 3.46 | 5.75 |
| PROTEIN | UPREG. | TU__0120963__0 | chr2: 172658361-172662549 | 27.56 | 5.66 |
| PROTEIN | UPREG. | TU__0044977__0 | chr13: 94524392-94621526 | 3.64 | 5.64 |
| PROTEIN | UPREG. | TU__0052614__0 | chr16: 20542057-20616514 | 6.65 | 5.63 |
| NOVEL | UPREG. | TU__0084303__0 | chr5: 15899476-15955226 | 7.46 | 5.61 |
| PROTEIN | UPREG. | TU__0060406__0 | chr1: 28134091-28158290 | 3.03 | 5.61 |
| PROTEIN | UPREG. | TU__0060407__0 | chr1: 28155047-28170460 | 2.41 | 5.60 |
| ncRNA | UPREG. | TU__0103252__0 | chr9: 96357168-96369978 | 5.00 | 5.58 |
| PROTEIN | UPREG. | TU__0034719__0 | chr14: 73490756-73555773 | 2.51 | 5.57 |
| PROTEIN | UPREG. | TU__0070457__0 | chr20: 2258975-2269890 | 6.49 | 5.56 |
| NOVEL | UPREG. | TU__0114240__0 | chr2: 1534883-1538193 | 5.25 | 5.54 |
| PROTEIN | UPREG. | TU__0087676__0 | chr5: 138643394-138648458 | 2.75 | 5.50 |
| PROTEIN | UPREG. | TU__0084138__0 | chr5: 13976388-13981285 | 4.09 | 5.48 |
| ncRNA | UPREG. | TU__0046237__0 | chr4: 1162036-1195088 | 4.29 | 5.47 |
| ncRNA | UPREG. | TU__0060421__0 | chr1: 28157480-28158290 | 3.12 | 5.44 |
| PROTEIN | UPREG. | TU__0061436__0 | chr1: 37954250-37957136 | 2.66 | 5.41 |
| PROTEIN | UPREG. | TU__0044894__0 | chr13: 94470096-94752898 | 2.85 | 5.38 |
| PROTEIN | UPREG. | TU__0034720__0 | chr14: 73486609-73503474 | 2.20 | 5.38 |
| PROTEIN | UPREG. | TU__0090153__0 | chr11: 4969009-4970186 | 7.37 | 5.34 |
| PROTEIN | UPREG. | TU__0061432__0 | chr1: 37954250-37958679 | 2.65 | 5.31 |
| PROTEIN | UPREG. | TU__0090268__0 | chr11: 6659768-6661138 | 1.76 | 5.30 |
| PROTEIN | UPREG. | TU__0084120__0 | chr5: 13743434-13864864 | 3.59 | 5.29 |
| PROTEIN | UPREG. | TU__0045059__0 | chr13: 94638351-94639152 | 2.93 | 5.28 |
| ncRNA | UPREG. | TU__0075807__0 | chr10: 101676895-101680049 | 2.61 | 5.27 |
| PROTEIN | UPREG. | TU__0078285__0 | chr12: 32150992-32421799 | 3.02 | 5.26 |
| PROTEIN | UPREG. | TU__0103019__0 | chr9: 87826642-87905011 | 2.77 | 5.22 |
| PROTEIN | UPREG. | TU__0046244__0 | chr4: 1185645-1216291 | 3.51 | 5.21 |
| PROTEIN | UPREG. | TU__0075664__0 | chr10: 98752046-98935267 | 4.15 | 5.20 |
| PROTEIN | UPREG. | TU__0090949__0 | chr11: 24475021-25059245 | 3.50 | 5.19 |
| NOVEL | UPREG. | TU__0099864__0 | chr8: 128094589-128103681 | 3.56 | 5.17 |
| PROTEIN | UPREG. | TU__0030273__0 | chrX: 106690714-106735138 | 3.52 | 5.15 |
| PROTEIN | UPREG. | TU__0090128__0 | chr11: 4656012-4675667 | 5.26 | 5.15 |
| PROTEIN | UPREG. | TU__0017700__0 | chr17: 51183394-51209728 | 2.05 | 5.13 |
| ncRNA | UPREG. | TU__0018760__0 | chr17: 71645643-71652049 | 6.41 | 5.08 |
| PROTEIN | UPREG. | TU__0018765__0 | chr17: 71652262-71747927 | 5.18 | 5.06 |
| ncRNA | UPREG. | TU__0114235__0 | chr2: 1521347-1608386 | 4.22 | 5.04 |
| PROTEIN | UPREG. | TU__0084132__0 | chr5: 13964466-13969509 | 4.30 | 5.03 |
| NOVEL | UPREG. | TU__0049368__0 | chr4: 106772318-106772770 | 3.40 | 5.03 |
| PROTEIN | UPREG. | TU__0115204__0 | chr2: 27175274-27195587 | 2.37 | 4.99 |
| PROTEIN | UPREG. | TU__0115205__0 | chr2: 27163593-27178264 | 2.49 | 4.98 |
| PROTEIN | UPREG. | TU__0062449__0 | chr1: 46418568-46424753 | 1.95 | 4.96 |
| PROTEIN | UPREG. | TU__0072027__0 | chr20: 35964872-36007156 | 3.91 | 4.95 |
| ncRNA | UPREG. | TU__0086706__0 | chr5: 116818427-116835522 | 2.91 | 4.92 |
| PROTEIN | UPREG. | TU__0084136__0 | chr5: 13972327-13976416 | 3.37 | 4.91 |
| PROTEIN | UPREG. | TU__0042761__0 | chr13: 23200813-23363662 | 3.54 | 4.90 |
| PROTEIN | UPREG. | TU__0114168__0 | chr15: 99658271-99847175 | 2.25 | 4.89 |
| ncRNA | UPREG. | TU__0018764__0 | chr17: 71650143-71652049 | 6.28 | 4.86 |
| PROTEIN | UPREG. | TU__0085832__0 | chr5: 76150810-76167055 | 3.84 | 4.86 |
| NOVEL | UPREG. | TU__0090142__0 | chr11: 4748677-4760303 | 12.08 | 4.86 |
| PROTEIN | UPREG. | TU__0103018__0 | chr9: 87745936-87851451 | 2.41 | 4.83 |
| NOVEL | UPREG. | TU__0096472__0 | chr11: 133844590-133862924 | 6.85 | 4.82 |
| PROTEIN | UPREG. | TU__0029229__0 | chrX: 70349443-70377690 | 2.34 | 4.81 |
| NOVEL | UPREG. | TU__0084306__0 | chr5: 15896315-15947088 | 5.37 | 4.78 |
| PROTEIN | UPREG. | TU__0024934__0 | chr19: 54352845-54407356 | 1.88 | 4.77 |
| NOVEL | UPREG. | TU__0096473__0 | chr11: 133844590-133862995 | 6.96 | 4.76 |
| ncRNA | UPREG. | TU__0101131__0 | chr21: 36994126-37041774 | 3.57 | 4.74 |
| PROTEIN | UPREG. | TU__0008239__0 | chr7: 7362390-7537552 | 3.00 | 4.73 |
| PROTEIN | UPREG. | TU__0000022__0 | chr6: 1567640-2190842 | 2.14 | 4.72 |
| PROTEIN | UPREG. | TU__0065193__0 | chr1: 145122471-145183544 | 2.72 | 4.72 |
| PROTEIN | UPREG. | TU__0061439__0 | chr1: 37954250-37971671 | 2.46 | 4.71 |
| ncRNA | UPREG. | TU__0096470__0 | chr11: 133841573-133850753 | 6.44 | 4.70 |

TABLE 4-continued

| Category | Type | Name | Interval | Fold change (Unlogged) | SAM score ((r)/(s + s0)) |
|---|---|---|---|---|---|
| PROTEIN | UPREG. | TU_0046219_0 | chr4: 993725-995193 | 3.90 | 4.69 |
| NOVEL | UPREG. | TU_0078288_0 | chr12: 32393283-32405731 | 2.47 | 4.67 |
| PROTEIN | UPREG. | TU_0101115_0 | chr21: 37000839-37005920 | 3.31 | 4.67 |
| NOVEL | UPREG. | TU_0099884_0 | chr8: 128301493-128307576 | 2.65 | 4.66 |
| PROTEIN | UPREG. | TU_0008489_0 | chr7: 23685881-23708938 | 1.70 | 4.64 |
| PROTEIN | UPREG. | TU_0042767_0 | chr13: 23186666-23204319 | 4.82 | 4.64 |
| PROTEIN | UPREG. | TU_0061430_0 | chr1: 37930752-37957012 | 2.30 | 4.64 |
| PROTEIN | UPREG. | TU_0079451_0 | chr12: 52696814-52736068 | 3.77 | 4.64 |
| PROTEIN | UPREG. | TU_0069545_0 | chr1: 226711356-226712534 | 2.36 | 4.63 |
| PROTEIN | UPREG. | TU_0045837_0 | chr13: 113151239-113151444 | 3.73 | 4.61 |
| PROTEIN | UPREG. | TU_0101138_0 | chr21: 36994126-37004010 | 3.54 | 4.61 |
| PROTEIN | UPREG. | TU_0049362_0 | chr4: 106693102-106771686 | 3.06 | 4.58 |
| PROTEIN | UPREG. | TU_0055044_0 | chr16: 88589437-88613428 | 2.23 | 4.55 |
| PROTEIN | UPREG. | TU_0038605_0 | chr3: 52689830-52704651 | 1.54 | 4.55 |
| ncRNA | UPREG. | TU_0062653_0 | chr1: 51756544-51799759 | 2.52 | 4.54 |
| PROTEIN | UPREG. | TU_0080359_0 | chr12: 63512292-63558861 | 1.87 | 4.53 |
| PROTEIN | UPREG. | TU_0012481_0 | chr7: 111155336-111217889 | 2.04 | 4.52 |
| PROTEIN | UPREG. | TU_0076355_0 | chr10: 115970327-115995953 | 10.34 | 4.52 |
| PROTEIN | UPREG. | TU_0099892_0 | chr8: 128817416-128822629 | 2.33 | 4.52 |
| ncRNA | UPREG. | TU_0050484_0 | chr1: 28706931-28707187 | 2.53 | 4.51 |
| PROTEIN | UPREG. | TU_0046232_0 | chr4: 1147069-1175181 | 2.75 | 4.50 |
| PROTEIN | UPREG. | TU_0107858_0 | chr22: 40664589-40673116 | 2.27 | 4.50 |
| PROTEIN | UPREG. | TU_0042794_0 | chr13: 23228589-23228839 | 3.47 | 4.49 |
| PROTEIN | UPREG. | TU_0057850_0 | chr1: 1523259-1525373 | 2.80 | 4.48 |
| PROTEIN | UPREG. | TU_0023156_0 | chr19: 40109515-40127909 | 2.56 | 4.48 |
| PROTEIN | UPREG. | TU_0102821_0 | chr9: 78263916-78312152 | 2.98 | 4.48 |
| PROTEIN | UPREG. | TU_0081659_0 | chr12: 108636297-108700791 | 2.90 | 4.47 |
| PROTEIN | UPREG. | TU_0049370_0 | chr4: 106776991-106847697 | 2.15 | 4.47 |
| PROTEIN | UPREG. | TU_0047672_0 | chr4: 41807710-41840313 | 2.51 | 4.47 |
| PROTEIN | UPREG. | TU_0114959_0 | chr2: 24865860-24869912 | 1.68 | 4.46 |
| PROTEIN | UPREG. | TU_0037043_0 | chr3: 13332730-13436812 | 1.77 | 4.46 |
| PROTEIN | UPREG. | TU_0087443_0 | chr5: 135237637-135247034 | 4.09 | 4.46 |
| PROTEIN | UPREG. | TU_0086635_0 | chr5: 114489075-114543909 | 2.02 | 4.43 |
| PROTEIN | UPREG. | TU_0107859_0 | chr22: 40664589-40665721 | 2.38 | 4.42 |
| NOVEL | UPREG. | TU_0106548_0 | chr22: 22209111-22212055 | 6.49 | 4.42 |
| PROTEIN | UPREG. | TU_0067165_0 | chr1: 160797907-160845907 | 1.81 | 4.40 |
| PROTEIN | UPREG. | TU_0020146_0 | chr19: 3728970-3737293 | 2.53 | 4.39 |
| PROTEIN | UPREG. | TU_0107642_0 | chr22: 39046992-39047479 | 1.69 | 4.38 |
| PROTEIN | UPREG. | TU_0016185_0 | chr17: 31415814-31422953 | 3.63 | 4.38 |
| NOVEL | UPREG. | TU_0104717_0 | chr9: 130697833-130698832 | 2.79 | 4.36 |
| PROTEIN | UPREG. | TU_0052105_0 | chr16: 4785874-4786488 | 2.99 | 4.36 |
| PROTEIN | UPREG. | TU_0059663_0 | chr1: 21795295-21850886 | 1.99 | 4.35 |
| PROTEIN | UPREG. | TU_0108030_0 | chr22: 43527117-43638770 | 1.74 | 4.34 |
| PROTEIN | UPREG. | TU_0093781_0 | chr11: 67151991-67154057 | 2.48 | 4.33 |
| PROTEIN | UPREG. | TU_0086924_0 | chr5: 126233852-126241807 | 2.89 | 4.32 |
| PROTEIN | UPREG. | TU_0048191_0 | chr4: 72423780-72424347 | 2.93 | 4.32 |
| PROTEIN | UPREG. | TU_0034727_0 | chr14: 73508223-73508442 | 2.29 | 4.32 |
| PROTEIN | UPREG. | TU_0096297_0 | chr11: 128342286-128353900 | 1.84 | 4.31 |
| PROTEIN | UPREG. | TU_0007829_0 | chr7: 3625233-4275129 | 4.39 | 4.30 |
| PROTEIN | UPREG. | TU_0116252_0 | chr2: 47449810-47467636 | 1.93 | 4.30 |
| PROTEIN | UPREG. | TU_0115216_0 | chr2: 27175274-27177799 | 2.02 | 4.27 |
| PROTEIN | UPREG. | TU_0018409_0 | chr17: 65013419-65049811 | 2.02 | 4.26 |
| PROTEIN | UPREG. | TU_0099847_0 | chr8: 126511614-126519830 | 2.75 | 4.25 |
| PROTEIN | UPREG. | TU_0035152_0 | chr14: 81062791-81063412 | 2.22 | 4.25 |
| PROTEIN | UPREG. | TU_0040936_0 | chr3: 155391785-155458293 | 2.10 | 4.25 |
| PROTEIN | UPREG. | TU_0027558_0 | chrX: 23595491-23614436 | 1.66 | 4.25 |
| PROTEIN | UPREG. | TU_0076460_0 | chr10: 121248954-121292235 | 1.66 | 4.24 |
| PROTEIN | UPREG. | TU_0067170_0 | chr1: 160826739-160826994 | 2.10 | 4.23 |
| PROTEIN | UPREG. | TU_0103050_0 | chr9: 89409681-89512477 | 2.30 | 4.23 |
| PROTEIN | UPREG. | TU_0112868_0 | chr15: 77390455-77402242 | 1.55 | 4.23 |
| PROTEIN | UPREG. | TU_0090960_0 | chr11: 25059388-25060757 | 3.35 | 4.23 |
| PROTEIN | UPREG. | TU_0072165_0 | chr20: 40142077-40204030 | 4.69 | 4.22 |
| PROTEIN | UPREG. | TU_0044687_0 | chr13: 74756644-74954891 | 2.04 | 4.21 |
| ncRNA | UPREG. | TU_0096477_0 | chr11: 133879414-133850753 | 4.43 | 4.21 |
| PROTEIN | UPREG. | TU_0093947_0 | chr11: 68208575-68215238 | 1.41 | 4.20 |
| PROTEIN | UPREG. | TU_0103253_0 | chr9: 96405246-96442373 | 1.69 | 4.20 |
| PROTEIN | UPREG. | TU_0099863_0 | chr11: 57008498-57039966 | 2.69 | 4.20 |
| PROTEIN | UPREG. | TU_0106199_0 | chr22: 18308042-18314411 | 3.94 | 4.20 |
| NOVEL | UPREG. | TU_0090140_0 | chr11: 4748163-4759145 | 6.33 | 4.20 |
| PROTEIN | UPREG. | TU_0103051_0 | chr9: 89302442-89409890 | 2.37 | 4.19 |
| NOVEL | UPREG. | TU_0078290_0 | chr12: 32394534-32410898 | 3.20 | 4.19 |
| PROTEIN | UPREG. | TU_0029336_0 | chrX: 70669659-70712461 | 1.70 | 4.18 |
| PROTEIN | UPREG. | TU_0092155_0 | chr11: 60871597-60886554 | 1.80 | 4.18 |
| PROTEIN | UPREG. | TU_0095597_0 | chr11: 114549577-114880335 | 1.75 | 4.18 |
| PROTEIN | UPREG. | TU_0082724_0 | chr12: 120230545-120274615 | 1.42 | 4.17 |
| PROTEIN | UPREG. | TU_0079770_0 | chr12: 55040666-55042824 | 4.25 | 4.16 |

TABLE 4-continued

| Category | Type | Name | Interval | Fold change (Unlogged) | SAM score ((r)/(s + s0)) |
|---|---|---|---|---|---|
| PROTEIN | UPREG. | TU_0000263_0 | chr6: 4060925-4080831 | 1.55 | 4.16 |
| NOVEL | UPREG. | TU_0040394_0 | chr3: 133418632-133441282 | 3.46 | 4.16 |
| PROTEIN | UPREG. | TU_0066594_0 | chr1: 154245443-154257363 | 1.40 | 4.15 |
| PROTEIN | UPREG. | TU_0099852_0 | chr8: 126515081-126519830 | 2.81 | 4.15 |
| PROTEIN | UPREG. | TU_0100363_0 | chr8: 144891741-144899598 | 2.24 | 4.14 |
| PROTEIN | UPREG. | TU_0096461_0 | chr11: 133751095-133757235 | 2.10 | 4.13 |
| ncRNA | UPREG. | TU_0044488_0 | chr13: 51641093-51641330 | 2.76 | 4.13 |
| PROTEIN | UPREG. | TU_0048990_0 | chr4: 95592056-95804933 | 2.30 | 4.13 |
| NOVEL | UPREG. | TU_0078293_0 | chr12: 32396393-32414822 | 2.90 | 4.13 |
| PROTEIN | UPREG. | TU_0046201_0 | chr4: 991841-1010686 | 2.57 | 4.12 |
| PROTEIN | UPREG. | TU_0091866_0 | chr11: 57008498-57010253 | 2.54 | 4.12 |
| PROTEIN | UPREG. | TU_0011133_0 | chr7: 94378726-94759741 | 1.77 | 4.12 |
| PROTEIN | UPREG. | TU_0122941_0 | chr2: 234410713-234427931 | 3.28 | 4.12 |
| PROTEIN | UPREG. | TU_0084131_0 | chr5: 13929889-13953380 | 2.62 | 4.12 |
| NOVEL | UPREG. | TU_0084142_0 | chr5: 14017046-14021379 | 3.59 | 4.11 |
| PROTEIN | UPREG. | TU_0087955_0 | chr5: 140931645-140931865 | 2.00 | 4.10 |
| PROTEIN | UPREG. | TU_0085953_0 | chr5: 79410392-79410908 | 3.35 | 4.10 |
| PROTEIN | UPREG. | TU_0022288_0 | chr19: 18357973-18360121 | 2.75 | 4.09 |
| PROTEIN | UPREG. | TU_0085951_0 | chr5: 79366959-79414885 | 3.01 | 4.09 |
| PROTEIN | UPREG. | TU_0060849_0 | chr1: 32572021-32574435 | 1.81 | 4.09 |
| PROTEIN | UPREG. | TU_0087441_0 | chr5: 134934290-134942617 | 2.74 | 4.09 |
| PROTEIN | UPREG. | TU_0042725_0 | chr13: 23148223-23200531 | 4.96 | 4.09 |
| PROTEIN | UPREG. | TU_0039018_0 | chr3: 66510805-66634168 | 1.69 | 4.08 |
| PROTEIN | UPREG. | TU_0096299_0 | chr11: 128340164-128347506 | 1.70 | 4.07 |
| PROTEIN | UPREG. | TU_0022290_0 | chr19: 18357973-18359195 | 2.64 | 4.07 |
| PROTEIN | UPREG. | TU_0100684_0 | chr8: 146190487-146191030 | 1.89 | 4.06 |
| PROTEIN | UPREG. | TU_0042974_0 | chr13: 26148671-26148967 | 2.81 | 4.06 |
| NOVEL | UPREG. | TU_0084308_0 | chr5: 15938753-15949124 | 4.09 | 4.06 |
| NOVEL | UPREG. | TU_0082746_0 | chr12: 120197102-120197416 | 4.97 | 4.06 |
| PROTEIN | UPREG. | TU_0014355_0 | chr17: 2650561-2887730 | 1.92 | 4.05 |
| PROTEIN | UPREG. | TU_0114110_0 | chr15: 99250537-99274351 | 2.01 | 4.05 |
| PROTEIN | UPREG. | TU_0096341_0 | chr11: 129534843-129585464 | 1.64 | 4.04 |
| PROTEIN | UPREG. | TU_0052083_0 | chr16: 4784094-4805339 | 2.71 | 4.04 |
| NOVEL | UPREG. | TU_0078196_0 | chr12: 32394534-32405549 | 2.92 | 4.04 |
| PROTEIN | UPREG. | TU_0084126_0 | chr5: 13892443-13903812 | 3.64 | 4.03 |
| NOVEL | UPREG. | TU_0047312_0 | chr4: 39217669-39222163 | 3.83 | 4.02 |
| PROTEIN | UPREG. | TU_0008287_0 | chr7: 8119340-8268973 | 1.65 | 4.02 |
| PROTEIN | UPREG. | TU_0018937_0 | chr17: 73714011-73714967 | 1.61 | 4.01 |
| PROTEIN | UPREG. | TU_0048995_0 | chr4: 95805027-95808417 | 2.47 | 4.00 |
| PROTEIN | UPREG. | TU_0038694_0 | chr3: 53810226-53855769 | 2.03 | 3.99 |
| ncRNA | UPREG. | TU_0046233_0 | chr4: 1202157-1232168 | 2.45 | 3.99 |
| PROTEIN | UPREG. | TU_0019018_0 | chr17: 75372094-75381243 | 2.25 | 3.98 |
| PROTEIN | UPREG. | TU_0042326_0 | chr3: 199123974-199125319 | 1.77 | 3.98 |
| PROTEIN | UPREG. | TU_0099893_0 | chr8: 128817416-128819105 | 2.23 | 3.98 |
| PROTEIN | UPREG. | TU_0012491_0 | chr7: 111304238-111362856 | 1.91 | 3.98 |
| PROTEIN | UPREG. | TU_0112335_0 | chr15: 70816880-70864494 | 1.71 | 3.97 |
| PROTEIN | UPREG. | TU_0047964_0 | chr4: 57020861-57038533 | 1.74 | 3.97 |
| PROTEIN | UPREG. | TU_0052565_0 | chr16: 19362784-19409995 | 1.98 | 3.96 |
| NOVEL | UPREG. | TU_0042717_0 | chr13: 23149908-23200198 | 4.95 | 3.96 |
| PROTEIN | UPREG. | TU_0017374_0 | chr17: 43380086-43404182 | 1.53 | 3.96 |
| PROTEIN | UPREG. | TU_0071058_0 | chr20: 20318209-20549154 | 2.02 | 3.96 |
| PROTEIN | UPREG. | TU_0105741_0 | chrY: 6971017-6998339 | 2.20 | 3.95 |
| PROTEIN | UPREG. | TU_0018995_0 | chr17: 74491566-74517485 | 1.64 | 3.94 |
| PROTEIN | UPREG. | TU_0103055_0 | chr9: 89512509-8913285 | 1.92 | 3.93 |
| PROTEIN | UPREG. | TU_0041139_0 | chr3: 171237964-171285906 | 1.91 | 3.93 |
| PROTEIN | UPREG. | TU_0042325_0 | chr3: 199124975-199143480 | 1.74 | 3.93 |
| PROTEIN | UPREG. | TU_0020688_0 | chr19: 8180084-8237335 | 1.60 | 3.93 |
| PROTEIN | UPREG. | TU_0118314_0 | chr2: 99086923-99100654 | 1.78 | 3.92 |
| PROTEIN | UPREG. | TU_0017875_0 | chr17: 54652767-54706896 | 2.33 | 3.92 |
| PROTEIN | UPREG. | TU_0037277_0 | chr3: 24134438-24511318 | 1.75 | 3.92 |
| PROTEIN | UPREG. | TU_0047593_0 | chr4: 40446539-40457235 | 1.90 | 3.91 |
| PROTEIN | UPREG. | TU_0114108_0 | chr15: 99235494-99274389 | 2.00 | 3.91 |
| ncRNA | UPREG. | TU_0024530_0 | chr19: 50889160-50909766 | 1.72 | 3.91 |
| PROTEIN | UPREG. | TU_0008957_0 | chr7: 38308886-38325338 | 2.62 | 3.91 |
| PROTEIN | UPREG. | TU_0043122_0 | chr13: 28981555-28989371 | 1.73 | 3.90 |
| PROTEIN | UPREG. | TU_0076644_0 | chr10: 127398227-127398596 | 2.06 | 3.90 |
| PROTEIN | UPREG. | TU_0045423_0 | chr13: 100053877-100125079 | 2.02 | 3.89 |
| PROTEIN | UPREG. | TU_0045495_0 | chr13: 107720446-107737194 | 2.06 | 3.88 |
| PROTEIN | UPREG. | TU_0076648_0 | chr10: 127412714-127442685 | 1.64 | 3.88 |
| NOVEL | UPREG. | TU_0088857_0 | chr5: 172259171-172275517 | 1.69 | 3.87 |
| NOVEL | UPREG. | TU_0044453_0 | chr13: 51505777-51524522 | 2.96 | 3.86 |
| NOVEL | UPREG. | TU_0047330_0 | chr4: 39217641-39222163 | 3.43 | 3.86 |
| PROTEIN | UPREG. | TU_0100838_0 | chr21: 30508275-30510244 | 2.43 | 3.86 |
| NOVEL | UPREG. | TU_0106544_0 | chr22: 22210421-22220506 | 4.27 | 3.85 |
| ncRNA | UPREG. | TU_0100275_0 | chr8: 144520506-144537551 | 2.11 | 3.85 |
| PROTEIN | UPREG. | TU_0057466_0 | chr18: 72853744-72866791 | 1.58 | 3.84 |

TABLE 4-continued

| Category | Type | Name | Interval | Fold change (Unlogged) | SAM score ((r)/(s + s0)) |
|---|---|---|---|---|---|
| PROTEIN | UPREG. | TU_0040010_0 | chr3: 126311839-126412928 | 2.16 | 3.84 |
| PROTEIN | UPREG. | TU_0042800_0 | chr13: 23360816-23370548 | 2.73 | 3.84 |
| PROTEIN | UPREG. | TU_0117501_0 | chr2: 74065748-74174193 | 1.71 | 3.83 |
| PROTEIN | UPREG. | TU_0053389_0 | chr16: 45673980-45701001 | 2.66 | 3.83 |
| PROTEIN | UPREG. | TU_0087944_0 | chr5: 140874777-140978925 | 1.47 | 3.83 |
| PROTEIN | UPREG. | TU_0017393_0 | chr17: 43389397-43390300 | 1.90 | 3.82 |
| PROTEIN | UPREG. | TU_0008919_0 | chr7: 38257158-38271020 | 1.93 | 3.82 |
| PROTEIN | UPREG. | TU_0033383_0 | chr14: 50259793-50367616 | 1.51 | 3.82 |
| PROTEIN | UPREG. | TU_0049911_0 | chr4: 139304784-139382952 | 2.48 | 3.82 |
| PROTEIN | UPREG. | TU_0024366_0 | chr19: 50100808-50104487 | 1.86 | 3.82 |
| PROTEIN | UPREG. | TU_0070109_0 | chr1: 243979271-244159914 | 1.56 | 3.81 |
| PROTEIN | UPREG. | TU_0120975_0 | chr2: 182104631-182107832 | 1.86 | 3.80 |
| NOVEL | UPREG. | TU_0044933_0 | chr13: 94755992-94760688 | 2.52 | 3.80 |
| PROTEIN | UPREG. | TU_0103689_0 | chr9: 111019219-111122750 | 1.75 | 3.80 |
| PROTEIN | UPREG. | TU_0096460_0 | chr11: 133734857-133786962 | 2.09 | 3.79 |
| PROTEIN | UPREG. | TU_0071115_0 | chr20: 24934888-24986948 | 1.48 | 3.79 |
| PROTEIN | UPREG. | TU_0093783_0 | chr11: 67153661-67153870 | 2.48 | 3.79 |
| PROTEIN | UPREG. | TU_0047591_0 | chr4: 40457999-40506655 | 1.79 | 3.79 |
| PROTEIN | UPREG. | TU_0112336_0 | chr15: 70830765-70838346 | 1.63 | 3.78 |
| PROTEIN | UPREG. | TU_0066664_0 | chr1: 154481433-154485049 | 2.29 | 3.78 |
| PROTEIN | UPREG. | TU_0018812_0 | chr17: 72119376-72151549 | 3.38 | 3.78 |
| PROTEIN | UPREG. | TU_0110225_0 | chr15: 48510091-48912722 | 3.60 | 3.78 |
| ncRNA | UPREG. | TU_0054545_0 | chr16: 79431010-79431852 | 10.26 | 3.78 |
| PROTEIN | UPREG. | TU_0107643_0 | chr22: 39072466-39093168 | 1.36 | 3.78 |
| PROTEIN | UPREG. | TU_0025230_0 | chr19: 55992773-56000199 | 1.86 | 3.78 |
| PROTEIN | UPREG. | TU_0012480_0 | chr7: 111153704-111155311 | 1.81 | 3.77 |
| PROTEIN | UPREG. | TU_0070821_0 | chr20: 8997167-9409281 | 1.64 | 3.77 |
| PROTEIN | UPREG. | TU_0103873_0 | chr9: 115151636-115178163 | 1.52 | 3.77 |
| PROTEIN | UPREG. | TU_0018813_0 | chr17: 72128611-72133119 | 3.56 | 3.76 |
| NOVEL | UPREG. | TU_0112004_0 | chr15: 67644390-67650387 | 3.56 | 3.76 |
| PROTEIN | UPREG. | TU_0043118_0 | chr13: 28981555-29067829 | 1.76 | 3.76 |
| NOVEL | UPREG. | TU_0112003_0 | chr15: 67645590-67775246 | 3.12 | 3.76 |
| NOVEL | UPREG. | TU_0060446_0 | chr1: 28438629-28450156 | 2.23 | 3.75 |
| PROTEIN | UPREG. | TU_0122972_0 | chr2: 236068012-236482693 | 1.69 | 3.75 |
| NOVEL | UPREG. | TU_0106545_0 | chr22: 22218478-22219162 | 3.99 | 3.74 |
| PROTEIN | UPREG. | TU_0087283_0 | chr5: 133753241-133766074 | 1.85 | 3.74 |
| ncRNA | UPREG. | TU_0025312_0 | chr19: 57059515-57145170 | 1.89 | 3.74 |
| PROTEIN | UPREG. | TU_0079679_0 | chr12: 54760142-54783545 | 1.58 | 3.73 |
| PROTEIN | UPREG. | TU_0074564_0 | chr10: 64241765-64246112 | 2.62 | 3.73 |
| PROTEIN | UPREG. | TU_0106189_0 | chr22: 18235213-18328816 | 1.82 | 3.73 |
| PROTEIN | UPREG. | TU_0078994_0 | chr12: 49412412-49428706 | 1.41 | 3.72 |
| ncRNA | UPREG. | TU_0003229_0 | chr6: 41598975-41621874 | 2.05 | 3.72 |
| PROTEIN | UPREG. | TU_0040937_0 | chr3: 155439710-155458293 | 1.96 | 3.72 |
| PROTEIN | UPREG. | TU_0040093_0 | chr3: 128830731-128874336 | 1.87 | 3.72 |
| NOVEL | UPREG. | TU_0106542_0 | chr22: 22211315-22220506 | 3.77 | 3.71 |
| PROTEIN | UPREG. | TU_0019375_0 | chr17: 77608812-77616980 | 1.63 | 3.71 |
| PROTEIN | UPREG. | TU_0042563_0 | chr13: 20264762-20334966 | 1.85 | 3.71 |
| PROTEIN | UPREG. | TU_0103386_0 | chr9: 9905734-99110148 | 1.89 | 3.71 |
| PROTEIN | UPREG. | TU_0030004_0 | chrX: 100534013-100534540 | 1.84 | 3.71 |
| NOVEL | UPREG. | TU_0089906_0 | chr11: 1042845-1045705 | 2.94 | 3.71 |
| NOVEL | UPREG. | TU_0089014_0 | chr5: 176014905-176015351 | 2.01 | 3.71 |
| ncRNA | UPREG. | TU_0056173_0 | chr18: 22523074-22537627 | 3.31 | 3.70 |
| PROTEIN | UPREG. | TU_0052880_0 | chr16: 28393117-28411069 | 1.48 | 3.70 |
| PROTEIN | UPREG. | TU_0100355_0 | chr8: 144884230-144910177 | 2.00 | 3.69 |
| PROTEIN | UPREG. | TU_0096216_0 | chr11: 125271293-125271517 | 2.08 | 3.69 |
| PROTEIN | UPREG. | TU_0092161_0 | chr11: 60884289-60892364 | 1.99 | 3.68 |
| PROTEIN | UPREG. | TU_0086926_0 | chr5: 126241953-126394149 | 2.27 | 3.68 |
| NOVEL | UPREG. | TU_0088230_0 | chr5: 148864170-148864752 | 1.94 | 3.68 |
| ncRNA | UPREG. | TU_0099940_0 | chr8: 129065546-129182684 | 1.61 | 3.68 |
| PROTEIN | UPREG. | TU_0089017_0 | chr5: 176222085-176240501 | 10.21 | 3.67 |
| PROTEIN | UPREG. | TU_0078586_0 | chr12: 46643629-46648944 | 1.47 | 3.67 |
| PROTEIN | UPREG. | TU_0053467_0 | chr16: 51028455-51138080 | 2.19 | 3.67 |
| PROTEIN | UPREG. | TU_0089452_0 | chr5: 179258704-179258997 | 1.62 | 3.67 |
| PROTEIN | UPREG. | TU_0076329_0 | chr10: 115501382-115531028 | 2.60 | 3.67 |
| PROTEIN | UPREG. | TU_0047688_0 | chr4: 42105164-42354144 | 1.68 | 3.67 |
| PROTEIN | UPREG. | TU_0059142_0 | chr1: 16203274-16206548 | 12.41 | 3.67 |
| PROTEIN | UPREG. | TU_0116906_0 | chr2: 63135968-63138462 | 2.81 | 3.66 |
| PROTEIN | UPREG. | TU_0000154_0 | chr6: 3063923-3099152 | 1.53 | 3.66 |
| PROTEIN | UPREG. | TU_0088782_0 | chr5: 170625426-170659593 | 1.78 | 3.66 |
| NOVEL | UPREG. | TU_0089905_0 | chr11: 1042845-1045705 | 2.77 | 3.66 |
| PROTEIN | UPREG. | TU_0101704_0 | chr9: 3265495-3516005 | 2.33 | 3.64 |
| ncRNA | UPREG. | TU_0044897_0 | chr13: 94746488-94760688 | 2.17 | 3.64 |
| PROTEIN | UPREG. | TU_0071059_0 | chr20: 20549245-20641260 | 2.39 | 3.64 |
| ncRNA | UPREG. | TU_0046268_0 | chr4: 1199698-1211108 | 1.93 | 3.63 |
| PROTEIN | UPREG. | TU_0071601_0 | chr20: 32827590-32828002 | 1.75 | 3.62 |
| PROTEIN | UPREG. | TU_0100712_0 | chr21: 15258179-15359100 | 2.14 | 3.62 |

TABLE 4-continued

| Category | Type | Name | Interval | Fold change (Unlogged) | SAM score ((r)/(s + s0)) |
|---|---|---|---|---|---|
| PROTEIN | UPREG. | TU_0092156_0 | chr11: 60885030-60893249 | 1.45 | 3.62 |
| PROTEIN | UPREG. | TU_0091402_0 | chr11: 46255779-46299542 | 1.71 | 3.62 |
| PROTEIN | UPREG. | TU_0039018_0 | chr3: 66376322-66514060 | 1.50 | 3.62 |
| PROTEIN | UPREG. | TU_0100378_0 | chr8: 144899799-144900640 | 2.00 | 3.62 |
| NOVEL | UPREG. | TU_0112025_0 | chr15: 67780574-67782345 | 3.42 | 3.62 |
| PROTEIN | UPREG. | TU_0106031_0 | chr22: 16336630-16412806 | 2.01 | 3.62 |
| PROTEIN | UPREG. | TU_0050785_0 | chr4: 174395360-174453821 | 2.36 | 3.61 |
| PROTEIN | UPREG. | TU_0058834_0 | chr1: 11768665-11783670 | 1.50 | 3.61 |
| PROTEIN | UPREG. | TU_0039496_0 | chr3: 106753939-106754201 | 1.99 | 3.61 |
| ncRNA | UPREG. | TU_0098397_0 | chr8: 69379259-69406175 | 2.73 | 3.61 |
| PROTEIN | UPREG. | TU_0017847_0 | chr17: 54188675-54413808 | 2.82 | 3.61 |
| PROTEIN | UPREG. | TU_0108299_0 | chr22: 49267227-49270226 | 2.03 | 3.60 |
| PROTEIN | UPREG. | TU_0076846_0 | chr10: 135042714-135056670 | 2.27 | 3.59 |
| PROTEIN | UPREG. | TU_0096351_0 | chr11: 129611827-129689996 | 1.61 | 3.59 |
| PROTEIN | UPREG. | TU_0019298_0 | chr17: 77242472-77300154 | 1.51 | 3.59 |
| PROTEIN | UPREG. | TU_0057465_0 | chr18: 72830973-7297379 | 1.56 | 3.59 |
| PROTEIN | UPREG. | TU_0013475_0 | chr7: 148137800-148212367 | 1.74 | 3.59 |
| PROTEIN | UPREG. | TU_0001426_0 | chr6: 28655044-28662198 | 2.56 | 3.59 |
| NOVEL | UPREG. | TU_0106541_0 | chr22: 22209111-22219162 | 4.02 | 3.58 |
| PROTEIN | UPREG. | TU_0073803_0 | chr10: 19005554-19007053 | 1.84 | 3.58 |
| PROTEIN | UPREG. | TU_0040100_0 | chr3: 129253916-129289610 | 1.39 | 3.58 |
| PROTEIN | UPREG. | TU_0001431_0 | chr6: 28978594-28999755 | 1.33 | 3.58 |
| PROTEIN | UPREG. | TU_0076643_0 | chr10: 127398227-127407663 | 1.73 | 3.57 |
| PROTEIN | UPREG. | TU_0089137_0 | chr5: 176814485-176815986 | 1.93 | 3.57 |
| PROTEIN | UPREG. | TU_0098700_0 | chr8: 82806988-82833618 | 1.76 | 3.57 |
| PROTEIN | UPREG. | TU_0093785_0 | chr11: 67186209-67198838 | 3.74 | 3.57 |
| NOVEL | UPREG. | TU_0056168_0 | chr18: 22477042-22477886 | 3.05 | 3.57 |
| PROTEIN | UPREG. | TU_0067222_0 | chr1: 164063363-164147501 | 1.63 | 3.57 |
| PROTEIN | UPREG. | TU_0052172_0 | chr16: 8799176-8799379 | 1.61 | 3.57 |
| PROTEIN | UPREG. | TU_0008360_0 | chr7: 16652301-16712672 | 1.46 | 3.57 |
| PROTEIN | UPREG. | TU_0035610_0 | chr14: 93580687-93582188 | 2.08 | 3.56 |
| PROTEIN | UPREG. | TU_0000168_0 | chr6: 3100128-3102765 | 2.10 | 3.56 |
| PROTEIN | UPREG. | TU_0039649_0 | chr3: 115160992-115164502 | 1.72 | 3.56 |
| PROTEIN | UPREG. | TU_0052843_0 | chr16: 27143818-27187607 | 1.42 | 3.56 |
| NOVEL | UPREG. | TU_0024950_0 | chr19: 54450100-54452968 | 2.11 | 3.55 |
| PROTEIN | UPREG. | TU_0008504_0 | chr7: 24656812-24693891 | 1.99 | 3.55 |
| PROTEIN | UPREG. | TU_0061102_0 | chr1: 35671678-35795597 | 1.44 | 3.55 |
| PROTEIN | UPREG. | TU_0032890_0 | chr14: 36736878-36788106 | 2.36 | 3.55 |
| ncRNA | UPREG. | TU_0046241_0 | chr4: 1158292-1167160 | 2.53 | 3.55 |
| NOVEL | UPREG. | TU_0008499_0 | chr7: 24236191-24236455 | 5.44 | 3.54 |
| PROTEIN | UPREG. | TU_0100172_0 | chr8: 142471307-142511866 | 1.78 | 3.54 |
| NOVEL | UPREG. | TU_0086543_0 | chr5: 110311813-110312092 | 1.53 | 3.53 |
| PROTEIN | UPREG. | TU_0072450_0 | chr20: 44619899-44747359 | 1.83 | 3.53 |
| NOVEL | UPREG. | TU_0044931_0 | chr13: 94755980-94759335 | 2.15 | 3.53 |
| PROTEIN | UPREG. | TU_0093950_0 | chr11: 68214746-68215218 | 1.49 | 3.53 |
| PROTEIN | UPREG. | TU_0006239_0 | chr6: 138649313-138671427 | 2.22 | 3.53 |
| PROTEIN | UPREG. | TU_0065894_0 | chr1: 150044684-150070988 | 1.54 | 3.52 |
| PROTEIN | UPREG. | TU_0078675_0 | chr12: 47602047-47602939 | 1.58 | 3.52 |
| PROTEIN | UPREG. | TU_0052150_0 | chr16: 8799176-8864674 | 1.42 | 3.52 |
| NOVEL | UPREG. | TU_0112021_0 | chr15: 67762926-67783593 | 2.66 | 3.52 |
| PROTEIN | UPREG. | TU_0041581_0 | chr3: 185450132-185459240 | 1.77 | 3.52 |
| PROTEIN | UPREG. | TU_0017269_0 | chr17: 42127174-42189979 | 1.59 | 3.52 |
| PROTEIN | UPREG. | TU_0103138_0 | chr9: 94055563-94056563 | 1.61 | 3.52 |
| PROTEIN | UPREG. | TU_0078683_0 | chr12: 47603989-47604485 | 1.69 | 3.52 |
| PROTEIN | UPREG. | TU_0099209_0 | chr11: 6453771-6453210 | 1.44 | 3.51 |
| ncRNA | UPREG. | TU_0045193_0 | chr13: 97851959-97852689 | 1.98 | 3.51 |
| PROTEIN | UPREG. | TU_0050499_0 | chr4: 156862572-156862939 | 1.82 | 3.51 |
| PROTEIN | UPREG. | TU_0088025_0 | chr5: 142130134-142254088 | 1.89 | 3.51 |
| PROTEIN | UPREG. | TU_0052554_0 | chr16: 19329285-19424714 | 1.78 | 3.51 |
| PROTEIN | UPREG. | TU_0085653_0 | chr5: 70918890-70990273 | 2.39 | 3.51 |
| PROTEIN | UPREG. | TU_0101238_0 | chr21: 41610494-41651888 | 1.89 | 3.50 |
| PROTEIN | UPREG. | TU_0098689_0 | chr8: 82355436-82355977 | 4.15 | 3.49 |
| PROTEIN | UPREG. | TU_0100271_0 | chr8: 144522379-144537551 | 1.93 | 3.49 |
| PROTEIN | UPREG. | TU_0013258_0 | chr7: 139750340-139773086 | 1.85 | 3.49 |
| PROTEIN | UPREG. | TU_0122559_0 | chr2: 224338108-224338327 | 2.32 | 3.49 |
| PROTEIN | UPREG. | TU_0068947_0 | chr1: 212567070-212567723 | 1.74 | 3.48 |
| PROTEIN | UPREG. | TU_0101300_0 | chr21: 42512421-42593934 | 1.60 | 3.48 |
| PROTEIN | UPREG. | TU_0105268_0 | chr9: 138238011-138277254 | 1.49 | 3.47 |
| PROTEIN | UPREG. | TU_0080269_0 | chr12: 62524730-62664317 | 2.05 | 3.47 |
| PROTEIN | UPREG. | TU_0001992_0 | chr6: 31939105-31955076 | 1.56 | 3.47 |
| PROTEIN | UPREG. | TU_0018485_0 | chr17: 70458432-70480451 | 1.58 | 3.47 |
| ncRNA | UPREG. | TU_0050493_0 | chr1: 28705947-28706605 | 1.60 | 2.46 |
| PROTEIN | UPREG. | TU_0085975_0 | chr5: 79478814-79495113 | 1.91 | 3.46 |
| PROTEIN | UPREG. | TU_0018919_0 | chr17: 73678343-73714970 | 1.48 | 3.46 |
| ncRNA | UPREG. | TU_0054534_0 | chr16: 79404014-79431652 | 9.85 | 3.46 |
| PROTEIN | UPREG. | TU_0076107_0 | chr10: 104454315-104488075 | 1.67 | 3.45 |

TABLE 4-continued

| Category | Type | Name | Interval | Fold change (Unlogged) | SAM score ((r)/(s + s0)) |
|---|---|---|---|---|---|
| ncRNA | UPREG. | TU_0069658_0 | chr1: 229724782-229731269 | 1.75 | 3.45 |
| NOVEL | UPREG. | TU_0120387_0 | chr2: 170267824-170281386 | 2.10 | 3.45 |
| PROTEIN | UPREG. | TU_0015665_0 | chr17: 24073407-24077926 | 1.52 | 3.45 |
| ncRNA | UPREG. | TU_0070414_0 | chr20: 1254059-1303172 | 1.68 | 3.45 |
| NOVEL | UPREG. | TU_0072624_0 | chr20: 47335522-47338977 | 1.65 | 3.45 |
| PROTEIN | UPREG. | TU_0012495_0 | chr7: 111373031-111411626 | 2.29 | 3.45 |
| PROTEIN | UPREG. | TU_0076659_0 | chr10: 127514501-127526128 | 1.31 | 3.45 |
| PROTEIN | UPREG. | TU_0088525_0 | chr5: 156625701-156755178 | 1.53 | 3.45 |
| PROTEIN | UPREG. | TU_0046096_0 | chr4: 759449-809939 | 2.01 | 3.44 |
| ncRNA | UPREG. | TU_0074332_0 | chr10: 43420869-43421283 | 1.52 | 3.44 |
| PROTEIN | UPREG. | TU_0082983_0 | chr12: 121778239-121779189 | 2.65 | 3.44 |
| PROTEIN | UPREG. | TU_0008361_0 | chr7: 16759923-16790805 | 1.58 | 3.44 |
| PROTEIN | UPREG. | TU_0061443_0 | chr1: 38032067-38039550 | 1.67 | 3.44 |
| PROTEIN | UPREG. | TU_0042715_0 | chr13: 23148223-23204319 | 3.68 | 3.43 |
| ncRNA | UPREG. | TU_0119128_0 | chr2: 118310197-118313068 | 1.62 | 3.43 |
| PROTEIN | UPREG. | TU_0112349_0 | chr15: 70834440-70835126 | 1.67 | 3.43 |
| PROTEIN | UPREG. | TU_0027543_0 | chrX: 21921233-21922374 | 2.48 | 3.43 |
| PROTEIN | UPREG. | TU_0062582_0 | chr1: 47489058-47552320 | 1.83 | 3.43 |
| ncRNA | UPREG. | TU_0050791_0 | chr4: 174322695-174323924 | 2.13 | 3.41 |
| PROTEIN | UPREG. | TU_0048346_0 | chr4: 77175264-77176185 | 2.48 | 3.41 |
| NOVEL | UPREG. | TU_0093068_0 | chr11: 64956616-64961189 | 2.13 | 3.41 |
| PROTEIN | UPREG. | TU_0033869_0 | chr14: 60248258-60260801 | 1.21 | 3.41 |
| PROTEIN | UPREG. | TU_0000031_0 | chr6: 2190031-2190908 | 2.44 | 3.41 |
| PROTEIN | UPREG. | TU_0082131_0 | chr12: 111151572-111152227 | 1.88 | 3.40 |
| PROTEIN | UPREG. | TU_0038169_0 | chr3: 49035494-49041923 | 1.35 | 3.40 |
| NOVEL | UPREG. | TU_0044898_0 | chr13: 94753009-94760688 | 2.11 | 3.40 |
| PROTEIN | UPREG. | TU_0089144_0 | chr5: 176814489-176815986 | 1.86 | 3.40 |
| PROTEIN | UPREG. | TU_0094504_0 | chr11: 74812477-74817273 | 2.40 | 3.40 |
| PROTEIN | UPREG. | TU_0035633_0 | chr14: 94304291-94305127 | 2.17 | 3.40 |
| PROTEIN | UPREG. | TU_0085819_0 | chr5: 75734806-76039614 | 1.64 | 3.40 |
| PROTEIN | UPREG. | TU_0061431_0 | chr1: 37961347-37973585 | 2.62 | 3.40 |
| NOVEL | UPREG. | TU_0078299_0 | chr12: 32290896-32292169 | 3.67 | 3.39 |
| PROTEIN | UPREG. | TU_0004059_0 | chr6: 52976378-53034598 | 1.65 | 3.39 |
| PROTEIN | UPREG. | TU_0098927_0 | chr8: 95722432-95788870 | 1.48 | 3.39 |
| ncRNA | UPREG. | TU_0013886_0 | chr7: 155957953-156090820 | 2.50 | 3.39 |
| PROTEIN | UPREG. | TU_0068377_0 | chr1: 201452418-201458956 | 1.84 | 3.39 |
| NOVEL | UPREG. | TU_0101035_0 | chr21: 35419563-36421930 | 1.84 | 3.39 |
| PROTEIN | UPREG. | TU_0062957_0 | chr1: 54089897-54128073 | 1.43 | 3.39 |
| PROTEIN | UPREG. | TU_0099854_0 | chr8: 127633901-127639897 | 1.65 | 3.38 |
| PROTEIN | UPREG. | TU_0048743_0 | chr4: 87924751-87955166 | 1.47 | 3.38 |
| PROTEIN | UPREG. | TU_0086478_0 | chr5: 102510255-102521832 | 1.95 | 3.38 |
| PROTEIN | UPREG. | TU_0120565_0 | chr2: 172672776-172675279 | 4.31 | 3.38 |
| PROTEIN | UPREG. | TU_0122360_0 | chr2: 219554051-219557439 | 2.92 | 3.38 |
| PROTEIN | UPREG. | TU_0092154_0 | chr11: 60857271-60874474 | 1.44 | 3.37 |
| PROTEIN | UPREG. | TU_0015718_0 | chr17: 24095069-24100305 | 1.64 | 3.37 |
| PROTEIN | UPREG. | TU_0039284_0 | chr3: 95208586-95249573 | 2.23 | 3.37 |
| PROTEIN | UPREG. | TU_0082089_0 | chr12: 111082307-111187476 | 1.44 | 3.37 |
| PROTEIN | UPREG. | TU_0035148_0 | chr14: 81009021-81069951 | 1.64 | 3.37 |
| PROTEIN | UPREG. | TU_0054849_0 | chr16: 87403253-87406669 | 1.47 | 3.37 |
| PROTEIN | UPREG. | TU_0113376_0 | chr15: 87432680-87545107 | 2.13 | 3.36 |
| PROTEIN | UPREG. | TU_0019481_0 | chr17: 77998514-77999441 | 1.55 | 3.36 |
| PROTEIN | UPREG. | TU_0007004_0 | chr6: 158396021-158440190 | 1.47 | 3.36 |
| PROTEIN | UPREG. | TU_0092190_0 | chr11: 60876795-60877493 | 1.85 | 3.36 |
| ncRNA | UPREG. | TU_0001996_0 | chr6: 31941546-31959679 | 1.43 | 3.36 |
| NOVEL | UPREG. | TU_0066689_0 | chr1: 154509233-154510967 | 1.61 | 3.36 |
| PROTEIN | UPREG. | TU_0035151_0 | chr14: 81015445-81021875 | 2.00 | 3.35 |
| PROTEIN | UPREG. | TU_0092866_0 | chr11: 63975211-63975675 | 3.20 | 3.35 |
| PROTEIN | UPREG. | TU_0050482_0 | chr4: 156807332-156877628 | 1.69 | 3.35 |
| PROTEIN | UPREG. | TU_0022391_0 | chr19: 19076718-19094443 | 1.60 | 3.35 |
| PROTEIN | UPREG. | TU_0048729_0 | chr4: 87734463-87924734 | 1.74 | 3.35 |
| PROTEIN | UPREG. | TU_0103472_0 | chr9: 100534124-100570357 | 1.61 | 3.35 |
| PROTEIN | UPREG. | TU_0087465_0 | chr5: 136431191-136431490 | 2.47 | 3.35 |
| PROTEIN | UPREG. | TU_0058833_0 | chr1: 11768665-11788581 | 1.45 | 3.34 |
| PROTEIN | DOWNREG. | TU_0009047_0 | chr7: 41967123-41970103 | 0.65 | -3.35 |
| PROTEIN | DOWNREG. | TU_0020039_0 | chr19: 2948637-2980244 | 0.65 | -3.36 |
| PROTEIN | DOWNREG. | TU_0024046_0 | chr19: 47194316-47201741 | 0.53 | -3.36 |
| PROTEIN | DOWNREG. | TU_0120035_0 | chr2: 154042114-154043553 | 0.49 | -3.36 |
| PROTEIN | DOWNREG. | TU_0014542_0 | chr17: 4790024-4790984 | 0.77 | -3.36 |
| PROTEIN | DOWNREG. | TU_0058703_0 | chr1: 10457547-10613394 | 0.66 | -3.37 |
| NOVEL | DOWNREG. | TU_0084922_0 | chr5: 44337219-44338127 | 0.51 | -3.37 |
| PROTEIN | DOWNREG. | TU_0067333_0 | chr1: 167362572-167539064 | 0.68 | -3.37 |
| PROTEIN | DOWNREG. | TU_0030086_0 | chrX: 101794939-101798995 | 0.64 | -3.37 |
| PROTEIN | DOWNREG. | TU_0031101_0 | chrX: 134247418-134254372 | 0.69 | -3.37 |
| PROTEIN | DOWNREG. | TU_0063762_0 | chr1: 87566944-87583813 | 0.66 | -3.38 |
| PROTEIN | DOWNREG. | TU_0107584_0 | chr22: 38075931-38123808 | 0.66 | -3.38 |
| PROTEIN | DOWNREG. | TU_0102296_0 | chr9: 34979701-34988409 | 0.57 | -3.38 |

TABLE 4-continued

| Category | Type | Name | Interval | Fold change (Unlogged) | SAM score $((r)/(s + s0))$ |
|---|---|---|---|---|---|
| PROTEIN | DOWNREG. | TU_0038455_0 | chr3: 51951847-51958668 | 0.65 | −3.38 |
| PROTEIN | DOWNREG. | TU_0062948_0 | chr1: 53744574-53746867 | 0.46 | −3.38 |
| PROTEIN | DOWNREG. | TU_0092655_0 | chr11: 63282470-63288729 | 0.73 | −3.38 |
| PROTEIN | DOWNREG. | TU_0035606_0 | chr14: 93470258-93500717 | 0.58 | −3.38 |
| PROTEIN | DOWNREG. | TU_0055588_0 | chr18: 10470831-10478699 | 0.58 | −3.38 |
| PROTEIN | DOWNREG. | TU_0056462_0 | chr18: 41558112-41584622 | 0.49 | −3.39 |
| PROTEIN | DOWNREG. | TU_0002739_0 | chr6: 35321958-35328561 | 0.55 | −3.39 |
| PROTEIN | DOWNREG. | TU_0030147_0 | chrX: 102727067-102729284 | 0.65 | −3.39 |
| NOVEL | DOWNREG. | TU_0030209_0 | chrX: 103250901-103253228 | 0.66 | −3.39 |
| ncRNA | DOWNREG. | TU_0068206_0 | chr1: 200132176-200134973 | 0.60 | −3.39 |
| PROTEIN | DOWNREG. | TU_0081627_0 | chr12: 108186419-108190411 | 0.63 | −3.40 |
| PROTEIN | DOWNREG. | TU_0068194_0 | chr1: 200132176-200182322 | 0.59 | −3.40 |
| PROTEIN | DOWNREG. | TU_0049308_0 | chr4: 104220026-104220361 | 0.46 | −3.40 |
| NOVEL | DOWNREG. | TU_0068431_0 | chr1: 202350966-202363482 | 0.62 | −3.40 |
| PROTEIN | DOWNREG. | TU_0073506_0 | chr10: 7630096-7723984 | 0.60 | −3.40 |
| PROTEIN | DOWNREG. | TU_0054695_0 | chr16: 83411105-83499914 | 0.62 | −3.40 |
| PROTEIN | DOWNREG. | TU_0012556_0 | chr7: 115934290-115935899 | 0.50 | −3.41 |
| PROTEIN | DOWNREG. | TU_0018647_0 | chr17: 71259157-71294839 | 0.74 | −3.41 |
| NOVEL | DOWNREG. | TU_0030577_0 | chrX: 118036531-118036860 | 0.43 | −3.41 |
| PROTEIN | DOWNREG. | TU_0089961_0 | chr11: 2248339-2247566 | 0.52 | −3.41 |
| PROTEIN | DOWNREG. | TU_0000888_0 | chr6: 19947236-19950403 | 0.56 | −3.41 |
| PROTEIN | DOWNREG. | TU_0002212_0 | chr6: 32224073-32226328 | 0.56 | −3.41 |
| PROTEIN | DOWNREG. | TU_0024749_0 | chr19: 52937559-52939100 | 0.58 | −3.41 |
| PROTEIN | DOWNREG. | TU_0101225_0 | chr21: 40161189-40161418 | 0.52 | −3.41 |
| ncRNA | DOWNREG. | TU_0100030_0 | chr8: 134653589-134655310 | 0.41 | −3.41 |
| PROTEIN | DOWNREG. | TU_0102256_0 | chr9: 34356684-34366854 | 0.56 | −3.41 |
| PROTEIN | DOWNREG. | TU_0039040_0 | chr3: 69107066-69108860 | 0.62 | −3.42 |
| ncRNA | DOWNREG. | TU_0115808_0 | chr2: 37722515-37725828 | 0.61 | −3.42 |
| PROTEIN | DOWNREG. | TU_0115807_0 | chr2: 37722515-37725828 | 0.61 | −3.42 |
| NOVEL | DOWNREG. | TU_0038811_0 | chr3: 57890130-57890834 | 0.43 | −3.43 |
| PROTEIN | DOWNREG. | TU_0107000_0 | chr22: 29790122-29830660 | 0.60 | −3.43 |
| PROTEIN | DOWNREG. | TU_0065126_0 | chr1: 144274405-144279906 | 0.53 | −3.43 |
| PROTEIN | DOWNREG. | TU_0065093_0 | chr1: 144167535-144181746 | 0.72 | −3.43 |
| PROTEIN | DOWNREG. | TU_0066887_0 | chr1: 158352167-158379985 | 0.56 | −3.44 |
| PROTEIN | DOWNREG. | TU_0034681_0 | chr14: 73248261-73250867 | 0.61 | −3.44 |
| PROTEIN | DOWNREG. | TU_0064872_0 | chr1: 115373945-115394701 | 0.60 | −3.44 |
| PROTEIN | DOWNREG. | TU_0115146_0 | chr2: 26806070-26809827 | 0.49 | −3.44 |
| PROTEIN | DOWNREG. | TU_0023552_0 | chr19: 43433715-43439100 | 0.52 | −3.44 |
| PROTEIN | DOWNREG. | TU_0013056_0 | chr2: 134269121-134269574 | 0.41 | −3.44 |
| PROTEIN | DOWNREG. | TU_0078015_0 | chr12: 21809160-21817495 | 0.61 | −3.45 |
| PROTEIN | DOWNREG. | TU_0010849_0 | chr7: 84462824-84464278 | 0.41 | −3.45 |
| PROTEIN | DOWNREG. | TU_0018278_0 | chr17: 62235564-62237319 | 0.62 | −3.45 |
| PROTEIN | DOWNREG. | TU_0106896_0 | chr22: 28206216-28217370 | 0.46 | −3.46 |
| PROTEIN | DOWNREG. | TU_0086308_0 | chr5: 95158335-95154222 | 0.54 | −3.46 |
| PROTEIN | DOWNREG. | TU_0059500_0 | chr1: 19842799-19857540 | 0.66 | −3.46 |
| PROTEIN | DOWNREG. | TU_0030156_0 | chrX: 102749504-102752161 | 0.61 | −3.46 |
| PROTEIN | DOWNREG. | TU_0053209_0 | chr16: 30815439-30839057 | 0.45 | −3.46 |
| PROTEIN | DOWNREG. | TU_0102372_0 | chr9: 35672000-35681106 | 0.58 | −3.46 |
| PROTEIN | DOWNREG. | TU_0040491_0 | chr3: 134947802-134980329 | 0.35 | −3.46 |
| PROTEIN | DOWNREG. | TU_0063025_0 | chr1: 54832256-54849445 | 0.56 | −3.46 |
| PROTEIN | DOWNREG. | TU_0016741_0 | chr17: 37808007-37818100 | 0.61 | −3.47 |
| PROTEIN | DOWNREG. | TU_0079872_0 | chr12: 53272841-55276238 | 0.70 | −3.47 |
| NOVEL | DOWNREG. | TU_0072214_0 | chr20: 42166331-42172501 | 0.45 | −3.47 |
| PROTEIN | DOWNREG. | TU_0069254_0 | chr1: 223745864-223750945 | 0.54 | −3.48 |
| PROTEIN | DOWNREG. | TU_0014474_0 | chr17: 4410320-4410614 | 0.34 | −3.48 |
| PROTEIN | DOWNREG. | TU_0002034_0 | chr6: 31975375-31977685 | 0.61 | −3.48 |
| ncRNA | DOWNREG. | TU_0115805_0 | chr2: 37722515-37727509 | 0.64 | −3.48 |
| PROTEIN | DOWNREG. | TU_0106487_0 | chr22: 21742726-21797216 | 0.56 | −3.48 |
| PROTEIN | DOWNREG. | TU_0100880_0 | chr21: 32808766-32809639 | 0.62 | −3.48 |
| PROTEIN | DOWNREG. | TU_0028960_0 | chrX: 64873768-64873981 | 0.59 | −3.48 |
| PROTEIN | DOWNREG. | TU_0103717_0 | chr9: 112675334-112676369 | 0.59 | −3.48 |
| PROTEIN | DOWNREG. | TU_0016732_0 | chr17: 37807991-37828819 | 0.65 | −3.48 |
| PROTEIN | DOWNREG. | TU_0075573_0 | chr10: 96987317-97040810 | 0.65 | −3.48 |
| PROTEIN | DOWNREG. | TU_0108979_0 | chr15: 34659121-34889737 | 0.68 | −3.48 |
| PROTEIN | DOWNREG. | TU_0039868_0 | chr3: 123526763-123543198 | 0.51 | −3.48 |
| PROTEIN | DOWNREG. | TU_0032236_0 | chr14: 22885061-22893832 | 0.61 | −3.48 |
| PROTEIN | DOWNREG. | TU_0103902_0 | chr9: 115957988-116128421 | 0.59 | −3.49 |
| PROTEIN | DOWNREG. | TU_0004251_0 | chr6: 71069214-71069482 | 0.36 | −3.49 |
| PROTEIN | DOWNREG. | TU_0115344_0 | chr2: 27568254-27571592 | 0.64 | −3.49 |
| NOVEL | DOWNREG. | TU_0094307_0 | chr11: 7977293-7979927 | 0.69 | −3.49 |
| NOVEL | DOWNREG. | TU_0020914_0 | chr19: 9718612-9721799 | 0.47 | −3.49 |
| PROTEIN | DOWNREG. | TU_0014009_0 | chr7: 158513133-158630217 | 0.48 | −3.50 |
| PROTEIN | DOWNREG. | TU_0111467_0 | chr15: 62817064-62854842 | 0.58 | −3.50 |
| NOVEL | DOWNREG. | TU_0088552_0 | chr5: 157103352-157120455 | 0.64 | −3.50 |
| PROTEIN | DOWNREG. | TU_0016616_0 | chr17: 36992038-37034423 | 0.44 | −3.50 |
| PROTEIN | DOWNREG. | TU_0109820_0 | chr15: 41600571-41611159 | 0.56 | −3.51 |

TABLE 4-continued

| Category | Type | Name | Interval | Fold change (Unlogged) | SAM score ((r)/(s + s0)) |
|---|---|---|---|---|---|
| PROTEIN | DOWNREG. | TU_0083744_0 | chr5: 236838-237985 | 0.50 | −3.51 |
| PROTEIN | DOWNREG. | TU_0038899_0 | chr3: 58465926-58495812 | 0.58 | −3.51 |
| PROTEIN | DOWNREG. | TU_0018817_0 | chr17: 72183287-72184800 | 0.61 | −3.51 |
| PROTEIN | DOWNREG. | TU_0096362_0 | chr11: 129779777-129794214 | 0.56 | −3.51 |
| ncRNA | DOWNREG. | TU_0104765_0 | chr9: 131134480-131144297 | 0.53 | −3.51 |
| PROTEIN | DOWNREG. | TU_0047809_0 | chr4: 52581019-52582331 | 0.62 | −3.52 |
| PROTEIN | DOWNREG. | TU_0114638_0 | chr2: 11804193-11884972 | 0.68 | −3.52 |
| PROTEIN | DOWNREG. | TU_0110215_0 | chr15: 43246574-43254766 | 0.63 | −3.52 |
| PROTEIN | DOWNREG. | TU_0117024_0 | chr2: 66515747-66653430 | 0.61 | −3.52 |
| PROTEIN | DOWNREG. | TU_0109004_0 | chr15: 35178588-35180010 | 0.39 | −3.53 |
| PROTEIN | DOWNREG. | TU_0114005_0 | chr15: 97462760-97493368 | 0.56 | −3.53 |
| PROTEIN | DOWNREG. | TU_0079534_0 | chr12: 53260191-53268540 | 0.41 | −3.53 |
| PROTEIN | DOWNREG. | TU_0058435_0 | chr1: 202366748-202385528 | 0.62 | −3.53 |
| PROTEIN | DOWNREG. | TU_0014730_0 | chr17: 7034460-7061662 | 0.61 | −3.53 |
| PROTEIN | DOWNREG. | TU_0111099_0 | chr15: 57738640-57756015 | 0.70 | −3.54 |
| PROTEIN | DOWNREG. | TU_0079355_0 | chr12: 51906937-51912605 | 0.54 | −3.54 |
| PROTEIN | DOWNREG. | TU_0107389_0 | chr22: 36670710-36671784 | 0.59 | −3.54 |
| PROTEIN | DOWNREG. | TU_0105434_0 | chr9: 138991774-138996018 | 0.54 | −3.54 |
| ncRNA | DOWNREG. | TU_0122441_0 | chr2: 220000172-220002664 | 0.38 | −3.54 |
| PROTEIN | DOWNREG. | TU_0074041_0 | chr10: 29785041-30065975 | 0.64 | −3.55 |
| PROTEIN | DOWNREG. | TU_0114819_0 | chr2: 23779564-23785016 | 0.65 | −3.55 |
| PROTEIN | DOWNREG. | TU_0013666_0 | chr7: 150180552-150189309 | 0.34 | −3.55 |
| PROTEIN | DOWNREG. | TU_0036844_0 | chr3: 9930678-9933062 | 0.54 | −3.56 |
| PROTEIN | DOWNREG. | TU_0014467_0 | chr17: 4407802-4410614 | 0.49 | −3.56 |
| NOVEL | DOWNREG. | TU_0036397_0 | chr14: 104617328-104624500 | 0.45 | −3.56 |
| PROTEIN | DOWNREG. | TU_0014721_0 | chr17: 6882853-6884238 | 0.60 | −3.57 |
| PROTEIN | DOWNREG. | TU_0061867_0 | chr1: 41618433-41621890 | 0.61 | −3.57 |
| PROTEIN | DOWNREG. | TU_0090901_0 | chr11: 20061238-20099725 | 0.60 | −3.57 |
| PROTEIN | DOWNREG. | TU_0089503_0 | chr5: 179949721-179951068 | 0.47 | −3.57 |
| NOVEL | DOWNREG. | TU_0112056_0 | chr15: 69658838-69678469 | 0.46 | −3.57 |
| NOVEL | DOWNREG. | TU_0052454_0 | chr16: 15702084-15702374 | 0.40 | −3.57 |
| PROTEIN | DOWNREG. | TU_0004248_0 | chr6: 70983350-71069482 | 0.52 | −3.57 |
| PROTEIN | DOWNREG. | TU_0111118_0 | chr15: 58426685-58428608 | 0.59 | −3.58 |
| PROTEIN | DOWNREG. | TU_0047256_0 | chr4: 38781223-38804739 | 0.63 | −3.58 |
| PROTEIN | DOWNREG. | TU_0092308_0 | chr11: 61395022-61326508 | 0.62 | −3.58 |
| PROTEIN | DOWNREG. | TU_0037381_0 | chr3: 33159367-33165995 | 0.70 | −3.59 |
| PROTEIN | DOWNREG. | TU_0088765_0 | chr5: 169737435-169749043 | 0.53 | −3.60 |
| PROTEIN | DOWNREG. | TU_0039072_0 | chr3: 70098064-70100160 | 0.63 | −3.60 |
| NOVEL | DOWNREG. | TU_0112059_0 | chr15: 69667695-69691724 | 0.41 | −3.60 |
| PROTEIN | DOWNREG. | TU_0030975_0 | chrX: 130235170-130235814 | 0.49 | −3.60 |
| PROTEIN | DOWNREG. | TU_0038532_0 | chr3: 52258212-52287726 | 0.77 | −3.60 |
| PROTEIN | DOWNREG. | TU_0014418_0 | chr17: 3748115-3749717 | 0.39 | −3.60 |
| PROTEIN | DOWNREG. | TU_0001986_0 | chr6: 31791087-31793378 | 0.48 | −3.61 |
| PROTEIN | DOWNREG. | TU_0111109_0 | chr15: 58426685-58477514 | 0.66 | −3.61 |
| PROTEIN | DOWNREG. | TU_0064151_0 | chr1: 98933515-98937074 | 0.46 | −3.61 |
| PROTEIN | DOWNREG. | TU_0111253_0 | chr15: 61121812-61151157 | 0.63 | −3.61 |
| PROTEIN | DOWNREG. | TU_0058947_0 | chr1: 13782811-13817026 | 0.61 | −3.62 |
| PROTEIN | DOWNREG. | TU_0031484_0 | chrX: 151890690-151892673 | 0.59 | −3.62 |
| PROTEIN | DOWNREG. | TU_0076212_0 | chr10: 105781059-105835687 | 0.47 | −3.62 |
| PROTEIN | DOWNREG. | TU_0062567_0 | chr1: 47050692-47056967 | 0.47 | −3.62 |
| NOVEL | DOWNREG. | TU_0020667_0 | chr19: 7888598-7889980 | 0.41 | −3.62 |
| PROTEIN | DOWNREG. | TU_0029358_0 | chrX: 71263703-71268507 | 0.66 | −3.63 |
| PROTEIN | DOWNREG. | TU_0065339_0 | chr1: 148457403-148475104 | 0.56 | −3.63 |
| PROTEIN | DOWNREG. | TU_0063765_0 | chr1: 87583567-87587269 | 0.58 | −3.63 |
| NOVEL | DOWNREG. | TU_0036395_0 | chr14: 104617328-104623671 | 0.53 | −3.63 |
| PROTEIN | DOWNREG. | TU_0103872_0 | chr9: 115178483-115203441 | 0.59 | −3.63 |
| PROTEIN | DOWNREG. | TU_0050244_0 | chr4: 148665059-148685558 | 0.63 | −3.63 |
| PROTEIN | DOWNREG. | TU_0031913_0 | chr14: 20554755-20563715 | 0.64 | −3.63 |
| PROTEIN | DOWNREG. | TU_0065343_0 | chr1: 148501147-148501585 | 0.37 | −3.63 |
| PROTEIN | DOWNREG. | TU_0084946_0 | chr5: 50715235-50726033 | 0.60 | −3.64 |
| PROTEIN | DOWNREG. | TU_0090342_0 | chr11: 8671475-8849482 | 0.64 | −3.64 |
| PROTEIN | DOWNREG. | TU_0120044_0 | chr2: 155422693-155423038 | 0.26 | −3.64 |
| PROTEIN | DOWNREG. | TU_0023267_0 | chr19: 40937280-40940189 | 0.52 | −3.64 |
| PROTEIN | DOWNREG. | TU_0023553_0 | chr19: 43433715-43434071 | 0.51 | −3.65 |
| PROTEIN | DOWNREG. | TU_0115806_0 | chr2: 37722515-37725663 | 0.60 | −3.65 |
| PROTEIN | DOWNREG. | TU_0085256_0 | chr5: 59099679-59100724 | 0.53 | −3.65 |
| PROTEIN | DOWNREG. | TU_0038056_0 | chr3: 48563574-48623119 | 0.68 | −3.65 |
| PROTEIN | DOWNREG. | TU_0022088_0 | chr19: 16864768-16929718 | 0.55 | −3.65 |
| ncRNA | DOWNREG. | TU_0083408_0 | chr12: 129197899-129212499 | 0.58 | −3.65 |
| PROTEIN | DOWNREG. | TU_0059155_0 | chr1: 16397144-16405288 | 0.61 | −3.65 |
| PROTEIN | DOWNREG. | TU_0046595_0 | chr4: 3264594-3411502 | 0.68 | −3.65 |
| PROTEIN | DOWNREG. | TU_0099476_0 | chr8: 108331106-108578694 | 0.58 | −3.66 |
| PROTEIN | DOWNREG. | TU_0091498_0 | chr11: 46834081-46849744 | 0.65 | −3.66 |
| PROTEIN | DOWNREG. | TU_0098389_0 | chr8: 68586418-68699042 | 0.45 | −3.66 |
| PROTEIN | DOWNREG. | TU_0046627_0 | chr4: 3735533-3740037 | 0.45 | −3.67 |
| NOVEL | DOWNREG. | TU_0103946_0 | chr9: 116821701-116822181 | 0.48 | −3.67 |

TABLE 4-continued

| Category | Type | Name | Interval | Fold change (Unlogged) | SAM score ((r)/(s + s0)) |
|---|---|---|---|---|---|
| PROTEIN | DOWNREG. | TU_0008057_0 | chr7: 5519816-5536775 | 0.62 | −3.67 |
| PROTEIN | DOWNREG. | TU_0100219_0 | chr8: 143849604-143856276 | 0.59 | −3.67 |
| PROTEIN | DOWNREG. | TU_0087532_0 | chr5: 137802544-137810548 | 0.53 | −3.68 |
| PROTEIN | DOWNREG. | TU_0066743_0 | chr1: 154859563-154862200 | 0.43 | −3.68 |
| PROTEIN | DOWNREG. | TU_0052586_0 | chr16: 19637116-19779369 | 0.64 | −3.68 |
| PROTEIN | DOWNREG. | TU_0075808_0 | chr10: 88708340-88712998 | 0.51 | −3.68 |
| PROTEIN | DOWNREG. | TU_0032240_0 | chr14: 22894093-22905632 | 0.57 | −3.68 |
| PROTEIN | DOWNREG. | TU_0046399_0 | chr4: 2031053-2040569 | 0.44 | −3.70 |
| PROTEIN | DOWNREG. | TU_0081487_0 | chr12: 104248577-104289423 | 0.56 | −3.70 |
| PROTEIN | DOWNREG. | TU_0096978_0 | chr8: 22133174-22140355 | 0.47 | −3.70 |
| PROTEIN | DOWNREG. | TU_0054692_0 | chr16: 83411105-83500616 | 0.62 | −3.70 |
| PROTEIN | DOWNREG. | TU_0067818_0 | chr1: 180809414-180811333 | 0.72 | −3.71 |
| PROTEIN | DOWNREG. | TU_0098841_0 | chr8: 92038228-92039575 | 0.39 | −3.71 |
| PROTEIN | DOWNREG. | TU_0121595_0 | chr2: 202193170-202196672 | 0.62 | −3.71 |
| PROTEIN | DOWNREG. | TU_0023218_0 | chr19: 40679964-40694184 | 0.55 | −3.71 |
| PROTEIN | DOWNREG. | TU_0112386_0 | chr15: 71818130-71820041 | 0.55 | −3.71 |
| PROTEIN | DOWNREG. | TU_0024601_0 | chr19: 51605296-51609005 | 0.56 | −3.71 |
| PROTEIN | DOWNREG. | TU_0055238_0 | chr18: 2561572-2606627 | 0.59 | −3.71 |
| PROTEIN | DOWNREG. | TU_0085908_0 | chr5: 78401241-78420780 | 0.52 | −3.72 |
| ncRNA | DOWNREG. | TU_0111315_0 | chr15: 61676589-61681634 | 0.55 | −3.72 |
| PROTEIN | DOWNREG. | TU_0111311_0 | chr15: 61676589-61681634 | 0.55 | −3.72 |
| PROTEIN | DOWNREG. | TU_0023241_0 | chr19: 40856254-40861198 | 0.41 | −3.72 |
| PROTEIN | DOWNREG. | TU_0068139_0 | chr1: 199127296-199147465 | 0.42 | −3.72 |
| ncRNA | DOWNREG. | TU_0102684_0 | chr9: 70336502-70344481 | 0.56 | −3.73 |
| PROTEIN | DOWNREG. | TU_0068764_0 | chr1: 207854842-207892483 | 0.49 | −3.73 |
| PROTEIN | DOWNREG. | TU_0053636_0 | chr16: 55846971-55853340 | 0.58 | −3.74 |
| PROTEIN | DOWNREG. | TU_0084025_0 | chr5: 6501949-6545706 | 0.54 | −3.74 |
| NOVEL | DOWNREG. | TU_0032151_0 | chr14: 22508055-22508830 | 0.58 | −3.74 |
| PROTEIN | DOWNREG. | TU_0014680_0 | chr17: 6295379-6305574 | 0.62 | −3.74 |
| PROTEIN | DOWNREG. | TU_0076124_0 | chr10: 104619299-104651033 | 0.60 | −3.75 |
| PROTEIN | DOWNREG. | TU_0085198_0 | chr5: 58300638-58305429 | 0.60 | −3.75 |
| PROTEIN | DOWNREG. | TU_0102686_0 | chr9: 70337677-70344573 | 0.55 | −3.76 |
| PROTEIN | DOWNREG. | TU_0112385_0 | chr15: 71818130-71831566 | 0.54 | −3.76 |
| PROTEIN | DOWNREG. | TU_0100875_0 | chr21: 32705500-32809639 | 0.61 | −3.78 |
| PROTEIN | DOWNREG. | TU_0065928_0 | chr1: 151800274-151855449 | 0.49 | −3.78 |
| PROTEIN | DOWNREG. | TU_0063298_0 | chr1: 62474433-62474872 | 0.36 | −3.78 |
| PROTEIN | DOWNREG. | TU_0100851_0 | chr21: 32604246-32608457 | 0.62 | −3.79 |
| PROTEIN | DOWNREG. | TU_0101015_0 | chr21: 35010830-35012376 | 0.55 | −3.79 |
| ncRNA | DOWNREG. | TU_0031086_0 | chrX: 133993992-133995935 | 0.73 | −3.79 |
| PROTEIN | DOWNREG. | TU_0068759_0 | chr1: 207669209-207672813 | 0.45 | −3.79 |
| NOVEL | DOWNREG. | TU_0069253_0 | chr1: 223741202-223745600 | 0.62 | −3.79 |
| PROTEIN | DOWNREG. | TU_0020150_0 | chr19: 3877291-3879097 | 0.52 | −3.79 |
| ncRNA | DOWNREG. | TU_0084069_0 | chr5: 9599340-9603383 | 0.50 | −3.80 |
| PROTEIN | DOWNREG. | TU_0016922_0 | chr17: 38430856-38435173 | 0.51 | −3.80 |
| PROTEIN | DOWNREG. | TU_0013053_0 | chr7: 134114695-134305949 | 0.56 | −3.81 |
| PROTEIN | DOWNREG. | TU_0017406_0 | chr17: 43458534-43470076 | 0.58 | −3.81 |
| PROTEIN | DOWNREG. | TU_0014681_0 | chr17: 6295379-6305877 | 0.50 | −3.81 |
| PROTEIN | DOWNREG. | TU_0058447_0 | chr1: 9040090-9052233 | 0.36 | −3.81 |
| PROTEIN | DOWNREG. | TU_0055624_0 | chr18: 11872611-11875972 | 0.64 | −3.82 |
| PROTEIN | DOWNREG. | TU_0003717_0 | chr6: 43381215-43381963 | 0.49 | −3.82 |
| NOVEL | DOWNREG. | TU_0016578_0 | chr17: 35881203-35884855 | 0.52 | −3.82 |
| PROTEIN | DOWNREG. | TU_0101224_0 | chr21: 40161189-40223184 | 0.50 | −3.82 |
| PROTEIN | DOWNREG. | TU_0064871_0 | chr1: 115391459-115433611 | 0.59 | −3.83 |
| PROTEIN | DOWNREG. | TU_0097462_0 | chr8: 37773618-37822041 | 0.55 | −3.83 |
| PROTEIN | DOWNREG. | TU_0066742_0 | chr1: 154860755-154862200 | 0.42 | −3.83 |
| PROTEIN | DOWNREG. | TU_0090638_0 | chr11: 14242208-14246823 | 0.55 | −3.83 |
| PROTEIN | DOWNREG. | TU_0046626_0 | chr4: 3735533-3740037 | 0.46 | −3.83 |
| PROTEIN | DOWNREG. | TU_0024608_0 | chr19: 51842682-51856041 | 0.53 | −3.83 |
| PROTEIN | DOWNREG. | TU_0071146_0 | chr20: 25381375-25432639 | 0.58 | −3.84 |
| PROTEIN | DOWNREG. | TU_0080097_0 | chr12: 56301840-56307003 | 0.56 | −3.85 |
| PROTEIN | DOWNREG. | TU_0062615_0 | chr1: 48974664-48997227 | 0.51 | −3.85 |
| PROTEIN | DOWNREG. | TU_0013669_0 | chr7: 150272983-150305963 | 0.52 | −3.86 |
| PROTEIN | DOWNREG. | TU_0102682_0 | chr9: 70197177-70337519 | 0.56 | −3.86 |
| PROTEIN | DOWNREG. | TU_0104855_0 | chr9: 131689287-131691419 | 0.64 | −3.86 |
| PROTEIN | DOWNREG. | TU_0116336_0 | chr2: 48677181-48685259 | 0.65 | −3.86 |
| PROTEIN | DOWNREG. | TU_0116619_0 | chr2: 60532630-60533546 | 0.47 | −3.87 |
| PROTEIN | DOWNREG. | TU_0034452_0 | chr14: 69415893-69568826 | 0.48 | −3.87 |
| PROTEIN | DOWNREG. | TU_0067213_0 | chr1: 163086189-163087684 | 0.59 | −3.87 |
| PROTEIN | DOWNREG. | TU_0065337_0 | chr1: 148457403-148475119 | 0.56 | −3.87 |
| NOVEL | DOWNREG. | TU_0062461_0 | chr1: 46461750-46463004 | 0.51 | −3.88 |
| PROTEIN | DOWNREG. | TU_0080098_0 | chr12: 56302807-56307707 | 0.56 | −3.88 |
| PROTEIN | DOWNREG. | TU_0034421_0 | chr14: 68410559-68412495 | 0.62 | −3.88 |
| PROTEIN | DOWNREG. | TU_0016601_0 | chr17: 36911114-36928728 | 0.39 | −3.88 |
| PROTEIN | DOWNREG. | TU_0079221_0 | chr12: 51194638-51200498 | 0.43 | −3.89 |
| PROTEIN | DOWNREG. | TU_0112752_0 | chr15: 76184009-76210733 | 0.55 | −3.90 |
| PROTEIN | DOWNREG. | TU_0028410_0 | chrX: 48910899-48929704 | 0.68 | −3.91 |

TABLE 4-continued

| Category | Type | Name | Interval | Fold change (Unlogged) | SAM score ((r)/(s + s0)) |
|---|---|---|---|---|---|
| PROTEIN | DOWNREG. | TU_0076498_0 | chr10: 123227854-123347940 | 0.55 | −3.92 |
| NOVEL | DOWNREG. | TU_0093208_0 | chr11: 65396931-65397655 | 0.45 | −3.92 |
| PROTEIN | DOWNREG. | TU_0078129_0 | chr12: 27016771-27017190 | 0.47 | −3.92 |
| PROTEIN | DOWNREG. | TU_0064620_0 | chr1: 111962071-112059304 | 0.61 | −3.92 |
| PROTEIN | DOWNREG. | TU_0005224_0 | chr6: 107917248-108088034 | 0.60 | −3.93 |
| PROTEIN | DOWNREG. | TU_0023668_0 | chr19: 44114820-44158190 | 0.56 | −3.93 |
| PROTEIN | DOWNREG. | TU_0041856_0 | chr3: 190990156-191097717 | 0.44 | −3.93 |
| PROTEIN | DOWNREG. | TU_0107364_0 | chr22: 36658502-36671784 | 0.62 | −3.93 |
| PROTEIN | DOWNREG. | TU_0079224_0 | chr12: 51194638-51199100 | 0.43 | −3.94 |
| PROTEIN | DOWNREG. | TU_0027357_0 | chrX: 17728093-17737982 | 0.57 | −3.94 |
| PROTEIN | DOWNREG. | TU_0071013_0 | chr20: 19141491-19652034 | 0.55 | −3.95 |
| PROTEIN | DOWNREG. | TU_0060281_0 | chr1: 27204050-27211524 | 0.48 | −3.95 |
| PROTEIN | DOWNREG. | TU_0096007_0 | chr11: 119487208-119514087 | 0.45 | −3.95 |
| PROTEIN | DOWNREG. | TU_0058810_0 | chr1: 11631005-11637486 | 0.50 | −3.95 |
| ncRNA | DOWNREG. | TU_0102668_0 | chr9: 67902293-67904671 | 0.52 | −3.96 |
| PROTEIN | DOWNREG. | TU_0103126_0 | chr9: 93524079-93559558 | 0.55 | −3.96 |
| PROTEIN | DOWNREG. | TU_0098384_0 | chr8: 68508843-68581618 | 0.43 | −3.96 |
| NOVEL | DOWNREG. | TU_0084058_0 | chr5: 9602147-9603383 | 0.49 | −3.96 |
| ncRNA | DOWNREG. | TU_0018887_0 | chr17: 73068191-73068659 | 0.29 | −3.97 |
| PROTEIN | DOWNREG. | TU_0020916_0 | chr19: 9720305-9727203 | 0.55 | −3.97 |
| PROTEIN | DOWNREG. | TU_0018819_0 | chr17: 72184340-72195820 | 0.59 | −3.97 |
| NOVEL | DOWNREG. | TU_0042081_0 | chr3: 197374550-197376798 | 0.46 | −3.97 |
| PROTEIN | DOWNREG. | TU_0065864_0 | chr1: 149850009-149852238 | 0.46 | −3.98 |
| PROTEIN | DOWNREG. | TU_0111301_0 | chr15: 61676589-51684028 | 0.54 | −3.98 |
| PROTEIN | DOWNREG. | TU_0073443_0 | chr10: 5556713-3558609 | 0.43 | −3.99 |
| PROTEIN | DOWNREG. | TU_0030581_0 | chrX: 118096546-118104692 | 0.38 | −3.99 |
| PROTEIN | DOWNREG. | TU_0039780_0 | chr3: 120843508-120866813 | 0.55 | −4.00 |
| PROTEIN | DOWNREG. | TU_0081660_0 | chr12: 108705678-108718771 | 0.50 | −4.00 |
| PROTEIN | DOWNREG. | TU_0046397_0 | chr4: 2032569-2050090 | 0.46 | −4.00 |
| PROTEIN | DOWNREG. | TU_0122440_0 | chr2: 219991398-219999705 | 0.53 | −4.01 |
| PROTEIN | DOWNREG. | TU_0011534_0 | chr7: 99083477-99096154 | 0.36 | −4.01 |
| PROTEIN | DOWNREG. | TU_0047206_0 | chr4: 37815997-37817190 | 0.59 | −4.02 |
| PROTEIN | DOWNREG. | TU_0017005_0 | chr17: 39308253-39337366 | 0.52 | −4.02 |
| PROTEIN | DOWNREG. | TU_0052436_0 | chr16: 15704489-15858435 | 0.54 | −4.03 |
| PROTEIN | DOWNREG. | TU_0014761_0 | chr17: 7128572-7131411 | 0.46 | −4.03 |
| PROTEIN | DOWNREG. | TU_0080075_0 | chr12: 56290183-56301803 | 0.53 | −4.03 |
| PROTEIN | DOWNREG. | TU_0089295_0 | chr5: 177597111-177621358 | 0.48 | −4.03 |
| PROTEIN | DOWNREG. | TU_0062594_0 | chr16: 19775320-19780719 | 0.60 | −4.03 |
| PROTEIN | DOWNREG. | TU_0068168_0 | chr1: 199700556-199742901 | 0.61 | −4.04 |
| ncRNA | DOWNREG. | TU_0102657_0 | chr9: 67902293-67908869 | 0.54 | −4.04 |
| PROTEIN | DOWNREG. | TU_0003729_0 | chr6: 43525496-43528789 | 0.55 | −4.04 |
| PROTEIN | DOWNREG. | TU_0071246_0 | chr20: 29913077-29921837 | 0.42 | −4.05 |
| NOVEL | DOWNREG. | TU_0050224_0 | chr4: 147115887-147190781 | 0.25 | −4.06 |
| PROTEIN | DOWNREG. | TU_0110166_0 | chr15: 43172154-43198892 | 0.49 | −4.07 |
| PROTEIN | DOWNREG. | TU_0030085_0 | chrX: 101782933-101800062 | 0.56 | −4.07 |
| PROTEIN | DOWNREG. | TU_0021042_0 | chr19: 10435466-10441506 | 0.61 | −4.08 |
| PROTEIN | DOWNREG. | TU_0097463_0 | chr8: 37812227-37826549 | 0.58 | −4.08 |
| PROTEIN | DOWNREG. | TU_0101681_0 | chr9: 734412-736069 | 0.67 | −4.08 |
| PROTEIN | DOWNREG. | TU_0030157_0 | chrX: 102750729-102751737 | 0.44 | −4.09 |
| NOVEL | DOWNREG. | TU_0098190_0 | chr8: 61704765-61708199 | 0.40 | −4.09 |
| PROTEIN | DOWNREG. | TU_0062947_0 | chr1: 53744955-53838542 | 0.42 | −4.09 |
| PROTEIN | DOWNREG. | TU_0078008_0 | chr12: 21679541-21702042 | 0.57 | −4.09 |
| PROTEIN | DOWNREG. | TU_0017582_0 | chr17: 45858594-45907395 | 0.54 | −4.09 |
| PROTEIN | DOWNREG. | TU_0000021_0 | chr6: 1555144-1559122 | 0.53 | −4.09 |
| PROTEIN | DOWNREG. | TU_0031424_0 | chrX: 149432223-149433104 | 0.47 | −4.10 |
| PROTEIN | DOWNREG. | TU_0065603_0 | chr1: 149275738-149286201 | 0.42 | −4.10 |
| PROTEIN | DOWNREG. | TU_0037859_0 | chr3: 45240966-45242817 | 0.49 | −4.11 |
| PROTEIN | DOWNREG. | TU_0102271_0 | chr9: 34511045-34512853 | 0.50 | −4.11 |
| PROTEIN | DOWNREG. | TU_0035605_0 | chr14: 93254401-93273368 | 0.49 | −4.11 |
| PROTEIN | DOWNREG. | TU_0064621_0 | chr1: 112047963-112062396 | 0.54 | −4.11 |
| ncRNA | DOWNREG. | TU_0031098_0 | chrX: 134057388-134058604 | 0.47 | −4.11 |
| PROTEIN | DOWNREG. | TU_0018799_0 | chr17: 72061371-72080938 | 0.61 | −4.11 |
| PROTEIN | DOWNREG. | TU_0011129_0 | chr7: 94135058-94136943 | 0.41 | −4.11 |
| NOVEL | DOWNREG. | TU_0036396_0 | chr14: 104617328-104619095 | 0.41 | −4.12 |
| PROTEIN | DOWNREG. | TU_0086255_0 | chr5: 92944260-92956054 | 0.57 | −4.12 |
| ncRNA | DOWNREG. | TU_0074501_0 | chr10: 60429298-60431091 | 0.42 | −4.12 |
| PROTEIN | DOWNREG. | TU_0073757_0 | chr10: 16672547-17699461 | 0.56 | −4.13 |
| PROTEIN | DOWNREG. | TU_0015457_0 | chr17: 19581898-19587356 | 0.45 | −4.13 |
| PROTEIN | DOWNREG. | TU_0122402_0 | chr2: 219821926-219824741 | 0.61 | −4.13 |
| PROTEIN | DOWNREG. | TU_0116618_0 | chr2: 60532830-60633902 | 0.49 | −4.13 |
| PROTEIN | DOWNREG. | TU_0029963_0 | chrX: 100220537-100238005 | 0.51 | −4.15 |
| PROTEIN | DOWNREG. | TU_0028949_0 | chrX: 64804077-64878518 | 0.61 | −4.15 |
| PROTEIN | DOWNREG. | TU_0088443_0 | chr5: 154178336-154210363 | 0.57 | −4.16 |
| PROTEIN | DOWNREG. | TU_0107371_0 | chr22: 36668731-36671784 | 0.56 | −4.17 |
| PROTEIN | DOWNREG. | TU_0016830_0 | chr17: 38070906-38071660 | 0.57 | −4.17 |
| PROTEIN | DOWNREG. | TU_0016596_0 | chr17: 36923524-36946925 | 0.50 | −4.17 |

TABLE 4-continued

| Category | Type | Name | Interval | Fold change (Unlogged) | SAM score ((r)/(s + s0)) |
|---|---|---|---|---|---|
| PROTEIN | DOWNREG. | TU_0014764_0 | chr17: 7131441-7134452 | 0.45 | −4.18 |
| PROTEIN | DOWNREG. | TU_0070473_0 | chr20: 2621571-2702522 | 0.60 | −4.18 |
| PROTEIN | DOWNREG. | TU_0065602_0 | chr1: 149282206-149286718 | 0.40 | −4.19 |
| PROTEIN | DOWNREG. | TU_0105435_0 | chr9: 138997874-138999099 | 0.37 | −4.19 |
| PROTEIN | DOWNREG. | TU_0015445_0 | chr17: 19415396-19422913 | 0.46 | −4.20 |
| PROTEIN | DOWNREG. | TU_0019012_0 | chr17: 74597027-74990278 | 0.42 | −4.21 |
| PROTEIN | DOWNREG. | TU_0048538_0 | chr4: 81336928-81344460 | 0.41 | −4.22 |
| PROTEIN | DOWNREG. | TU_0098385_0 | chr8: 68508843-68509111 | 0.41 | −4.22 |
| PROTEIN | DOWNREG. | TU_0076499_0 | chr10: 123227854-123248042 | 0.53 | −4.23 |
| PROTEIN | DOWNREG. | TU_0117482_0 | chr2: 73973507-74000287 | 0.56 | −4.23 |
| PROTEIN | DOWNREG. | TU_0114778_0 | chr2: 20264034-20288661 | 0.45 | −4.24 |
| PROTEIN | DOWNREG. | TU_0018316_0 | chr17: 33917848-33935788 | 0.53 | −4.25 |
| PROTEIN | DOWNREG. | TU_0071893_0 | chr20: 34603301-34611746 | 0.59 | −4.25 |
| PROTEIN | DOWNREG. | TU_0073523_0 | chr10: 8136827-8157157 | 0.44 | −4.26 |
| PROTEIN | DOWNREG. | TU_0064500_0 | chr1: 110061334-110079791 | 0.42 | −4.27 |
| PROTEIN | DOWNREG. | TU_0065862_0 | chr1: 149850009-149852444 | 0.41 | −4.27 |
| PROTEIN | DOWNREG. | TU_0030064_0 | chrX: 101268429-101269091 | 0.44 | −4.28 |
| PROTEIN | DOWNREG. | TU_0060278_0 | chr1: 27192773-27200190 | 0.51 | −4.28 |
| PROTEIN | DOWNREG. | TU_0000013_0 | chr6: 1257191-1259972 | 0.36 | −4.29 |
| PROTEIN | DOWNREG. | TU_0120707_0 | chr2: 176665581-176669190 | 0.46 | −4.31 |
| PROTEIN | DOWNREG. | TU_0016744_0 | chr17: 37790368-37809206 | 0.54 | −4.31 |
| PROTEIN | DOWNREG. | TU_0016827_0 | chr17: 38065830-38071660 | 0.63 | −4.31 |
| PROTEIN | DOWNREG. | TU_0056190_0 | chr18: 26824024-26842486 | 0.43 | −4.33 |
| PROTEIN | DOWNREG. | TU_0096964_0 | chr8: 22027917-22043914 | 0.47 | −4.35 |
| PROTEIN | DOWNREG. | TU_0030062_0 | chrX: 101267701-101269091 | 0.41 | −4.36 |
| ncRNA | DOWNREG. | TU_0120711_0 | chr2: 176690351-176696560 | 0.49 | −4.36 |
| PROTEIN | DOWNREG. | TU_0011537_0 | chr7: 99085728-99111736 | 0.39 | −4.39 |
| PROTEIN | DOWNREG. | TU_0107366_0 | chr22: 36668731-36673469 | 0.54 | −4.39 |
| PROTEIN | DOWNREG. | TU_0065341_0 | chr1: 148496551-148500610 | 0.35 | −4.39 |
| PROTEIN | DOWNREG. | TU_0015076_0 | chr17: 12510065-12612990 | 0.50 | −4.40 |
| PROTEIN | DOWNREG. | TU_0087752_0 | chr5: 139206352-139211418 | 0.44 | −4.40 |
| PROTEIN | DOWNREG. | TU_0108990_0 | chr15: 34970176-35180015 | 0.51 | −4.41 |
| PROTEIN | DOWNREG. | TU_0062566_0 | chr1: 47037330-47057598 | 0.43 | −4.42 |
| PROTEIN | DOWNREG. | TU_0018825_0 | chr17: 72192513-72192794 | 0.47 | −4.43 |
| PROTEIN | DOWNREG. | TU_0002566_0 | chr6: 33797424-33798978 | 0.37 | −4.44 |
| PROTEIN | DOWNREG. | TU_0074074_0 | chr10: 29814868-29815135 | 0.26 | −4.44 |
| PROTEIN | DOWNREG. | TU_0110179_0 | chr15: 43196205-43235205 | 0.43 | −4.46 |
| PROTEIN | DOWNREG. | TU_0082372_0 | chr12: 116130336-116130610 | 0.41 | −4.47 |
| ncRNA | DOWNREG. | TU_0102658_0 | chr9: 67902293-67908683 | 0.46 | −4.48 |
| PROTEIN | DOWNREG. | TU_0024160_0 | chr19: 48777171-48778386 | 0.51 | −4.49 |
| PROTEIN | DOWNREG. | TU_0031081_0 | chrX: 133993992-134013925 | 0.64 | −4.49 |
| PROTEIN | DOWNREG. | TU_0015447_0 | chr17: 19421649-19423000 | 0.46 | −4.50 |
| PROTEIN | DOWNREG. | TU_0016834_0 | chr17: 38072130-38072515 | 0.54 | −4.50 |
| PROTEIN | DOWNREG. | TU_0120709_0 | chr2: 176677352-176697902 | 0.49 | −4.50 |
| PROTEIN | DOWNREG. | TU_0041205_0 | chr3: 171619688-171634575 | 0.48 | −4.53 |
| PROTEIN | DOWNREG. | TU_0110178_0 | chr15: 43196270-43241274 | 0.43 | −4.54 |
| PROTEIN | DOWNREG. | TU_0064473_0 | chr1: 110000292-110079791 | 0.51 | −4.58 |
| ncRNA | DOWNREG. | TU_0120715_0 | chr2: 176692475-176697902 | 0.50 | −4.58 |
| PROTEIN | DOWNREG. | TU_0110180_0 | chr15: 43196205-43243358 | 0.43 | −4.63 |
| PROTEIN | DOWNREG. | TU_0024922_0 | chr19: 54253368-54259943 | 0.42 | −4.64 |
| ncRNA | DOWNREG. | TU_0115816_0 | chr2: 38109039-38116939 | 0.32 | −4.64 |
| ncRNA | DOWNREG. | TU_0067289_0 | chr1: 166307141-166318970 | 0.48 | −4.69 |
| NOVEL | DOWNREG. | TU_0095765_0 | chr11: 117640504-117642734 | 0.36 | −4.69 |
| PROTEIN | DOWNREG. | TU_0058445_0 | chr1: 9017797-9040122 | 0.33 | −4.70 |
| PROTEIN | DOWNREG. | TU_0047068_0 | chr4: 23402764-23403824 | 0.41 | −4.72 |
| PROTEIN | DOWNREG. | TU_0016882_0 | chr17: 38260060-38263683 | 0.51 | −4.82 |
| NOVEL | DOWNREG. | TU_0098382_0 | chr8: 68494189-68495887 | 0.29 | −4.83 |
| PROTEIN | DOWNREG. | TU_0110177_0 | chr15: 43196768-43245735 | 0.47 | −4.86 |
| PROTEIN | DOWNREG. | TU_0089598_0 | chr11: 303980-310982 | 0.35 | −4.87 |
| PROTEIN | DOWNREG. | TU_0107527_0 | chr22: 37740155-37746215 | 0.44 | −4.88 |
| PROTEIN | DOWNREG. | TU_0107528_0 | chr22: 37741248-37746215 | 0.43 | −4.90 |
| PROTEIN | DOWNREG. | TU_0032311_0 | chr14: 23612588-23617134 | 0.32 | −5.04 |

TABLE 5

| PCAT ID | Gene | Chromosomal Location | Expected score (dExp) | Observed score(d) | Fold change (PCA vs Benign) | q-value (%) |
|---|---|---|---|---|---|---|
| PCAT-1 | TU_0099865_0 | chr8:128087842-128095202 | −2.2654014 | 5.44088 | 6.9071784 | 0 |
| PCAT-2 | TU_0090142_0 | chr11:4745677-4768303 | −2.4400573 | 4.6781354 | 11.39653 | 0 |
| PCAT-3 | TU_0054606_0 | chr16:82380936-82394836 | −2.1786725 | 4.4512455 | 5.8916535 | 0 |
| PCAT-4 | TU_0090140_0 | chr11:4748163-4759145 | −2.1153426 | 4.4345 | 7.1999154 | 0 |

TABLE 5-continued

| PCAT ID | Gene | Chromosomal Location | Expected score (dExp) | Observed score(d) | Fold change (PCA vs Benign) | q-value (%) |
|---|---|---|---|---|---|---|
| PCAT-5 | TU_0078288_0 | chr12:32393283-32405731 | −1.9164219 | 4.312603 | 3.5655262 | 0 |
| PCAT-6 | TU_0099664_0 | chr8:128034589-128103681 | −1.7214081 | 4.265536 | 3.8997242 | 0 |
| PCAT-7 | TU_0084308_0 | chr5:15938753-15949124 | −1.9636476 | 4.124071 | 4.747601 | 0 |
| PCAT-8 | TU_0084303_0 | chr5:15899476-15955226 | −2.0245785 | 4.0520086 | 7.1035967 | 0 |
| PCAT-9 | TU_0082746_0 | chr12:120197102-120197416 | −1.861408 | 3.7551165 | 5.1431665 | 0 |
| PCAT-10 | TU_0078296_0 | chr12:32394534-32406549 | −1.5944241 | 3.6902914 | 3.084959 | 0 |
| PCAT-11 | TU_0078290_0 | chr12:32394534-32410898 | −1.5337954 | 3.675318 | 3.1572607 | 0 |
| PCAT-12 | TU_0002597_0 | chr6:34335202-34338521 | −1.6263145 | 3.6469774 | 3.352418 | 0 |
| PCAT-13 | TU_0049368_0 | chr4:106772318-106772770 | −1.6894234 | 3.6079375 | 2.8299346 | 0 |
| PCAT-14 | TU_0106548_0 | chr22:22209111-22212055 | −1.939075 | 3.591358 | 5.962547 | 0 |
| PCAT-15 | TU_0076293_0 | chr12:32395393-32414822 | −1.5212961 | 3.5705945 | 2.9219175 | 0 |
| PCAT-16 | TU_0099884_0 | chr8:128301493-128307576 | −1.4445064 | 3.5658643 | 2.516981 | 0 |
| PCAT-17 | TU_0112014_0 | chr15:67722165-67739990 | −1.6325295 | 3.562463 | 3.6594224 | 0 |
| PCAT-18 | TU_0084306_0 | chr5:15896315-15947088 | −1.845 | 3.5603988 | 5.746707 | 0 |
| PCAT-19 | TU_0114240_0 | chr2:1534883-1538193 | −1.6970209 | 3.5233572 | 4.339947 | 0 |
| PCAT-20 | TU_0008499_0 | chr7:24236191-24236455 | −1.8302058 | 3.571697 | 6.6821446 | 0 |
| PCAT-21 | TU_0078299_0 | chr12:32290896-32292169 | −1.7297358 | 3.506232 | 3.2923684 | 0 |
| PCAT-22 | TU_0000033_0 | chr6:1619606-1668581 | −1.7680657 | 3.494188 | 2.2470818 | 0 |
| PCAT-23 | TU_0096472_0 | chr11:133844590-133862924 | −1.8782617 | 3.410355 | 5.9854198 | 0 |
| PCAT-24 | TU_0114259_0 | chr2:1606782-2607314 | −1.6662377 | 3.3919659 | 5.060926 | 0 |
| PCAT-25 | TU_0096473_0 | chr11:133844590-133862995 | −1.8963361 | 3.3859823 | 6.1071715 | 0 |
| PCAT-26 | TU_0100362_0 | chr5:144914456-144930753 | −1.6521469 | 3.3805158 | 3.8420251 | 0 |
| PCAT-27 | TU_0040394_0 | chr3:133418632-133441262 | −1.6208395 | 3.3201025 | 2.9724674 | 0 |
| PCAT-28 | TU_0043432_0 | chr13:34032994-34050503 | −1.6739471 | 3.2037551 | 3.2093527 | 0 |
| PCAT-29 | TU_0112020_0 | chr15:67764259-67801825 | −1.5603316 | 3.1937351 | 3.593551 | 0 |
| PCAT-30 | TU_0042717_0 | chr13:23149908-23200198 | −2.0654948 | 3.1685438 | 4.9699407 | 0 |
| PCAT-31 | TU_0078292_0 | chr12:32290485-32406307 | −1.4503003 | 3.151379 | 2.8911364 | 0 |
| PCAT-32 | TU_0084146_0 | chr5:14025126-14862770 | −1.6452767 | 3.1257985 | 2.6199455 | 0 |
| PCAT-33 | TU_0056168_0 | chr18:22477042-22477656 | −1.5381516 | 3.0557241 | 3.1951044 | 0 |
| PCAT-34 | TU_0040383_0 | chr3:133360541-133429262 | −1.5558791 | 3.0416908 | 3.7478442 | 0 |
| PCAT-35 | TU_0112025_0 | chr15:67780574-67758345 | −1.6815377 | 3.0412362 | 3.433415 | 0 |
| PCAT-36 | TU_0041688_0 | chr3:186741299-186741933 | −1.4749297 | 3.0062308 | 2.543465 | 0 |
| PCAT-37 | TU_0103642_0 | chr9:109187089-109187455 | −1.7387192 | 2.998956 | 6.6124363 | 0 |
| PCAT-38 | TU_0040375_0 | chr3:133280694-133394609 | −1.5469999 | 2.97533568 | 3.9068055 | 0 |
| PCAT-39 | TU_0047312_0 | chr4:39217669-39222153 | −1.6388936 | 2.9124916 | 3.161209 | 0 |
| PCAT-40 | TU_0106545_0 | chr22:22216478-22219162 | −1.7586497 | 2.889856 | 3.7357745 | 0 |
| PCAT-41 | TU_0054541_0 | chr16:79408800-79435066 | −1.7485934 | 2.8699164 | 6.647557 | 0 |
| PCAT-42 | TU_0050446_0 | chr1:28438629-2845056 | −1.4880521 | 2.857332 | 1.9824111 | 0 |
| PCAT-43 | TU_0072907_0 | chr20:55759486-55771563 | −1.5254781 | 2.7966201 | 2.812179 | 0 |
| PCAT-44 | TU_0043403_0 | chr13:33844637-33845921 | −1.5793877 | 2.7919009 | 3.6403422 | 0 |
| PCAT-45 | TU_0038678_0 | chr3:53515951-53517078 | −1.7047809 | 2.7858517 | 3.6905987 | 0 |
| PCAT-46 | TU_0101706_0 | chr9:3408690-3415374 | −1.4780945 | 2.7822099 | 3.3066912 | 0 |
| PCAT-47 | TU_0101709_0 | chr9:3411967-3415374 | −1.4652373 | 2.7522206 | 3.1886175 | 0 |
| PCAT-48 | TU_0106544_0 | chr22:22210421-22220506 | −1.6153399 | 2.7578135 | 3.7418716 | 0 |
| PCAT-49 | TU_0046121_0 | chr4:766363-766599 | −1.5697786 | 2.7578307 | 1.435532 | 0 |
| PCAT-50 | TU_0106542_0 | chr22:22211315-22220506 | −1.6098742 | 2.755721 | 3.3781004 | 0 |
| PCAT-51 | TU_0106541_0 | chr22:22209111-22219162 | −1.6593721 | 2.7341027 | 3.654146 | 0 |
| PCAT-52 | TU_0044453_0 | chr13:51505777-51524522 | −1.3416 | 2.732018 | 2.536953 | 0 |
| PCAT-53 | TU_0104717_0 | chr9:130697233-158698332 | −1.2938 | 2.7219732 | 2.3344588 | 0 |
| PCAT-54 | TU_0039014_0 | chr5:176814905-176015351 | −1.3967873 | 2.7047258 | 1.7803552 | 0 |
| PCAT-55 | TU_0108452_0 | chr15:19344745-19362916 | −1.5839852 | 2.6759455 | 1.8484153 | 0 |
| PCAT-56 | TU_0112003_0 | chr15:67645590-67775246 | −1.4386703 | 2.668052 | 3.045022 | 0 |
| PCAT-57 | TU_0078286_0 | chr12:32395583-32405731 | −1.3580605 | 2.6660874 | 2.6121044 | 0 |
| PCAT-58 | TU_0078303_0 | chr12:32274210-37274530 | −1.5020599 | 2.65866 | 3.3306372 | 0 |
| PCAT-59 | TU_0112064_0 | chr15:67644390-67650887 | −1.5175762 | 2.6509888 | 2.9933636 | 0 |
| PCAT-60 | TU_0071087_0 | chr20:21428679-21429454 | −1.4916688 | 2.649109 | 4.6481714 | 0 |
| PCAT-61 | TU_0072906_0 | chr20:35759768-53770657 | −1.5059631 | 2.645004 | 2.95755 | 0 |
| PCAT-62 | TU_0054240_0 | chr16:70155175-7013873 | −1.4715649 | 2.6437716 | 3.5309577 | 0 |
| PCAT-63 | TU_0047330_0 | chr4:39217641-39222163 | −1.5139307 | 2.6277255 | 3.0695639 | 0 |
| PCAT-64 | TU_0055435_0 | chr18:6715938-6719172 | −1.5048826 | 2.6173768 | 2.9221427 | 0 |
| PCAT-65 | TU_0079791_0 | chr12:54971063-54971481 | −1.4415668 | 2.6010823 | 2.041602 | 0 |
| PCAT-66 | TU_0043411_0 | chr13:33918267-33926769 | −1.495064 | 2.5991623 | 3.3860352 | 0 |
| PCAT-67 | TU_0056121_0 | chr18:20196762-20197522 | −1.2526748 | 2.5938754 | 1.7191441 | 0 |
| PCAT-68 | TU_0043412_0 | chr13:33918267-33935946 | 1.5891836 | 2.590199 | 4.2804045 | 0 |
| PCAT-69 | TU_0065837_0 | chr1:149791252-149795934 | −1.3852053 | 2.5882297 | 2.9343975 | 0 |
| PCAT-70 | TU_0043401_0 | chr13:33825711-33845275 | −1.5994886 | 2.5853698 | 4.3461533 | 0 |
| PCAT-71 | TU_0006463_0 | chr6:144659819-144660143 | −1.4985942 | 2.5744107 | 2.2007995 | 0 |
| PCAT-72 | TU_0048506_0 | chr4:50329017-80348239 | −1.5744382 | 1.5590413 | 2.8022916 | 0 |
| PCAT-73 | TU_0084140_0 | chr5:14003669-14054874 | −1.4040573 | 2.5472755 | 2.5979335 | 0 |
| PCAT-74 | TU_0082982_0 | chr12:121776584-139001515 | −1.5293782 | 2.5458217 | 2.6197583 | 0 |
| PCAT-75 | TU_0013212_0 | chr7:138990883-139001515 | −1.2295493 | 1.544434 | 1.6879753 | 0 |
| PCAT-76 | TU_0072912_0 | chr20:65779532-55780817 | −1.4302964 | 2.5406737 | 3.8653345 | 0 |

TABLE 5-continued

| PCAT ID | Gene | Chromosomal Location | Expected score (dExp) | Observed score(d) | Fold change (PCA vs Benign) | q-value (%) |
|---|---|---|---|---|---|---|
| PCAT-77 | TU_0112281_0 | chr15:70586704-70590792 | −1.4590155 | 2.5375097 | 2.4288568 | 0 |
| PCAT-78 | TU_0048767_0 | chr4:88120066-88124880 | −1.3735119 | 2.5328846 | 2.233308 | 0 |
| PCAT-79 | TU_0108455_0 | chr15:19358326-19365341 | −1.5651321 | 2.5261333 | 1.9462687 | 0 |
| PCAT-80 | TU_0091997_0 | chr11:585603-58573012 | −1.3149309 | 2.5185204 | 2.1176686 | 0 |
| PCAT-81 | TU_0121656_0 | chr2:202985284-202998534 | −1.4014161 | 2.476237 | 2.2194188 | 0.859614 |
| PCAT-82 | TU_0071798_0 | chr20:33775260-33778511 | −1.3356665 | 2.4645917 | 1.6566333 | 0.850371 |
| PCAT-83 | TU_0049200_0 | chr4:102469973-102476087 | −1.3222212 | 2.456723 | 1.9456172 | 0.832468 |
| PCAT-84 | TU_0121714_0 | chr2:203295212-203514868 | −1.3457565 | 2.4496653 | 1.7624274 | 0.832486 |
| PCAT-85 | TU_0098937_0 | chr8:95748751-95751321 | −1.4532137 | 2.42248 | 2.2326854 | 0.823797 |
| PCAT-86 | TU_0108453_0 | chr15:19356996-19364013 | −1.8033699 | 2.4094539 | 3.839975 | 0.767811 |
| PCAT-87 | TU_0114170_0 | chr15:99659312-99669199 | −1.4358851 | 2.4062114 | 2.1252658 | 0.767811 |
| PCAT-88 | TU_0089906_0 | chr11:1042845-1045706 | −1.3899238 | 2.401665 | 2.6399955 | 0.767811 |
| PCAT-89 | TU_0001559_0 | chr6:30283700-30286011 | −1.3517065 | 2.3987799 | 1.5110756 | 0.767811 |
| PCAT-90 | TU_0050557_0 | chr4:159976338-160016453 | −1.17525 | 2.598688 | 2.0524442 | 0.767811 |
| PCAT-91 | TU_0078294_0 | chr12:32395632-32413064 | −1.3568982 | 2.3969867 | 2.1863208 | 0.767811 |
| PCAT-92 | TU_0044933_0 | chr13:94755901-94760688 | −1.2906197 | 2.3965187 | 2.189938 | 0.767811 |
| PCAT-93 | TU_0017730_0 | chr17:52345638-52346880 | −1.4169512 | 2.3874657 | 1.4708191 | 0.760428 |
| PCAT-94 | TU_0039020_0 | chr3:66578329-66607777 | −1.2662895 | 2.3720088 | 1.7112706 | 0.712473 |
| PCAT-95 | TU_0049213_0 | chr4:102461960-102476087 | −1.2726139 | 2.3671806 | 1.8876821 | 0.712473 |
| PCAT-96 | TU_0093070_0 | chr11:64945809-64961189 | −1.2954472 | 2.3545105 | 1.9128959 | 0.712473 |
| PCAT-97 | TU_0051063_0 | chr4:187244297-187244767 | 1.8922831 | −2.8485844 | 0.50983155 | 0.732268 |
| PCAT-98 | TU_0098190_0 | chr8:61704763-61706199 | 1.9825526 | −2.8612907 | 0.4027831 | 0.732264 |
| PCAT-99 | TU_0038811_0 | chr3:57890130-57890834 | 1.9620296 | −2.8837616 | 0.44431657 | 0.732264 |
| PCAT-100 | TU_0020914_0 | chr19:9715612-8731799 | 1.6433232 | −2.9243097 | 0.50623006 | 0.732264 |
| PCAT-101 | TU_0132056_0 | chr15:69655838-69678469 | 1.837833 | −3.0355222 | 0.4616976 | 0 |
| PCAT-102 | TU_0056396_0 | chr14:104617328-104619095 | 1.549756 | −3.1192882 | 0.45514825 | 0 |
| PCAT-103 | TU_0095765_0 | chr11:117640604-117642734 | 2.1002219 | −3.2632742 | 0.38160567 | 0 |
| PCAT-104 | TU_0060224_0 | chr4:147115887-147190783 | 2.1981242 | −3.2975357 | 0.28569755 | 0 |
| PCAT-105 | TU_0112059_0 | chr15:59667695-69691724 | 1.8148681 | −3.3816626 | 0.43667468 | 0 |
| PCAT-106 | TU_0098382_0 | chr8:68494189-68495887 | 2.5413978 | −4.0586042 | 0.30793378 | 0 |

TABLE 6

| PCAT ID | Gene | Chromosomal Location | Outlier Score | Median Expression (RPKM) | Maximum Expression (RPKM) |
|---|---|---|---|---|---|
| PCAT-107 | TU_0029004_0 | chrX: 66691350-66692032 | 130.7349145 | 1 | 90.921 |
| PCAT-108 | TU_0054542_0 | chr16: 79420131-79423590 | 127.0430957 | 5.60998 | 135.85 |
| PCAT-109 | TU_0120899_0 | chr2: 180689090-180696402 | 123.5416436 | 1.0525222 | 94.6932 |
| PCAT-110 | TU_0054540_0 | chr16: 79419351-79423673 | 119.090847 | 4.161985 | 94.4461 |
| PCAT-111 | TU_0120918_0 | chr2: 181297540-181400892 | 112.710111 | 1.4533705 | 92.1795 |
| PCAT-112 | TU_0054538_0 | chr16: 79408946-79450819 | 98.01851659 | 1.830343 | 93.1207 |
| PCAT-113 | TU_0059541_0 | chr1: 20685471-20686432 | 68.3572507 | 1.783109 | 1375.15 |
| PCAT-114 | TU_0120924_0 | chr2: 181331111-181427485 | 63.95455962 | 1.3891845 | 365.202 |
| PCAT-115 | TU_0074308_0 | chr10: 42652247-42653596 | 60.91841567 | 1.393607 | 65.7712 |
| PCAT-116 | TU_0049192_0 | chr4: 102257900-102306678 | 59.24997694 | 1.3854525 | 69.2423 |
| PCAT-117 | TU_0054537_0 | chr16: 79406933-79430041 | 58.04481977 | 1.8534395 | 42.751 |
| PCAT-118 | TU_0120900_0 | chr2: 180926864-180985967 | 55.8438747 | 1 | 67.6582 |
| PCAT-119 | TU_0114527_0 | chr2: 10858318-10858530 | 54.76455104 | 1.2969775 | 35.0059 |
| PCAT-120 | TU_0120923_0 | chr2: 181328093-181419226 | 52.9793227 | 1.2821 | 232.556 |
| PCAT-121 | TU_0049231_0 | chr4: 102257900-102259695 | 52.77001947 | 1.34042 | 67.6276 |

TABLE 7

| Rank | Gene | Chromosomal location | Outlier Score | Median Expression (RPKM) | Maximum Expression (RPKM) |
|---|---|---|---|---|---|
| 1 | CRISP3 | chr6: 49803053-49813070 | 294.56446 | 1.5414775 | 478.812 |
| 2 | SPINK1 | chr5: 147184335-147191453 | 177.19518 | 2.484455 | 624.733 |
| 3 | TU_0029004_0 | chrX: 66691350-66692032 | 130.73491 | 1 | 90.921 |
| 4 | TU_0054542_0 | chr16: 79420131-79423590 | 127.0431 | 5.60998 | 135.85 |
| 5 | TU_0120899_0 | chr2: 180689090-180696402 | 123.54164 | 1.0525222 | 94.6932 |
| 6 | ERG | chr21: 38673821-38792298 | 119.446 | 3.421615 | 178.826 |
| 7 | TU_0054540_0 | chr16: 79419351-79423673 | 119.09085 | 4.161985 | 94.4461 |
| 8 | ERG | chr21: 38673821-38792298 | 117.60294 | 3.470755 | 176.186 |
| 9 | ERG | chr21: 38673821-38955574 | 117.26408 | 3.385695 | 170.663 |
| 10 | ERG | chr21: 38673821-38955574 | 116.33448 | 3.40077 | 170.443 |

TABLE 7-continued

| Rank | Gene | Chromosomal location | Outlier Score | Median Expression (RPKM) | Maximum Expression (RPKM) |
| --- | --- | --- | --- | --- | --- |
| 11 | TU_0120918_0 | chr2: 181297540-181400892 | 112.71011 | 1.4533705 | 92.1795 |
| 12 | C7orf68 | chr7: 127883119-127885708 | 105.18504 | 6.835525 | 336.148 |
| 13 | CSRP3 | chr11: 19160153-19180106 | 101.12947 | 1 | 148.45 |
| 14 | C7orf68 | chr7: 127883119-127885708 | 100.63202 | 7.08303 | 337.76 |
| 15 | COL2A1 | chr12: 46653014-46684552 | 99.166329 | 1.2285615 | 96.0977 |
| 16 | C1orf64 | chr1: 16203317-16205771 | 98.085922 | 3.62012 | 252.013 |
| 17 | TU_0054538_0 | chr16: 79408946-79450819 | 98.018517 | 1.830343 | 93.1207 |
| 18 | COL2A1 | chr12: 46653014-46684552 | 97.347905 | 1.2416035 | 94.6672 |
| 19 | CSRP3 | chr11: 19160153-19180165 | 96.730187 | 1 | 141.963 |
| 20 | COL9A2 | chr1: 40538749-40555526 | 74.408443 | 19.24815 | 570.961 |
| 21 | PLA2G7 | chr6: 46780012-46811389 | 69.521175 | 10.83567 | 97.8331 |
| 22 | AGT | chr1: 228904891-228916959 | 69.319886 | 4.797365 | 189.281 |
| 23 | TU_0059541_0 | chr1: 20685471-20686432 | 68.357259 | 1.783109 | 1375.15 |
| 24 | ETV1 | chr7: 13897382-13992664 | 68.218569 | 1.932797 | 138.519 |
| 25 | ETV1 | chr7: 13897382-13992664 | 67.723331 | 1.9899945 | 142.406 |
| 26 | ETV1 | chr7: 13897382-13992664 | 67.680571 | 1.9915925 | 143.632 |
| 27 | PLA2G7 | chr6: 46780011-46811110 | 67.089039 | 10.62 | 95.3551 |
| 28 | ETV1 | chr7: 13897382-13997390 | 66.381191 | 2.097225 | 143.975 |
| 29 | ETV1 | chr7: 13897382-13997575 | 65.563724 | 2.074935 | 141.069 |
| 30 | MUC6 | chr11: 1002823-1026706 | 64.7328 | 1.466194 | 351.862 |
| 31 | TU_0120924_0 | chr2: 181331111-181427485 | 63.95456 | 1.3891845 | 365.202 |
| 32 | ETV1 | chr7: 13897382-13996167 | 63.929225 | 2.05648 | 135.131 |
| 33 | ETV1 | chr7: 13897382-13996167 | 62.424072 | 2.03086 | 131.644 |
| 34 | TU_0074308_0 | chr10: 42652247-42653596 | 60.918416 | 1.393607 | 65.7712 |
| 35 | TU_0049192_0 | chr4: 102257900-102306678 | 59.249977 | 1.3854525 | 69.2423 |
| 36 | TU_0054537_0 | chr16: 79406933-79430041 | 58.04482 | 1.8534395 | 42.751 |
| 37 | RGL3 | chr19: 11365731-11391018 | 57.528689 | 7.660035 | 91.2238 |
| 38 | RGL3 | chr19: 11365731-11391018 | 57.393056 | 7.6327 | 90.6937 |
| 39 | TMEM45B | chr11: 129190950-129235108 | 55.587846 | 4.87695 | 60.0414 |
| 40 | TU_0120900_0 | chr2: 180926864-180985967 | 55.843875 | 1 | 67.6582 |
| 41 | PTK6 | chr20: 61630219-61639151 | 55.101291 | 3.420545 | 114.116 |
| 42 | TU_0114527_0 | chr2: 10858318-10858530 | 54.764551 | 1.2969775 | 35.0059 |
| 43 | TU_0112020_0 | chr15: 67764259-67801825 | 53.882769 | 2.0281615 | 88.99 |
| 44 | TU_0120923_0 | chr2: 181328093-181419226 | 52.979323 | 1.2821 | 232.556 |
| 45 | TU_0049231_0 | chr4: 102257900-102259695 | 52.770019 | 1.34042 | 67.6276 |
| 46 | MON1B | chr16: 75782336-75791044 | 51.717027 | 26.00355 | 187.807 |
| 47 | TU_0054541_0 | chr16: 79408800-79435066 | 50.445248 | 1.7164375 | 32.5832 |
| 48 | TU_0087466_0 | chr5: 136779809-136798173 | 50.285169 | 1.2738505 | 42.0309 |
| 49 | DLX1 | chr2: 172658453-172662647 | 50.048039 | 2.088625 | 43.0035 |
| 50 | TU_0108209_0 | chr22: 46993579-46531245 | 47.753833 | 1.0491419 | 26.6643 |
| 51 | DLX1 | chr2: 172658453-172662647 | 47.159314 | 1.9682735 | 38.4705 |
| 52 | SMC4 | chr3: 161600123-161635435 | 47.127047 | 4.581655 | 63.2353 |
| 53 | SMC4 | chr3: 161601040-161635435 | 46.967013 | 4.442065 | 61.2756 |
| 54 | TU_0102399_0 | chr9: 35759438-35761676 | 46.664973 | 6.44675 | 179.711 |
| 55 | TU_0029005_0 | chrX: 66690414-66704178 | 46.155567 | 1.0870047 | 38.3022 |
| 56 | C15orf48 | chr15: 43510054-43512939 | 45.732475 | 19.02125 | 223.42 |
| 57 | C15orf48 | chr15: 43510054-43512939 | 45.549287 | 21.28355 | 248.097 |
| 58 | EFNA3 | chr1: 153317971-153326638 | 44.993943 | 3.68358 | 70.5016 |
| 59 | TU_0043412_0 | chr13: 33918267-33935946 | 44.506741 | 1.311142 | 15.1968 |
| 60 | TU_0069093_0 | chr1: 220878648-220886461 | 42.645673 | 1.443496 | 160.898 |
| 61 | UGT1A6 | chr2: 234265059-234346684 | 42.500058 | 1.937622 | 45.753 |
| 62 | TU_0057051_0 | chr18: 54524352-54598419 | 42.108622 | 2.418785 | 56.0712 |
| 63 | AMH | chr19: 2200112-2203072 | 41.744334 | 2.16026 | 91.244 |
| 64 | TU_0120908_0 | chr2: 181147971-181168431 | 41.650097 | 1.0750564 | 48.7957 |
| 65 | TU_0099873_0 | chr8: 128138926-128140075 | 41.420293 | 1.51101 | 38.7353 |
| 66 | HN1 | chr17: 70642938-70662369 | 40.495209 | 16.35625 | 110.208 |
| 67 | TU_0022570_0 | chr19: 20341299-20343938 | 39.984803 | 2.912835 | 98.5739 |
| 68 | TU_0098937_0 | chr8: 95748751-95751321 | 39.740546 | 1.4422495 | 51.5935 |
| 69 | TU_0040375_0 | chr3: 133280694-133394609 | 39.664781 | 2.149005 | 90.9787 |
| 70 | HN1 | chr17: 70642938-70662370 | 39.655603 | 16.34725 | 109.587 |
| 71 | TU_0120929_0 | chr2: 181328093-181423017 | 39.419483 | 1.2116475 | 189.765 |
| 72 | TU_0112004_0 | chr15: 67644390-67650387 | 39.300923 | 6.10665 | 76.723 |
| 73 | TU_0108439_0 | chr15: 19293567-19296333 | 39.131646 | 1 | 27.7534 |
| 74 | HN1 | chr17: 70642938-70662369 | 39.00893 | 15.53595 | 103.782 |
| 75 | SULT1C2 | chr2: 108271526-108292803 | 39.007062 | 1.2259165 | 91.5617 |
| 76 | STX19 | chr3: 95215904-95230144 | 38.954223 | 4.521255 | 46.0375 |
| 77 | TU_0030420_0 | chrX: 112642982-112685485 | 38.715477 | 1.0890785 | 62.9419 |
| 78 | TU_0099875_0 | chr8: 128138047-128140075 | 38.489447 | 1.393413 | 35.8984 |
| 79 | UBE2T | chr1: 200567408-200577717 | 38.387515 | 3.070345 | 85.9738 |
| 80 | SULT1C2 | chr2: 108271526-108292803 | 37.817555 | 1.215033 | 88.0858 |
| 81 | TU_0049429_0 | chr4: 109263508-109272353 | 37.794245 | 1.09915225 | 29.1838 |
| 82 | STMN1 | chr1: 26099193-26105955 | 37.319869 | 14.3784 | 187.062 |
| 83 | UGT1A1 | chr2: 234333657-234346684 | 37.267194 | 1.660554 | 35.9476 |
| 84 | LRRN1 | chr3: 3816120-3864387 | 37.229013 | 3.8912 | 137.117 |
| 85 | TU_0086631_0 | chr5: 113806149-113806936 | 36.896806 | 1.0501165 | 29.6561 |
| 86 | ORM2 | chr9: 116131889-116135357 | 36.878688 | 3.614505 | 120.139 |

TABLE 7-continued

| Rank | Gene | Chromosomal location | Outlier Score | Median Expression (RPKM) | Maximum Expression (RPKM) |
|---|---|---|---|---|---|
| 87 | TU_0084060_0 | chr5: 7932238-7932523 | 36.807599 | 1 | 23.1979 |
| 88 | TU_0098644_0 | chr8: 81204784-81207034 | 36.779294 | 1.6013735 | 64.9663 |
| 89 | ACSM1 | chr16: 20542059-20610079 | 36.280896 | 13.3707 | 317.077 |
| 90 | STMN1 | chr1: 26099193-26105231 | 35.882914 | 12.73275 | 164.721 |
| 91 | STMN1 | chr1: 26099193-26105580 | 35.823453 | 14.31935 | 185.329 |
| 92 | TU_0120914_0 | chr2: 181265370-181266053 | 35.551458 | 1.053468 | 30.7074 |
| 93 | UGT1A7 | chr2: 234255322-234346684 | 35.073998 | 1.667349 | 33.4378 |
| 94 | TU_0087462_0 | chr5: 136386339-136403134 | 34.992335 | 1.4450115 | 27.1703 |
| 95 | UGT1A3 | chr2: 234302511-234346684 | 34.952247 | 1.6889365 | 33.4202 |
| 96 | UGT1A5 | chr2: 234286376-234346684 | 34.950003 | 1.6639345 | 33.2718 |
| 97 | FOXD1 | chr5: 72777840-72780108 | 34.875512 | 1.2373575 | 10.80944 |
| 98 | ADM | chr11: 10283217-10285499 | 34.855767 | 11.83635 | 276.194 |
| 99 | PPFIA4 | chr1: 201286933-201314487 | 34.769924 | 1.566044 | 43.9812 |
| 100 | UGT1A10 | chr2: 234209861-234346690 | 34.738527 | 1.652799 | 32.7318 |
| 101 | UGT1A4 | chr2: 234292176-234346684 | 34.663597 | 1.655824 | 32.9264 |
| 102 | UGT1A9 | chr2: 234245282-234346690 | 34.648086 | 1.655272 | 32.852 |
| 103 | TU_0090142_0 | chr11: 4748677-4760303 | 34.517072 | 1.6226305 | 51.3411 |
| 104 | TU_0082746_0 | chr12: 120197102-120197416 | 34.499713 | 2.531095 | 59.9026 |
| 105 | UGT1A8 | chr2: 234191029-234346684 | 34.433379 | 1.6498025 | 32.5849 |
| 106 | TU_0112207_0 | chr15: 70278422-70286121 | 34.308752 | 10.40266 | 112.274 |
| 107 | LOC145837 | chr15: 67641112-67650833 | 34.291574 | 7.59729 | 74.8194 |
| 108 | TU_0050712_0 | chr4: 170217424-170228463 | 34.23107 | 1.504313 | 65.5606 |
| 109 | TU_0043410_0 | chr13: 33929484-33944669 | 34.112491 | 1.393529 | 24.8401 |
| 110 | SNHG1 | chr11: 62376035-62379936 | 33.971989 | 33.74365 | 270.512 |
| 111 | MUC1 | chr1: 153424923-153429324 | 33.838228 | 16.3238 | 664.278 |
| 112 | MUC1 | chr1: 153424923-153429324 | 33.823147 | 15.8436 | 644.44 |
| 113 | TU_0099871_0 | chr8: 128138047-128143500 | 33.697285 | 1.412872 | 33.2958 |
| 114 | TU_0040383_0 | chr3: 133360541-133429262 | 33.548813 | 2.553955 | 85.8384 |
| 115 | MUC1 | chr1: 153424923-153429324 | 33.495501 | 15.91355 | 627.622 |
| 116 | TU_0049202_0 | chr4: 102257900-102304755 | 33.391066 | 1.5555505 | 39.7522 |
| 117 | TU_0120913_0 | chr2: 181254530-181266950 | 33.188328 | 1 | 43.8515 |
| 118 | B4GALNT4 | chr11: 359794-372116 | 33.176248 | 6.3749 | 80.9639 |
| 119 | TU_0100059_0 | chr8: 141258835-141260573 | 33.169029 | 1.3615865 | 44.8943 |
| 120 | TOP2A | chr17: 35798321-35827695 | 33.132056 | 1.9725825 | 34.1032 |
| 121 | MUC1 | chr1: 153424923-153429324 | 33.081326 | 15.9539 | 632.042 |
| 122 | TU_0001265_0 | chr6: 27081719-27082291 | 33.045746 | 1.3381905 | 100.5401 |
| 123 | C7orf53 | chr7: 111908143-111918171 | 33.024251 | 2.820945 | 32.2465 |
| 124 | SLC45A2 | chr5: 33980477-34020537 | 32.952911 | 2.012104 | 54.8589 |
| 125 | TU_0099869_0 | chr8: 128138047-128225937 | 32.928048 | 1.308804 | 30.4667 |
| 126 | UGT1A6 | chr2: 234266250-234346690 | 32.918772 | 1.662221 | 31.4671 |
| 127 | TU_0120917_0 | chr2: 181265370-181266950 | 32.796137 | 1.0771403 | 36.3557 |
| 128 | CACNA1D | chr3: 53504070-53821532 | 32.608694 | 4.51306 | 44.9904 |
| 129 | UBE2C | chr20: 43874661-43879003 | 32.456813 | 1.6391285 | 58.398 |
| 130 | ALDOC | chr17: 23924259-23928078 | 32.455953 | 14.98415 | 228.812 |
| 131 | MUC1 | chr1: 153424923-153429324 | 32.44845 | 15.5895 | 599.062 |
| 132 | MMP11 | chr22: 22445035-22456503 | 32.411555 | 3.257735 | 73.9158 |
| 133 | TU_0084303_0 | chr5: 15899476-15955226 | 32.39036 | 2.21168 | 14.4385 |
| 134 | CACNA1D | chr3: 53504070-53821532 | 32.381439 | 4.484655 | 44.6867 |
| 135 | UBE2C | chr20: 43874661-43879003 | 32.358151 | 1.705223 | 57.8559 |
| 136 | CACNA1D | chr3: 53504070-53821532 | 32.353332 | 4.463805 | 44.2455 |
| 137 | FGFRL1 | chr4: 995609-1010686 | 32.275762 | 26.0133 | 450.449 |
| 138 | FGFRL1 | chr4: 996251-1010686 | 32.075261 | 27.0148 | 468.809 |
| 139 | FGFRL1 | chr4: 995759-1010686 | 32.069901 | 26.92945 | 467.246 |
| 140 | MUC1 | chr1: 153424923-153429324 | 32.011017 | 15.3218 | 586.058 |
| 141 | TU_0099922_0 | chr8: 128979617-128981414 | 31.833339 | 3.32544 | 32.6893 |
| 142 | TU_0001173_0 | chr6: 26385234-26386052 | 31.823293 | 2.339595 | 71.3388 |
| 143 | MUC1 | chr1: 153424923-153429324 | 31.781267 | 15.22945 | 587.582 |
| 144 | TMEM178 | chr2: 39746141-39798605 | 31.614406 | 13.40605 | 182.08 |
| 145 | UBE2C | chr20: 43874661-43879003 | 31.37539 | 1.7154185 | 58.1531 |
| 146 | KCNC2 | chr12: 73720162-73889778 | 31.294059 | 1.8783795 | 104.225 |
| 147 | MAGEC2 | chrX: 141117794-141120742 | 31.286618 | 1 | 34.1099 |
| 148 | SERHL2 | chr22: 41279868-41300332 | 31.131788 | 3.670135 | 61.9969 |
| 149 | KCNC2 | chr12: 73720162-73889778 | 31.126593 | 1.868714 | 108.199 |
| 150 | GRAMD4 | chr22: 45401321-45454352 | 31.063732 | 5.977725 | 79.8338 |

TABLE 7

| | | | | | |
|---|---|---|---|---|---|
| 123 | C7orf53 | chr7: 111908143-111918171 | 33.024251 | 2.820945 | 32.2465 |
| 124 | SLC45A2 | chr5: 33980477-34020537 | 32.952911 | 2.012104 | 54.8589 |
| 125 | TU_0099869_0 | chr8: 128138047-128225937 | 32.928048 | 1.308804 | 30.4667 |
| 126 | UGT1A6 | chr2: 234266250-234346690 | 32.918772 | 1.662221 | 31.4671 |
| 127 | TU_0120917_0 | chr2: 181265370-181266950 | 32.796137 | 1.0771403 | 36.3557 |

TABLE 7-continued

| | | | | | |
|---|---|---|---|---|---|
| 128 | CACNA1D | chr3: 53504070-53821532 | 32.608994 | 4.51306 | 44.9904 |
| 129 | UBE2C | chr20: 438746561-43879003 | 32.456813 | 1.6391285 | 58.398 |
| 130 | ALDOC | chr17: 23924259-23928078 | 32.455953 | 14.98415 | 228.812 |
| 131 | MUC1 | chr1: 153424923-153429324 | 32.44845 | 15.5895 | 599.062 |
| 132 | MMP11 | chr22: 22445035-22456503 | 32.411555 | 3.257735 | 73.9158 |
| 133 | TU_0084303_0 | chr5: 15899476-15955226 | 32.39036 | 2.21168 | 14.4385 |
| 134 | CACNA1D | chr3: 53504070-53821532 | 32.381439 | 4.484655 | 44.6867 |
| 135 | UBE2C | chr20: 43874661-43873603 | 32.358151 | 1.705223 | 57.8559 |
| 136 | CACNA1D | chr3: 53504070-53821532 | 32.353332 | 4.463805 | 44.2455 |
| 137 | FGFRL1 | chr4: 995609-1010686 | 32.275762 | 26.0133 | 450.449 |
| 138 | FGFRL1 | chr4: 996251-1010686 | 32.075261 | 27.0148 | 468.809 |
| 139 | FGFRL1 | chr4: 995759-1010686 | 32.069901 | 26.92945 | 467.246 |
| 140 | MUC1 | chr1: 153424923-153429324 | 32.011017 | 15.3218 | 586.058 |
| 141 | TU_0099922_0 | chr8: 128979617-128981414 | 31.833339 | 3.32544 | 32.6893 |
| 142 | TU_0001173_0 | chr6: 26385234-26386052 | 31.823293 | 2.339595 | 71.3388 |
| 143 | MUC1 | chr1: 153424923-153429324 | 31.781267 | 15.22945 | 587.582 |
| 144 | TMEM178 | chr2: 39746141-39798605 | 31.614406 | 13.40605 | 182.03 |
| 145 | UBE2C | chr20: 43874661-43879003 | 31.37539 | 1.7154185 | 58.1531 |
| 146 | KCNC2 | chr12: 73720162-73889778 | 31.294059 | 1.8783795 | 104.225 |
| 147 | MAGEC2 | chrX: 141117794-141120742 | 31.286618 | 1 | 34.1099 |
| 148 | SERHL2 | chr22: 41279868-41300332 | 31.131788 | 3.670135 | 61.9969 |
| 149 | KCNC2 | chr12: 73720162-73889778 | 31.126593 | 1.868714 | 108.199 |
| 150 | GRAMD4 | chr22: 45401321-45454352 | 31.063732 | 5.977725 | 79.8338 |

Table 8 shows the number of cancer-associated lncRNAs nominated for four major cancer types. The number validated is indicated in the column on the right. This table reflects ongoing efforts.

TABLE 8

| | # of cancer-specific lncRNAs nominated | # validated to date |
|---|---|---|
| Prostate cancer | 121 | 11 |
| Breast cancer | 6 | 6 |
| Lung cancer | 36 | 32 |
| Pancreatic cancer | 34 | 0 |

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method of screening for the level of expression of one or more non-coding RNAs in a subject, comprising
   (a) contacting a biological sample from a subject with a reagent for detecting the level of expression of one or more non-coding RNAs (ncRNA) selected from PCAT1 or PCAT14, wherein said PCTA1 has a nucleic acid sequence comprising SEQ ID NOs: 1 and 2 and said PCAT14 has a nucleic acid sequence selected from the group consisting of SEQ IDs 3-6; SEQ ID NOs: 7 and 8; and SEQ ID NOs 9; and
   (b) detecting the level of expression of said ncRNA in said sample using an in vitro assay.

2. The method of claim 1, wherein the sample is selected from the group consisting of tissue, blood, plasma, serum, urine, urine supernatant, urine cell pellet, semen, prostatic secretions and prostate cells.

3. The method of claim 1, wherein detection is carried out utilizing a method selected from the group consisting of a sequencing technique, a nucleic acid hybridization technique, a nucleic acid amplification technique, and an immunoassay.

4. The method of claim 3, wherein the nucleic acid amplification technique is selected from the group consisting of polymerase chain reaction, reverse transcription polymerase chain reaction, transcription-mediated amplification, ligase chain reaction, strand displacement amplification, and nucleic acid sequence based amplification.

5. The method of claim 1, wherein said subject has or is suspected of having a cancer selected from the group consisting of localized prostate cancer and metastatic prostate cancer.

6. The method of claim 1, wherein said reagent is selected from the group consisting of a pair of amplification oligonucleotides and an oligonucleotide probe.

7. The method of claim 1, wherein said one or more ncRNAs are PCAT1 and PCAT14.

* * * * *

UNITED STATES PATENT AND TRADEMARK OFFICE
CERTIFICATE OF CORRECTION

PATENT NO. : 11,390,923 B2
APPLICATION NO. : 16/453195
DATED : July 19, 2022
INVENTOR(S) : Arul Chinnaiyan, John Prensner and Matthew Iyer It is certified that error appears in the above-identified patent and that said Letters Patent is hereby corrected as shown below:

In the Claims

Claim 1, Column 97, Line 63 reads:
"PCAT1 or PCAT14, wherein said PCTA1 has a nucleic"
Whereas it should read:
"PCAT1 or PCAT14, wherein said PCAT1 has a nucleic" and Claim 1, Column 97, Line 66 reads:
"the group consisting of SEQ IDs 3-6; SEQ ID NOs: 7"
Whereas it should read:
"the group consisting of SEQ ID NOs: 3-6; SEQ ID NOs: 7" and Claim 1, Column 97, Line 67 reads:
"and 8; and SEQ ID NOs 9; and"
Whereas it should read:
"and 8; and SEQ ID NO: 9; and"

Signed and Sealed this
Thirtieth Day of August, 2022

Katherine Kelly Vidal
*Director of the United States Patent and Trademark Office*

SEQUENCE LISTING

<160> NUMBER OF SEQ ID NOS: 21

<210> SEQ ID NO 1
<211> LENGTH: 621
<212> TYPE: DNA
<213> ORGANISM: Homo sapiens

<400> SEQUENCE: 1

```
acacatggat attggatatc tgcataggca gcttgctcca cgccagtgcc tacctgtgca      60
gatgggaagg aaaggaaagt ggcaaggagg cagagaaagc atctgtaccc ttacaatttg     120
gtgagacaag aatgtatgaa ttcccacagg tcaaattata atgaagaaag gaacctctct     180
tgagtacaaa gagctaccta tggtggtctg gagccggagg accacagcat caaaggatat     240
aagatgcata gccaactgag gaacctgagc aattaaagag atccacagtt aagtcacact     300
taactggcac ttgtggaagc cccgcaaggc ctgaaggaga gctgacatag gcaccccgga     360
gagccagaat ctggatccca tcttaataag gccatgaaca ccagtggaga agaggcagaa     420
acaccaatgg ataaggaaca ttcacatctt tcttcccatg tgcctctaag tgccagtgca     480
ggccccacag gccaagctac agggagaaag gagatgacgc aaaggaacct aactggactt     540
taatcactag aagtgagaag agaaatctat tggaacctcc caagataatg ccaagggtca     600
```
aagggtgcgc agatacataa g                                              621

<210> SEQ ID NO 2
<211> LENGTH: 1371
<212> TYPE: DNA
<213> ORGANISM: Homo sapiens

<400> SEQUENCE: 2
accatggaaa taatatcaga caaaaagcag attagagcaa ttttcttttt cgagttcaaa    60
atgggttata aagcagcgga gacaaaccgc aacatcacca acgcctttgg cccaggaact   120
gctaatgaag gtacagtgca gtcactgttc aggaagtttt gcaaaggaga ctagagcctt   180
gaagatgagg agcatagtga ccagccattg gaagtcgaca agaccaatt gagaggaatc   240 attgaagctg atcatcttac aactacacga gaagttgtca agaacgcaa tgttgaccat   300 tgtgtggtct tttcgcattt gaagcaaatt ggaaaggtga aaaacttgat aagtgggtgc   360
cttgtgagct cagcaaaaat ccaaaaaaat aatcattttt aagtgttgtc ttctcttatt   420
ctacgcaaca acaataacca ttttgcaatc ggattgtgat gtgcaatgaa aagtggattt   480
ggggccgggc gcggtggctc acgcctgtaa tctcagcact ttggaaggcc aaggcgggca   540
gatcacgagg tcaggagatc aagaccgtcc tggctaacac ggtgaaaccc cgtctctact   600
gaaaatacaa aaattagcc gggtgtggtg gctggcgcct gtagtccag ctacaggctg    660 aggcaggaga atggcatgaa cctgggaggc ggagcttgca gtgagccgag accgtgccac   720
tgcactccag cctgggcgac agagcgatac tccgtcaaaa aaaaaaaaaa aaaaaaaaa    780 agacaagtgg attttatata tggcaaccag caatgaccag ctcagtggct ggactgagaa   840
gaagctccaa agcacttccc aaagccaaac ttgcaccaaa aaaaggtca gggtcactgt    900 ttggtggtct gctgctggtc tgatccaccg ctgctctctg aatcctggca aaaccattac   960
atctgagaag tatgctcaac aaatcaatga gctacgccaa aaactgcagc atctgcagct  1020
ggcattggtc aacataacgg gtccaattct tctccacgac aacgctcaac tgcaccttgc  1080
gcaagcagcg cttcaaaagt tgaacaaatt gggctacata gttttcctc atccgccata   1140 ttcacctgac gtcttgccaa ctaactacca cttcttcaag tatctcaaca acttttgca   1200 gggaaaacac ttccacaacc agcaggatgc agaacacgct ttccaagagt tgtcgaatc   1260 ctgacgcaca gattttttatg ctacaggaat aaactaactt attttctcatt ggcaaaaatg  1320 tgttgattgt aatggttcct attttgatga ataaatgtgt gtttgagcct a           1371

<210> SEQ ID NO 3
<211> LENGTH: 238
<212> TYPE: DNA
<213> ORGANISM: Homo sapiens

<400> SEQUENCE: 3
atgctgagcg ccggtcccct gggcccactt ttctttctct atactttgtc tctgttgtct    60 ttctttctc aagtctctcg ttccacctga ggagaaatgc ccacagctgt ggaggcgcag   120
gccactccat ctggtgccca acgtggatgc ttttctctag ggtgaaggga ctctcgagtg   180
tggtcattga ggacaagtca acgagagatt cccgagtacg tctacagtga gccttgtg     238

<210> SEQ ID NO 4
<211> LENGTH: 79
<212> TYPE: DNA
<213> ORGANISM: Homo sapiens

<400> SEQUENCE: 4

```
ggtgaaggta ctctacagtg tggtcattga ggacaagttg acgagagagt cccaagtacg    60
tccacggtca gccttgcgg                                                  79
```

<210> SEQ ID NO 5
<211> LENGTH: 79
<212> TYPE: DNA
<213> ORGANISM: Homo sapiens

<400> SEQUENCE: 5

```
acatttaaag ttctacaatg aactcactgg agatgcaaag aaaagtgtgg agatggagac    60
accccaatcg actcgccag                                                  79
```

<210> SEQ ID NO 6
<211> LENGTH: 682
<212> TYPE: DNA
<213> ORGANISM: Homo sapiens

<400> SEQUENCE: 6

```
tctacaggtg tatccagcag ctccaaagag acagcaacca gcaagaatgg gccatagtga    60
cgatggtggt tttgtcaaaa agaaaagggg gggatatgta aggaaaagag agatcagact   120
ttcactgtgt ctatgtagaa aaggaagaca taagaaactc cattttgatc tgtactaaga   180
aaaattgttt tgccttgaga tgctgttaat ctgtaacttt agcccaacc ctgtgctcac    240 ggaaacatgt gctgtaaggt ttaagggatc tagggctgtg caggatgtac cttgttaaca   300
atatgtttgc aggcagtatg tttggtaaaa gtcatcgcca ttctccattc tcgattaacc   360
aggggctcaa tgcactgtgg aaagccacag gaacctctgc caagaaagc ctggctgttg    420 tgggaagtca ggaccccga atggaggac cagctggtgc tgcatcagga aacataaatt     480
gtgaagattt cttggacatt tatcagtttc caaaattaat acttttataa tttcttacac   540
ctgtcttact ttaatctctt aatcctgtta tctttgtaag ctgaggatat acgtcacctc   600
aggaccacta ttgtacaaat tgattgtaaa acatgttcac atgtgtttga acaatatgaa   660
atcagtgcac cttgaaaatg aa                                            682
```

<210> SEQ ID NO 7
<211> LENGTH: 238
<212> TYPE: DNA
<213> ORGANISM: Homo sapiens

<400> SEQUENCE: 7

```
atgctgagcg ccggtcccct gggcccactt ttctttctct atactttgtc tctgttgtct    60
ttcttttctc aagtctctcg ttccacctga ggagaaatgc ccacagctgt ggaggcgcag   120
gccactccat ctggtgccca acgtggatgc ttttctctag ggtgaaggga ctctcgagtg   180
tggtcattga ggacaagtca acgagagatt cccgagtacg tctacagtga gccttgtg    238
```

<210> SEQ ID NO 8
<211> LENGTH: 5553
<212> TYPE: DNA
<213> ORGANISM: Homo sapiens

<400> SEQUENCE: 8

```
tctctcatcc ctcctgacga gaaatacccca caggtgtgga ggggctggcc cccttcatct    60
gatgcccaat gtgggtgcct ttctctaggg tgaaggtact ctacagtgtg gtcattgagg   120
acaagttgac gagagagtcc caagtacgtc cacggtcagc cttgcggtaa gcttgtgtgc   180
```

-continued

```
ttagaggaac ccagggtaac gatggggcaa actgaaagta aatatgcctc ttatctcagc    240
tttattaaaa ttcttttaag aagaggggga gttagagctt ctacagaaaa tctaattacg    300
ctatttcaaa caatagaaca attctgccca tggtttccag aacagggaac tttagatcta    360
aaagattggg aaaaaattgg caaagaatta aaacaagcaa ataggaagg taaaatcatc     420 ccacttacag tatggaatga ttgggccatt attaaagcaa ctttagaacc atttcaaaca    480
ggagaagata ttgtttcagt ttctgatgcc cctaaaagct gtgtaacaga ttgtgaagaa    540
gaggcaggga cagaatccca gcaaggaacg gaaagttcac attgtaaata tgtagcagag    600
tctgtaatgg ctcagtcaac gcaaaatgtt gactacagtc aattacagga gataatatac    660
cctgaatcat caaaattggg ggaaggaggt ccagaatcat gggggccatc agagcctaaa    720
ccacgatcgc catcaactcc tcctcccgtg gttcagatgc ctgtaacatt acaacctcaa    780
acgcaggtta gacaagcaca aaccccaaga gaaaatcaag tagaaaggga cagagtctct    840
atcccggcaa tgccaactca gatacagtat ccacaatatc agccggtaga aaataagacc    900
caaccgctgg tagtttatca ataccggctg ccaaccgagc ttcagtatcg gcctccttca    960
gaggttcaat acagacctca agcggtgtgt cctgtgccaa atagcacggc accataccag   1020
caacccacag cgatggcgtc taattcacca gcaacacagg acgcggcgct gtatcctcag   1080
ccgcccactg tgagacttaa tcctacagca tcacgtagtg gacagggtgg tgcactgcat   1140
gcagtcattg atgaagccag aaaacagggc gatcttgagg catggcggtt cctggtaatt   1200
ttacaactgg tacaggccgg ggaagagact caagtaggag cgcctgcccg agctgagact   1260
agatgtgaac ctttcaccat gaaaatgtta aagatataa aggaaggagt taaacaatat    1320
ggatccaact ccccttatat aagaacatta ttagattcca ttgctcatgg aaatagactt    1380
actcctcatg actgggaaat tttggccaaa tcttcccttt catcctctca gtatctacag   1440
tttaaaacct ggtggattga tggagtacaa gaacaggtac gaaaaaatca ggctactaag    1500
cccactgtta atatagacgc agaccaattg ttaggaacag gtccaaattg gagcaccatt   1560
aaccaacaat cagtgatgca gaatgaggct attgaacaag taagggctat ttgcctcagg   1620
gcctggggaa aaattcagga cccaggaaca gcttttccct ttaattcaat tagacaaggc   1680
tctaaagagc catatcctga ctttgtggca agattacaag atgctgctca aaagtctatt   1740
acagatgaca atgcccgaaa agttattgta gaattaatgg cctatgaaaa tgcaaatcca    1800
gaatgtcagt cggccataaa gccattaaaa ggaaaagttc cagcaggagt tgatgtaatt   1860
acagaatatg tgaaggcttg tgatgggatt ggaggagcta tgcataaggc aatgctaatg   1920
gctcaagcaa tgaggggct cactctagga ggacaagtta aacatttgg gaaaaaatgt     1980 tataattgtg gtcaaatcgg tcatctgaaa aggagttgcc caggcttaaa taaacagaat   2040
ataataaatc aagctattaa cagcaaaaaa taaaagcca tctggcctgt gtccaaaatg     2100
tggaaaagca aaacattggg ccaatcaatg tcattctaaa tttgataaag atgggcaacc   2160
attgtctgga aacaggaaga ggggccagcc tcaggccccc caacaaactg ggcattccc     2220 agttaaactg tttgttcctc agggttttca aggacaacaa ccctacagaa aataccacc    2280 acttcaggga gtcagccaat tacaacaatc aacagctgt cccgcgccac agcaggcagc    2340
accgcagtag atttatgttc cacccaaatg gtcttttac tccctggaaa gcccccacaa    2400
aagattccta gaggggtata tggcccgctg ccagaaggga gggtaggcct ttagggagg    2460 tcgtctaaat ttgaagggag tccaaattca tactgggta atttattcag attataaagg    2520
gggaattcag ttagtgatca gctccactgt tccccggagt gccaatccag gtgatagaat    2580
```

```
tgctcaatta ctgcttttgc cttatgttaa aattggggaa aacaaaaagg aaagaacagg   2640
agggtttgga agtaccaacc ctgcaggaaa agctgcttat tgggctaatc aggtctcaga   2700
ggatagaccc gtgtgtacag tcactattca gggaaagagt ttgaaggatt agtggatacc   2760
caggctgatg tttctgtcat cggcataggt actgcctcag aagtgtatca aagtgccatg   2820
attttacatt gtccaggatc tgataatcaa gaaagtacgg ttcagcctgt gatcacttca   2880
ttccaatcaa tttatggggc cgagacttgt tacaacaatg gcatgcagag attactatcc   2940
cagcctccct atacagcccc aggaataaaa aaatcatgac taaaatggga tagctcccta   3000
aaaagggact aggaaagaag tcccaattga ggctgaaaaa aatcaaaaaa gaaaaggaat   3060
agggcatcct ttttaggagc ggtcactgta gagcctccaa aacccattcc attaacttgg   3120
gggaaaaaaa aacaactgta tggtaaatca gcagcgcttc caaaacaaaa actgagggct   3180
ttacatttat tagcaaagaa acaattagaa aaggacatt gagccttcat tttcgccttg    3240
gaattctgtt tgtaattcag aaaaaatccg gcagatggcg tataatgccg taattcaacc   3300
catgggggct ctcccacccc ggttgccctc tccagccatg gtcccctta attataattg    3360 atctgaagga ttgcttttt accattcctc tggcaaaaca ggattttgaa aaatttgctt    3420
ttaccacacc agcctaaata ataaagaacc agccaccagg tttcagtgga aagtattgcc   3480
tcagggaatg cttaatagtt caactatttg tcagctcaag ctctgcaacc agttagagac   3540
aagttttcag actgttacat cgttcactat gttgatattt tgtgtgctgc agaaacgaga   3600
gacaaattaa ttgaccgtta cacatttctg cagacagagg ttgccaacgc gggactgaca   3660
ataacatctg ataagattca aacctctact cctttccgtt acttgggaat gcaggtagag   3720
gaaaggaaaa ttaaaccaca aaaaatagaa ataagaaaag acacattaaa agcattaaat   3780
gagtttcaaa agttgctagg agatactaat tggatttgga gatattaatt ggatttggcc   3840
aactctaggc attcctactt atgccatgtc aaatttgttc tctttcttaa gaggggactc   3900
ggaattaaat agtgaaagaa cgttaactcc agaggcaact aaagaaatta aattaattga   3960
agaaaaaatt cggtcagcac aagtaaatag aatagatcac ttggccccac tccaaatttt   4020 gattttgct actgcacatt ccctaacagg catcattgtt caaaatacag atcttgtgga    4080
gtggtccttc cttcctcaca gtacaattaa gacttttaca ttgtacttgg atcaaatggc   4140
tacattaatt ggtcagggaa gattatgaat aataacattg tgtggaaatg acccagataa   4200
aatcactgtt cctttcaaca agcaacaggt tagacaagcc tttatcaatt ctggtgcatg   4260
gcagattggt cttgccgatt ttgtgggaat tattgacaat cgttacccca aaacaaaaat   4320
cttccagttt ttaaaattga ctacttggat tttacctaaa gttaccaaac ataagccttt   4380
aaaaaatgct ctggcagtgt ttactgatgg ttccagcaat ggaaaagtgg cttacaccgg   4440
gccaaaagaa tgagtcatca aaactcagta tcacttgact caaagagcag agttggttgc   4500
cgtcattaca gtgttaacaa gatttttaatc agtctattaa cattgtatca gattctgcat   4560
atgtagtaca ggctacaaag gatattgaga gagccctaat caaatacatt atggatgatc   4620
agttaaaccc gctgtttaat ttgttacaac aaaatgtaag aaaaagaaat ttcccatttt   4680
atattactca tattcgagca cacactaatt taccagggcc tttaactaaa gcaaatgaac   4740
aagctgactt gctagtatca tctgcattca tggaagcaca agaacttcat gccttgactc   4800
atgtaaatgc aataggatta aaaaataaat ttgatatcac atggaaacag acaaaaaata   4860
ttgtacaaca ttgcacccag tgtcagattc tacacctggc cactcaggag gcaagagtta   4920
```

| | | | | |
|---|---|---|---|---|
| atcccagagg | tctatgtcct | aatgtgttat | ggcaaatgga | tgtcatgcac | gtaccttcat | 4980 |
| ttggaaaatt | gtcatttgtc | catgtgacag | ttgatactta | ttcacatttc | atatgggcaa | 5040 |
| cctgccagac | aggagaaagt | acttcccatg | ttaaaagaca | tttattatct | tgttttcctg | 5100 |
| tcatgggagt | tccagaaaaa | gttaaaacag | acaatgggcc | aggttactgt | agtaaagcag | 5160 |
| ttcaaaaatt | cttaaatcag | tggaaaatta | cacatacaat | aggaattctc | tataattccc | 5220 |
| aaggacaggc | cataattgaa | agaactaata | gaacactcaa | agctcaattg | gttaaacaaa | 5280 |
| aaaaggaaa | agacaggagt | ataacactcc | ccagatgcaa | cttaatctag | cactctatac | 5340 |
| tttaaatgtt | ttaaacattt | atagaaatca | gaccactacc | tctgcagaac | aacatcttac | 5400 |
| tggtaaaagg | aacagcccac | atgaaggaaa | actgatttgg | tggaaagata | taaaaataa | 5460 |
| aacatgggaa | atggggaagg | tgataacgtg | ggggagaggt | tttgcttgtg | tttcaccagg | 5520 |
| agaaaatcag | cttcctgttt | ggatacccac | tag | | | 5553 |

<210> SEQ ID NO 9
<211> LENGTH: 2179
<212> TYPE: DNA
<213> ORGANISM: Homo sapiens

<400> SEQUENCE: 9

| | | | | | | |
|---|---|---|---|---|---|---|
| gtaaacaaaa | tggtgatatc | agaagaacag | aaaaagttgc | cttccatcaa | ggaagcagag | 60 |
| ttgccaatat | aggcacaatt | aaagaagctg | acacagttag | ctaaaaaaaa | aagcctagag | 120 |
| aatacaaagg | tgacaccaac | tccagagaat | atgctgcttg | cagctctgat | gattgtatca | 180 |
| acggtggtaa | gtcttcccaa | gtctgcagga | gcagctgcag | ctaattatac | ttactgggcc | 240 |
| tatgtgcctt | tcccacccct | aattcgggca | gttacataga | tggataatcc | tattgaagta | 300 |
| gatgttaata | atagtgcatg | ggtgcctggc | cccacagatg | actgttgccc | tgcccaacct | 360 |
| gaagaaggaa | tgatgatgaa | tatttccatt | gggtatcctt | atcctcctgt | ttgcctaggg | 420 |
| aaggcaccag | gatgcttaat | gcctacaacc | caaaattggt | tggtagaagt | acctacagtc | 480 |
| agtgctacca | gtagatttac | ttatcacatg | gtaagtggaa | tgtcacagat | aaataattta | 540 |
| caggacccct | cttatcaaag | atcattacaa | tgtaggccta | aggggaaggc | ttgccccaag | 600 |
| gaaattccca | agaatcaaa | agcccagaa | gtcttagtct | gcggagaatg | tgtggctgat | 660 |
| actgcagtgt | agtacaaaac | aatgaatttt | gaactatgat | agactgggtc | ccttgaggcc | 720 |
| aattatatca | taactgtaca | ggccagactc | attcatgttc | acaggcccca | tccatctggc | 780 |
| ccattaatcc | agcctatgac | ggtgatgtaa | ctgaaaggct | ggaccaggtt | tatagaaggt | 840 |
| tagaatcact | ctgtccaagg | aaatggggtg | aaaagggaat | ttcatcacct | tgaccaaagt | 900 |
| tagtcctgtt | actggtcctg | aacatccaga | attaggaagc | ttactgtggc | ctcacaccac | 960 |
| attagaattt | gttctggaaa | tcaagctata | ggaacaagag | atcgtaagtc | atattatact | 1020 |
| atcaacctaa | attccagtct | gacaattcct | ttgcaaaatt | gtgtaaaact | cccttatatt | 1080 |
| gctagttgta | ggaaaaacat | agttattaaa | cctgattccc | aaaccataat | ctgtgaaaat | 1140 |
| tgtggaatgt | ttacttgcat | tgatttgact | tttaattggc | agcaccgtat | tctactagga | 1200 |
| agagcaagag | agggtgtgtg | gatccttgtg | tccatggacc | gaccatggga | ggcttcgcta | 1260 |
| tccatccata | ttttaacgga | agtattaaaa | ggaattctaa | ctagatccaa | aagattcatt | 1320 |
| tttactttga | tggcagtgat | tatgggcctc | attgcagtca | cagctactgc | tgcggctgct | 1380 |
| ggaattgctt | tacactcctc | tgttcaaact | gcagaatacg | taaatgattg | gcaaaagaat | 1440 |
| tcctcaaaat | tgtggaattc | tcagatccaa | atagatcaaa | aattggcaaa | ccaaattaat | 1500 |

```
gatcttagac aaactgtcat ttggatggga gaggctcatg agcttggaat atctttttca    1560
gttacgatgt gactggaata catcagattt ttgtgttaca ccacaagcct ataatgagtc    1620
tgagcatcac tgggacatgg ttagatgcca tctgcaagga ggagaagata atcttacttt    1680
agacatttca aaattaaaag aattttttt ttctttgaga cagagtctcg ctctgtcgcc     1740
caggctggag tgcagtggcg tgatctcagc tcactgcaag ttccgcctcc tgggtttaca    1800
ccattctcct gcctcagcct cccaagtagt tgggactaca ggagcccacc accatgcctg    1860 gctaatttt tttgggtttt taatagagat ggagtttcac cgtgttagcc aggatggtct     1920
cgatctcctg accttgtgat ctgcccacct tggcctccca aagtgctggg attacagtcg    1980
tgagccaccg tgcccagcca agaaaaaatt tttgaggcat caaaagccca tttaaatttg    2040
gtgccaggaa cggagacaat cgtgaaagct gctgatagcc tcacaaatct taagccagtc    2100
acttgggtta aaagcatcag aagtttcact attgtaaatt tcatattaat ccttgtatgc    2160
ctgttctgtc tgttgttag                                                2179
```

```
<210> SEQ ID NO 10
<211> LENGTH: 16
<212> TYPE: DNA
<213> ORGANISM: Artificial Sequence
<220> FEATURE:
<223> OTHER INFORMATION: Synthetic

<400> SEQUENCE: 10
ccgaaccaca catgga                                                     16

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagatacata aggtaagc                                                   18

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12 tttatttag accatggaaa ta                                               22

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13
gatgaataaa tgtgtgtttg agcctagtta tg                                   32

<210> SEQ ID NO 14
<211> LENGTH: 261
<212> TYPE: DNA
<213> ORGANISM: Artificial Sequence
<220> FEATURE:
```

<223> OTHER INFORMATION: Synthetic

<400> SEQUENCE: 14

| cgggtcctcc atatgctgag cgccggtccc ctgggcccac ttttcttct ctatactttg | 60 |
| tctctgttgt ctttcttttc tcaagtctct cgttccacct gaggagaaat gcccacagct | 120 |
| gtggaggcgc aggccactcc atctggtgcc caacgtggat gcttttctct agggtgaagg | 180 |
| gactctcgag tgtggtcatt gaggacaagt caacgagaga ttcccgagta cgtctacagt | 240 |
| gagccttgtg gtaagcttgg g | 261 |

<210> SEQ ID NO 15
<211> LENGTH: 101
<212> TYPE: DNA
<213> ORGANISM: Artificial Sequence
<220> FEATURE:
<223> OTHER INFORMATION: Synthetic

<400> SEQUENCE: 15

| tctttcctca gggtgaaggt actctacagt gtggtcattg aggacaagtt gacgagagag | 60 |
| tcccaagtac gtccacggtc agccttgcgg gtgaaggtac t | 101 |

<210> SEQ ID NO 16
<211> LENGTH: 101
<212> TYPE: DNA
<213> ORGANISM: Artificial Sequence
<220> FEATURE:
<223> OTHER INFORMATION: Synthetic

<400> SEQUENCE: 16

| atacccacta gacatttaaa gttctacaat gaactcactg gagatgcaaa gaaaagtgtg | 60 |
| gagatggaga caccccaatc gactcgccag gtaaacaaaa t | 101 |

<210> SEQ ID NO 17
<211> LENGTH: 701
<212> TYPE: DNA
<213> ORGANISM: Artificial Sequence
<220> FEATURE:
<223> OTHER INFORMATION: Synthetic

<400> SEQUENCE: 17

| tgttgttagt ctacaggtgt atccagcagc tccaaagaga cagcaaccag caagaatggg | 60 |
| ccatagtgac gatggtggtt ttgtcaaaaa gaaaaggggg ggatatgtaa ggaaaagaga | 120 |
| gatcagactt tcactgtgtc tatgtagaaa aggaagacat aagaaactcc attttgatct | 180 |
| gtactaagaa aaattgtttt gccttgagat gctgttaatc tgtaacttta gccccaaccc | 240 |
| tgtgctcacg gaaacatgtg ctgtaaggtt taagggatct agggctgtgc aggatgtacc | 300 |
| ttgttaacaa tatgtttgca ggcagtatgt ttggtaaaag tcatcgccat tctccattct | 360 |
| cgattaacca ggggctcaat gcactgtgga aagccacagg aacctctgcc caagaaagcc | 420 |
| tggctgttgt gggaagtcag ggaccccgaa tggagggacc agctggtgct gcatcaggaa | 480 |
| acataaattg tgaagatttc ttggacattt atcagtttcc aaaattaata ctttttataat | 540 |
| ttcttacacc tgtcttactt taatctctta atcctgttat ctttgtaagc tgaggatata | 600 |
| cgtcacctca ggaccactat tgtacaaatt gattgtaaaa catgttcaca tgtgtttgaa | 660 |
| caatatgaaa tcagtgcacc ttgaaaatga acagaataac a | 701 |

<210> SEQ ID NO 18
<211> LENGTH: 644

```
<212> TYPE: DNA
<213> ORGANISM: Artificial Sequence
<220> FEATURE:
<223> OTHER INFORMATION: Synthetic

<400> SEQUENCE: 18
ggctccgaac acacatggat attggatatc tgcataggca gcttgctcca cgccagtgcc      60
tacctgtgca gatgggaagg aaaggaaagt ggcaaggagg cagagaaagc atctgtaccc     120
ttacaatttg gtgagacaag aatgtatgaa ttcccacagg tcaaattata atgaagaaag     180
gaacctctct tgagtacaaa gagctaccta tggtggtctg gagccggagg accacagcat     240
caaaggatat aagatgcata gccaactgag gaacctgagc aattaaagag atccacagtt     300
aagtcacact taactggcac ttgtggaagc cccgcaaggc ctgaaggaga gctgacatag     360
gcaccccgga gagccagaat ctggatccca tcttaataag gccatgaaca ccagtggaga     420
agaggcagaa acaccaatgg ataaggaaca ttcacatctt tcttcccatg tgcctctaag     480
tgccagtgca ggccccacag gccaagctac agggagaaag gagatgacgc aaaggaacct     540
aactggactt taatcactag aagtgagaag agaaatctat tggaacctcc caagataatg     600
ccaagggtca aagggtgcgc agatacataa ggtaagccct tcgg                      644

<210> SEQ ID NO 19
<211> LENGTH: 1376
<212> TYPE: DNA
<213> ORGANISM: Artificial Sequence
<220> FEATURE:
<223> OTHER INFORMATION: Synthetic

<400> SEQUENCE: 19
tttagaccat ggaaataata tcagacaaaa agcagattag agcaatttc tttttcgagt        60 tcaaaatggg ttataaagca gcggagacaa accgcaacat caccaacgcc tttggcccag     120
gaactgctaa tgaaggtaca gtgcagtcac tgttcaggaa gttttgcaaa ggagactaga     180
gccttgaaga tgaggagcat agtgaccagc cattggaagt cgacaaagac caattgagag     240
gaatcattga agctgatcat cttacaacta cacgagaagt tgtcaaagaa cgcaatgttg     300
accattgtgt ggtcttttcg catttgaagc aaattggaaa ggtgaaaaac ttgataagtg     360
ggtgccttgt gagctcagca aaaatccaaa aaaataatca tttttaagtg ttgtcttctc     420
ttattctacg caacaacaat aaccattttg caatcggatt gtgatgtgca atgaaaagtg     480
gatttggggc cgggcgcggt ggctcacgcc tgtaatctca gcactttgga aggccaaggc     540
gggcagatca cgaggtcagg agatcaagac cgtcctggct aacacggtga accccgtct     600 ctactgaaaa tacaaaaaat tagccgggtg tggtggctgg cgcctgtagt cccagctaca     660
ggctgaggca ggagaatggc atgaacctgg gaggcggagc ttgcagtgag ccgagaccgt     720
gccactgcac tccagcctgg gcgacagagc gatactccgt caaaaaaaaa aaaaaaaaaa     780
aaaaaagaca agtggatttt atatatggca accagcaatg accagctcag tggctggact     840
gagaagaagc tccaaagcac ttcccaaagc caaacttgca ccaaaaaaa ggtcagggtc      900 actgtttggt ggtctgctgc tggtctgatc caccgctgct ctctgaatcc tggcaaaacc     960
attacatctg agaagtatgc tcaacaaatc aatgagctac gccaaaaact gcagcatctg    1020
cagctggcat tggtcaacat aacgggtcca attcttctcc acgacaacgc tcaactgcac    1080
cttgcgcaag cagcgcttca aaagttgaac aaattgggct acatagtttt tcctcatccg    1140
ccatattcac ctgacgtctt gccaactaac taccacttct tcaagtatct caacaacttt    1200
```

-continued

```
ttgcagggaa aacacttcca caaccagcag gatgcagaac acgctttcca agagtttgtc   1260
gaatcctgac gcacagattt ttatgctaca ggaataaact aacttatttc tcattggcaa   1320
aaatgtgttg attgtaatgg ttcctatttt gatgaataaa tgtgtgtttg agccta       1376

<210> SEQ ID NO 20
<211> LENGTH: 813
<212> TYPE: DNA
<213> ORGANISM: Homo sapiens

<400> SEQUENCE: 20
tttctcaggt ctggatgtag ggttagatgc cagttagata taagtgaaat agccggttta     60
cttaccaata gacaggaaag tagtcttttg tgattccctt ctccactaaa tacaaatcag    120
tgctactcag gggctcttta agaaggagt tggccaggtg tggtgactca cgcctgtaat     180
cttagcactt tgggaggttg aggcgggtgg atcacctgag gtcaggagtt cgagaccatt    240
cctgaccaac atgagaaac cctgtctcta aaaatacaaa atcagctggg cgtggtggcg     300
catgcctgta atcccagcta cttgggaggc tgaggcagga gaatcgcttg aacccgggag    360
gcggaggttg tagtgagccg agattgtgcc attgcactcc agcctgggca acaagagcga    420
aactccgact acatgtaccc taaaacttaa agtataataa taataaaatt aaaaaaaaaa    480
aaaaagaaca gcagcagtaa aaaataaata aagaaataaa taaataaata aatgaagaag    540
tcaatcggta ccataagaaa ggacaaaaac caaaacaaac ccaaagcaaa accaaaaact    600
ccccacaaac cagcctcccc taacccttt aactcaaagc ttcgtaatgt ctctgaattt     660
ataattacga ttttaaagag cactgtttct catgccccat cccccaaccc atttcgggag    720 taaaccttt ctgtcagggt gaggagaaag tgggtaaagg acttcagcat ttacagttga    780
gttagtattt gttgttctcc aaatgtgcag gaa                                813

<210> SEQ ID NO 21
<211> LENGTH: 404
<212> TYPE: DNA
<213> ORGANISM: Homo sapiens

<400> SEQUENCE: 21
tccttggtgg cttagggtac agttattaat gctggctgtg atgaagtttt gctggggacc     60
aggataacag atggtccagt catggggcct cagtggtggc agtgattagc tgatcatgcc    120
tgtcctttgg ccccaggttg gcttatgctg gcacttgtgt tgttaggccc aagcagtctg    180
atttgggggc ctccacatgg tttgctggga tgttggtagt ttctgcttcc tggcctgatg    240
tggtacatct gggtgagtgc cagctctggt ggtattagca tgttatgtca gcctgtcctt    300
agaccctggg agaagtgttc atgtgccaat ggtggtagac tgtgctgagt gatttccagg    360
cccctggaca gcatactgaa ttactgagag gatgggactg agca                    404
```